US012735494B2

(12) United States Patent
Devorkin et al.

(10) Patent No.: US 12,735,494 B2
(45) Date of Patent: Sep. 15, 2026

(54) CD3 T-CELL ENGAGERS AND METHODS OF USE

(71) Applicant: AbCellera Biologics Inc., Vancouver (CA)

(72) Inventors: Lindsay Devorkin, Vancouver (CA); Aaron Paul Yamniuk, Vancouver (CA); Bryan Crawford Barnhart, Vancouver (CA); Wei Wei, Vancouver (CA); Kevin Albert Heyries, Vancouver (CA); Harveer Dhupar, Vancouver (CA); Sherie Duncan, Vancouver (CA); Timothy M. Jacobs, Vancouver (CA)

(73) Assignee: AbCellera Biologics Inc. (CA)

( * ) Notice: Subject to any disclaimer, the term of this patent is extended or adjusted under 35 U.S.C. 154(b) by 677 days.

(21) Appl. No.: 18/186,429

(22) Filed: Mar. 20, 2023

(65) Prior Publication Data

US 2023/0295310 A1 Sep. 21, 2023

Related U.S. Application Data

(60) Provisional application No. 63/321,745, filed on Mar. 20, 2022.

(51) Int. Cl.
*C07K 16/28* (2006.01)
*A61K 47/68* (2017.01)
*C12N 15/86* (2006.01)

(52) U.S. Cl.
CPC ...... *C07K 16/2863* (2013.01); *A61K 47/6849* (2017.08); *C07K 16/2809* (2013.01); *C12N 15/86* (2013.01); *C07K 2317/31* (2013.01); *C07K 2317/92* (2013.01); *C12N 2740/15043* (2013.01)

(58) Field of Classification Search
None
See application file for complete search history.

(56) References Cited

U.S. PATENT DOCUMENTS 9,657,102 B2 * 5/2017 Smith ..................... A61P 35/02
2015/0166661 A1 6/2015 Chen et al.

FOREIGN PATENT DOCUMENTS

EP 3527590 A1 8/2019
EP 3561057 A1 10/2019
WO 2015181098 A1 12/2015
WO 2018197502 A1 11/2018
WO 2020132574 A1 6/2020
WO 2021104430 A1 6/2021

OTHER PUBLICATIONS

Dondelinger et al., Front Immunol 9: 1-15 (Year: 2018).*
"Bispecific Antibody Drug Conjugates (ADCs): Emerging Trends", at https://www.biochempeg.com/article/290.html, downloaded Jul. 19, 2023.
Chothia et al., "Conformations of immunoglobulin hypervariable regions", Nature 342, 877-883 (1989).
Chothia, et al., "Canonical structures for the hypervariable regions of immunoglobulins." Journal of molecular biology 196.4 (1987): 901-917.
Groth, et al., "Phase I/II Trial of a Combination of Anti-CD3/CD7 Immunotoxins for Steroid-Refractory Acute Graft- versus-Host Disease", Biology of Blood and Marrow Transplantation, vol. 25, Issue 4, 2019, pp. 712-719.
Hotzel et al., "A strategy for risk mitigation of antibodies with fast clearance", mAbs vol. 4, 6 (2012): 753-60.
International Search Report and Written Opinion issued in International Patent Appln. No. PCT/US2023/064693 dated Sep. 1, 2023.
Invitation to Pay Additional Fees and Partial Search Report mailed Jul. 11, 2023, for International Patent Application No. PCT/US2023/064693.
Leo et al., "Identification of a monoclonal antibody specific for a murine T3 polypeptide." Proceedings of the National Academy of Sciences 84.5 (1987): 1374-1378.
Liu et al., "High-throughput screening for developability during early-stage antibody discovery using self-interaction hanoparticle spectroscopy", mAbs, 6:2, 483-492.
Maccallum et al., "Antibody-antigen interactions: contact analysis and binding site topography", J Mol Biol. Oct. 1, 19961;262(5):732-45.
Wei et al., "Current landscape and future directions of bispecific antibodies in cancer immunotherapy", Front Immunol. Oct. 28, 2022;13.
Zhao et al., "Bispecific Antibodies for Autoimmune and Inflammatory Diseases: Clinical Progress to Date", BioDrugs. Apr. 2020;34(2):111-119.

* cited by examiner

*Primary Examiner* — Phuong Huynh
(74) *Attorney, Agent, or Firm* — Potomac Law Group, PLLC

(57) ABSTRACT

Anti-CD3 antibodies for use in the diagnosis or treatment of hyperproliferative or autoimmune disorders methods of using the same for detecting and/or treating a hyperproliferative or autoimmune disorders.

6 Claims, 3 Drawing Sheets

Specification includes a Sequence Listing.

```
                                SEQUENCE LISTING


Sequence total quantity: 592
SEQ ID NO: 1              moltype = AA  length = 124
FEATURE                   Location/Qualifiers
source                    1..124
                          mol_type = protein
                          organism = synthetic construct
SEQUENCE: 1
QAQLVQSGSE LKKPGASVKV SCKASGYTFT KHSMNWVRQA PGQGLEWMGW INTNTGNPTY  60
AQGFTGRFVF SLDTSVTTAY LQISSLKAED TAVYYCAREG DYDFWSGFFN FDYWGQGTLV  120
TVSS                                                               124

SEQ ID NO: 2              moltype = AA  length = 107
FEATURE                   Location/Qualifiers
source                    1..107
                          mol_type = protein
                          organism = synthetic construct
SEQUENCE: 2
DIQMTQSPSS LSASVGDRVT ITCRASQGIR NDLGWYQQKP GKAPKRLIYA ASSLQSGVPS  60
RFSGSGSGAE FTLTISSLQP EDFATYYCLQ HNSYPRTFGQ GTKVEIK                107

SEQ ID NO: 3              moltype = AA  length = 124
FEATURE                   Location/Qualifiers
source                    1..124
                          mol_type = protein
                          organism = synthetic construct
SEQUENCE: 3
QAQLVQSGSE LKKPGASVKV SCKASGYTFT KHSMNWVRQA PGQGLEWMGW INTNTGNPMY  60
AQGFTGRFVF SLDTSVTTAY LQISSLKAED TAVYYCAREG DYDFWSGFFN FDYWGQGTLV  120
TVSS                                                               124

SEQ ID NO: 4              moltype = AA  length = 107
FEATURE                   Location/Qualifiers
source                    1..107
                          mol_type = protein
                          organism = synthetic construct
SEQUENCE: 4
DIQMTQSPSS LSASVGDRVT ITCRASQGIR NDLGWYQQKP GKAPKRLIYA ASSLQSGVPS  60
RFSGSGSGAE FTLTISSLQP EDFATYYCLQ HNSYPRTFGQ GTKVEIK                107

SEQ ID NO: 5              moltype = AA  length = 124
FEATURE                   Location/Qualifiers
source                    1..124
                          mol_type = protein
                          organism = synthetic construct
SEQUENCE: 5
QAQLVQSGSE LKKPGASVKV SCKASGYTFT RHAMNWVRQA PGQGLEWMGW INTNTGNPTY  60
AQGFTGRFVF SLDTSVSTAY LKISSLKAED TAVYYCVREG DYDFWSGFFN FDYWGQGTLV  120
TVSS                                                               124

SEQ ID NO: 6              moltype = AA  length = 107
FEATURE                   Location/Qualifiers
source                    1..107
                          mol_type = protein
                          organism = synthetic construct
SEQUENCE: 6
DIQMTQSPSS LSASVGDRVT ITCRASQGIR NDLGWFQQKP GKAPTRLIYA ASSLQSGVPS  60
RFSGSGSGAE FTLTISSLQP EDFATYYCLQ HNSYPRTFGQ GTKVEIK                107

SEQ ID NO: 7              moltype = AA  length = 124
FEATURE                   Location/Qualifiers
```

```
source                  1..124
                        mol_type = protein
                        organism = synthetic construct
SEQUENCE: 7
QAQLVQSGSE LKKPGASVKV SCKASGYTFT KHSMNWVRQA PGQGLEWMGW INTNTGNPMY  60
GQGFTGRFVF SLDTSMTTTY LQISSLKAED TAIYYCAREG DYDLWRGFFN FDYWGQGTLV  120
TVSS                                                              124

SEQ ID NO: 8            moltype = AA  length = 107
FEATURE                 Location/Qualifiers
source                  1..107
                        mol_type = protein
                        organism = synthetic construct
SEQUENCE: 8
DIQMTQSPSS LSASVGDRVT ITCRASQGIR NDLGWYQQKP GKAPKRLIYA ASSLQSGVPS  60
RFSGSGSGAE FTLTISSLQP EDFATYYCLQ HNSYPRTFGQ GTKVEIK               107

SEQ ID NO: 9            moltype = AA  length = 120
FEATURE                 Location/Qualifiers
source                  1..120
                        mol_type = protein
                        organism = synthetic construct
SEQUENCE: 9
EGQLVESGGG LVQPGGSLRL SCVASGFTLS SYTLNWVRQA PGKGLEWVSY ISSTSRTIYY  60
SDSVKGRFTI SRDNAKNSLY LQMNSLRDED TALYYCARED YYDSSGFDYW GQGTLVTVSS  120

SEQ ID NO: 10           moltype = AA  length = 120
FEATURE                 Location/Qualifiers
source                  1..120
                        mol_type = protein
                        organism = synthetic construct
SEQUENCE: 10
EGQLVESGGG LVQPGGSLRL SCVASGFTLS SYTLNWVRQA PGKGLEWVSY ISSTSRTIYY  60
SDSVKGRFTI SRDNAKNSLY LQMNSLRDED TALYYCARED YYDSSGFDYW GQGTLVTVSS  120

SEQ ID NO: 11           moltype = AA  length = 124
FEATURE                 Location/Qualifiers
source                  1..124
                        mol_type = protein
                        organism = synthetic construct
SEQUENCE: 11
QAQLVQSGSE LKKPGASVKV SCKASGYTFT KHSMNWVRQA PGQGLEWMGW INTNTGNPTY  60
AQGFTGRFVF SLDTSVTTAY LQISSLKAED TAVYYCAREG DYDFWSGFFN FDYWGQGTLV  120
TVSS                                                              124

SEQ ID NO: 12           moltype = AA  length = 124
FEATURE                 Location/Qualifiers
source                  1..124
                        mol_type = protein
                        organism = synthetic construct
SEQUENCE: 12
QAQLVQSGSE LKKPGASVKV SCKASGYTFT KHSMNWVRQA PGQGLEWMGW INTNTGNPTY  60
AQGFTGRFVF SLDTSVTTAY LQISSLKAED TAVYYCAREG DYDFWSGFFN FDYWGQGTLV  120
TVSS                                                              124

SEQ ID NO: 13           moltype = AA  length = 117
FEATURE                 Location/Qualifiers
source                  1..117
                        mol_type = protein
                        organism = synthetic construct
SEQUENCE: 13
QVQLVQSGAE VKKPGASVKV SCKASGYTFT GYYIHWVRQA PGQGLEWMGW INPKSGNRNY  60
AQKFQGRVTM TRDTSIDTAY MELTRLRSDD TAVYYCARIE QLVFDYWGQG TLVTVSS     117

SEQ ID NO: 14           moltype = AA  length = 113
FEATURE                 Location/Qualifiers
source                  1..113
                        mol_type = protein
                        organism = synthetic construct
SEQUENCE: 14
DIVMTQSPDS LAVSLGERAT INCKSSQSVL YSSNNKNYLA WYQQKPGQPP KLLIYWASTR  60
ESGVPDRFSG SGSGTDFTLT ISSLQAEDVA VYYCQQYYST PYTFGQGTKL EIK         113

SEQ ID NO: 15           moltype = AA  length = 120
FEATURE                 Location/Qualifiers
source                  1..120
                        mol_type = protein
                        organism = synthetic construct
SEQUENCE: 15
```

```
EVQLVESGGG LVPPGGSLRL SCVASGFTLR SYTMNWVRQA PGQGLEWISY ISSTSRTIYY  60
SDSVKGRFTI SRDNAKNSLY LQVNSLRDED TALYYCARED YYDSSGFDCW GQGTLVTVSS  120

SEQ ID NO: 16          moltype = AA  length = 107
FEATURE                Location/Qualifiers
source                 1..107
                       mol_type = protein
                       organism = synthetic construct
SEQUENCE: 16
AIRMTQSPSS FSASTGDRVT ITCRASQGIF NYLAWYQQKP GKAPKLLIYS TSTLQSGVPS  60
RFSGSGSGTD FTLTIRGLQS EDLATYYCQQ YYSFPRTFGQ GTKVDIK              107

SEQ ID NO: 17          moltype = AA  length = 124
FEATURE                Location/Qualifiers
source                 1..124
                       mol_type = protein
                       organism = synthetic construct
SEQUENCE: 17
QAQLVQSGSE LKKPGASVKV SCKASGYTFT RHAMNWVRQA PGQGLEWMGW INTNTGNPTY  60
AQGFTGRFVF SLDTSVTTAY LQISSLKAED TAVYYCAREG DYDFWSGFFN FDYWGQGTLV  120
TVSS                                                              124

SEQ ID NO: 18          moltype = AA  length = 107
FEATURE                Location/Qualifiers
source                 1..107
                       mol_type = protein
                       organism = synthetic construct
SEQUENCE: 18
DIQMTQSPSS LSASVGDRVT ITCRASQGIR NDLGWFQQKP GKAPTRLIYA ASSLQSGVPS  60
RFSGSGSGAE FTLTISSLQP EDFATYYCLQ HNSYPRTFGQ GTKVEIK              107

SEQ ID NO: 19          moltype = AA  length = 120
FEATURE                Location/Qualifiers
source                 1..120
                       mol_type = protein
                       organism = synthetic construct
SEQUENCE: 19
EVQLVESGGG LVQPGGSLRL SCAASGFTLS SYTMNWVRQA PGKGLEWVSY ISSSSRTIYY  60
SDSVKGRFSI SRDNAKNSLY LQMNSLRDED TALYYCARED YYDSSGFDNW GQGTLVTVSS  120

SEQ ID NO: 20          moltype = AA  length = 107
FEATURE                Location/Qualifiers
source                 1..107
                       mol_type = protein
                       organism = synthetic construct
SEQUENCE: 20
AIRMTQSPSS FSASTGDRVT ITCRASQGIS SYLAWYQQKP GKAPKLLIYT ASTLQSGVPS  60
RFSGSGSGTD FTLTIRSLQS EDFATYYCQQ YYSYPRTFGQ GTKVEIK              107

SEQ ID NO: 21          moltype = AA  length = 124
FEATURE                Location/Qualifiers
source                 1..124
                       mol_type = protein
                       organism = synthetic construct
SEQUENCE: 21
QVQLVQSGAE VKKPGASVKV SCKASGYTFT SHDINWVRQA TGQGLEWMGW LNPNSGKTGY  60
AQKFQGRVTM ARDTSMYTAD MELSSLRFED TAVYYCARVG HYDMWPGFFS FDYWGQGTLV  120
TVSS                                                              124

SEQ ID NO: 22          moltype = AA  length = 107
FEATURE                Location/Qualifiers
source                 1..107
                       mol_type = protein
                       organism = synthetic construct
SEQUENCE: 22
DIQMTQSPSS LSASVGDRII ITCRASQDIR NDLGWYQQKP GKAPKRLIYA ASSLQSGVPS  60
RFSGSRSGTE FTLTISSLHP EDFATYYCLQ HRSYPYTFGQ GTNLEIK              107

SEQ ID NO: 23          moltype = AA  length = 124
FEATURE                Location/Qualifiers
source                 1..124
                       mol_type = protein
                       organism = synthetic construct
SEQUENCE: 23
QVQLVQSGAE VKKPGASVKV SCKASGYTFT SYDINWVRQA TGQGLEWMGW MNPKSGKTGY  60
AQKFQGRITM TRNTPISTVY MDLSSLRSED TAVYYCAREG HYDFWTGYYS FDYWGQGTLV  120
TVSS                                                              124

SEQ ID NO: 24          moltype = AA  length = 107
```

```
FEATURE                Location/Qualifiers
source                 1..107
                       mol_type = protein
                       organism = synthetic construct
SEQUENCE: 24
DIQMTQSPSS LSASVGDRVT ITCRASQGIR NDLGWYQQTP GKAPKRLIYA ASSLQSGVPS  60
RFSGSGSGTE FTLTISSLQP EDFATYYCLQ HYSYPYTFGQ GTKLEIK               107

SEQ ID NO: 25          moltype = AA  length = 120
FEATURE                Location/Qualifiers
source                 1..120
                       mol_type = protein
                       organism = synthetic construct
SEQUENCE: 25
EVQLEESGGG LVQPGGSLRL SCAASGFTFS RYSMNWVRQA PGKGLEWFSY ISSSSRTIYY  60
ADSVKGRFTM SRDNAKNSLY LQMNSLRDED TAVYFCARGD YYDSEGMDVW GKGTTVTVSS  120

SEQ ID NO: 26          moltype = AA  length = 107
FEATURE                Location/Qualifiers
source                 1..107
                       mol_type = protein
                       organism = synthetic construct
SEQUENCE: 26
DIQMTQSPST LSASVGDRVT ITCRASQTIT TWLAWYQQKP GKAPKLLIYK ASTLESGVPS  60
RFSGSGSGTE FTLTISSLQP DDFATYHCQQ YKTFSYTFGQ GTKLDIK               107

SEQ ID NO: 27          moltype = AA  length = 124
FEATURE                Location/Qualifiers
source                 1..124
                       mol_type = protein
                       organism = synthetic construct
SEQUENCE: 27
QVQLEQSGAE VKKPGASVKV SCKTSGYIFA NYDINWVRQA TGQGLEWMGW MNPKSGKAGY  60
AQKFQGRVTM TSNTPINTAY MELSSLRSED TAVYYCAREG HYDFWRGFYS FDYWGQGILV  120
TVSS                                                              124

SEQ ID NO: 28          moltype = AA  length = 107
FEATURE                Location/Qualifiers
source                 1..107
                       mol_type = protein
                       organism = synthetic construct
SEQUENCE: 28
DIQMTQSPSS LSASVGDRVT ITCRASQGIR NDLGWYQQKP GKAPKRLIYT ASSLQSGVPS  60
RFSGSGSGTE FTLTISSLQP EDFATYFCLQ YNTYPYTFGQ GTKLEIK               107

SEQ ID NO: 29          moltype = AA  length = 118
FEATURE                Location/Qualifiers
source                 1..118
                       mol_type = protein
                       organism = synthetic construct
SEQUENCE: 29
QVQLVQSGAE VRKPGASVKV SCKASGYTFT GNHMHWVRQA PGQGLEWMGW INPKSGRTNF  60
AQNFQGRVTM TRDTSISTAF MELSRLRSDD TAVYYCARMG DLLLFDFWGQ GTLVTVSS    118

SEQ ID NO: 30          moltype = AA  length = 113
FEATURE                Location/Qualifiers
source                 1..113
                       mol_type = protein
                       organism = synthetic construct
SEQUENCE: 30
DIVMTQSPDS LAVSLGERAT INCKSSQSVL YSSNNKNYLA WYQQKPGQPP KLLIYWASTR  60
ESGVPDRFSG SGSGTDFTLT ISSLQAEDVA VYYCQQYYST PLTFGGGTKV EIK        113

SEQ ID NO: 31          moltype = AA  length = 117
FEATURE                Location/Qualifiers
source                 1..117
                       mol_type = protein
                       organism = synthetic construct
SEQUENCE: 31
QVQLMPSGAE VKEPGASVKV SCKASGYTFT GYYMHWVRQA PGQGLEWMGW INPNSGRTSY  60
AKNFQGRVTM TRDTSISTAY MELSRLRSDD TAVYYCARIE QLVFDYWGQG TLVTVSS     117

SEQ ID NO: 32          moltype = AA  length = 112
FEATURE                Location/Qualifiers
source                 1..112
                       mol_type = protein
                       organism = synthetic construct
SEQUENCE: 32
DIVMTQSPLS LPVTPGEPAS ISCRSSQSLL HSNGYNYLDW YLQKPGQSPQ LLIYLGSNRA  60
```

-continued

```
SGVPDRFSGS GSGTDFTLKI SRVEAEDVGV YYCMQALQTP LTFGGGTKVE IK         112

SEQ ID NO: 33           moltype = AA  length = 118
FEATURE                 Location/Qualifiers
source                  1..118
                        mol_type = protein
                        organism = synthetic construct
SEQUENCE: 33
QVQLVESGGG VVQPGRSLRL SCAASGFTFS GYGMHWVRQA PGKGLDWVAI IYYNGNNKYY  60
ADSVKGRFTI SRDNSKNTLY LQMNSLRAED TAVYYCARGG GYNWFDPWGQ GTLVIVSS    118

SEQ ID NO: 34           moltype = AA  length = 107
FEATURE                 Location/Qualifiers
source                  1..107
                        mol_type = protein
                        organism = synthetic construct
SEQUENCE: 34
DIQMTQSPSS LSASVGDRVT ITCRPSQSIS NYLNWYQQKP GKAPKLLIYA ASSLQSGVPS  60
RFSGSGSGTD FTLTISSLQP EDFATYYCQQ SYSTPFTFGR GTRLEIK               107

SEQ ID NO: 35           moltype = AA  length = 121
FEATURE                 Location/Qualifiers
source                  1..121
                        mol_type = protein
                        organism = synthetic construct
SEQUENCE: 35
QVQLVQSGAE VKKPGASVKV SCKASGYTVT GYYMHWVRQA PGQGLEWMGW INPNSGGTNF  60
AQNFQGRVTM TRDTSISTFY MDLSRLRSDD TAVYYCARGG APVSYWFFDL WGRGTLVTVS  120
S                                                                 121

SEQ ID NO: 36           moltype = AA  length = 107
FEATURE                 Location/Qualifiers
source                  1..107
                        mol_type = protein
                        organism = synthetic construct
SEQUENCE: 36
DIQMTQSPSS LSASVGDRVT ITCRASQSIS RYLNWYQQKP GKAPKVLIYN TSSLKSGVPS  60
RFSGSGSGTD FTLTISSLQP EDFATLYCQQ SHSTPFTFGP GTKVDIK               107

SEQ ID NO: 37           moltype = AA  length = 126
FEATURE                 Location/Qualifiers
source                  1..126
                        mol_type = protein
                        organism = synthetic construct
SEQUENCE: 37
EVQLVESGGD LVQPGRSLRL SCAASGFTFD DCVIHWVRQA PGKGLEWVSG ITWNSGRIGY  60
ADSVKGRFTI SRDNAKNSLY LQMNSLRVED TALYYCAKEG NYDFWSTYYR GYFDLWGRGT  120
LVTVSS                                                            126

SEQ ID NO: 38           moltype = AA  length = 107
FEATURE                 Location/Qualifiers
source                  1..107
                        mol_type = protein
                        organism = synthetic construct
SEQUENCE: 38
DIQMTQSPSS LSASVGDRVT ITCRASQGIR NDLGWYQQKP GIAPKRLIYA ASSLQGGVPL  60
RFSGSGSGTE FTLTISSLQP EDFATYYCLQ HNSYPYTFGQ GTKLEIK               107

SEQ ID NO: 39           moltype = AA  length = 121
FEATURE                 Location/Qualifiers
source                  1..121
                        mol_type = protein
                        organism = synthetic construct
SEQUENCE: 39
EVQLVDSGGG LVQPGGSLRL SCSGSGFTFS SYWMSWVRQA PGKGLEWVAN IKQDGSQKYY  60
VDSVKGRFTI SRDNVKNSLY LQMNSLRVED TAVYYCARDE SSSWYWYFDL WGRGTLVTVS  120
S                                                                 121

SEQ ID NO: 40           moltype = AA  length = 107
FEATURE                 Location/Qualifiers
source                  1..107
                        mol_type = protein
                        organism = synthetic construct
SEQUENCE: 40
DIQMTQSPST LSASVGDRVT LTCRASQNIV KWLAWYQQKP GKAPKLLIYK ASSLESGVPS  60
WFSGSGSGTE FTLTINSLQP DDFATYYCQQ YYTYSRTFGQ GTKVEIK               107

SEQ ID NO: 41           moltype = AA  length = 118
FEATURE                 Location/Qualifiers
```

```
source                  1..118
                        mol_type = protein
                        organism = synthetic construct
SEQUENCE: 41
QMLLVESGGG VVQPGRSLTL SCAASGFTFR SYGMHWVRQA PGRGLEWVAI IWYDGSTEYY  60
ADSVKGRFTI SRANSKNMLY LQMNSLRAED TAVYYCAAFD YTNSFDIWGQ GTMVTVSS    118

SEQ ID NO: 42           moltype = AA  length = 112
FEATURE                 Location/Qualifiers
source                  1..112
                        mol_type = protein
                        organism = synthetic construct
SEQUENCE: 42
DIVVTQTPLS SPVTLGQPAS ISCRSSQRFV HSDGNTYLSW LQQRPGQPPR LLIYKISNRI  60
SGVPDRFSGS GAGTDFKLKI SRVEAEDVGI YYCMQATQFP YTFGQGTKLE IK          112

SEQ ID NO: 43           moltype = AA  length = 118
FEATURE                 Location/Qualifiers
source                  1..118
                        mol_type = protein
                        organism = synthetic construct
SEQUENCE: 43
QGQLVESGGG VVQPGRSLRL SCEASGFTFR SYGMHWVRQP PGKGLEWVAI IWYDGGKKYY  60
GDSVKGRFTI SRDNPKNTLY LQMNSLRPED TAVYYCMAYD YSNGFDIWGQ GTMVTVSS    118

SEQ ID NO: 44           moltype = AA  length = 112
FEATURE                 Location/Qualifiers
source                  1..112
                        mol_type = protein
                        organism = synthetic construct
SEQUENCE: 44
DIVMTQTPLS SPVTLGQPAS ISCRSSQSFV HSDGSTYLSW LQQRPGQPPR LLIYKISNRF  60
SGVPDRFSGR GAGTDFTLKI SRVEAEDVGI YYCMQNTQFP YTFGQGTKLE IK          112

SEQ ID NO: 45           moltype = AA  length = 124
FEATURE                 Location/Qualifiers
source                  1..124
                        mol_type = protein
                        organism = synthetic construct
SEQUENCE: 45
QVQLVQSGAE VRKPGASVKV SCKASGYTFT KYDVNWVRQA PGQGLEWMGW MNSNNGNIGY  60
AQKFQGRVTM TRKTSISTAY MELSSLRSED TAVYYCAREG HYDFWRGFYN FDYWGQGTLV  120
TVSS                                                              124

SEQ ID NO: 46           moltype = AA  length = 107
FEATURE                 Location/Qualifiers
source                  1..107
                        mol_type = protein
                        organism = synthetic construct
SEQUENCE: 46
DIQMTQSPSS LSASVGDRVT ITCRASQDIK NDLGWYQQKP GKAPKRLIYA ASSLQSGVPS  60
RFSGSGSGTE FTLTISSLQP EDFATYYCLQ HNFYPITFGQ GTRLEIK               107

SEQ ID NO: 47           moltype = AA  length = 121
FEATURE                 Location/Qualifiers
source                  1..121
                        mol_type = protein
                        organism = synthetic construct
SEQUENCE: 47
EVQLVDSGGG LVQPGGSLRL SCAASGFTFS SYWMSWVRQA PGKGLEWVAN IKQDGSEKYY  60
VDSVKGRFTI SRDNVKNSLS LEMNSLRAED TALYYCARDE SSSWYWYFDL WGRGTLVTVS  120
S                                                                 121

SEQ ID NO: 48           moltype = AA  length = 107
FEATURE                 Location/Qualifiers
source                  1..107
                        mol_type = protein
                        organism = synthetic construct
SEQUENCE: 48
DIQMTQSPST LSASVGDRVT ITCRASQSIS KWLAWYQQKP GKAPKLLIYK ASSLENGVPS  60
RFSGSGSGTE FTLTISSLQP DDFATYYCQQ YSSYSRTFGQ GTKVEIK               107

SEQ ID NO: 49           moltype = AA  length = 126
FEATURE                 Location/Qualifiers
source                  1..126
                        mol_type = protein
                        organism = synthetic construct
SEQUENCE: 49
EVELVESGGG LVQPGRSLRL SCAASGFTFD DKVMHWVRQA PGKGLEWVSC INWNSGHIGY  60
```

```
ADSVKGRFTI SRDNARTSLY LQMNSLRPED TALYYCVREG NYDFWSGYYR GFFDLWGRGT  120
LVTVSS                                                            126

SEQ ID NO: 50          moltype = AA  length = 107
FEATURE                Location/Qualifiers
source                 1..107
                       mol_type = protein
                       organism = synthetic construct
SEQUENCE: 50
DIQMTQSPSS LSASVGDRVT ITCRASQGIR NDLGWYQQKP GKAPKRLIYA ASSLQGGVPS  60
RFSGSGSGTE FTLTISSLQP EDFATYYCLQ HTSYPFTFGQ GTKLEIK               107

SEQ ID NO: 51          moltype = AA  length = 126
FEATURE                Location/Qualifiers
source                 1..126
                       mol_type = protein
                       organism = synthetic construct
SEQUENCE: 51
EVQLVESGGG LVQPGRSLRL SCAASGFTFA DYVMHWVRQA PGKGLEWVSG INWNNARIGY  60
VGSVKGRFTI SRDNAKNSLY LQMTSLRVED TALYHCVREG NFDFWSAYYR GFLDLWGRGT  120
LVTVSS                                                            126

SEQ ID NO: 52          moltype = AA  length = 107
FEATURE                Location/Qualifiers
source                 1..107
                       mol_type = protein
                       organism = synthetic construct
SEQUENCE: 52
DIQMTQSPSS LSASVGDRVT ITCRASQGIR SDLGWYQQKP GKAPKRLIYG ASSLQGGVPS  60
RFSGSGSGTE FTLTISSLQP EDFATYYCLQ HNSYPYTFGQ GTKLEIK               107

SEQ ID NO: 53          moltype = AA  length = 118
FEATURE                Location/Qualifiers
source                 1..118
                       mol_type = protein
                       organism = synthetic construct
SEQUENCE: 53
QVQLVQSGAE VKKPGASVRV SCKASGYTFT GNYIHWVRLA PGQGLEWMGW INPKSGRTQF  60
VQKFQGRVTM TRDTSITTVY MELSRLRSDD TAVYYCARLG DLLNFDYWGQ GTLVTVSS   118

SEQ ID NO: 54          moltype = AA  length = 107
FEATURE                Location/Qualifiers
source                 1..107
                       mol_type = protein
                       organism = synthetic construct
SEQUENCE: 54
DIQMTQSPSS LSASVGDRVT ITCQASQDIS NYLNWYQQKP GKAPKLLIYD ASNLETGVPS  60
RFSGSGSGTD FTFTISSLQP EDIATYYCQQ YDNLPLTFGG GTKVEIK               107

SEQ ID NO: 55          moltype = AA  length = 117
FEATURE                Location/Qualifiers
source                 1..117
                       mol_type = protein
                       organism = synthetic construct
SEQUENCE: 55
QVHLVQSGAE VKKPGASVKV SCKASGHTFT GFYVHWARQA PGQGLEWMGW IYSNSGRTSY  60
SQKFQGRVAM TRDTSISTIY MDLSRLRSDD TAVYYCARLE QLVFDFWGQG TLVTVSS    117

SEQ ID NO: 56          moltype = AA  length = 106
FEATURE                Location/Qualifiers
source                 1..106
                       mol_type = protein
                       organism = synthetic construct
SEQUENCE: 56
EIVMTQSPAT LSVSPGERAT LSCRASQSVS SNLAWYQQKP GQAPRLLIYG ASTRATGIPA  60
RFSGSGSGTE FTLTISSLQS EDFAVYYCQQ YNNWWTFGQG TKVEIK                106

SEQ ID NO: 57          moltype = AA  length = 121
FEATURE                Location/Qualifiers
source                 1..121
                       mol_type = protein
                       organism = synthetic construct
SEQUENCE: 57
EVQLVESGGG LVQPGGSLRL SCAASGFTFS NYWMSWVRQA PGKGLEWVAN IKQDGSEKYY  60
VDSVRGRFTI SRDNAKKSLY LQMNSLRAED TAVYYCARDN SNYAYWYFDI WGRGTLVTVS  120
S                                                                 121

SEQ ID NO: 58          moltype = AA  length = 107
FEATURE                Location/Qualifiers
```

```
source                  1..107
                        mol_type = protein
                        organism = synthetic construct
SEQUENCE: 58
DIQMTQSPST LSVSVGDRVT ITCRASQSIR KWLAWYQQKP GKAPKLLIFK ASSLESGVPS  60
RFSGSGSGTE FTLTISSLQP DDFATYYCQQ YDTYSRTFGQ GTKVEIK                107

SEQ ID NO: 59           moltype = AA  length = 121
FEATURE                 Location/Qualifiers
source                  1..121
                        mol_type = protein
                        organism = synthetic construct
SEQUENCE: 59
EVQLVESGGG LVQPGGSLRL SCAASGFTFS SYWMSWVRQA PGKGLEWVAN IKQDGSEKYY  60
VDSVKGRFTI SRDNAKNSLY LQMNSLRAED TAVYYCARDN SPSFYWYFDL WGRGTLVTVS  120
S                                                                  121

SEQ ID NO: 60           moltype = AA  length = 107
FEATURE                 Location/Qualifiers
source                  1..107
                        mol_type = protein
                        organism = synthetic construct
SEQUENCE: 60
DIQMTQSPST LSASVGDRVT ITCRASQSLS RWLAWYQQKP GKAPKLLIYK ASSLESGVPS  60
RFSGSGSGTE FTLTISSLQP DDFATYYCQQ YYTYSRTFGQ GTKVEIK                107

SEQ ID NO: 61           moltype = AA  length = 121
FEATURE                 Location/Qualifiers
source                  1..121
                        mol_type = protein
                        organism = synthetic construct
SEQUENCE: 61
QVQLVQSGAE VKKPGASVKV SCKASGYIVT GYYMHWVRQA PGHGLEWMGW INPNSGGTNF  60
AQNFQGRVTM TRDTSISTFY MDLNRLTSDD TAVYYCARGG APVSYWFFDL WGRGTLVTVS  120
S                                                                  121

SEQ ID NO: 62           moltype = AA  length = 107
FEATURE                 Location/Qualifiers
source                  1..107
                        mol_type = protein
                        organism = synthetic construct
SEQUENCE: 62
DIQMTQSPSS LSASVGDRVT ITCRASQNIN SYLNWYHQKP GKAPKVLIYN TSTLKSGVPS  60
RFSGSGSGTY FTLTISSLQP EDFATFYCQQ SHSTPFTFGP GTKVDIK                107

SEQ ID NO: 63           moltype = AA  length = 117
FEATURE                 Location/Qualifiers
source                  1..117
                        mol_type = protein
                        organism = synthetic construct
SEQUENCE: 63
QVQLVQSGAE VKKPGASVKV SCKASGYTFA GYYLHWVRQA PGQGLEWMGW INPNSGRTES  60
AQKFQGRVTL TRDTSITTAY MALSRLRSDD TAIYYCTRLE QLVFDYWGQG TLVTVSS     117

SEQ ID NO: 64           moltype = AA  length = 106
FEATURE                 Location/Qualifiers
source                  1..106
                        mol_type = protein
                        organism = synthetic construct
SEQUENCE: 64
EIVLTQSPDF QSVTPKEKVT ITCRASQSIG SSLHWYQQKP DQSPKLLIKY ASQSFSGVPS  60
RFSGSGSGTD FTLTINSLEA EDAATYYCHQ SSSLPTFGQG TKVEIK                 106

SEQ ID NO: 65           moltype = AA  length = 118
FEATURE                 Location/Qualifiers
source                  1..118
                        mol_type = protein
                        organism = synthetic construct
SEQUENCE: 65
QVQLAESGGG VVQPGRSLRL SCAASGFTFS GYGMHWVRQA PGKGLDWVAI IYYDGKNKYY  60
ADSVKGRFTI SRDNSKNTLY LQMNSLRAED TAVYYCARGG GYNWFDPWGQ GTLVTVSS    118

SEQ ID NO: 66           moltype = AA  length = 107
FEATURE                 Location/Qualifiers
source                  1..107
                        mol_type = protein
                        organism = synthetic construct
SEQUENCE: 66
DIQMTQSPSS LSASVGDRVT ITCRPSQTIS NYLNWYQQDP GKAPKLLIYA ASSLQSGVPS  60
```

```
RFSGSGSGTD FTLTISSLQP EDFATYYCQQ SYSTPITFGR GTRLEIK              107

SEQ ID NO: 67          moltype = AA  length = 117
FEATURE                Location/Qualifiers
source                 1..117
                       mol_type = protein
                       organism = synthetic construct
SEQUENCE: 67
QVHLVQSGAE VKKPGASVKV SCKASGHTFT GYYVHWARQA PGQGLEWMGW IYSNSGRTSY  60
SQKFQGRVAM TRDTSISTIY MDLSRLRSDD TAVYYCARLE QLVFDFWGQG TLVTVSS     117

SEQ ID NO: 68          moltype = AA  length = 108
FEATURE                Location/Qualifiers
source                 1..108
                       mol_type = protein
                       organism = synthetic construct
SEQUENCE: 68
DIQMTQSPSS LSASVGDRVT ITCQASQDIS NYLNWYQQKP GKAPKLLIYD ASNLETGVPS  60
RFSGSGSGTD FTFTISSLQP EDIATYYCQQ YDNLPLFTFG PGTKVDIK             108

SEQ ID NO: 69          moltype = AA  length = 118
FEATURE                Location/Qualifiers
source                 1..118
                       mol_type = protein
                       organism = synthetic construct
SEQUENCE: 69
QVQLVESGGG VVQPGRSLRL SCAASGFTFS GYGMHWVRQA PGKGLDWVAI IYYNGNNKYY  60
ADSVKGRFTI SRDNSKNTLY LQMNSLRAED TAVYYCARGG GYNWFDPWGQ GTLVIVSS    118

SEQ ID NO: 70          moltype = AA  length = 107
FEATURE                Location/Qualifiers
source                 1..107
                       mol_type = protein
                       organism = synthetic construct
SEQUENCE: 70
DIQMTQSPSS LSASVGDRVT ITCRPSQIII NYLNWYQQKP GKAPKLLIYA ASSLQSGVPS  60
RFSGSGSGTD FTLTISSLQP EDFATYYCQQ SYSTPFTFGR GTRLEIK              107

SEQ ID NO: 71          moltype = AA  length = 117
FEATURE                Location/Qualifiers
source                 1..117
                       mol_type = protein
                       organism = synthetic construct
SEQUENCE: 71
QVHLVQSGAE VKKPGASVKV SCKASGHSFT GYYVHWARQA PGQGLEWMGW IYSNSGRTSY  60
AQKFQGRVTM TRDTSISTTY MELSRLRSDD TAVYYCARLD QLVFDYWGQG TLVTVSS     117

SEQ ID NO: 72          moltype = AA  length = 107
FEATURE                Location/Qualifiers
source                 1..107
                       mol_type = protein
                       organism = synthetic construct
SEQUENCE: 72
DIQMTQSPSS LSASVGDRVT ITCQASQDIS NYLNWYQQKP GKAPKLLIYD ASNLETGVPS  60
RFSGSGSGTD FTFTISSLQP EDIATYYCQQ YDNLPLTFGG GTKVEIK              107

SEQ ID NO: 73          moltype = AA  length = 121
FEATURE                Location/Qualifiers
source                 1..121
                       mol_type = protein
                       organism = synthetic construct
SEQUENCE: 73
QVQLVQSGAE VKKPGASVKV SCKASGYTVT GYYMHWVRQA PGQGLEWMGW INPNSGGTNF  60
AQNFQGRVTM TRDTSISTFY MDLNRLRSDD TAVYYCARGG APVSYWFFDL WGRGTLVTVS  120
S                                                                 121

SEQ ID NO: 74          moltype = AA  length = 107
FEATURE                Location/Qualifiers
source                 1..107
                       mol_type = protein
                       organism = synthetic construct
SEQUENCE: 74
DIQMTQSPSS LSASVGDRVT ITCRASQSIS RYLNWYQQKP GKAPKVLIYN TSSLKSGVPS  60
RFSGSGSGTD FTLTISSLQP EDFGTFYCQQ SHSTPFTFGP GTKVDIK              107

SEQ ID NO: 75          moltype = AA  length = 118
FEATURE                Location/Qualifiers
source                 1..118
                       mol_type = protein
```

```
                         organism = synthetic construct
SEQUENCE: 75
QVQLAESGGG VVQPGRSLRL SCEASGFTFS GYGMHWVRQA PGKGLDWVAI IYYDGKNKYY  60
ADSVKGRFTI SRDNSKNTLY LQMNSLRAED TAVYYCARGG GYNWFDPWGQ GTLVTVSS    118

SEQ ID NO: 76            moltype = AA  length = 107
FEATURE                  Location/Qualifiers
source                   1..107
                         mol_type = protein
                         organism = synthetic construct
SEQUENCE: 76
DIQMTQSPSS LSASVGDRVT ITCRPSQTIS KYLNWYQQKP GKAPKLLIYA ASSLQSGVPS  60
RFSGSGSGTD FTLTISSLQP EDFATYYCQQ SYITPITFGR GTRLEIK                107

SEQ ID NO: 77            moltype = AA  length = 117
FEATURE                  Location/Qualifiers
source                   1..117
                         mol_type = protein
                         organism = synthetic construct
SEQUENCE: 77
QVQLVQSGAE MKKPGASVKV SCKASGYTFT DYYLHWVRRA PGHGLEWMGW IYPKSGRRNY  60
AQHFQGRVTM TRDTSINTAY MELSSLRSDD SAVYFCVRLE QLVFDYWGQG TLVTVSS     117

SEQ ID NO: 78            moltype = AA  length = 108
FEATURE                  Location/Qualifiers
source                   1..108
                         mol_type = protein
                         organism = synthetic construct
SEQUENCE: 78
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYGSSPLTFG GGTKVEIK               108

SEQ ID NO: 79            moltype = AA  length = 117
FEATURE                  Location/Qualifiers
source                   1..117
                         mol_type = protein
                         organism = synthetic construct
SEQUENCE: 79
QVHLVQSGAE VKKPGASVKV SCKASGHTFT GYYVHWARQA PGQGLEWMGW IYSNSGRTSY  60
SQKFQGRVAM TRDTSINTIY MDLSRLRSDD TAVYYCARLE QLVFDFWGQG TLVTVSS     117

SEQ ID NO: 80            moltype = AA  length = 106
FEATURE                  Location/Qualifiers
source                   1..106
                         mol_type = protein
                         organism = synthetic construct
SEQUENCE: 80
EIVMTQSPAT LSVSPGERAT LSCRASQSVS SNLAWYQQKP GQAPRLLIYG ASTRATGIPA  60
RFSGSGSGTE FTLTISSLQS EDFAVYYCQQ YNNWWTFGQG TKVEIK                 106

SEQ ID NO: 81            moltype = AA  length = 117
FEATURE                  Location/Qualifiers
source                   1..117
                         mol_type = protein
                         organism = synthetic construct
SEQUENCE: 81
QVQLVQSGAE VKKPGASVKV SCKASGYTFA GYYLHWVRQA PGQGLEWMGW INPNSGRTES  60
AQKFQGRVTL TRDTSITTAY MALSRLRSDD TAIYYCTRLE QLVFDYWGQG TLVTVSS     117

SEQ ID NO: 82            moltype = AA  length = 107
FEATURE                  Location/Qualifiers
source                   1..107
                         mol_type = protein
                         organism = synthetic construct
SEQUENCE: 82
DIQMTQSPSS LSASVGDRVT ITCRASQGIS NYLAWFQQKP GKAPKSLIYA ASSLQSGVPS  60
KFSGSGSGTD FTLTISSLQP EDFATYYCQQ YNSYPITFGQ GTRLEIK                107

SEQ ID NO: 83            moltype = AA  length = 116
FEATURE                  Location/Qualifiers
source                   1..116
                         mol_type = protein
                         organism = synthetic construct
SEQUENCE: 83
EVQLVESGGG LVQPGGSLKL SCAASGFTFS GSAMHWVRQA SGKGLEWVGR IRTKPNSYAT  60
SYAASVKDRF TISRDDSKNT AYLQMNSLKT EDTAVYYCIR GELEPWGQGT LVTVSS      116

SEQ ID NO: 84            moltype = AA  length = 113
FEATURE                  Location/Qualifiers
```

```
source                  1..113
                        mol_type = protein
                        organism = synthetic construct
SEQUENCE: 84
DIVMTQSPDS LAVSLGERAT INCKSSQSVL YRSNNKNYLA WYQQKPGQPP KLFIYWASTR  60
ESGVPDRFSG SGSGTDFTLT ISSLQAEDVA VYYCQQFYTT PWTFGQGTKV EIK         113

SEQ ID NO: 85           moltype = AA  length = 117
FEATURE                 Location/Qualifiers
source                  1..117
                        mol_type = protein
                        organism = synthetic construct
SEQUENCE: 85
QVQLVQSGAE VKKPGASVKV SCKASGYTFT GYYIHWVRQA PGQGLEWMGW INPKSGNTVY  60
AQRFQGRVTM TRDTSISTAY MDLSRLKSDD TAVYYCARLE QLVFDYWGQG ALVTVSS     117

SEQ ID NO: 86           moltype = AA  length = 112
FEATURE                 Location/Qualifiers
source                  1..112
                        mol_type = protein
                        organism = synthetic construct
SEQUENCE: 86
DIVMTQSPDS LAVSLGERAT INCKSSQSVL YSSNNKNYLA WYQQKPGQPP KLLIYWASTR  60
ESGVPDRFSG SGSGTDFTLT ISSLQAEDVA VYYCQQYYST ITFGQGTRLE IK          112

SEQ ID NO: 87           moltype = AA  length = 118
FEATURE                 Location/Qualifiers
source                  1..118
                        mol_type = protein
                        organism = synthetic construct
SEQUENCE: 87
QVQLVESGGG VVQPGRSLRL SCAASGFTFR GYGMHWVRQA PGKGLEWVAI IYYNGNNKYY  60
ADSVKGRFTI SRDNSKNTLY LQMNSLRAED TAVYYCARGG GYNWFDPWGQ GTLVTVSS    118

SEQ ID NO: 88           moltype = AA  length = 107
FEATURE                 Location/Qualifiers
source                  1..107
                        mol_type = protein
                        organism = synthetic construct
SEQUENCE: 88
DIQMTQSPSS LSASVGDRVT ITCRASQSIS NYLNWYQQEP GKAPKLLIYT ASSLQSGVPS  60
RFSGSGSGTA FTLTISSLQP EDFAIYYCQR SSSPPFTFGP GTKLDIK               107

SEQ ID NO: 89           moltype = AA  length = 118
FEATURE                 Location/Qualifiers
source                  1..118
                        mol_type = protein
                        organism = synthetic construct
SEQUENCE: 89
QVHLVESGGG VVQPGRSLRL SCSASGFTFS GYGMHWVRQA PGKGLEWVAL IYFDGRNKYY  60
ADSVKGRFTI SRDNSKNTLY LQMNSLRAED TAVYYCARGG GYNWFDPWGQ GTLVTVSS    118

SEQ ID NO: 90           moltype = AA  length = 107
FEATURE                 Location/Qualifiers
source                  1..107
                        mol_type = protein
                        organism = synthetic construct
SEQUENCE: 90
DIQMTQSPSS LSASVGDRVT ITCRASQSIS NYLNWYQQKP GKAPKLLIYL ASSLQSGVPS  60
RFSGSGSGTD FTLTINSLQP EDFASYYCQL SYSSPFTFGP GTKVDVN               107

SEQ ID NO: 91           moltype = AA  length = 118
FEATURE                 Location/Qualifiers
source                  1..118
                        mol_type = protein
                        organism = synthetic construct
SEQUENCE: 91
QAHLVESGGG VVQPGRSLRL SCSASGFTFS GYGMHWVRQA PGKGLEWVAL IYFDGRNKYY  60
ADSVKGRFTI SRDNSKNTLY LQMNSLRAED TAVYYCARGG GYNWFDPWGQ GTLVTVSS    118

SEQ ID NO: 92           moltype = AA  length = 107
FEATURE                 Location/Qualifiers
source                  1..107
                        mol_type = protein
                        organism = synthetic construct
SEQUENCE: 92
DIQMTQSPSS LSASVGDRVT ITCRASQSIN NYLSWYQQKP GKAPKLLIYL ASNLQSGVPS  60
RFSGSGSGTD FTLTISSLQP EDFATYYCQL SYRSPFTFGP GTKVDVK               107
```

```
SEQ ID NO: 93           moltype = AA  length = 118
FEATURE                 Location/Qualifiers
source                  1..118
                        mol_type = protein
                        organism = synthetic construct
SEQUENCE: 93
QAHLVESGGG VVQPGRSLRL SCSASGFTFS GYGMHWVRQA PGKGLEWVSL IYFDGRNKYY  60
ADSVKGRFTI SRDNSKNTLY LQMNSLRAED TAVYYCARGG GYNWFDPWGQ GTLVTVSS    118

SEQ ID NO: 94           moltype = AA  length = 107
FEATURE                 Location/Qualifiers
source                  1..107
                        mol_type = protein
                        organism = synthetic construct
SEQUENCE: 94
DIQMTQSPSS LSASVGDRVT ITCRASQSIN NYLSWYQQKP GKAPKLLIYL ASNLQSGVPS  60
RFSGNGSGTD FTLTISSLQP EDFATYYCQL SYRSPFTFGP GTKVDVK               107

SEQ ID NO: 95           moltype = AA  length = 118
FEATURE                 Location/Qualifiers
source                  1..118
                        mol_type = protein
                        organism = synthetic construct
SEQUENCE: 95
QGQLVESGGG VVQPGRSLRL SCAASGFTFR GYGMHWVRQA PGKGLEWVAI IYYDGKNKYY  60
ADSVKGRFTI SRDNSKNTLY LQMNNLRVED TAVYYCARGG GYNWFDPWGQ GTLVTVSS    118

SEQ ID NO: 96           moltype = AA  length = 107
FEATURE                 Location/Qualifiers
source                  1..107
                        mol_type = protein
                        organism = synthetic construct
SEQUENCE: 96
DIQMTQSPSS LSASIGDRVT ITCRASQSIS NYLNWYQQKP GKAPKLLIYS ASSLQSGVPS  60
RFSGSGSGTD FTLTISNLQP EDFAIYYCQR SYSPPFTFGP GTKLDIR               107

SEQ ID NO: 97           moltype = AA  length = 118
FEATURE                 Location/Qualifiers
source                  1..118
                        mol_type = protein
                        organism = synthetic construct
SEQUENCE: 97
QVHLVESGGD VVQPGRSLRL SCSASGFTFS GYGMHWVRQA PGKGLEWVAL IYFDGRNKYY  60
ADSVKGRFTI SRDNSKNTLY LQMNSLRAED TAVYYCARGG GYNWFDPWGQ GTLVTVSS    118

SEQ ID NO: 98           moltype = AA  length = 107
FEATURE                 Location/Qualifiers
source                  1..107
                        mol_type = protein
                        organism = synthetic construct
SEQUENCE: 98
DIQMTQSPSS LSASVGDRVT ITCRASQSIN NYLNWYQQKP GKAPKLLIYL ASSLQSGVPS  60
RFSGSGSGTD FTLTISSLQP EDLATYYCQL SYSSPFTFGP GTKVDVK               107

SEQ ID NO: 99           moltype = AA  length = 118
FEATURE                 Location/Qualifiers
source                  1..118
                        mol_type = protein
                        organism = synthetic construct
SEQUENCE: 99
QGQLVESGGG VVQPGRSLRL SCAASGFTFR GFGMHWVRQA PGKGLEWVAI IYYDGKNKYY  60
ADSVKGRFTI SRDNSKNTLY LQMNSLRAED TAVYYCAKGG GYNWFDPWGQ GTLVTVSS    118

SEQ ID NO: 100          moltype = AA  length = 107
FEATURE                 Location/Qualifiers
source                  1..107
                        mol_type = protein
                        organism = synthetic construct
SEQUENCE: 100
DIQMTQSPSS LSASVGDRVT ITCRASQSIS TYLNWYQQKP GKAPKLLIYS ASSLQSGVPS  60
RFSGSGSGTD FTLTISNLQP EDFAIYYCQR SYSPPFTFGP GTKLDIR               107

SEQ ID NO: 101          moltype = AA  length = 118
FEATURE                 Location/Qualifiers
source                  1..118
                        mol_type = protein
                        organism = synthetic construct
SEQUENCE: 101
QVQLVESGGG VVQPGRSLRL SCVASGFTFR GYGMHWVRQA PGKGLEWVAI IYYDGKNKYY  60
```

```
ADSVKGRFTI SRDNSKNTLY LQMNSLRVED TALYYCARGG GYNWFDPWGQ GTLVTVSS    118

SEQ ID NO: 102          moltype = AA  length = 107
FEATURE                 Location/Qualifiers
source                  1..107
                        mol_type = protein
                        organism = synthetic construct
SEQUENCE: 102
DIQMTQSPSS LSASVGDRVT ITCRASQSIS TYLNWYQQKP GKAPKLLIYT ASSLQSGVPS  60
RFSGSGSGTV FTLTISSLQP EDFAIYYCQR SYSPPFTFGP GTRLDIK               107

SEQ ID NO: 103          moltype = AA  length = 118
FEATURE                 Location/Qualifiers
source                  1..118
                        mol_type = protein
                        organism = synthetic construct
SEQUENCE: 103
QGQLVESGGG VVQPGRSLRL SCAASGFTFR GFGMHWVRQA PGKGLEWVAI IYYDGKNKYY  60
ADSVKGRFTI SRDNSKNMLY LQMNSLRAED TAVYYCAKGG GYNWFDPWGQ GTLVTVSS    118

SEQ ID NO: 104          moltype = AA  length = 107
FEATURE                 Location/Qualifiers
source                  1..107
                        mol_type = protein
                        organism = synthetic construct
SEQUENCE: 104
DIQMTQSPSS LSASVGDRVT ITCRASQSIS TYLNWYQQKP GKAPKLLIYS ASSLQSGVPS  60
RFSGSGSGTD FTLTISNLQP EDFAIYYCQR SYSPPFTFGP GTKLDIR               107

SEQ ID NO: 105          moltype = AA  length = 121
FEATURE                 Location/Qualifiers
source                  1..121
                        mol_type = protein
                        organism = synthetic construct
SEQUENCE: 105
QVQLVESGGG VVQPGRSLRL SCAASGFSFR SYGMHWVRQA PGKGLEWVSV ISYDGGNKYY  60
ADSVKGRFTI SRDNSKNTLF LQMKSLRAED TALYYCAKGG GTYWRGLFEY WGQGTLVTVS  120
S                                                                  121

SEQ ID NO: 106          moltype = AA  length = 107
FEATURE                 Location/Qualifiers
source                  1..107
                        mol_type = protein
                        organism = synthetic construct
SEQUENCE: 106
DIQLTQSPSF LSASVGDRVT ITCRASQGIS SYLAWYQKKP GKAPKLLIYA ASTLHSGVPS  60
RFSGGGSGTA FTLTISSLQP EDFATYYCQQ LNNYPFTFGP GTKVDIK               107

SEQ ID NO: 107          moltype = AA  length = 118
FEATURE                 Location/Qualifiers
source                  1..118
                        mol_type = protein
                        organism = synthetic construct
SEQUENCE: 107
QVQLVQSGAE VMKPGASVKV SCKASGYTFT DFYIHWVRQA PGQGLEWMGW INPKSGNTRF  60
AQKFQGRVTM TRDTSIATSY MELSRLRSDD TAVFYCARMG DLLALDYWGQ GTLVTVSS    118

SEQ ID NO: 108          moltype = AA  length = 106
FEATURE                 Location/Qualifiers
source                  1..106
                        mol_type = protein
                        organism = synthetic construct
SEQUENCE: 108
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWYTFGQG TKLEIK                106

SEQ ID NO: 109          moltype = AA  length = 118
FEATURE                 Location/Qualifiers
source                  1..118
                        mol_type = protein
                        organism = synthetic construct
SEQUENCE: 109
QVQLVQSGAE VKKPGASVKV SCKASGYTFT DFYIHWVRQA PGQGLEWMGW INPKSGNTRF  60
AQRFQGRVTM TRDTSITTSY MELSRLRSDD TAVFYCARMG DLLALDYWGQ GTLVTVSS    118

SEQ ID NO: 110          moltype = AA  length = 108
FEATURE                 Location/Qualifiers
source                  1..108
                        mol_type = protein
```

```
                         organism = synthetic construct
SEQUENCE: 110
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYGSSPRTFG QGTKVEIK               108

SEQ ID NO: 111           moltype = AA  length = 119
FEATURE                  Location/Qualifiers
source                   1..119
                         mol_type = protein
                         organism = synthetic construct
SEQUENCE: 111
QVQLQESGPG LVKPSATLSL TCTVSGGSIS TYYWSWIRQS PGKGLEWIGY ISYSVNTNPS  60
LKSRVTISVD KSKNQLSLNL RSATGADTAV YYCARGGLYG GNAGRFDLWG QGTLVTVSS   119

SEQ ID NO: 112           moltype = AA  length = 108
FEATURE                  Location/Qualifiers
source                   1..108
                         mol_type = protein
                         organism = synthetic construct
SEQUENCE: 112
EIVLTQSPGT LSLSPGERAT LSCRASQSVI NNYVAWYQQK PGQAPSLIIT GVSRRATGIP  60
DRFIGSGSGT DFILIISRLE PEDFAVYCCQ QYGNSPWTFG QGTRVEIK               108

SEQ ID NO: 113           moltype = AA  length = 118
FEATURE                  Location/Qualifiers
source                   1..118
                         mol_type = protein
                         organism = synthetic construct
SEQUENCE: 113
QVQLVESGGG VVQPGRSLRL SCAASGFTFR SYGMHWVRQA PGKGLEWVAI IWYNGNKKDY  60
VDSVKGRFTI SRDNSKNTLY LQMNSLRAED TALYYCARGP GYNWFDPWGQ GTLVTVSS    118

SEQ ID NO: 114           moltype = AA  length = 107
FEATURE                  Location/Qualifiers
source                   1..107
                         mol_type = protein
                         organism = synthetic construct
SEQUENCE: 114
DIQMTQSPPS LSASVGDRVT ITCRASQRIS SYLNWYQQKP GKAPKLLIYA ASSLQSGVPS  60
RFSGSGSGTD FTLTISSLQP EDFATYYCQQ SDSFPLTFGG GTKVEII                107

SEQ ID NO: 115           moltype = AA  length = 121
FEATURE                  Location/Qualifiers
source                   1..121
                         mol_type = protein
                         organism = synthetic construct
SEQUENCE: 115
QVQLQESGPG LVKPSETLSL TCTVSGGSIS SYCWSWIRQP PGKGLEWIGY IYNIGSTNFN  60
PSLKSRVTIS VDTSKNQFSL KLNSVTAADT AVYYCARGGL YSGNGGRFDP WGRGTLVTVS  120
S                                                                  121

SEQ ID NO: 116           moltype = AA  length = 108
FEATURE                  Location/Qualifiers
source                   1..108
                         mol_type = protein
                         organism = synthetic construct
SEQUENCE: 116
EIVLTQSPGT LSLSPGQTAT LSCRASQGVR SNYLAWYQQK PGQAPRLLIY GASSRATGIP  60
VRFSGSGSGT GFTLTMSRLE PEDFAVYYCQ QYGSSPWTFG QGSKVEIK               108

SEQ ID NO: 117           moltype = AA  length = 115
FEATURE                  Location/Qualifiers
source                   1..115
                         mol_type = protein
                         organism = synthetic construct
SEQUENCE: 117
QVQLVESGGG VVQPGRSLRL SCAASGFTFS SYGMHWVRQA PGKGLEWVAV IWYDGSNKYY  60
EDSVKGRFTI SRDNSKNTLH LQMNSLRVED TAVYYCARGL EFDYWGQGTL VTVSS       115

SEQ ID NO: 118           moltype = AA  length = 112
FEATURE                  Location/Qualifiers
source                   1..112
                         mol_type = protein
                         organism = synthetic construct
SEQUENCE: 118
DIVMTQTPLS SPVTLGQPAS ISCRSSQSLV HSDGITYLNW LQQRPGQPPR LLIYKISNRF  60
SGVPDRFSGS GSGTDFTLKI SRVEAEDVGV YYCMQATQFP WTFGQGTKVE IK          112

SEQ ID NO: 119           moltype = AA  length = 119
```

```
FEATURE                 Location/Qualifiers
source                  1..119
                        mol_type = protein
                        organism = synthetic construct
SEQUENCE: 119
QVQLVESGGG VVQPGRSLRL SCVASGFPFR SYGMHWVRQA PGKGLEWVAF IWYDGSNKYY  60
ADSVRGRFTI SRDNFKKMVY LQMNSLRAED TAVYYCARDL AGIYAFDVWG QGTVVTVSS   119

SEQ ID NO: 120          moltype = AA  length = 108
FEATURE                 Location/Qualifiers
source                  1..108
                        mol_type = protein
                        organism = synthetic construct
SEQUENCE: 120
EIVMTQSPAT LSVSPGERAT LSCRASQSVS SNLAWYQQKP GQAPRLLIYG ASTRATGIPA  60
RFSGSGSGTE FTLTVSSLQS EDFAIYYCQQ YNNWRPLTFG GGTKVEIK               108

SEQ ID NO: 121          moltype = AA  length = 118
FEATURE                 Location/Qualifiers
source                  1..118
                        mol_type = protein
                        organism = synthetic construct
SEQUENCE: 121
QVQLVESGGG VVQPGRSLRL SCAASGFTFR SYGMHWVRQA PGKGLEWVAI IWYNGNKKDY  60
VDSVKGRFTI SRDNSKNMLY LQMNSLRAED TALYYCARGP GYNWFDPWGQ GTLVTVSS    118

SEQ ID NO: 122          moltype = AA  length = 107
FEATURE                 Location/Qualifiers
source                  1..107
                        mol_type = protein
                        organism = synthetic construct
SEQUENCE: 122
DIQMTQSPPS LSASVGDRVT ITCRASQRIS SYLNWYQQRP GKAPKLLIYA ASSLQSGVPS  60
RFSGSGSGTD FTLTISSLQP EDFATYYCQQ TDSFPLTFGG GTKVEII                107

SEQ ID NO: 123          moltype = AA  length = 126
FEATURE                 Location/Qualifiers
source                  1..126
                        mol_type = protein
                        organism = synthetic construct
SEQUENCE: 123
EVQLVESGGV LVKTGGSLRL SCVASGFSFK KAWMNWVRQA PGKGLEWVGR IKRNSDGGAA  60
DYAAPVKDRF TLSRDDSKNT LYLQMNSLKT EDTAVYYCTT LDSSSWYVGY YYMDVWGKGT  120
TVTVSS                                                             126

SEQ ID NO: 124          moltype = AA  length = 107
FEATURE                 Location/Qualifiers
source                  1..107
                        mol_type = protein
                        organism = synthetic construct
SEQUENCE: 124
DIHMTQSPSS VSASLGDRVT FTCRASQNIN NWLAWYQQKP GKAPKLLIYT ASSLQSGVPS  60
RFSGSGSGTD FTLTISSLQP DDFATYYCQQ AHSLPITFGQ GTRLGIK                107

SEQ ID NO: 125          moltype = AA  length = 126
FEATURE                 Location/Qualifiers
source                  1..126
                        mol_type = protein
                        organism = synthetic construct
SEQUENCE: 125
EVQLVESGGG LVKTGGSHRL SCVASGFSFK KAWMNWVRQA PGKGLEWVGR IKRNSDGGTT  60
DYAAPVKGRF ILSRDDSKNT LYLQMNSLKT EDTAVYYCTT LDSSSWYVGY YYMDVWGKGT  120
TVTVSS                                                             126

SEQ ID NO: 126          moltype = AA  length = 107
FEATURE                 Location/Qualifiers
source                  1..107
                        mol_type = protein
                        organism = synthetic construct
SEQUENCE: 126
DIQMTQSPSS VSASVGDRVT ITCRASQDIN NWLAWYQQKP GKAPKILIYT ASNLQSGVPS  60
RFSGSGSGTD FTLTISSLQP EDFATYFCQQ AHSLPITFGQ GTRLEIK                107

SEQ ID NO: 127          moltype = AA  length = 126
FEATURE                 Location/Qualifiers
source                  1..126
                        mol_type = protein
                        organism = synthetic construct
SEQUENCE: 127
```

```
EVQLVESGGG LVKTGGSLRL SCVASGFSFK KAWMNWVRQA PGKGLEWVGR IKRNTDGGTT  60
DYAAPVKGRF TLSRDDSKNT LYLQMNSLKT EDTAVYYCTT LDSSSWYVGY YYMDVWGKGT  120
TVTVSS                                                            126

SEQ ID NO: 128         moltype = AA  length = 107
FEATURE                Location/Qualifiers
source                 1..107
                       mol_type = protein
                       organism = synthetic construct
SEQUENCE: 128
DIQMTQSPSS VSASVGDRVT ITCRASQDIN NWLAWYQQKP GKAPKILIYT ASSLQSGVPS  60
RFSGSGSGTD FTLTISSLQP EDFATYYCQQ AHSLPITFGQ GTRLEIK               107

SEQ ID NO: 129         moltype = AA  length = 126
FEATURE                Location/Qualifiers
source                 1..126
                       mol_type = protein
                       organism = synthetic construct
SEQUENCE: 129
EVQLVESGGG LVKTGGSLRL SCVASGFSFK KAWMNWVRQA PGKGLEWVGR IKRNTDGGPA  60
DYAAPVKGRF TLSRDDSKKT LYLQMNSLKT EDTAVYYCTT LDSSSWYVGY YYMDVWGKGT  120
TVTVSS                                                            126

SEQ ID NO: 130         moltype = AA  length = 107
FEATURE                Location/Qualifiers
source                 1..107
                       mol_type = protein
                       organism = synthetic construct
SEQUENCE: 130
DIQMTQSPSS VSASVGDRVI ITCRASQDIN NWLAWYLQRP GKAPKLLIYA ASSLQSGVPS  60
RFSGSGSGTD FTLTIGSLQP EDFATYYCQQ AHSLPITFGQ GTRLEIQ               107

SEQ ID NO: 131         moltype = AA  length = 126
FEATURE                Location/Qualifiers
source                 1..126
                       mol_type = protein
                       organism = synthetic construct
SEQUENCE: 131
EVQLVESGGG LVKTGGSHRL SCVASGFSFK KAWMNWVRQA PGKGLEWVGR IKRNSDGGTT  60
DYAAPVKGRF ILSRDDSKNT LYLQMNSLKT EDTAVYYCTT LDSSSWYVGY YYMDVWGKGT  120
TVTVSS                                                            126

SEQ ID NO: 132         moltype = AA  length = 107
FEATURE                Location/Qualifiers
source                 1..107
                       mol_type = protein
                       organism = synthetic construct
SEQUENCE: 132
DIQMTQSPSS VSASVGDRVT ITCRASQDIN NWLAWYQQKP GKAPKILIYT ASNLQSGVPS  60
RFSGSGSGTD FTLTISSLQP EDFATYFCQQ AHGLPITFGQ GTRLEIK               107

SEQ ID NO: 133         moltype = AA  length = 126
FEATURE                Location/Qualifiers
source                 1..126
                       mol_type = protein
                       organism = synthetic construct
SEQUENCE: 133
EVQLVESGGG LVKTGGSLRL SCVASGFSFK KAWMNWVRQA PGKGLEWVGR IKRNSDGGTT  60
DYAAPVKGRF TLSRDDSKNT LYLQMNSLKT EDTAVYYCTT LDSSSWYVGY YYMDVWGKGT  120
TVTVSS                                                            126

SEQ ID NO: 134         moltype = AA  length = 107
FEATURE                Location/Qualifiers
source                 1..107
                       mol_type = protein
                       organism = synthetic construct
SEQUENCE: 134
DIQMTQSPFS VSASVGDRVT ITCRASQDIN NWLAWYQQKP GKAPKILIYT ASSLQSGVPS  60
RFSGSGSGTD FTLTISSLQP EDFATYYCQQ AHSLPITFGQ GTRLEIK               107

SEQ ID NO: 135         moltype = AA  length = 126
FEATURE                Location/Qualifiers
source                 1..126
                       mol_type = protein
                       organism = synthetic construct
SEQUENCE: 135
EVQLVESGGG LVKTGGSLRL SCVASGFSFK KAWMNWVRQA PGKGLEWVGR IKRNTDGGTT  60
DYAAPVKGRF TLSRDDSKNT LYLQMNSLKT EDTAVYYCTT LDSSSLYVGY YYMDVWGKGT  120
TVTVSS                                                            126
```

```
SEQ ID NO: 136          moltype = AA  length = 107
FEATURE                 Location/Qualifiers
source                  1..107
                        mol_type = protein
                        organism = synthetic construct
SEQUENCE: 136
DIQMTQSPSS VSASVGDRVT ITCRASQDIN NWLAWYQQKP GKAPKLLIYT ASSLQSGVPS  60
RFSGSGSGTD FTLTISSLQP EDFATYYCQQ AHSLPITFGQ GTRLEIK                107

SEQ ID NO: 137          moltype = AA  length = 124
FEATURE                 Location/Qualifiers
source                  1..124
                        mol_type = protein
                        organism = synthetic construct
SEQUENCE: 137
EVQLVESGGG LVQPGRSLRL SCAASGFTFD DYTMHWVRQA PGKGLEWVSG ISWNSGSIGY  60
ADSVKGRFTI SRDNAKNSLY LQMNSLRAED TALYYCSKDS SGYGYYLNYS LDVWGKGTTV  120
TVSS                                                               124

SEQ ID NO: 138          moltype = AA  length = 106
FEATURE                 Location/Qualifiers
source                  1..106
                        mol_type = protein
                        organism = synthetic construct
SEQUENCE: 138
EIVMTQSPAT LSVSPGERAT LSCRASQSVS SNLAWYQQKP GQAPRLLIYG ASTRATGIPA  60
RFSGSGSGTE FTLTISSLQS EDFAVYYCQQ YNNWPHFGQG TRLEIK                 106

SEQ ID NO: 139          moltype = AA  length = 124
FEATURE                 Location/Qualifiers
source                  1..124
                        mol_type = protein
                        organism = synthetic construct
SEQUENCE: 139
EVQLVESGGG LVQPGRSLRL SCAASGFTFD DYTMHWVRQA PGKGLEWVSG ISWNSGSIGY  60
ADSVKGRFTI SRDNAKNSLY LQMNSLRAED TALYYCSKDS SGYGYYLNYS LDVWGKGTTV  120
TVSS                                                               124

SEQ ID NO: 140          moltype = AA  length = 105
FEATURE                 Location/Qualifiers
source                  1..105
                        mol_type = protein
                        organism = synthetic construct
SEQUENCE: 140
EIVMTQSPAT LSVSPGERAT LSCRASQSVS NLAWYQQKPG QAPRLLIYGA STRATGIPAR  60
FSGSGSGTEF TLTISSLQSE DFAVYYCQQY NNWPHFGQGT RLQIK                  105

SEQ ID NO: 141          moltype = AA  length = 126
FEATURE                 Location/Qualifiers
source                  1..126
                        mol_type = protein
                        organism = synthetic construct
SEQUENCE: 141
EVQLVESGGG LVKTGGSLRL SCVASGFSFK KAWMNWVRQA PGKGLEWVGR IKRNTDGGTA  60
DYAAPVKGRF TLSRDDSKKT LFLQMNSLKT EDTAVYYCTT LDSSSYYVGY YYMDVWGKGT  120
TVTVSS                                                             126

SEQ ID NO: 142          moltype = AA  length = 107
FEATURE                 Location/Qualifiers
source                  1..107
                        mol_type = protein
                        organism = synthetic construct
SEQUENCE: 142
DIQMTQSPSS VSASVGDRVT ITCRASQDIN NWLAWYQQKP GKAPKLLIYT ASSLQSGVPS  60
RFSGSGSGTD FTLTIGSLQP EDFATYYCQQ AHSLPITFGQ GTRLEIK                107

SEQ ID NO: 143          moltype = AA  length = 124
FEATURE                 Location/Qualifiers
source                  1..124
                        mol_type = protein
                        organism = synthetic construct
SEQUENCE: 143
EVQLVESGGG LVQPGRSLRL SCATSGFTFA DYTMHWVRQA PGKGLEWVSG ISWNSGSIDY  60
ADSVKGRFTI SRDNAKKSLY LQMNSLRAED TALYFCAKDS SGYGHYYFYY LDVWGKGTTV  120
TVSS                                                               124

SEQ ID NO: 144          moltype = AA  length = 106
FEATURE                 Location/Qualifiers
```

```
source                  1..106
                        mol_type = protein
                        organism = synthetic construct
SEQUENCE: 144
EIVMTQSPGT LSVSPGKRAT LSCRASQSVS SNLAWYQQKP GQGPRLLIYS TSTRATGIPA  60
RFSGSGSGTE FTLTISSLQS EDSAVYYCQH YNNWPHFGQG TRLEIK                106

SEQ ID NO: 145          moltype = AA  length = 126
FEATURE                 Location/Qualifiers
source                  1..126
                        mol_type = protein
                        organism = synthetic construct
SEQUENCE: 145
EVQLVESGGG LVKTGGSLRL SCVASGFSFK KAWMNWVRQA PGKGLEWVGR IKRNTDGGTA  60
DYAAPVKGRF TLSRDDSKKT LYLQMNSLKT EDTAVYYCTT LDSSSRYVGY YYMDVWGKGT  120
TVTVSS                                                            126

SEQ ID NO: 146          moltype = AA  length = 107
FEATURE                 Location/Qualifiers
source                  1..107
                        mol_type = protein
                        organism = synthetic construct
SEQUENCE: 146
DIQMTQSPSS VSASVGDRVI ITCRASQDIN NWLAWYQQKP GKVPKLLIYT ASSLQSGVPS  60
RFSGSGSGTD FTLTIGSLQP EDFATYYCQQ AHSLPITFGQ GTRLEIK               107

SEQ ID NO: 147          moltype = AA  length = 126
FEATURE                 Location/Qualifiers
source                  1..126
                        mol_type = protein
                        organism = synthetic construct
SEQUENCE: 147
DVQLVESGGG TVKTGGSLRL SCVASGFSFK KAWMNWVRQA PGKGLEWVGR IKKNSDDGTA  60
DYAAPVKGRF TISRDDSKRT LFLQMNSLQT EDTAVYYCTT LDSSSWFVGY YYMDVWGKGT  120
TVTVSS                                                            126

SEQ ID NO: 148          moltype = AA  length = 107
FEATURE                 Location/Qualifiers
source                  1..107
                        mol_type = protein
                        organism = synthetic construct
SEQUENCE: 148
DIQMTQSPSS VSASVGDRVI ITCRASQDIN NWLAWYQQKP GKAPKLLIYT ASSLQSGVPS  60
RFSGSGSVSD FTLTIDSLQP EDFATYYCQQ AHSLPITFGQ GTRLEIK               107

SEQ ID NO: 149          moltype = AA  length = 122
FEATURE                 Location/Qualifiers
source                  1..122
                        mol_type = protein
                        organism = synthetic construct
SEQUENCE: 149
EVQVVESGGD LVQPGGSLRL SCAASGFTFS TYAMTWVRQA PGKGLEWIST ISGSGHNTYY  60
ADSVKGRFTI SRGNSKNTLF LQMNSLRAED TAVYYCAKEN CGGDCLYYMD VWGKGTTVTV  120
SS                                                                122

SEQ ID NO: 150          moltype = AA  length = 107
FEATURE                 Location/Qualifiers
source                  1..107
                        mol_type = protein
                        organism = synthetic construct
SEQUENCE: 150
DIQMTQSPSS LSASVGDRVT ITCRASQSIS NYLNWYQQKS GKAPKLLIYF ASSLQSGVPS  60
RFGGSGAGTD FTLTISSLQP EDFATYSCQQ SYSTPLTFGG GTKVEIK               107

SEQ ID NO: 151          moltype = AA  length = 126
FEATURE                 Location/Qualifiers
source                  1..126
                        mol_type = protein
                        organism = synthetic construct
SEQUENCE: 151
EVQLVESGGG LVKTGGSLRL SCVASGFSFK KAWMNWVRQA PGKGLEWVGR IKRNTDGGTA  60
DYAAPVKGRF TLSRDDSKKT LYLQMNSLKT EDTAVYYCTT LDSSSRYVGY YYMDVWGKGT  120
TVTVSS                                                            126

SEQ ID NO: 152          moltype = AA  length = 107
FEATURE                 Location/Qualifiers
source                  1..107
                        mol_type = protein
                        organism = synthetic construct
```

```
SEQUENCE: 152
DIQMTQSPSS VSASVGDRVI ITCRASQDIN NWLAWYQQKP GKVPKLLIYT ASSLQSGVPS  60
RFSGSGSGTD FTLTIGTLQP EDFATYYCQQ AHSLPITFGQ GTRLDIK               107

SEQ ID NO: 153         moltype = AA  length = 124
FEATURE                Location/Qualifiers
source                 1..124
                       mol_type = protein
                       organism = synthetic construct
SEQUENCE: 153
EVQLVESGGG LVQPGRSLRL SCAASGFTFN DYTMHWVRQV PGKGLEWVSG ISWNSGSIDY  60
ADSVKGRFTI SRDNAKNSLY LQMNSLRAED TALYYCAKDS SGYGYYYYYY MDVWGKGTTV  120
TVSS                                                              124

SEQ ID NO: 154         moltype = AA  length = 106
FEATURE                Location/Qualifiers
source                 1..106
                       mol_type = protein
                       organism = synthetic construct
SEQUENCE: 154
EIVMTQSPAT LSVSPGERAT LSCRASQSVS INLAWYQQKP GQAPRLLIYG ASTRATGIPA  60
RFSGSGSGTE FTLTISSLQS EDFAVYYCQL YHNWPHFGQG TRLEIK                106

SEQ ID NO: 155         moltype = AA  length = 126
FEATURE                Location/Qualifiers
source                 1..126
                       mol_type = protein
                       organism = synthetic construct
SEQUENCE: 155
EVQLVESGGG LVKTGGSHRL SCVASGFSFK KAWMNWVRQA PGKGLEWVGR IKRNSDGGTT  60
DYAAPVKGRF ILSRDDSKNT LYLQMNSLKT EDTAVYYCTT LDSSSWYVGY YYMDVWGKGT  120
TVTVSS                                                            126

SEQ ID NO: 156         moltype = AA  length = 107
FEATURE                Location/Qualifiers
source                 1..107
                       mol_type = protein
                       organism = synthetic construct
SEQUENCE: 156
DIQMTQSPSS VSASVGDRVT ITCRASQDIN NWLAWYQQKP GKAPKILIYT ASNLQSGVPS  60
RFSGSGSGTD FTLTISTLQP EDFATYFCQQ AHGLPITFGQ GTRLEIK               107

SEQ ID NO: 157         moltype = AA  length = 124
FEATURE                Location/Qualifiers
source                 1..124
                       mol_type = protein
                       organism = synthetic construct
SEQUENCE: 157
EVQLVESGGG LVQPGRSLRL SCAASGFTFD DYTMHWVRQA PGKGLEWVSG ISWNSGSIGY  60
ADSVKGRFTI SRDNAKNSLY LQMNSLRAED TALYYCAKDS SGYGYYYYYS MDVWGKGTTV  120
TVSS                                                              124

SEQ ID NO: 158         moltype = AA  length = 106
FEATURE                Location/Qualifiers
source                 1..106
                       mol_type = protein
                       organism = synthetic construct
SEQUENCE: 158
EIVMTQSPAT LSVSPGERAT LSCRASQSVS SNLAWYQQKP GQAPRLLIYG ASTRATGIPA  60
RFSGSGSGTE FTLTISSLQS EDFAVYYCQL YYNWPHFGQG TRLAIK                106

SEQ ID NO: 159         moltype = AA  length = 126
FEATURE                Location/Qualifiers
source                 1..126
                       mol_type = protein
                       organism = synthetic construct
SEQUENCE: 159
EVQLVESGGD LVKTGGSLRL SCVASGFSFK KAWMNWVRQA PGKGLEWVGR IKRNTDGGAT  60
DYAAPVKDRF TLSRDDSKNT LYLQMNSLKT EDTAVYYCTT LDSSSWYVGY YYMDVWGKGT  120
TVTVSS                                                            126

SEQ ID NO: 160         moltype = AA  length = 107
FEATURE                Location/Qualifiers
source                 1..107
                       mol_type = protein
                       organism = synthetic construct
SEQUENCE: 160
DIHMTQSPSS VSASLGDRVT FTCRASQDIN NWLAWYQQKP GKAPRLLIYT ASSLQSGVPS  60
RFSGSGSGTD FTLTISSLQP DDFATYYCQQ AHSLPITFGQ GTRLGIE               107
```

```
SEQ ID NO: 161          moltype = AA  length = 126
FEATURE                 Location/Qualifiers
source                  1..126
                        mol_type = protein
                        organism = synthetic construct
SEQUENCE: 161
EVQLVESGGG LVKTGGSLRL SCVASGFSFK KAWMNWVRQA PGKGLEWVGR IKRNSDGGAT  60
DYAAPVKDRF TLSRDDSKNT LYLQMNSLKT EDTAVYYCTT LDSSSWYVGY YYMDVWGKGT  120
TVTVSS                                                             126

SEQ ID NO: 162          moltype = AA  length = 107
FEATURE                 Location/Qualifiers
source                  1..107
                        mol_type = protein
                        organism = synthetic construct
SEQUENCE: 162
DIHMTQSPSS VSASLGDRVT FTCRASQDIN NWLAWYQQRP GKAPKLLIYT ASSLQSGVPS  60
RFSGSGSGTD FTLTISSLQP EDFATYYCQQ AHSLPITFGQ GTRLGIK                107

SEQ ID NO: 163          moltype = AA  length = 126
FEATURE                 Location/Qualifiers
source                  1..126
                        mol_type = protein
                        organism = synthetic construct
SEQUENCE: 163
EVQLVESGGG LVKTGGSLRI SCVASGFSFK KAWMNWVRQA PGKGLEWVGR IKRNTDGGTI  60
DYAAPVKGRF SLSRDDSKNT LFLQMNSLKT EDTAVYFCTT LDSSSYYVGY YYMDVWGKGT  120
TVTVSS                                                             126

SEQ ID NO: 164          moltype = AA  length = 107
FEATURE                 Location/Qualifiers
source                  1..107
                        mol_type = protein
                        organism = synthetic construct
SEQUENCE: 164
DIHMTQSPSS VSASVGDRVT ITCRASQDIN NWLAWYQQKP GKAPKLLIYT ASSLQSGVPS  60
RFSGSGSGTD FTLTISSLQP EDFATYFCQQ AHSLPITFGQ GTRLGIK                107

SEQ ID NO: 165          moltype = AA  length = 126
FEATURE                 Location/Qualifiers
source                  1..126
                        mol_type = protein
                        organism = synthetic construct
SEQUENCE: 165
DVQLVESGGG TVKTGGSLRL SCVASGFSFK KAWMNWVRQA PGKGLEWVGR IKKNSDGGTA  60
DYAAPVKGRF TISRDDSKKT LYLQMNSLQT EDTAVYYCTT LDSSSWYVGY YYMDVWGKGT  120
TVTVSS                                                             126

SEQ ID NO: 166          moltype = AA  length = 107
FEATURE                 Location/Qualifiers
source                  1..107
                        mol_type = protein
                        organism = synthetic construct
SEQUENCE: 166
DIQMTQSPSS VSASVGDRVI ITCRASQDIN NWLAWYQQKP GIAPKLLIYT ASSLQSGVPS  60
RFSGSGSVSD FTLTIGSLQP EDFATYYCQQ AHSLPITFGQ GTRLEIK                107

SEQ ID NO: 167          moltype = AA  length = 126
FEATURE                 Location/Qualifiers
source                  1..126
                        mol_type = protein
                        organism = synthetic construct
SEQUENCE: 167
EVQLVESGGG LVKTGGSLRL SCVASGFSFK KAWMSWVRQA PGKGLEWVGR IKRNTDGGTA  60
DYAAPVKGRF TLSRDDSKKT LFLQMNSLKT EDSAVYYCVT LDSSSYYVGY YYMDVWGKGT  120
TVTVSS                                                             126

SEQ ID NO: 168          moltype = AA  length = 107
FEATURE                 Location/Qualifiers
source                  1..107
                        mol_type = protein
                        organism = synthetic construct
SEQUENCE: 168
DIQMTQSPSS VSASVGDRVS ITCRASQDIN NWLAWYQQKP GKAPKLLIYT ASSLQSGVPS  60
RFSGSGSGTD FTLTIGSLQP EDFATYYCQQ AHSLPITFGQ GTRLEIK                107

SEQ ID NO: 169          moltype = AA  length = 126
FEATURE                 Location/Qualifiers
```

```
source                1..126
                      mol_type = protein
                      organism = synthetic construct
SEQUENCE: 169
EVQLVESGGG LVKTGGSLRL SCVASGFSFK KAWMNWVRQA PGKGLEWVGR IKRNTDGGTA  60
DYAAPVKGRF TLSRDDSKKT LFLQMNSLKT EDTAVYYCTT LDSSSWYVGY YYMDVWGKGT  120
TVTVSS                                                             126

SEQ ID NO: 170        moltype = AA  length = 107
FEATURE               Location/Qualifiers
source                1..107
                      mol_type = protein
                      organism = synthetic construct
SEQUENCE: 170
DIQMTQSPSS VSASVGDRVI ITCRASQDIN NWLAWYQQKP GKAPKLLIYT ASSLQSGVPS  60
RFSGSGSGTD FTLTIGSLQP EDFATYYCQQ AHSLPITFGQ GTRLEIK                107

SEQ ID NO: 171        moltype = AA  length = 126
FEATURE               Location/Qualifiers
source                1..126
                      mol_type = protein
                      organism = synthetic construct
SEQUENCE: 171
EVQLVESGGG LVKTGGSLRL SCVASGFSFK KAWMNWVRQA PGKGLEWVGR IKRNSDGGTT  60
DYAAPVKGRF TLSRDDSKNT LYLQMNSLKT EDTAVYYCTT LDSSSWYVGY YYMDVWGKGT  120
TVTVSS                                                             126

SEQ ID NO: 172        moltype = AA  length = 108
FEATURE               Location/Qualifiers
source                1..108
                      mol_type = protein
                      organism = synthetic construct
SEQUENCE: 172
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYGSSPLTFG GGTKVEIK               108

SEQ ID NO: 173        moltype = AA  length = 123
FEATURE               Location/Qualifiers
source                1..123
                      mol_type = protein
                      organism = synthetic construct
SEQUENCE: 173
QVQLVESGGG VVQPGRSLRL SCAASGFTFS IYGMHWVRQA PGKGLEWVAV IWHDGSNKYY  60
ADSVKGRFTI SRDNSKNTLY LQMNSLRAED TAVYYCARTG ITGTKAYFYF DYWGQGTLVT  120
VSS                                                                123

SEQ ID NO: 174        moltype = AA  length = 112
FEATURE               Location/Qualifiers
source                1..112
                      mol_type = protein
                      organism = synthetic construct
SEQUENCE: 174
DIVMTQSPDS LAVSLGERAT INCKSSQSVL YSSNNKNYLA WYQQKPGRPP KLFIYWASNR  60
ESGVPDRFSG RGSGTDFTLT ISSLQAEDVA VYYCQQYYST VTFGGGTKVE IK          112

SEQ ID NO: 175        moltype = AA  length = 123
FEATURE               Location/Qualifiers
source                1..123
                      mol_type = protein
                      organism = synthetic construct
SEQUENCE: 175
QVQLVESGGG VVQPGRSLRL SCAASGFTFS TYGMHWVRQA PGKGLEWVAV IWYDGSHKYY  60
ADSVKGRFTI SRDNSKKTLY LQMNSLRAED TGIYYCARTG ISGNMSYFYF DHWGQGILVT  120
VSS                                                                123

SEQ ID NO: 176        moltype = AA  length = 112
FEATURE               Location/Qualifiers
source                1..112
                      mol_type = protein
                      organism = synthetic construct
SEQUENCE: 176
DIVMTQSPDS LAVSLGERAT INCKSSQSVL YSSKNRNYLA WYQQKQGQPP KMFIYWASTR  60
ESGVPDRFSG SGSGTDFTLT ISSLQAEDVA VYYCQQYYGP VTFGGGTKVE IK          112

SEQ ID NO: 177        moltype = AA  length = 118
FEATURE               Location/Qualifiers
source                1..118
                      mol_type = protein
                      organism = synthetic construct
```

```
SEQUENCE: 177
QVLLVQSGPE VKKPGASVKV SCKASGYTFT DYYLHWVRQA PGQGLDWMGW INPKSGGTRN  60
AQKFQGRVTM TRDTSISTAY MDLTRLRSDD TAVYYCARVG GELLFDYWGQ GTLVTVSS    118

SEQ ID NO: 178          moltype = AA  length = 112
FEATURE                 Location/Qualifiers
source                  1..112
                        mol_type = protein
                        organism = synthetic construct
SEQUENCE: 178
DIVMTQSPLS LSVTPGEPAS ISCRSSQSLL HSDGYNYLDW FLQKPGQSPH LLIFLGSNRA  60
SGVPDRFSGS GSGTDFTLKI SRVEAEDVGI YYCMQALQTP LTFGGGTKVE IK          112

SEQ ID NO: 179          moltype = AA  length = 122
FEATURE                 Location/Qualifiers
source                  1..122
                        mol_type = protein
                        organism = synthetic construct
SEQUENCE: 179
QVQLVESGGG VVQPGRSLRL SCAASGFTFS SYAMHWVRQA PGKGLEWVAV IWFDGTNKYY  60
TDSVRGRFTI SRDNSKNTLY LQMNSLRAED TAVYYCATER GITETTRGFD YWGQGTLVTV  120
SS                                                                 122

SEQ ID NO: 180          moltype = AA  length = 107
FEATURE                 Location/Qualifiers
source                  1..107
                        mol_type = protein
                        organism = synthetic construct
SEQUENCE: 180
DIQMTQSPSS LSASVGDRVT ITCRTSQGIG NDLDWYQQNP GKAPKRLIYA TSNLQSGVPS  60
RFSGSGSGTE FTLTISGLQP EDFTTYYCLR HNSYPYTFGQ GTKLEIT                107

SEQ ID NO: 181          moltype = AA  length = 123
FEATURE                 Location/Qualifiers
source                  1..123
                        mol_type = protein
                        organism = synthetic construct
SEQUENCE: 181
QVQLVESGGG VVQPGRSLRL SCAASGFTFS TYGMHWVRQA PGKGLEWVAV IWYDGSHKYY  60
ADSVKGRFTI SRDNSKNTLY LQMNSLRAED TAVYYCARTG ITGTTAYFYF DYWGQGTLVT  120
VSS                                                                123

SEQ ID NO: 182          moltype = AA  length = 112
FEATURE                 Location/Qualifiers
source                  1..112
                        mol_type = protein
                        organism = synthetic construct
SEQUENCE: 182
DIVMTQSPDS LAVSLGERAT INCKSSQSVL YSSKNKNYLA WYQQKQGQPP KLFIYWASTR  60
ESGVPDRFSG SGSGTDFTLT ISSLQAEDVA VYYCQQYYST VTFGGGTKVE IK          112

SEQ ID NO: 183          moltype = AA  length = 122
FEATURE                 Location/Qualifiers
source                  1..122
                        mol_type = protein
                        organism = synthetic construct
SEQUENCE: 183
QVQLVQSGAE VKKPGASVKV SCKASGYTFT SYYIHWVRQA PGQGLDWMGI INPSGGITGY  60
AQKLQGRVTM TRDTSTTTVY MELSSLRSDD TAVYYCARGV RGNYYYYYMD VWGKGTTVTV  120
SS                                                                 122

SEQ ID NO: 184          moltype = AA  length = 107
FEATURE                 Location/Qualifiers
source                  1..107
                        mol_type = protein
                        organism = synthetic construct
SEQUENCE: 184
EIVLTQSPDF QSVTPKEKVT ITCRASQSIG SKLHWYQQKP DQSPKLLIKY ASQSFSGVPS  60
RFSGSGSGTD FNLTINSLEA EDAATFYCHQ SSGLPYTFGQ GTKLEIK                107

SEQ ID NO: 185          moltype = AA  length = 123
FEATURE                 Location/Qualifiers
source                  1..123
                        mol_type = protein
                        organism = synthetic construct
SEQUENCE: 185
QVQLVESGGG VVQPGRSLRL SCAASGFTFS SYGMHWVRQA PGKGLEWVAV IWYDGSNKYY  60
ADSVKGRFTI SRDNSKNTLY LQMNSLRAED TAVYYCARTG ITGTTAYFYF DSWGQGTLVT  120
VSS                                                                123
```

```
SEQ ID NO: 186          moltype = AA  length = 112
FEATURE                 Location/Qualifiers
source                  1..112
                        mol_type = protein
                        organism = synthetic construct
SEQUENCE: 186
DIVMTQSPDS LAVSLGERAT INCKSSQSVL YSSKNKNYLA WYQQKPGQTP KLLIYWASTR  60
ESGVPDRFSG SGSGTDFTLT ISSLQAEDVA LYYCQQYYST VTFGGGTKVE IK          112

SEQ ID NO: 187          moltype = AA  length = 119
FEATURE                 Location/Qualifiers
source                  1..119
                        mol_type = protein
                        organism = synthetic construct
SEQUENCE: 187
QVQLMQSGSE LEKPGASVKV SCKASGYTFT SFAINWVRQA PGQGLEWMGW INTITGNPSY  60
AQGFTGRFVF SLDTSVTTAF LQINSLKTED TAVYYCARYV TSSGKFDYWG QGTLVTVSS   119

SEQ ID NO: 188          moltype = AA  length = 107
FEATURE                 Location/Qualifiers
source                  1..107
                        mol_type = protein
                        organism = synthetic construct
SEQUENCE: 188
DIQMTQSPSS VSASVGDRVT ITCRASRGIS RWLDWYQQKP GKAPKLLIYA ASNLQGGVPS  60
RFSGSGSGTD FTLTIRSLQP EDFAIYYCQQ AKTFPFTFGP GTKVDIK                107

SEQ ID NO: 189          moltype = AA  length = 123
FEATURE                 Location/Qualifiers
source                  1..123
                        mol_type = protein
                        organism = synthetic construct
SEQUENCE: 189
QVQLVESGGY VVQPGRSLRL SCAASGFTFS NFGMHWVRQA PGKGLEWVAV IWYDGSHKYY  60
ADSVKGRFTI SRDNSKNTLY LQMNSLRAED TAVYYCARTG ITGTTAYFYF DYWGQGTLVT  120
VSS                                                                 123

SEQ ID NO: 190          moltype = AA  length = 112
FEATURE                 Location/Qualifiers
source                  1..112
                        mol_type = protein
                        organism = synthetic construct
SEQUENCE: 190
DIVMTQSPDS LAVSLGERAT INCKSSQSVL YSSKNKNYLA WYQQKQGQPP KLFIYWASTR  60
ESGVPDRFSG SGSGTDFTLT IRSLQAEDVA VYYCQQYYGP VTFGGGTKVE IK          112

SEQ ID NO: 191          moltype = AA  length = 122
FEATURE                 Location/Qualifiers
source                  1..122
                        mol_type = protein
                        organism = synthetic construct
SEQUENCE: 191
QVQLVQSGAE VKKPGASVKV SCKASGYTFT NYYIHWVRQA PGQGLDWMGI INPSGGITGY  60
AQKFQGRVTM TRDTSTTTVY MELSSLRSDD TAVYYCARGV RGNYYYYYMD VWGKGTTVTV  120
SS                                                                  122

SEQ ID NO: 192          moltype = AA  length = 107
FEATURE                 Location/Qualifiers
source                  1..107
                        mol_type = protein
                        organism = synthetic construct
SEQUENCE: 192
EIVLTQSPDF QSVTPKEKVT ITCRASQSIG SKLHWYQQKP DQSPKLLIKF ASQSFSGVPS  60
RFSGSGSGTD FNLTINSLEP EDAATFYCHQ SSGLPYTFGQ GTKLEIK                107

SEQ ID NO: 193          moltype = AA  length = 123
FEATURE                 Location/Qualifiers
source                  1..123
                        mol_type = protein
                        organism = synthetic construct
SEQUENCE: 193
QVQLVESGGG VVQPGRSLRL SCAASGFTFI TYGMHWVRQA PGKGLEWVAV IWYDGSHKYY  60
ADSVKGRFTI SRDNSKNMLY LQMNSLRVED TAVYYCARTG ITGTTAYFYF DNWGQGTLVT  120
VSS                                                                 123

SEQ ID NO: 194          moltype = AA  length = 112
FEATURE                 Location/Qualifiers
source                  1..112
```

```
                        mol_type = protein
                        organism = synthetic construct
SEQUENCE: 194
DIVMTQSPDS LAVSLGERAT INCKSSQSVL YRSKNKNYLA WYQQKQGQPP KMFISWASTR  60
ESGVPDRFSG SGSGTDFTLT ISSLQAEDVA VYYCQQYYGP VTFGGGTKVE IK          112

SEQ ID NO: 195          moltype = AA  length = 117
FEATURE                 Location/Qualifiers
source                  1..117
                        mol_type = protein
                        organism = synthetic construct
SEQUENCE: 195
QVQLVQSGAE VKKPGASVKV SCKASGYTFT AYHTHWVRQA PGQGLEWMGW IYPKSGRTTY  60
TQKFQGRVTM TRDTSISTVY MELSRLKSDD TAVYYCARVG ALLFDYWGQG TLVTVSS     117

SEQ ID NO: 196          moltype = AA  length = 113
FEATURE                 Location/Qualifiers
source                  1..113
                        mol_type = protein
                        organism = synthetic construct
SEQUENCE: 196
DIVMTQSPDS LAVSLGERAT INCKSSQSVL YSSNNKNYLA WYQQKPGQPP KLLIYWASTR  60
ESGVPDRFSG SGSGTDFTLT ISSLQAEDVA VYYCQQYYST PLTFGGGTKV EIK         113

SEQ ID NO: 197          moltype = AA  length = 117
FEATURE                 Location/Qualifiers
source                  1..117
                        mol_type = protein
                        organism = synthetic construct
SEQUENCE: 197
QVQLVQSGAE VKKPGASVKV SCKASGYTFT AYHTHWVRQA PGQGLEWMGW IYPKSGRTTY  60
TQKFQGRVTM TRDTSISTVY MELSRLKSDD TAVYYCARVG ALLFDYWGQG TLVTVSS     117

SEQ ID NO: 198          moltype = AA  length = 107
FEATURE                 Location/Qualifiers
source                  1..107
                        mol_type = protein
                        organism = synthetic construct
SEQUENCE: 198
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPFTFGP GTKVDIK                107

SEQ ID NO: 199          moltype = AA  length = 117
FEATURE                 Location/Qualifiers
source                  1..117
                        mol_type = protein
                        organism = synthetic construct
SEQUENCE: 199
QVQLVQSGAE VKKPGASVKV SCKASGYTFT AYHTHWVRQA PGQGLEWMGW IYPKSGRTTY  60
TQKFQGRVTM TRDTSISTVY MELSRLKSDD TAVYYCARVG ALLFDYWGQG TLVTVSS     117

SEQ ID NO: 200          moltype = AA  length = 112
FEATURE                 Location/Qualifiers
source                  1..112
                        mol_type = protein
                        organism = synthetic construct
SEQUENCE: 200
DIVMTQTPLS SPVTLGQPAS ISCRSSQSLV HSDGNTYLSW LQQRPGQPPR LLIYKISNRF  60
SGVPDRFSGS GAGTDFTLKI SRVEAEDVGV YYCMQATQFP QTFGQGTKVE IK          112

SEQ ID NO: 201          moltype = AA  length = 117
FEATURE                 Location/Qualifiers
source                  1..117
                        mol_type = protein
                        organism = synthetic construct
SEQUENCE: 201
QVQLVQSGAE VKKPGASVKV SCKASGYTFT AYHTHWVRQA PGQGLEWMGW IYPKSGRTTY  60
TQKFQGRVTM TRDTSISTVY MELSRLKSDD TAVYYCARVG ALLFDYWGQG TLVTVSS     117

SEQ ID NO: 202          moltype = AA  length = 107
FEATURE                 Location/Qualifiers
source                  1..107
                        mol_type = protein
                        organism = synthetic construct
SEQUENCE: 202
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPLTFGG GTKVEIK                107

SEQ ID NO: 203          moltype = AA  length = 117
```

```
FEATURE                Location/Qualifiers
source                 1..117
                       mol_type = protein
                       organism = synthetic construct
SEQUENCE: 203
QVQLVQSGAE VKKPGASVKV SCKASGYTFT AYHTHWVRQA PGQGLEWMGW IYPKSGRTTY  60
TQKFQGRVTM TRDTSISTVY MELSRLKSDD TAVYYCARVG ALLFDYWGQG TLVTVSS     117

SEQ ID NO: 204         moltype = AA  length = 107
FEATURE                Location/Qualifiers
source                 1..107
                       mol_type = protein
                       organism = synthetic construct
SEQUENCE: 204
DIQMTQSPSS LSASVGDRVT ITCRASQGIR NDLGWYQQKP GKAPKCLIYA ASNLQSGVPS  60
RFSGSGSGTE FTLTISSLQP EDFATYYCLQ HNSYPRTFGQ GTKVDVK               107

SEQ ID NO: 205         moltype = AA  length = 117
FEATURE                Location/Qualifiers
source                 1..117
                       mol_type = protein
                       organism = synthetic construct
SEQUENCE: 205
QVQLVQSGAE VKKPGASVKV SCKASGYTFT AYHTHWVRQA PGQGLEWMGW IYPKSGRTTY  60
TQKFQGRVTM TRDTSISTVY MELSRLKSDD TAVYYCARVG ALLFDYWGQG TLVTVSS     117

SEQ ID NO: 206         moltype = AA  length = 110
FEATURE                Location/Qualifiers
source                 1..110
                       mol_type = protein
                       organism = synthetic construct
SEQUENCE: 206
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYGSSPPEYT FGQGTKLEIK            110

SEQ ID NO: 207         moltype = AA  length = 123
FEATURE                Location/Qualifiers
source                 1..123
                       mol_type = protein
                       organism = synthetic construct
SEQUENCE: 207
QVQLVESGGG VVQPGRSLRL SCAASGFTFS TYGMHWVRQA PGKGLEWVAV IWYDGSHKYY  60
SDSVKGRFTI SRDNSKNTLY LQMNSLRVED TAIYYCARTG ITGTTAYFYF DSWGQGTLVT  120
VSS                                                                123

SEQ ID NO: 208         moltype = AA  length = 112
FEATURE                Location/Qualifiers
source                 1..112
                       mol_type = protein
                       organism = synthetic construct
SEQUENCE: 208
DIVMTQSPDS LAVSLGERAT INCKSSQSVL YRSKNKNYLA WYQQKQGQPP KLFIYWASTR  60
ESGVPDRFSG SGSGTDFTLT ISSLQTEDVA IYYCQQYYGP VTFGGGTKVE IK          112

SEQ ID NO: 209         moltype = AA  length = 119
FEATURE                Location/Qualifiers
source                 1..119
                       mol_type = protein
                       organism = synthetic construct
SEQUENCE: 209
QVQLMQSGSE LEKPGASVKV SCKASGYTFT SFAINWVRQA PGQGLEWMGW INTITGNPSY  60
AQGFTGRFVF SLDTSVSTAF LQINSLKTED TAVYYCARYV TSSGKFDYWG QGTLVTVSS   119

SEQ ID NO: 210         moltype = AA  length = 107
FEATURE                Location/Qualifiers
source                 1..107
                       mol_type = protein
                       organism = synthetic construct
SEQUENCE: 210
DIQMTQSPSS VSASVGDRVT ITCRASRGIS RWLDWYQQKP GKAPKLLIYA ASNLQGGVPS  60
RFSGSGSGTD FTLTIRSLQP EDFALYYCQQ AKTFPFTFGP GTKVDIR               107

SEQ ID NO: 211         moltype = AA  length = 126
FEATURE                Location/Qualifiers
source                 1..126
                       mol_type = protein
                       organism = synthetic construct
SEQUENCE: 211
EVQLVESGGG LVKTGGSLRL SCVASGFSFK KAWMNWVRQA PGKGLEWVGR IKRNTDGGTA  60
```

```
DYAAPVKGRF TLSRDDSKKT LFLQMNSLKT EDTAVYYCTT LDSSSYYVGY YYMDVWGKGT  120
TVTVSS                                                             126

SEQ ID NO: 212          moltype = AA  length = 107
FEATURE                 Location/Qualifiers
source                  1..107
                        mol_type = protein
                        organism = synthetic construct
SEQUENCE: 212
DIQMTQSPSS VSASVGDRVI ITCRASQDIN NWLAWYQQKP GKAPKLLIYT ASSLQSGVPS  60
RFSGSGSGTD FTLTIGSLQP EDFATYYCQQ AHSLPISFGQ GTRLDIK               107

SEQ ID NO: 213          moltype = AA  length = 126
FEATURE                 Location/Qualifiers
source                  1..126
                        mol_type = protein
                        organism = synthetic construct
SEQUENCE: 213
EVQLVESGGG LVKTGGSLRL SCVASGFSFK KAWMNWVRQA PGKGLEWVGR IKRNTDGGTA  60
DYAAPVKGRF TLSRDDSKKT LFLQMNSLKT EDTAVYYCTT LDSSSYYVGY YYMDVWGKGT  120
TVTVSS                                                             126

SEQ ID NO: 214          moltype = AA  length = 107
FEATURE                 Location/Qualifiers
source                  1..107
                        mol_type = protein
                        organism = synthetic construct
SEQUENCE: 214
DIQMTQSPSS VSASVGDRVI ITCRASQDIN NWLAWYQQKA GKAPKLLIYT ASSLQSGVPS  60
RFSGSGSGTD FTLTIGSLQP EDFATYYCQQ AHSLPITFGQ GTRLEIK               107

SEQ ID NO: 215          moltype = AA  length = 126
FEATURE                 Location/Qualifiers
source                  1..126
                        mol_type = protein
                        organism = synthetic construct
SEQUENCE: 215
EVQLVESGGG LVKTGGSLRL SCVASGFSFK KAWMNWVRQA PGKGLEWVGR IKRTADGGAT  60
DYAAPVKGRF TLSRDDSKNT LYLQMNSLKT EDTAVYYCTT LDSSSWYVGY YYMDVWGKGT  120
TVTVSS                                                             126

SEQ ID NO: 216          moltype = AA  length = 107
FEATURE                 Location/Qualifiers
source                  1..107
                        mol_type = protein
                        organism = synthetic construct
SEQUENCE: 216
DIHMTQAPSS VSASVGDRVT FTCRASQDIN NWLAWYQQKP GKAPKLLIYT ASSLQSGVPS  60
RFSGSGSGTD FTLTISSLQP EDFATYYCQQ AHSLPITFGQ GTRLGIK               107

SEQ ID NO: 217          moltype = AA  length = 124
FEATURE                 Location/Qualifiers
source                  1..124
                        mol_type = protein
                        organism = synthetic construct
SEQUENCE: 217
EVQLVESGGG LVQPGRSLRL SCAASGFTFA DYTMHWVRQV PGKGLEWVSG ISWNSGSVDY  60
ADSVKGRFTI SRDNAKKTLY LQMNSLRAED TALYYCAKDS SGYGHYYFYY LDVWGKGTTV  120
TVSS                                                               124

SEQ ID NO: 218          moltype = AA  length = 106
FEATURE                 Location/Qualifiers
source                  1..106
                        mol_type = protein
                        organism = synthetic construct
SEQUENCE: 218
EIVMTQSPAT LSVSPGERAT LSCRATQSVS SNLAWYQQKP GQAPRLLIYS TSTRATGIPA  60
RFSGSRSGTE FTLTISSLQS EDSAVYYCQQ YNNWPHFGQG TRLEIK                106

SEQ ID NO: 219          moltype = AA  length = 124
FEATURE                 Location/Qualifiers
source                  1..124
                        mol_type = protein
                        organism = synthetic construct
SEQUENCE: 219
EVQLVESGGG LVQPGRSLRL SCAASGFTFN GYTMHWVRQV PGKGLEWVSG ISWNSGSVGY  60
ADSVKGRFTI SRDNAKNSLF LQMNSLRAED TALYYCAKDS SGYGHYYYYY MDVWGKGTTV  120
TVSS                                                               124
```

```
SEQ ID NO: 220          moltype = AA  length = 106
FEATURE                 Location/Qualifiers
source                  1..106
                        mol_type = protein
                        organism = synthetic construct
SEQUENCE: 220
EIVMTQSPAT LSVSPGERAT LSCRASQSVR NNLAWYQQKP GQAPRLLIYG ASTRATGIPA  60
RFSGSGSGTE FTLTISSLQS EDFALYYCQL YNNWPHFGQG TRLEIK                106

SEQ ID NO: 221          moltype = AA  length = 124
FEATURE                 Location/Qualifiers
source                  1..124
                        mol_type = protein
                        organism = synthetic construct
SEQUENCE: 221
EVQLVESGGG LVQPGRSLRL SCAVSGFTFN DYTMHWVRQV PGKGLEWVSG ISWNSGSIGY  60
ADSVKGRFTI SRDNAKNSLY LQMNSLRAED TALYFCAKDS SGYGHYYYYY MDVWGRGTTV  120
TVSS                                                              124

SEQ ID NO: 222          moltype = AA  length = 106
FEATURE                 Location/Qualifiers
source                  1..106
                        mol_type = protein
                        organism = synthetic construct
SEQUENCE: 222
EIVMTQSPAT LSVSPGERAT LSCRASQSVR KNLAWYQQKP GQAPRLLIYG ASTRATGIPA  60
RFSGSGSGTE FTLTISSLQS EDFAVYYCQL YNNWPHFGQG TRLEIK                106

SEQ ID NO: 223          moltype = AA  length = 124
FEATURE                 Location/Qualifiers
source                  1..124
                        mol_type = protein
                        organism = synthetic construct
SEQUENCE: 223
EVQLVESGGG LVQPGRSLRL SCAASGITFA DYTMHWVRQA PGKGLEWVSG ISWNSGSIDY  60
ADSVKGRFTI SRDNAKKTLY LQMNRLRAED TALYYCAKDS SGYGHYYFYY LDVWGKGTTV  120
TVSS                                                              124

SEQ ID NO: 224          moltype = AA  length = 106
FEATURE                 Location/Qualifiers
source                  1..106
                        mol_type = protein
                        organism = synthetic construct
SEQUENCE: 224
EIVMTQSPAT LSVSPGERAT LSCRASQSVS NNLAWYQQKP GQAPRLLIYS TSTRATGIPA  60
RFSGSRSGTE FTLTISSLQS EDSAVYYCQQ YNNWPHFGQG TRLEIK                106

SEQ ID NO: 225          moltype = AA  length = 124
FEATURE                 Location/Qualifiers
source                  1..124
                        mol_type = protein
                        organism = synthetic construct
SEQUENCE: 225
EVQLVESGGG LVQPGRSLRL SCAASGFTFD NYAMHWVRQA PGKGLEWVSG ISWNSGSIGY  60
ADSVKGRFTI SRDNAKNSLY LELNSLRAED TALYYCAKDS SGYGYYYNYY MDVWGKGTTV  120
TVSS                                                              124

SEQ ID NO: 226          moltype = AA  length = 106
FEATURE                 Location/Qualifiers
source                  1..106
                        mol_type = protein
                        organism = synthetic construct
SEQUENCE: 226
EIVMTQSPAT LSVSPGERAT LSCRASQSVR SNLAWYQQKP GQAPRLLIYG ASTRATGIPA  60
KFSGSGSGTE FTLTISSLQS EDFAVYYCQY YYNWPHFGQG TRLEIK                106

SEQ ID NO: 227          moltype = AA  length = 126
FEATURE                 Location/Qualifiers
source                  1..126
                        mol_type = protein
                        organism = synthetic construct
SEQUENCE: 227
EVQLVESGGG LVKTGGSLRL SCVASGFSFK KAWMNWVRQV PGKGLEWVGR IKRNTDGGTA  60
DYAAPVKGRF TLSRDDSKKT LFLQMNSLKT EDTAVYYCTT LDSSSYYVGY YYMDVWGKGT  120
TVTVSS                                                            126

SEQ ID NO: 228          moltype = AA  length = 107
FEATURE                 Location/Qualifiers
source                  1..107
```

```
                         mol_type = protein
                         organism = synthetic construct
SEQUENCE: 228
DIQMTQSPSS VSASVGDRVI ITCRASQDIN NWLAWYQQKP GKAPKLLIYT ASSLQSGVPS  60
RFSGSGSGTD FTLTIGSLQP EDFATYYCQQ AHSLPITFGQ GTRLEIK              107

SEQ ID NO: 229           moltype = AA  length = 126
FEATURE                  Location/Qualifiers
source                   1..126
                         mol_type = protein
                         organism = synthetic construct
SEQUENCE: 229
EVQLVESGGG LVKTGGSLRL SCVASGFSFK KAWMNWVRQA PGKGLEWVGR IKRNTDGGTA  60
DYAAPVKGRF TLSRDDSKKT LFLQMNSLKT EDTAVYYCTT LDSSSYYVGY YYMDVWGKGT  120
TVTVSS                                                            126

SEQ ID NO: 230           moltype = AA  length = 107
FEATURE                  Location/Qualifiers
source                   1..107
                         mol_type = protein
                         organism = synthetic construct
SEQUENCE: 230
DIQMTQSPSS VSASVGDRVT ITCRASQDIK NWLAWYQQKP GKAPKLLIYT ASSLQSGVPS  60
RFSGSGSGTD FTLTIGSLQP EDFATYYCQQ AHSLPITFGQ GTRLEIK              107

SEQ ID NO: 231           moltype = AA  length = 126
FEATURE                  Location/Qualifiers
source                   1..126
                         mol_type = protein
                         organism = synthetic construct
SEQUENCE: 231
EVQLVESGGG LVKTGGSLRL SCVASGFSFK KAWMNWVRQA PGKGLEWVGR IKRNTDGGTA  60
DYAAPVKGRF TLSRDDSKRT LYLQMNSLKT EDTAVYYCTT LDSSSRYVGY YYMDVWGKGT  120
TVTVSS                                                            126

SEQ ID NO: 232           moltype = AA  length = 107
FEATURE                  Location/Qualifiers
source                   1..107
                         mol_type = protein
                         organism = synthetic construct
SEQUENCE: 232
DIQMTQSPSS VSASVGDRVI ITCRASQDIN NWLAWYQQKP GKVPKLLIYT ASSLQSGVPS  60
RFSGSGSGTD FTLTIGSLQP EDFATYYCQQ AHSLPITFGQ GTRLEIK              107

SEQ ID NO: 233           moltype = AA  length = 126
FEATURE                  Location/Qualifiers
source                   1..126
                         mol_type = protein
                         organism = synthetic construct
SEQUENCE: 233
EVQLVESGGG LVKTGGSLRL SCVASGFSFK KAWMNWVRQA PGRGLEWVGR IKRNTDGGTT  60
DYAAPVKGRF TLSRDDSKNM LYLQMNSLKT EDTAVYYCTT LDSSSLYVGY YYMDVWGKGT  120
TVTVSS                                                            126

SEQ ID NO: 234           moltype = AA  length = 107
FEATURE                  Location/Qualifiers
source                   1..107
                         mol_type = protein
                         organism = synthetic construct
SEQUENCE: 234
DIQMTQSPSS VSASVGDRVT ITCRASQDIN NWLAWYQQKP GKAPKLLIYT ASSLQSGVPS  60
RFSGSGSGTD FTLTISSLQP EDFATYFCQQ AHSLPITFGQ GTRLEIT              107

SEQ ID NO: 235           moltype = AA  length = 124
FEATURE                  Location/Qualifiers
source                   1..124
                         mol_type = protein
                         organism = synthetic construct
SEQUENCE: 235
EVHLVESGGG LVQPGRSLRL SCAASGFTFD DYAMHWVRQA PGKGLEWVSG ISWNSGTIGY  60
ADSVKGRFTI SRDNAKNSLY LEMNSLRAED TALYYCAKDS SGYGHYYHYY IDVWGTGTTV  120
TVSS                                                              124

SEQ ID NO: 236           moltype = AA  length = 106
FEATURE                  Location/Qualifiers
source                   1..106
                         mol_type = protein
                         organism = synthetic construct
SEQUENCE: 236
```

```
EIVMTQSPAT LSVSPGGRAT LSCRASQSVG SNLAWYQQKP GQAPRLLIYD ASTRATGIPA  60
RFRGSGSGTE FTLTISGLQS EDFAVYYCQL YYNWPHFGQG TRLEIK                106

SEQ ID NO: 237          moltype = AA  length = 118
FEATURE                 Location/Qualifiers
source                  1..118
                        mol_type = protein
                        organism = synthetic construct
SEQUENCE: 237
EVQLVQSGAE VKKPGESLKI SCKGSGYIFT SYWIGWVRQM PGKGLEWMGI IYPGDSDTRY  60
SPSFQGQVTI SADKSISTAY LQWSSLKASD TAMYYCARRN YYYYMDVWGK GTTVTVSS    118

SEQ ID NO: 238          moltype = AA  length = 113
FEATURE                 Location/Qualifiers
source                  1..113
                        mol_type = protein
                        organism = synthetic construct
SEQUENCE: 238
DIVMTQSPDS LAVSLGERAT INCKSSQSVL YSSNNKNYLA WYQQKPGQPP KLLIYWASTR  60
ESGVPDRFSG SGSGTDFTLT ISSLQAEDVA VYYCQQYYST PYTFGQGTKL EIK         113

SEQ ID NO: 239          moltype = AA  length = 126
FEATURE                 Location/Qualifiers
source                  1..126
                        mol_type = protein
                        organism = synthetic construct
SEQUENCE: 239
EVQLVESGGG LVKTGGSLRL SCVASGFSFK KAWMNWVRQA PGKGLEWVGR IKRNTDGGTA  60
DYAAPVKGRF TLSRDDSKKT LFLQMNSLKT EDTAVYYCTT LDSSSYYVGY YYMDVWGKGT  120
TVTVSS                                                            126

SEQ ID NO: 240          moltype = AA  length = 107
FEATURE                 Location/Qualifiers
source                  1..107
                        mol_type = protein
                        organism = synthetic construct
SEQUENCE: 240
DIQMTQSPSS VSASVGDRVI ITCRASQDIN NWLAWYQQKP GKAPKLLIYT ASSLQSGVPS  60
RFSGSGSGTD FILTIGSLQP EDFATYYCQQ AHSLPITFGQ GTRLEIK               107

SEQ ID NO: 241          moltype = AA  length = 124
FEATURE                 Location/Qualifiers
source                  1..124
                        mol_type = protein
                        organism = synthetic construct
SEQUENCE: 241
EVQLVESGGG LVRPGRSLRL SCAASGFTFD DYTMHWVRQA PGKGLEWVSG ISWNSGSIGY  60
ADSVKGRFTI SRDNAKNSLY LQMNSLRAED TALYYCSKDS SGYGYYLNYS LDVWGKGTTV  120
TVSS                                                              124

SEQ ID NO: 242          moltype = AA  length = 106
FEATURE                 Location/Qualifiers
source                  1..106
                        mol_type = protein
                        organism = synthetic construct
SEQUENCE: 242
EIVMTQSPAT LSVSPGERAT LSCRASLSVT SNLAWYQQKP GQAPRLLIYG ASTRATGVPA  60
RFSGSGSGTE FTLTISSLQS EDFAVYYCQQ YNNWPHFGQG TRLEIK                106

SEQ ID NO: 243          moltype = AA  length = 124
FEATURE                 Location/Qualifiers
source                  1..124
                        mol_type = protein
                        organism = synthetic construct
SEQUENCE: 243
EVQLVESGGG LVQPGRSLRL SCAASGFTFA DYTMHWVRQA PGQGLEWVSG ISWNSGSIDY  60
ADSVKGRFII SRDNAKKTLY LQMNSLRAED TALYYCAKDS SGYGHYYFYY LDVWGKGTTV  120
TVSS                                                              124

SEQ ID NO: 244          moltype = AA  length = 106
FEATURE                 Location/Qualifiers
source                  1..106
                        mol_type = protein
                        organism = synthetic construct
SEQUENCE: 244
EIVMTQSPAT LSVSPGERAT LSCRASQSVS SNLAWYQQKP GQAPRLLIYS TSTRATGIPA  60
RFSGSRSGTE FTLTISSLQS EDSAVYYCQQ YNNWPHFGQG TRLEIK                106

SEQ ID NO: 245          moltype = AA  length = 124
```

```
FEATURE                Location/Qualifiers
source                 1..124
                       mol_type = protein
                       organism = synthetic construct
SEQUENCE: 245
EVQLVESGGG LVQPGRSLRL SCTTSGFTFD DYTMHWVRQV PGKGLEWVSD ISWNSGSVGY  60
ADSVKGRFTI SRDNAKNSLY LQMNSLRAED TALYYCVKDS SGYGHYFHYY MDVWGKGTTV  120
TVSS                                                              124

SEQ ID NO: 246         moltype = AA  length = 124
FEATURE                Location/Qualifiers
source                 1..124
                       mol_type = protein
                       organism = synthetic construct
SEQUENCE: 246
EVQLVESGGG LVQPGRSLRL SCTTSGFTFD DYTMHWVRQV PGKGLEWVSD ISWNSGSVGY  60
ADSVKGRFTI SRDNAKNSLY LQMNSLRAED TALYYCVKDS SGYGHYFHYY MDVWGKGTTV  120
TVSS                                                              124

SEQ ID NO: 247         moltype = AA  length = 124
FEATURE                Location/Qualifiers
source                 1..124
                       mol_type = protein
                       organism = synthetic construct
SEQUENCE: 247
EVQLVESGGG LVQPGRSLRL SCAASGFTFD DYTMHWVRQV PGKGLEWVSD ISWNSGSVGY  60
ADSVKGRFTI SRDNAKNSLY LQMNSLRAED TALYYCVKDS SGYGHYFHYY MDVWGKGTTV  120
TVSS                                                              124

SEQ ID NO: 248         moltype = AA  length = 107
FEATURE                Location/Qualifiers
source                 1..107
                       mol_type = protein
                       organism = synthetic construct
SEQUENCE: 248
DIQMTQSPSS LSASVGDRVT ITCRASQSIS NYLNWYQVKP GKAPKVLIYA ASSLQSGVPS  60
RFSGSGSGTD FTLTISSLQP EDFVSYYCHQ SYNTPITFGQ GTRLEIK               107

SEQ ID NO: 249         moltype = AA  length = 121
FEATURE                Location/Qualifiers
source                 1..121
                       mol_type = protein
                       organism = synthetic construct
SEQUENCE: 249
EVQLVESGGG LVQPGGSLRL SCAASGFTFS SNWMSWVRQA PGKGLEWVAN IKQDGSEKYS  60
VDSVKGRFTI SRDNAKNSLY LQMNSLRAED TAVYYCARDR SRNYYWYFDL WGRGTLVTVS  120
S                                                                 121

SEQ ID NO: 250         moltype = AA  length = 107
FEATURE                Location/Qualifiers
source                 1..107
                       mol_type = protein
                       organism = synthetic construct
SEQUENCE: 250
DIQMTQSPST LSASVGDRVT ITCRASQTIS RWLAWYQQKP GKAPKLLIYK ASSLESGVPS  60
RFSGSGSGTE FTLTISSLQP DDFATYYCQQ YNSYSRTFGQ GTKVEIK               107

SEQ ID NO: 251         moltype = AA  length = 121
FEATURE                Location/Qualifiers
source                 1..121
                       mol_type = protein
                       organism = synthetic construct
SEQUENCE: 251
EVELVESGGG LVQPGGSLRL SCAASGFTFS SNWMSWVRQA PGKGLEWVAN IKQDGSEKYY  60
VDSVKGRFTI SRDNAKNSLY LKMNSLRAED TAVYYCARDC SSNWYWYFDL WGRGTLVTVS  120
S                                                                 121

SEQ ID NO: 252         moltype = AA  length = 107
FEATURE                Location/Qualifiers
source                 1..107
                       mol_type = protein
                       organism = synthetic construct
SEQUENCE: 252
DIQMTQSPST LSASVGDRVT ITCRASQSIS RWLAWYQQKP GKAPKLLIYK ASSLESGVPS  60
RFSGSGSGTE FILTISSLQP DDFATYYCQQ YNSYSRTFGQ GTKVEIK               107

SEQ ID NO: 253         moltype = AA  length = 124
FEATURE                Location/Qualifiers
source                 1..124
```

```
                         mol_type = protein
                         organism = synthetic construct
SEQUENCE: 253
EVELVESGGG LVQPGRSLRL SCAASGFKFD DYTMHWVRLP PGKGLEWVSG ISWNSGTIDY  60
GDSVKGRFTI SRDNAKNSLY LQMNSLRVED TALYYCAKDT SGYGHYFYYY MDVWGKGTTV  120
TVSS                                                               124

SEQ ID NO: 254           moltype = AA  length = 107
FEATURE                  Location/Qualifiers
source                   1..107
                         mol_type = protein
                         organism = synthetic construct
SEQUENCE: 254
DIQMTQSPSS LSASIGDRVS ITCRTSQIIN NYLNWYQQKP GKAPKVLIYS ASSLQSGVPS  60
RFSGSGSGTD FTLTINSLQP EDFATYYCQQ SYNFPITFGQ GTRLELK               107

SEQ ID NO: 255           moltype = AA  length = 124
FEATURE                  Location/Qualifiers
source                   1..124
                         mol_type = protein
                         organism = synthetic construct
SEQUENCE: 255
EVQLVESGGG LVQPGMSLRL SCAASGFTFD DYTMHWVRQS PGKGLEWVAG ISWNSGTIGY  60
GDSMKGRFTI SRDNAKNSLD LQMNSLRVED TALYYCAKDT SGYGHYYYYF MDVWGKGTTV  120
TVSS                                                               124

SEQ ID NO: 256           moltype = AA  length = 107
FEATURE                  Location/Qualifiers
source                   1..107
                         mol_type = protein
                         organism = synthetic construct
SEQUENCE: 256
DIQMTQSPSS LSASIGDRVS ITCRTSQIIN NYLNWYQQKP GKAPKLLIYS ASSLQSGVPS  60
RFSGSGSGTD FTLTLSSLQP EDFATYFCQQ SYNFPITFGQ GTRLELK               107

SEQ ID NO: 257           moltype = AA  length = 124
FEATURE                  Location/Qualifiers
source                   1..124
                         mol_type = protein
                         organism = synthetic construct
SEQUENCE: 257
EVQLVESGGG LVQPGRSLRL SCAASGFTFD DYTMHWVRQA PGKGLEWVSD ISWNSGTIGY  60
ADSVKGRFTI SRDNAKNSLY LQMNSLRAED TALYYCVKDS SGYGHYYKYY MDVWGKGTTV  120
TVSS                                                               124

SEQ ID NO: 258           moltype = AA  length = 107
FEATURE                  Location/Qualifiers
source                   1..107
                         mol_type = protein
                         organism = synthetic construct
SEQUENCE: 258
DIQMTQSPSS LSASVGDRVT ITCRASQSIS NYLNWYQQKA GKVPKVLIYG SSSLQSGVPS  60
RFSGSGSGTD FTLTISSLQP EDFASYYCQQ TYSSPLTFGG GTKVDFK               107

SEQ ID NO: 259           moltype = AA  length = 124
FEATURE                  Location/Qualifiers
source                   1..124
                         mol_type = protein
                         organism = synthetic construct
SEQUENCE: 259
EVQLVESGGG LVQPGRSLRL SCAASGFTFD DYTMHWVRQT PGKGLEWVSD ISWNSGSIGY  60
ADSVKGRFTI SRDNAKNTLY LQMNSLRAED TALYYCVKDS SGYGHYLYYY MDVWGKGTTV  120
TVSS                                                               124

SEQ ID NO: 260           moltype = AA  length = 107
FEATURE                  Location/Qualifiers
source                   1..107
                         mol_type = protein
                         organism = synthetic construct
SEQUENCE: 260
DIQMTQSPSS LSASVGDRVT ITCRASQSIR NYLNWYQQSP GRAPKLLIFS ASSLQSGVPS  60
RFSGSGSGTD FTLTISSLQP EDFVTYYCQQ RYSTPITFGQ GTRLEIK               107

SEQ ID NO: 261           moltype = AA  length = 124
FEATURE                  Location/Qualifiers
source                   1..124
                         mol_type = protein
                         organism = synthetic construct
SEQUENCE: 261
```

-continued

```
EVNLVESGGG LVQPGRSLRL SCAASGFTFD DYTMHWVRQV PGKGLEWVSN ISWNSGSLGY  60
ADSVKGRFTI SRDNAKDSLY LQMNSLRVED TALYYCAKDS SGYGHYNSYY MDVWGKGTTV  120
TVSS                                                              124

SEQ ID NO: 262         moltype = AA  length = 107
FEATURE                Location/Qualifiers
source                 1..107
                       mol_type = protein
                       organism = synthetic construct
SEQUENCE: 262
DIQMTQSPSS LSASVGDRVT ITCRASQSIR NYLNWYQQKP GKAPKVLIYS ASSLQSGVPS  60
RFSGSGSGTD FTLTISSLQP EDFASFYCQQ TYSTPITFGQ GTRLEIK               107

SEQ ID NO: 263         moltype = AA  length = 117
FEATURE                Location/Qualifiers
source                 1..117
                       mol_type = protein
                       organism = synthetic construct
SEQUENCE: 263
QVQLVQSGAD MKKPGASVKV SCKASGYTFT DYHIHWVRQA PGQGLEWMGW INPKSGRTMF  60
AQNFQDRVTM TRDTSISTAY MELNRLRSDD SAVYYCARVT QLVFDHWGQG TLVTVSF     117

SEQ ID NO: 264         moltype = AA  length = 107
FEATURE                Location/Qualifiers
source                 1..107
                       mol_type = protein
                       organism = synthetic construct
SEQUENCE: 264
AIQMTQSPSS LSASVGDRVT ITCRASQGIR NDLGWYQQKP GKAPKLLIYA ASSLQSGVPS  60
RFSGSGSGTD FTLTISSLQP EDFATYYCLQ DYNYMYTFGQ GTKLEIK               107

SEQ ID NO: 265         moltype = AA  length = 117
FEATURE                Location/Qualifiers
source                 1..117
                       mol_type = protein
                       organism = synthetic construct
SEQUENCE: 265
QVQLVQSGAG MKKPGASVRV SCKASGYNFI DYHIHWVRQA PGQGLEWMGW INPKSGRTMS  60
AQKFQGRVTM TRDTSITAAY MELNRLRSDD SAIYYCARVT QLVFDHWGQG TLVTVSL     117

SEQ ID NO: 266         moltype = AA  length = 113
FEATURE                Location/Qualifiers
source                 1..113
                       mol_type = protein
                       organism = synthetic construct
SEQUENCE: 266
DIVMTQSPDS LAVSLGERAT INCKSSQSVL YSSNNKNYLA WYQQKPGQPP KLLIYWASTR  60
ESGVPDRFSG SGSGTDFTLT ISSLQAEDVA VYYCQQYYST PYTFGQGTKL EIK         113

SEQ ID NO: 267         moltype = AA  length = 118
FEATURE                Location/Qualifiers
source                 1..118
                       mol_type = protein
                       organism = synthetic construct
SEQUENCE: 267
QVQLVQSGAE VKKPGASVRV SCKSSGYTFT GYYIHWVRQA PGQGLEWMGW INPKSGRTSY  60
AEKFQGSITM TRDTSINTAY MELTKLRSDD TAVYYCERMG ELLLFDYWGQ GTLVTVSS    118

SEQ ID NO: 268         moltype = AA  length = 111
FEATURE                Location/Qualifiers
source                 1..111
                       mol_type = protein
                       organism = synthetic construct
SEQUENCE: 268
DIVMTQTPLS SPVTLGQPAS ISCRSSQSLV HSDGNTYLSW LQQRPGQPPR LLIYKISNRF  60
SGVPDRFSGS GAGTDFTLKI SRVEAEDVGV YYCMQATQLY TFGQGTKLEI K           111

SEQ ID NO: 269         moltype = AA  length = 122
FEATURE                Location/Qualifiers
source                 1..122
                       mol_type = protein
                       organism = synthetic construct
SEQUENCE: 269
QVQLVESGGG VVQPGRSLRL SCAASGFTFS DYGMHWVRQA PGKGLEWVSV IWSDGLNKYY  60
KDSVKGRFTI SRDNSKNTLY LQMNSLRAAD TAVYYCARLY SGSHYHYFMD VWGKGTSVTV  120
SS                                                                122

SEQ ID NO: 270         moltype = AA  length = 107
FEATURE                Location/Qualifiers
```

```
source                  1..107
                        mol_type = protein
                        organism = synthetic construct
SEQUENCE: 270
DILLTQSPSF LSASVGDRVT ITCRASQDIS SSLAWYQQKP KKAPDLLIYT ASTLQSGVPS  60
RFSGRGSGTE FTLTISNLQP EDFATYYCQQ LKNYPITFGQ GTRLEIK              107

SEQ ID NO: 271          moltype = AA  length = 118
FEATURE                 Location/Qualifiers
source                  1..118
                        mol_type = protein
                        organism = synthetic construct
SEQUENCE: 271
QVQLVQSGSE VKKPGASVRV SCKASGYIFT GYHIHWVRQA PGQGLEWMGW INPKSGRTSY  60
AQNFQARVTM TRDTSINTIH MELSRLRSDD TAIYYCMRVG EQLLFDFWGQ GTLVTVSS   118

SEQ ID NO: 272          moltype = AA  length = 107
FEATURE                 Location/Qualifiers
source                  1..107
                        mol_type = protein
                        organism = synthetic construct
SEQUENCE: 272
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SYSTPLTFGG GTKVEIK              107

SEQ ID NO: 273          moltype = AA  length = 119
FEATURE                 Location/Qualifiers
source                  1..119
                        mol_type = protein
                        organism = synthetic construct
SEQUENCE: 273
EVQLLESGGG LVQPGGSLRL SCAASGFTFS SYAMNWVRQA PGKGLEWVSA ISSSGGRTYY  60
ADSVKGRFTI SRDNSKNTLY LQMNSLRAED TAVYYCAKDS TSHPYMDVWG KGTTVTVSS  119

SEQ ID NO: 274          moltype = AA  length = 107
FEATURE                 Location/Qualifiers
source                  1..107
                        mol_type = protein
                        organism = synthetic construct
SEQUENCE: 274
AIQMTQSPSS LSASVGDRVT ITCRASQGIR NDLGWYQQQP GKAPKLLIYD ASSLQSGVPS  60
RFSGSGSGTV FTLTISSLQP EDFATYFCLQ DYNYPFTFGP GTKVDIK              107

SEQ ID NO: 275          moltype = AA  length = 118
FEATURE                 Location/Qualifiers
source                  1..118
                        mol_type = protein
                        organism = synthetic construct
SEQUENCE: 275
QVQLVESGGG VVQPGRSLRL SCAASGFTFS GYGMHWVRQA PGKGLEWVAI IYYNGKKEYY  60
ADSVKGRFTI SRDNSKNTLY LQMNSLRAED TAVYYCTRGE GYNWFDPWGQ GTLVTVSS   118

SEQ ID NO: 276          moltype = AA  length = 107
FEATURE                 Location/Qualifiers
source                  1..107
                        mol_type = protein
                        organism = synthetic construct
SEQUENCE: 276
EIVMTQSPAT LSVSPGERAT LSCRASQSVS SNLAWYQQKP GQAPRLLIYG ASTRATGIPA  60
RFSGSGSGTE FTLTISSLQS EDFAVYYCQQ YNNWPLTFGG GTKVEIK              107

SEQ ID NO: 277          moltype = AA  length = 118
FEATURE                 Location/Qualifiers
source                  1..118
                        mol_type = protein
                        organism = synthetic construct
SEQUENCE: 277
QVQLVESGGG VVQPGRSLRL SCAASGFTFS GYGMHWVRQA PGKGLEWVAI IYYDGKNKYY  60
ADSVKGRFTI SRDNSKSTLY LQMNSLGADD TAVYYCTRGK GYNWFDPWGQ GTLVTVSS   118

SEQ ID NO: 278          moltype = AA  length = 107
FEATURE                 Location/Qualifiers
source                  1..107
                        mol_type = protein
                        organism = synthetic construct
SEQUENCE: 278
EIVMTQSPAT LSVSPGERAT LSCRASQSVS SNLAWYQQKP GQAPRLLIYG ASTRATGIPA  60
RFSGSGSGTE FTLTISSLQS EDFAVYYCQQ YNNWPLTFGG GTKVEIK              107
```

```
SEQ ID NO: 279          moltype = AA  length = 118
FEATURE                 Location/Qualifiers
source                  1..118
                        mol_type = protein
                        organism = synthetic construct
SEQUENCE: 279
QVQLVESGGG VVQPGRSLRL SCAASGFTFS GYGMHWVRQA PGKGLEWVAI IYYNGKKEYY  60
ADSVKGRFTI SRDNSKNTLY LQMNSLRAED TAVYYCTRGE GYNWFDPWGQ GTLVTVSS    118

SEQ ID NO: 280          moltype = AA  length = 107
FEATURE                 Location/Qualifiers
source                  1..107
                        mol_type = protein
                        organism = synthetic construct
SEQUENCE: 280
EIVMTQSPAT LSVSPGERAT LSCRASQSVS SNLAWYQQKP GQAPRLLIYG ASTRATGIPA  60
RFSGSGSGTE FTLTISSLQS EDFAVYYCKQ YNNWPLTFGG GTKVEIK               107

SEQ ID NO: 281          moltype = AA  length = 118
FEATURE                 Location/Qualifiers
source                  1..118
                        mol_type = protein
                        organism = synthetic construct
SEQUENCE: 281
QVQLVESGGG VVQPGRSLRL SCAASGFTFS GYGMHWVRQA PGKGLEWVAI IYYNGKKEYY  60
ADSVKGRFTI SRDNSKNTLY LQMNSLRAED TAVYYCTRGE GYNWFDPWGQ GTLVTVSS    118

SEQ ID NO: 282          moltype = AA  length = 107
FEATURE                 Location/Qualifiers
source                  1..107
                        mol_type = protein
                        organism = synthetic construct
SEQUENCE: 282
EIVMTQSPAT LSVSPGERAT LSCRASQSVS SNLAWYQQKP GQAPRLLIYG ASTRATGIPA  60
RFSGSGSGTD FTLTISSLQS EHFAVYYCQQ YTNWPLTFGG GTKVEIK               107

SEQ ID NO: 283          moltype = AA  length = 107
FEATURE                 Location/Qualifiers
source                  1..107
                        mol_type = protein
                        organism = synthetic construct
SEQUENCE: 283
EIVMTQSPAT LSVSPGERAT LSCRASQSVS SNLAWYQQKP GQAPRLLIYG ASTRATGIPA  60
RFSGSGSGTD FTLTISSLQS EHFAVYYCQQ YTNWPLTFGG GTKVEIK               107

SEQ ID NO: 284          moltype = AA  length = 107
FEATURE                 Location/Qualifiers
source                  1..107
                        mol_type = protein
                        organism = synthetic construct
SEQUENCE: 284
EIVMTQSPAT LSVSPGERAT LSCRASQSVS SNLAWYQQKP GQAPRLLIYG ASTRATGIPA  60
RFSGSGSGTE FTLTISSLQS EDFAVYYCKQ YKNWPLTFGG GTKVEIK               107

SEQ ID NO: 285          moltype = AA  length = 118
FEATURE                 Location/Qualifiers
source                  1..118
                        mol_type = protein
                        organism = synthetic construct
SEQUENCE: 285
QVQLVESGGG VVQPGRSLRL SCAASGFTFS GYGMHWVRQA PGKGLEWVAI IYYNGNNRKY  60
ADSVKGRFTI SRDNSKNTVS LQMNSLRVED TAIYYCTRGD GYNWFVTWGQ GTLVTVSS    118

SEQ ID NO: 286          moltype = AA  length = 107
FEATURE                 Location/Qualifiers
source                  1..107
                        mol_type = protein
                        organism = synthetic construct
SEQUENCE: 286
EIVMTQSPAT LSVSPGERAT LSCRASQSVS SNLAWYHQKP GQAPRLLIYG ASTRATGIPV  60
RFSGSGSGTE FTLTISSLQS DDFAVYYCQQ YNNWPLTFGG GTKVEIK               107

SEQ ID NO: 287          moltype = AA  length = 118
FEATURE                 Location/Qualifiers
source                  1..118
                        mol_type = protein
                        organism = synthetic construct
SEQUENCE: 287
QEQLVESGGG VVQPGGSLRL SCAASGFIFS GYGMHWVRQA PGKGLEWVAI IWYNGRKTYY  60
```

```
AESVKGRFTI SRDNSKNTLS LQMNSLRVED TAVYYCTAGQ GYNWFDPWGQ GTLVTVSS    118

SEQ ID NO: 288         moltype = AA  length = 107
FEATURE                Location/Qualifiers
source                 1..107
                       mol_type = protein
                       organism = synthetic construct
SEQUENCE: 288
EIVMTQSPAT LSVSPGERAT LSCRASQSVS SNLAWYQQKP GQAPRLLIYG ASTRATGIPA  60
RFSGSGSGTE FTLTISSLQS EDFAVYYCQQ FNAWPLTFGG GTKMEIK                107

SEQ ID NO: 289         moltype = AA  length = 118
FEATURE                Location/Qualifiers
source                 1..118
                       mol_type = protein
                       organism = synthetic construct
SEQUENCE: 289
QEQLVESGGG VVQSGRSLRL SCVASGFKFS GYGMHWVRQA PGKGLEWVAI IYYDGKNKYY  60
ADSVKGRFTI SRDNSKNTLY LQMNSLRAED TAVYYCTRGA GYNWFDSWGQ GTLVTVSS    118

SEQ ID NO: 290         moltype = AA  length = 107
FEATURE                Location/Qualifiers
source                 1..107
                       mol_type = protein
                       organism = synthetic construct
SEQUENCE: 290
EIVMTQSPAT LSVSPGERAT LSCRASQSVR NNLAWYQQKP GQAPRLLIYG VSTRATAFPA  60
RFSGSGSGTE FTLTISSLQS EDFAVYYCQQ YNNWPLTFGG GTKVEIK                107

SEQ ID NO: 291         moltype = AA  length = 118
FEATURE                Location/Qualifiers
source                 1..118
                       mol_type = protein
                       organism = synthetic construct
SEQUENCE: 291
QEQLVESGGG VVQSGRSLRL SCVASGFKFS GYGMHWVRQA PGKGLEWVAI IYYDGKNKYY  60
ADSVKGRFTV SRDNSKNTLY LQMNSLRAED TAVYYCTRGA GYNWFDSWGQ GTLVTVSS    118

SEQ ID NO: 292         moltype = AA  length = 107
FEATURE                Location/Qualifiers
source                 1..107
                       mol_type = protein
                       organism = synthetic construct
SEQUENCE: 292
EIVMTQSPAT LSVSPGERAT LSCRASQSVR NNLAWYQQKP GQAPRLLIYG VSTRATAFPA  60
RFSGSGSGTE FTLTISSLQS EDFAVYYCQQ YNNWPLTFGG GTKVEIK                107

SEQ ID NO: 293         moltype = AA  length = 118
FEATURE                Location/Qualifiers
source                 1..118
                       mol_type = protein
                       organism = synthetic construct
SEQUENCE: 293
QVQLVESGGG VVQPGGSLRL SCAASGFTFS GYGMHWVRQA PGKGLEWVAI IWYNGRKTYY  60
AESVKGRFTI SRDNSKNTLS LQMNSLRVED TAVYYCTTGQ GYNWFDPWGQ GTLVTVSS    118

SEQ ID NO: 294         moltype = AA  length = 107
FEATURE                Location/Qualifiers
source                 1..107
                       mol_type = protein
                       organism = synthetic construct
SEQUENCE: 294
EIVMTQSPAT LSVSPGERAT LSCRASQSVS SNLAWYQQKP GQAPRLLIYG ASTRATGIPA  60
RFSGSGSGTE FTLTISSLQS EDFAVYYCQQ FNAWPLTFGG GTKMEIK                107

SEQ ID NO: 295         moltype = AA  length = 118
FEATURE                Location/Qualifiers
source                 1..118
                       mol_type = protein
                       organism = synthetic construct
SEQUENCE: 295
QVQLVESGGG VVQPGGSLRL SCAASGFTFS GYGMHWVRQA PGKGLEWVAI IWYNGRKTYY  60
AESVKGRFTI SRDNSKNTLS LQMNSLRIED TAVYYCTTGQ GYNWFDPWGQ GTLVTVSS    118

SEQ ID NO: 296         moltype = AA  length = 107
FEATURE                Location/Qualifiers
source                 1..107
                       mol_type = protein
                       organism = synthetic construct
```

```
SEQUENCE: 296
EIVMTQSPAT LSVSPGERAT LSCRASQSVS SNLAWYQQKP GQAPRLLIYG ASTRATGIPA  60
RFSGSGSGTE FTLTISSLQS EDFAVYYCQQ FNAWPLTFGG GTKMEIK               107

SEQ ID NO: 297         moltype = AA  length = 118
FEATURE                Location/Qualifiers
source                 1..118
                       mol_type = protein
                       organism = synthetic construct
SEQUENCE: 297
QVQLVESGGG VVQPGRSLRL SCAASGFTFS GYGMHWVRQA PGKGLEWVAI IYYNGKKEYY  60
ADSVKGRFTI FRDNSKNTLY LHMNSLRAED TAVYYCTRGE GYNWFDPWGQ GTLVTVSS    118

SEQ ID NO: 298         moltype = AA  length = 107
FEATURE                Location/Qualifiers
source                 1..107
                       mol_type = protein
                       organism = synthetic construct
SEQUENCE: 298
EIVMTQSPAT LSVSPGERAT LSCRASQSVS RNLAWYQQKP GQAPRLLIYG ASTRATGIPA  60
RFSGSGSGTE FTLTISSLQS EDFAVYYCQQ YNNWPLTFGG GTKVEIK               107

SEQ ID NO: 299         moltype = AA  length = 118
FEATURE                Location/Qualifiers
source                 1..118
                       mol_type = protein
                       organism = synthetic construct
SEQUENCE: 299
QVQLAESGGG VVQPGRSLRL SCAASGFTFS GYGMHWVRQA PGKGLEWVAI IYYNGKKEYY  60
ADSVKGRFTI SRDNSKNTLY LQMNSLRAED TAVYFCTRGE GYNWFDPWGQ GTLVTVSS    118

SEQ ID NO: 300         moltype = AA  length = 107
FEATURE                Location/Qualifiers
source                 1..107
                       mol_type = protein
                       organism = synthetic construct
SEQUENCE: 300
EIVMTQSPAT LSVSPGERAT LSCRASQSVS SNLAWYQQKP GQAPRLLIYG ASTRATGIPA  60
RFSGSGSGTE FTLTISSLQS EDFAVYYCKQ YKNWPLTFGG GTKVEIK               107

SEQ ID NO: 301         moltype = AA  length = 118
FEATURE                Location/Qualifiers
source                 1..118
                       mol_type = protein
                       organism = synthetic construct
SEQUENCE: 301
QVQLVESGGG VVQPGRSLRL SCAASGFTFS GYGMHWVRQA PGKGLEWVAI IYYNGKKEYY  60
ADSVKGRFTI SRDNSKNTLY LQMNSLRAED TAVYYCTRGE GYNWFDPWGQ GTLVTVSS    118

SEQ ID NO: 302         moltype = AA  length = 107
FEATURE                Location/Qualifiers
source                 1..107
                       mol_type = protein
                       organism = synthetic construct
SEQUENCE: 302
EIVMTQSPAT LSVSPGERAT LSCRASQSVS SSLAWYQQKP GQAPRLLIYG ASTRATGIPA  60
RFSGSGSGTE FTLTISSLQS EDFAVYYCQQ YNNWPLTFGG GTKVEIK               107

SEQ ID NO: 303         moltype = AA  length = 118
FEATURE                Location/Qualifiers
source                 1..118
                       mol_type = protein
                       organism = synthetic construct
SEQUENCE: 303
QVQLVESGGG VVQPGRSLRL SCAASGFTFS GYGMHWVRQA PGKGLEWVAI IYYNGKKEYY  60
ADSVKGRFTI SRDNSKNTLY LQMNSLRAED TAVYFCTRGE GYNWFDPWGQ GTLVTVSS    118

SEQ ID NO: 304         moltype = AA  length = 107
FEATURE                Location/Qualifiers
source                 1..107
                       mol_type = protein
                       organism = synthetic construct
SEQUENCE: 304
EIVMTQSPAT LSVSPGERAT LSCRASQSVS SNLAWYQQKP GQAPRLLIYG ASTRATGIPA  60
RFSGSGSGTE FTLTISSLQS EDFAVYYCKQ YKNWPLTFGG GTKVEIK               107

SEQ ID NO: 305         moltype = AA  length = 118
FEATURE                Location/Qualifiers
source                 1..118
```

```
                         mol_type = protein
                         organism = synthetic construct
SEQUENCE: 305
QVQLVESGGG VVQPGGSLRL SCAASGFTFR GYGMHWVRQA PGKGLEWVAI IYYNGRKTYY  60
AESVKGRFTI SRDNSKNTLS LQMNSLRVED TAVYYCTAGQ GYNWFDPWGQ GTLVTVSS    118

SEQ ID NO: 306           moltype = AA  length = 107
FEATURE                  Location/Qualifiers
source                   1..107
                         mol_type = protein
                         organism = synthetic construct
SEQUENCE: 306
EIVMTQSPAT LSVSPGERAT LSCRASQSVS SNLAWYQQKP GQAPRLLIYG ASTRATGIPA  60
RFSGSGSGTE FTLTISSLQS EDFAVYYCQQ FNAWPLTFGG GTKMEIK                107

SEQ ID NO: 307           moltype = AA  length = 118
FEATURE                  Location/Qualifiers
source                   1..118
                         mol_type = protein
                         organism = synthetic construct
SEQUENCE: 307
QVQLVESGGG VVQSGRSLRL SCAASGFTFS GYGMHWVRQA PGKGLEWVAI VYYDGKNKYY  60
ADSVKGRFTI SRDNSKNTLY LQMNSLRAED TAVYYCVRGE GYNWFDPWGQ GTLVTVSS    118

SEQ ID NO: 308           moltype = AA  length = 107
FEATURE                  Location/Qualifiers
source                   1..107
                         mol_type = protein
                         organism = synthetic construct
SEQUENCE: 308
EIVMTQSPAT LSVSPGERAT LSCRASQSVS SNLAWYQQKP GQVPRLLIYG ASTRATGIPA  60
RFSGSGSGTQ FTLTISSLQS EDFAVYYCQQ YNNWPLTFGG GTKVEIK                107

SEQ ID NO: 309           moltype = AA  length = 118
FEATURE                  Location/Qualifiers
source                   1..118
                         mol_type = protein
                         organism = synthetic construct
SEQUENCE: 309
QVQLVESGGG VVQPGKSLRL SCAASGFTFS GYGMHWVRQA PGKGLEWVAI IYYNGKKEYY  60
ADSVKGRFTI SRDNSKNTLY LQMNSLRAED TAVYYCTRGE GYNWFDPWGQ GTLVTVSS    118

SEQ ID NO: 310           moltype = AA  length = 107
FEATURE                  Location/Qualifiers
source                   1..107
                         mol_type = protein
                         organism = synthetic construct
SEQUENCE: 310
EIVMTQSPAT LSVSPGERAT LSCRASQSVS SNLAWYQQKP GQAPRLLIYG ASTRATGIPA  60
RFSGSGSGTE FTLTISSLQS EDFAVYYCKQ YNNWPLTFGG GTKVEIK                107

SEQ ID NO: 311           moltype = AA  length = 118
FEATURE                  Location/Qualifiers
source                   1..118
                         mol_type = protein
                         organism = synthetic construct
SEQUENCE: 311
QVQLVESGGG VVQPGRSLRL SCAASGFTFS GYGMHWVRQA PGKGLEWVAI IYYNGNNRKY  60
ADSVKGRFTI SRDNSKNTVS LQMNSLRVED TAIYYCTRGD GYNWFVTWGQ GTLVTVSS    118

SEQ ID NO: 312           moltype = AA  length = 107
FEATURE                  Location/Qualifiers
source                   1..107
                         mol_type = protein
                         organism = synthetic construct
SEQUENCE: 312
EIVMTQSPAT LSVSPGERAT LSCRASQSVS SNLAWYHQKP GQAPRLLIYG ASTRATGIPV  60
RFSGSGSGTE FTLTISSLQS EDFAVYYCQQ YNNWPLTFGG GTKVEIK                107

SEQ ID NO: 313           moltype = AA  length = 118
FEATURE                  Location/Qualifiers
source                   1..118
                         mol_type = protein
                         organism = synthetic construct
SEQUENCE: 313
QVQLVESGGG VVQPGRSLRL SCAASGFTFS GYGMHWVRQA PGKGLEWVAI IYYNGKKEYY  60
ADSVKGRFTI SRDNSRNTLF LQMNSLRAED TAIYYCTRGE GYNWFDPWGQ GTLVTVSS    118

SEQ ID NO: 314           moltype = AA  length = 107
```

```
FEATURE                Location/Qualifiers
source                 1..107
                       mol_type = protein
                       organism = synthetic construct
SEQUENCE: 314
EIVMTQSPAT LSVSPGERAT LSCRASQSVS SNLAWYQQKP GQAPRLLIYG ASTRATGIPA  60
RFSGSGSGTE FTLTISSLLS EDFAVYYCKQ YNNWPLTFGG GTKVEIK                107

SEQ ID NO: 315         moltype = AA  length = 118
FEATURE                Location/Qualifiers
source                 1..118
                       mol_type = protein
                       organism = synthetic construct
SEQUENCE: 315
QEQLVESGGG VVQPGRSLRL SCAASGFTFS SYGMHWVRQA PGKGLEWVAI IWYNGKKKDY  60
ADSVKGRFTI SRDNSKSTLY LQMNSLRAED TAVYYCARGL GYNWFDPWGQ GTLVTVSS    118

SEQ ID NO: 316         moltype = AA  length = 107
FEATURE                Location/Qualifiers
source                 1..107
                       mol_type = protein
                       organism = synthetic construct
SEQUENCE: 316
EIVLTQSPDF QSVTPMEKVT IACRASQNIG SSLHWYQQKP DQSPKLLIKY ASQSFSGVPS  60
RFSGSGSGTD FTLTINSLEA EDAATYYCHQ SSSFPNTFGQ GTKLEIK                107

SEQ ID NO: 317         moltype = AA  length = 118
FEATURE                Location/Qualifiers
source                 1..118
                       mol_type = protein
                       organism = synthetic construct
SEQUENCE: 317
QVQLVESGGG VVQPGRSLRL SCAASGFTFS GYGMHWVRQA PGKGLEWVAI IYYNGKKEYY  60
ADSVKGRFTV SRDNSKNMLY LQMNSLRAED TAVYYCTRGE GYNWFDPWGQ GTLVTVSS    118

SEQ ID NO: 318         moltype = AA  length = 107
FEATURE                Location/Qualifiers
source                 1..107
                       mol_type = protein
                       organism = synthetic construct
SEQUENCE: 318
EIVMTQSPAT LSVSPGERAT LSCRASQTVS SNLAWYQQKP GQAPRLLIYG ASTRATGIPA  60
RFSGSGSGTE FTLTISSLQS EDFAVYYCKQ YNNRPLTFGG GTKVEIK                107

SEQ ID NO: 319         moltype = AA  length = 118
FEATURE                Location/Qualifiers
source                 1..118
                       mol_type = protein
                       organism = synthetic construct
SEQUENCE: 319
QVQLVESGGG VVQPGRSLRL SCAASGFTFS GYGMHWVRQA PGKGLEWLAI IYYNGNNRKY  60
ADSVKGRFTI SRDNSKNTVS LQMNSLRVED TAMYYCTRGD GYNWFVTWGQ GTLVTVSS    118

SEQ ID NO: 320         moltype = AA  length = 107
FEATURE                Location/Qualifiers
source                 1..107
                       mol_type = protein
                       organism = synthetic construct
SEQUENCE: 320
EIVMTQSPAT LSVSPGERAA LSCRASQSVT SNLAWYHQKP GQAPRLLIYG ASTRATGIPV  60
RFSGSGSGTE FTLTISSLQS EDFAVYYCQQ YNNWPLTFGG GTKVENK                107

SEQ ID NO: 321         moltype = AA  length = 118
FEATURE                Location/Qualifiers
source                 1..118
                       mol_type = protein
                       organism = synthetic construct
SEQUENCE: 321
QVQLVESGGG VVQPGRSLRL SCAASGFTFS GYGMHWVRQA PGKGLEWVAI IYYNGKREYY  60
ADSVKGRFTI SRDNSKNTLY LQMNSLRAED TAVYYCTRGE GYNWFDPWGQ GTLVTVSS    118

SEQ ID NO: 322         moltype = AA  length = 107
FEATURE                Location/Qualifiers
source                 1..107
                       mol_type = protein
                       organism = synthetic construct
SEQUENCE: 322
EIVMTQSPAT LSVSPGERAT LSCRASQSVS SNLAWYQQKP GQAPRLLIYG ASTRATGIPA  60
RFSGSGSGTE FTLTISSLQS EDFAVYYCKH YNNWPLTFGG GTKVEIK                107
```

```
SEQ ID NO: 323          moltype = AA  length = 123
FEATURE                 Location/Qualifiers
source                  1..123
                        mol_type = protein
                        organism = synthetic construct
SEQUENCE: 323
EVQLLESGGG LVQPGGSLRL SCAASGFTFS NYAMNWVRQA PGKGLEWVSA ISGSRSNTYY  60
ADSVKGRFTI SRDNSKNTLY LQMNSLRAED TGVYYCAKGA YSKYPYYYYM DVWGKGTTVT  120
VSS                                                                123

SEQ ID NO: 324          moltype = AA  length = 108
FEATURE                 Location/Qualifiers
source                  1..108
                        mol_type = protein
                        organism = synthetic construct
SEQUENCE: 324
EIVMTQSPAT LSLSPGERAT LSCRASQSVS SSYLSWYQQK PGQAPRLLIY GASTRAIGIP  60
ARFSGSGSGT DFTLTISSLQ AEDFAVYYCQ QDDNLPWTFG QGTKVEIK              108

SEQ ID NO: 325          moltype = AA  length = 118
FEATURE                 Location/Qualifiers
source                  1..118
                        mol_type = protein
                        organism = synthetic construct
SEQUENCE: 325
QEQLVESGGG VVQPGGSLRL SCAASGFTFS GYGMHWVRQA PGKGLEWVAI IWYNGRKTYY  60
AESVKGRFTI SRDNSKNTLS LQMNSLRVED TAVYYCTTGK GYNWFDPWGQ GTLVTVSS    118

SEQ ID NO: 326          moltype = AA  length = 107
FEATURE                 Location/Qualifiers
source                  1..107
                        mol_type = protein
                        organism = synthetic construct
SEQUENCE: 326
EIVMTQSPAT LSVSPGERAT LSCRASQSVS SNLAWYQQKP GQAPRLLIYG ASTRATGIPA  60
RFSGSGSGTE FTLTISSLQS EDFAVYYCQQ FNAWPLTFGG GTKMEIK               107

SEQ ID NO: 327          moltype = AA  length = 123
FEATURE                 Location/Qualifiers
source                  1..123
                        mol_type = protein
                        organism = synthetic construct
SEQUENCE: 327
EVQLLESGGG LVQPGGSLRL SCAASGFTFS NYAMNWVRQA PGKGLEWVSA ISGSRSNTYY  60
ADSVKGRFTI SRDNSKNTLY LQMNSLRAED TAVYYCAKGA YSKYPYYYYM DVWGKGTTVT  120
VSS                                                                123

SEQ ID NO: 328          moltype = AA  length = 108
FEATURE                 Location/Qualifiers
source                  1..108
                        mol_type = protein
                        organism = synthetic construct
SEQUENCE: 328
EIVMTQSPAT LSLSPGERAT LSCRASQSVS SSYLSWYQQK PGQAPRLLIY GASTRAIGIP  60
ARFSGSGSGT DFTLTISSLQ AEDFAVYYCQ QDDNLPWTFG QGTKVEIK              108

SEQ ID NO: 329          moltype = AA  length = 118
FEATURE                 Location/Qualifiers
source                  1..118
                        mol_type = protein
                        organism = synthetic construct
SEQUENCE: 329
QVQLVESGGG VVQPGRSLRL SCAATGFTFS GYGMHWVRQA PGKGLEWVAI IYYNGNNRKY  60
ADSVKGRFTI SRDNSKNTVS LQMNSLRVED TAIYYCTRGD GYNWFVTWGQ GTLVTVSS    118

SEQ ID NO: 330          moltype = AA  length = 107
FEATURE                 Location/Qualifiers
source                  1..107
                        mol_type = protein
                        organism = synthetic construct
SEQUENCE: 330
EIVMTQSPAT LSVSPGERAT LSCRASQSVS SNLAWYRQKP GQAPRLLIYG ASTRATGIPV  60
RFSGSGSGTE FTLTISSLQS EDFAVYYCQQ YNNWPLTFGG GTKVEIK               107

SEQ ID NO: 331          moltype = AA  length = 118
FEATURE                 Location/Qualifiers
source                  1..118
                        mol_type = protein
```

```
                         organism = synthetic construct
SEQUENCE: 331
QVQLVESGGG VVQPGRSLRL SCAASGFTFS GYGMHWVRQA PGKGLEWVAI IYYNGKKEYY  60
ADSVKGRFTI SRDNSKNTLY LQMNSLRAED TAVYYCTRGE GYNWFDPWGQ GTLVTVSS    118

SEQ ID NO: 332           moltype = AA  length = 107
FEATURE                  Location/Qualifiers
source                   1..107
                         mol_type = protein
                         organism = synthetic construct
SEQUENCE: 332
EIVMTQSPAT LSVSPGERAT LSCRASQSVS SNLAWYQQKP GQAPRLLIYG ASTRATGIPA  60
RFSGSGSGTE FTLTISSLQS EDFAVYYCKQ YKNWPLTFGG GTKVEIK                107

SEQ ID NO: 333           moltype = AA  length = 118
FEATURE                  Location/Qualifiers
source                   1..118
                         mol_type = protein
                         organism = synthetic construct
SEQUENCE: 333
QVQLVESGGG VVQPGRSLRL SCAASGFTFS GYGMHWVRQA PGKGLEWVAI IYYNGKKEYY  60
ADSVKGRFTI FRDNSKNTVY LQMKSLRAED TAVYYCTRGE GYNWFDPWGQ GTLVTVSS    118

SEQ ID NO: 334           moltype = AA  length = 107
FEATURE                  Location/Qualifiers
source                   1..107
                         mol_type = protein
                         organism = synthetic construct
SEQUENCE: 334
EIVMTQSPAT LSVSPGERAT LSCRASQSVS SNLAWYQQKP GQAPRLLIYG ASTRATGIPA  60
RFSGSGSGTE FTLTISSLQS EDFAVYYCQQ YNNWPLTFGG GTKVEIK                107

SEQ ID NO: 335           moltype = AA  length = 118
FEATURE                  Location/Qualifiers
source                   1..118
                         mol_type = protein
                         organism = synthetic construct
SEQUENCE: 335
QVQLVESGGG VVQPGRSLRL SCAASGFTFS GYGMHWVRQA PGKGLEWVAI IYYNGNNRKY  60
ADSVRGRFTI SRDNSKNTVS LQMNSLRVED TAIYYCTRGD GYNWFVTWGQ GTLVTVSS    118

SEQ ID NO: 336           moltype = AA  length = 107
FEATURE                  Location/Qualifiers
source                   1..107
                         mol_type = protein
                         organism = synthetic construct
SEQUENCE: 336
EIVMTQSPAT LSVSPGERAT LSCRASQSVS SNLAWYYQKP GQAPRLLIYG ASTRATGIPV  60
RFSGSGSGTE FTLTISSLQS EDFAVYYCQQ YNNWPLTFGG GTKVEIK                107

SEQ ID NO: 337           moltype = AA  length = 118
FEATURE                  Location/Qualifiers
source                   1..118
                         mol_type = protein
                         organism = synthetic construct
SEQUENCE: 337
QEQLVESGGG VVQPGGSLRL SCAASGFMFS GYGMHWVRQA PGKGLEWVAI IWYNGRKTYY  60
TESVKGRFTI SRDNSKNTLS LQMNSLRVED TAVYYCTAGQ GYNWFDPWGQ GTLVTVSS    118

SEQ ID NO: 338           moltype = AA  length = 107
FEATURE                  Location/Qualifiers
source                   1..107
                         mol_type = protein
                         organism = synthetic construct
SEQUENCE: 338
EIVMTQSPAT LSVSPGERAT LSCRASQSVS SNLAWYQQKP GQAPRLLIYG ASTRATGIPA  60
RFSGSGSGTE FTLTISSLQS EDFAVYYCQQ FNAWPLTFGG GTKMEIK                107

SEQ ID NO: 339           moltype = AA  length = 118
FEATURE                  Location/Qualifiers
source                   1..118
                         mol_type = protein
                         organism = synthetic construct
SEQUENCE: 339
QEQLVESGGG VVQPGGSLRL SCVASGFTFS GYGMHWVRQA PGKGLEWVAI IWYNGRKTYY  60
AESVKGRFTI SRDNSKNTLS LQMNSLRVED TAVYYCTTGK GYNWFDPWGQ GTLVTVSS    118

SEQ ID NO: 340           moltype = AA  length = 107
FEATURE                  Location/Qualifiers
```

```
source                  1..107
                        mol_type = protein
                        organism = synthetic construct
SEQUENCE: 340
EIVMTQSPAT LSVSPGERAT LSCRASQSVS SNLAWYQQKP GQAPRLLIYG ASTRATGIPA  60
RFSGSGSGTE FTLTISSLQS EDFAVYYCQQ FNAWPLTFGG GTKMEIK               107

SEQ ID NO: 341          moltype = AA  length = 118
FEATURE                 Location/Qualifiers
source                  1..118
                        mol_type = protein
                        organism = synthetic construct
SEQUENCE: 341
QVQLVESGGG VVQPGGSLRL SCAASGFTFS GYGMHWVRQA PGKGLEWVAI IWYNGRKTYY  60
AESVKGRFTI SRDNSKNTLS LQMNSLRVED TAVYYCTAGQ GYNWFDPWGQ GTLVTVSS    118

SEQ ID NO: 342          moltype = AA  length = 107
FEATURE                 Location/Qualifiers
source                  1..107
                        mol_type = protein
                        organism = synthetic construct
SEQUENCE: 342
EIVMTQSPAT LSVSPGERAT LSCRASQSVS SNLAWYQQKP GQAPRLLIYG ASTRATGIPA  60
RFSGSGSGTE FTLTISSLQS EDFAVYYCQQ FNAWPLTFGG GTKMEIK               107

SEQ ID NO: 343          moltype = AA  length = 118
FEATURE                 Location/Qualifiers
source                  1..118
                        mol_type = protein
                        organism = synthetic construct
SEQUENCE: 343
QVQLVESGGG VVQPGRSLRL SCAASGFTFS GYGMHWVRQA PGKGLEWVAI IYYNGKKEYY  60
ADSVKGRFTI SRDNSKNTVY LQMNSLRAED TAVYYCTRGE GYNWFDPWGQ GTLVTVSS    118

SEQ ID NO: 344          moltype = AA  length = 107
FEATURE                 Location/Qualifiers
source                  1..107
                        mol_type = protein
                        organism = synthetic construct
SEQUENCE: 344
KIVMTQSPAT LSVSPGERAT LSCRASQSVS SNLAWYQQKP GQAPRLLIYG ASTRATGIPA  60
RFSGSGSGTE FTLTISSLQS EDFAVYYCKQ YNNWPLTFGG GTKVEIK               107

SEQ ID NO: 345          moltype = AA  length = 118
FEATURE                 Location/Qualifiers
source                  1..118
                        mol_type = protein
                        organism = synthetic construct
SEQUENCE: 345
QVQLVESGGG VVQPGRSLRL SCAASGFTFS GYGMHWVRQA PGKGLEWVAI IYYNGNNRKY  60
ADSVKGRFTI SRDNSKNMVS LQMNSLRVED TAIYYCTRGD GYNWFVTWGQ GTLVTVSS    118

SEQ ID NO: 346          moltype = AA  length = 107
FEATURE                 Location/Qualifiers
source                  1..107
                        mol_type = protein
                        organism = synthetic construct
SEQUENCE: 346
EIVMTQSPAT LSVSPGEGAT LSCRASQSVS SNLAWYHQKP GQAPRLLIYG ASTRATGIPV  60
RFSGSGSGTE FTLTISSLQS DDFAVYFCQQ YNNWPLTFGG GTKVEIK               107

SEQ ID NO: 347          moltype = AA  length = 118
FEATURE                 Location/Qualifiers
source                  1..118
                        mol_type = protein
                        organism = synthetic construct
SEQUENCE: 347
QVQLVESGGG VVQPGRSLRL SCAASGFTFS GYGMHWVRQA PGKGLEWVAI IYYNGKKEYY  60
ADSVKGRFTI SRDNSKNMLY LQMNGLRAED TAIYYCTRGE GYNWFDPWGQ GTLVTVSS    118

SEQ ID NO: 348          moltype = AA  length = 107
FEATURE                 Location/Qualifiers
source                  1..107
                        mol_type = protein
                        organism = synthetic construct
SEQUENCE: 348
EIVMTQSPAT LSVSPGERTT LSCRASQSVS NNLAWYQQKP GQAPRLLIYG ASTRATGIPA  60
RFSGSGSGTE FTLTISSLQS EDFAVYYCQQ YNNWPLTFGG GTKVEIK               107
```

```
SEQ ID NO: 349          moltype = AA  length = 118
FEATURE                 Location/Qualifiers
source                  1..118
                        mol_type = protein
                        organism = synthetic construct
SEQUENCE: 349
QEQLVESGGG VVQPGGSLRL SCAASGFKFS GYGMHWVRQA PGKGLEWVAI IWYNGRKTYY  60
AESVKGRFTI SRDNSKNTLS LQMNRLRVED TAVYYCTAGQ GYNWFDPWGQ GTLVTVSS    118

SEQ ID NO: 350          moltype = AA  length = 107
FEATURE                 Location/Qualifiers
source                  1..107
                        mol_type = protein
                        organism = synthetic construct
SEQUENCE: 350
EIVMTQSPAT LSVSPGERAT LSCRASQSVS SNLAWYQQKP GQAPRLLIYG ASTRATGIPA  60
RFSGSGSGTE FTLTISSLQS EDFAVYYCQQ FNAWPLTFGG GTKMEIK               107

SEQ ID NO: 351          moltype = AA  length = 118
FEATURE                 Location/Qualifiers
source                  1..118
                        mol_type = protein
                        organism = synthetic construct
SEQUENCE: 351
QVQLVESGGG VVQPGRSLRL SCAASGFTFS GYGMHWVRQA PGKGLEWVAI IYYNGNNRKY  60
ADSVKGRFTI SRDNSKNTVS LQMNSLRVED TAIYYCTRGD GYNWFVTWGQ GTLVTVSS    118

SEQ ID NO: 352          moltype = AA  length = 107
FEATURE                 Location/Qualifiers
source                  1..107
                        mol_type = protein
                        organism = synthetic construct
SEQUENCE: 352
EIVMTQSPAT LSVSPGERAT LSCRASQSIS SNLAWYHQKP GQAPRLLIYG ASTRATGIPV  60
RFSGSGSGTE FTLTISSLQS EDFALYYCQQ YNNWPLTFGG GTKVEIK               107

SEQ ID NO: 353          moltype = AA  length = 118
FEATURE                 Location/Qualifiers
source                  1..118
                        mol_type = protein
                        organism = synthetic construct
SEQUENCE: 353
QEQLVESGGG VVQPGRSLRL SCAASGFIFS SYGMHWVRQA PGKGLEWVAI IWYNGKKRDY  60
ADSVKGRFTI SRDNSKNTLY LQMNSLRAED TAVYYCARGL GYNWFDPWGQ GTLVTVSS    118

SEQ ID NO: 354          moltype = AA  length = 107
FEATURE                 Location/Qualifiers
source                  1..107
                        mol_type = protein
                        organism = synthetic construct
SEQUENCE: 354
EIVLTQSPDF QSVTPKEKVT ITCRASQSIG SSLHWYQQKP DQSPKLLIKY ASQSFSGVPS  60
RFSGSGSGTD FTLTINSLEA EDAATYYCHQ SSSLPYTFGQ GTKLEIK               107

SEQ ID NO: 355          moltype = AA  length = 125
FEATURE                 Location/Qualifiers
source                  1..125
                        mol_type = protein
                        organism = synthetic construct
SEQUENCE: 355
EVQLLESGGG LVQPGGSLRL SCAASGFTFS NYAMNWVRQA PGKGLEWVST ISGSGGGKYY  60
ADSVKGRFTI SRDNSKNTLY LHMNSLRAED TAVYYCAKDP VQDRYYFYYY YMDVWGKGTT  120
VTVSS                                                             125

SEQ ID NO: 356          moltype = AA  length = 107
FEATURE                 Location/Qualifiers
source                  1..107
                        mol_type = protein
                        organism = synthetic construct
SEQUENCE: 356
EIVLTQSPDF QSVTPKEKVT ITCRASQSIG SSLHWYQQKP DQSPKLLIKY ASQSISGVPS  60
RFSGSGSGTD FTLTINSLEA EDAAAYYCHQ SSSLPHTFGQ GTKLEIK               107

SEQ ID NO: 357          moltype = AA  length = 118
FEATURE                 Location/Qualifiers
source                  1..118
                        mol_type = protein
                        organism = synthetic construct
SEQUENCE: 357
```

```
QEQLVESGGG VVQPGRSLRL SCAASGFTFS SYGMHWVRQA PGKGLEWVAI IYYNGKKKDY  60
ADSVKGRFTI SRDNSKNTLY LQMNSLRAED TAVYYCARGL GYNWFDPWGQ GTLVTVSS    118

SEQ ID NO: 358         moltype = AA  length = 107
FEATURE                Location/Qualifiers
source                 1..107
                       mol_type = protein
                       organism = synthetic construct
SEQUENCE: 358
EIVLTQSPDF QSVTPKEKVT ITCRASQSIG SSLHWYQQKP DQSPKLLIKY ASQSFSGVPS  60
RFSGSGSGTD FTLTINSLEA EDAATYYCHQ SSSLPYTFGQ GTKLEIK               107

SEQ ID NO: 359         moltype = AA  length = 125
FEATURE                Location/Qualifiers
source                 1..125
                       mol_type = protein
                       organism = synthetic construct
SEQUENCE: 359
EVQLLESGGG LVQPGGSLRL SCAASGFTFS SYAMSWVRQA PGKGLEWVSS ISGSGGSRYY  60
ADSVKGRFTI SRDNSKNTLY LQMNSLRAED TAVYYCAKDP VQDRYYFYYY YMDVWGKGTT  120
VTVSS                                                              125

SEQ ID NO: 360         moltype = AA  length = 107
FEATURE                Location/Qualifiers
source                 1..107
                       mol_type = protein
                       organism = synthetic construct
SEQUENCE: 360
EIVLTQSPDF QSVTPKEKVT ITCRASQSIG SSLHWYQQKP DQSPKLLIKY ASQSISGVPS  60
RFSGSGSGTD FTLTINSLEA EDAAAYYCHQ SSSLPHTFGQ GTKLEIK               107

SEQ ID NO: 361         moltype = AA  length = 118
FEATURE                Location/Qualifiers
source                 1..118
                       mol_type = protein
                       organism = synthetic construct
SEQUENCE: 361
QEQLVESGGG VVQPGRSLRL SCAASGFTFS SYGMHWVRQA PGKGLEWVAI IYYNGKKKDY  60
ADSVKGRFTI SRDNSKNTLY LQMNSLRAED TAVYYCVRGL GYNWFDPWGQ GTLVTVSS    118

SEQ ID NO: 362         moltype = AA  length = 107
FEATURE                Location/Qualifiers
source                 1..107
                       mol_type = protein
                       organism = synthetic construct
SEQUENCE: 362
EIVLTQSPDF QSVTPKEKVT ITCRASQSIG SSLHWYQQKP DQSPKLLIKY ASQSFSGVPS  60
RFSGSGSGTD FTLTINSLEA EDAATYYCHQ SSNLPYTFGQ GTKLEIK               107

SEQ ID NO: 363         moltype = AA  length = 118
FEATURE                Location/Qualifiers
source                 1..118
                       mol_type = protein
                       organism = synthetic construct
SEQUENCE: 363
QEQLVESGGG VVQPGRSLRL SCAASGFTFS SYGMHWVRQA PGKGLEWVAI IWYNGRKKDY  60
ADSVKGRFTI SRDNSKNTLY LQMNSLRAED TAVYYCARGL GYNWFDPWGQ GTLVTVSS    118

SEQ ID NO: 364         moltype = AA  length = 107
FEATURE                Location/Qualifiers
source                 1..107
                       mol_type = protein
                       organism = synthetic construct
SEQUENCE: 364
EIVLTQSPDF QSVTPMEKVT IACRASQSIG SSLHWYQQKP DQSPKLLIKY ASQSFSGVPS  60
RFSGSGSGTD FTLTINSLEA EDAATYYCHQ SSSLPYTFGQ GTKLEIK               107

SEQ ID NO: 365         moltype = AA  length = 118
FEATURE                Location/Qualifiers
source                 1..118
                       mol_type = protein
                       organism = synthetic construct
SEQUENCE: 365
QGKLVESGGG VVQPGRSLRL SCVASGFTFS GYGMHWVRQV PNKGLEWVAI IYYDGKNKYY  60
ADSVKGRFTI SRDNSKNMLY LQMNSLRAED TAVYYCVRGP GYNWFDPWGQ GTLVTVSS    118

SEQ ID NO: 366         moltype = AA  length = 107
FEATURE                Location/Qualifiers
source                 1..107
```

```
                         mol_type = protein
                         organism = synthetic construct
SEQUENCE: 366
EIVLTQSPDF QSVTPKEKVT ITCRASQNIG SSLHWYQQKP DQSPKLLIKL TSQSFSGVPS  60
RFSGSGSGTD FTLTINSLEA EDAATYYCHQ SSSLPYTFGQ GTKLEIK               107

SEQ ID NO: 367           moltype = AA  length = 118
FEATURE                  Location/Qualifiers
source                   1..118
                         mol_type = protein
                         organism = synthetic construct
SEQUENCE: 367
QEQLVESGGG VVQPGRSLRL SCAASGFIFS SYGMHWVRQA PGKGLEWVAI IWYNGKKRDY  60
ADSVKGRFTI SRDNSKNTLY LQMNSLRVED TAVYYCARGL GYNWFDSWGQ GTLVTVSS    118

SEQ ID NO: 368           moltype = AA  length = 107
FEATURE                  Location/Qualifiers
source                   1..107
                         mol_type = protein
                         organism = synthetic construct
SEQUENCE: 368
EIVLTQSPDF QSVTPKEKVT ITCRASQSIG SSLHWYQQKP DQSPKLLIKY ASQSFSGVPS  60
RFSGSGSGTD FTLTINSLEA EDAATYYCHQ SSSLPYTFGQ GTKLEIK               107

SEQ ID NO: 369           moltype = AA  length = 118
FEATURE                  Location/Qualifiers
source                   1..118
                         mol_type = protein
                         organism = synthetic construct
SEQUENCE: 369
QGKLVESGGG VVQPGRSLRL SCVASGFTFS GYGMHWVRQA PNKGLEWVAI IYYDGKNKYY  60
ADSVKGRFTV SRDNSKNTLY LQLNNLRAED TAVYYCVRGP GYNWFDPWGQ GTLVTVSS    118

SEQ ID NO: 370           moltype = AA  length = 107
FEATURE                  Location/Qualifiers
source                   1..107
                         mol_type = protein
                         organism = synthetic construct
SEQUENCE: 370
EIVLTQSPDF QSVTPKEKVT ITCRASQNIG SSLHWYQQKP DQSPKLFIKH ASQSFSGVPS  60
RFSGSGSGTD FTLTINSLEA EDAATYYCHQ SSSLPYTFGQ GTKLEIK               107

SEQ ID NO: 371           moltype = AA  length = 118
FEATURE                  Location/Qualifiers
source                   1..118
                         mol_type = protein
                         organism = synthetic construct
SEQUENCE: 371
QVKLVESGGG VVQPGRSLRL SCVASGFTFS GYGMHWVRQA PGKGLEWVAI IYYDGKNKYY  60
ADSAKGRFTV SRDNSKNTLY LQLNSLRAED TAVYYCVRGP GYNWFDSWGQ GTLVTVSS    118

SEQ ID NO: 372           moltype = AA  length = 107
FEATURE                  Location/Qualifiers
source                   1..107
                         mol_type = protein
                         organism = synthetic construct
SEQUENCE: 372
EIVLTQSPDF QSVTPKEKVT ITCRASQSIG SNLHWYQQKP DQSPKLLIKY TSQSFSGVPS  60
RFSGSGSGTD FTLTINSLEA EDAATYYCHQ SSSLPYTFGQ GTKLEIK               107

SEQ ID NO: 373           moltype = AA  length = 120
FEATURE                  Location/Qualifiers
source                   1..120
                         mol_type = protein
                         organism = synthetic construct
SEQUENCE: 373
EVQLLESGGD LVQPGGSLRL TCAASGFTFR SYAMNWVRQA PGKGLEWVST ISSRGDTTNY  60
ADSVKGRFTI SRDTSKNTLY LQMDNLRADD TAVYYCSKMF SYYYYYMDVW GKGTTVTVSS  120

SEQ ID NO: 374           moltype = AA  length = 106
FEATURE                  Location/Qualifiers
source                   1..106
                         mol_type = protein
                         organism = synthetic construct
SEQUENCE: 374
SYELTQPLSV SVALGQTARI TCGGNNIGSK DVHWYQQKPG QAPVLVIYRD SNRPSGIPER  60
FSGSNSGNTA TLTISRAQAG DEADYYCQVW DSRTAVFGGG TQLTAL                106

SEQ ID NO: 375           moltype = AA  length = 120
```

```
FEATURE                Location/Qualifiers
source                 1..120
                       mol_type = protein
                       organism = synthetic construct
SEQUENCE: 375
EVQLLESGGD LVQPGGSLRL TCAASGFTFR SYAMNWVRQA PGKGLEWVST ISSRGDTTNY  60
ADSVKGRFTI SRDTSKNTLY LQMDNLRADD TAVYYCSKMF SYYYYYMDVW GKGTTVTVSS  120

SEQ ID NO: 376         moltype = AA  length = 106
FEATURE                Location/Qualifiers
source                 1..106
                       mol_type = protein
                       organism = synthetic construct
SEQUENCE: 376
SYELTQPLSV SVALGQTARI TCGGNNIGSK DVHWYQQKPG QAPVLVIYRD SNRPSGIPER  60
FSGSNSGNTA TLTISRAQAG DEADYYCQVW DSSTAVFGGG TQLTAL                 106

SEQ ID NO: 377         moltype = AA  length = 118
FEATURE                Location/Qualifiers
source                 1..118
                       mol_type = protein
                       organism = synthetic construct
SEQUENCE: 377
QEKLVESGGG VVQPGRSLRL SCVASGFTFS GFGMHWVRQA PGKGLEWVAI IYYDGKNKYY  60
ADSVKGRFTI SRDNSKNTLY LQMNSLRAED TAVYYCVRGP GYNWFDPWGQ GTLVTVSS    118

SEQ ID NO: 378         moltype = AA  length = 107
FEATURE                Location/Qualifiers
source                 1..107
                       mol_type = protein
                       organism = synthetic construct
SEQUENCE: 378
EIVLTQSPDF QSVTPKEKVT ITCRASQSIG SSLHWYQQKP DQSPKLLIKY ASQSFSGVPS  60
RFSGSGSGTD FTLTINSLEA EDAATYYCHQ SSSLPYTFGQ GTKLEIK                107

SEQ ID NO: 379         moltype = AA  length = 118
FEATURE                Location/Qualifiers
source                 1..118
                       mol_type = protein
                       organism = synthetic construct
SEQUENCE: 379
QGKLVESGGG VVQPGRSLRL SCVASGFTFS GYGMHWVRQA PNKGLEWVAI IYYDGKNKYY  60
ADSVKGRFTI SRDNSKNTLY LQLNSLRAED TAVYYCVRGP GYNWFDPWGQ GTLVTVSS    118

SEQ ID NO: 380         moltype = AA  length = 107
FEATURE                Location/Qualifiers
source                 1..107
                       mol_type = protein
                       organism = synthetic construct
SEQUENCE: 380
EIVLTQSPDF QSVTPKEKVT ITCRASQNIG SSLHWYQQKP DQSPKLLIKH ASQSFSGVPS  60
RFSGSGSGTD FTLTINSLEA EDAATYYCHQ SSSLPYTFGQ GTKLEIK                107

SEQ ID NO: 381         moltype = AA  length = 118
FEATURE                Location/Qualifiers
source                 1..118
                       mol_type = protein
                       organism = synthetic construct
SEQUENCE: 381
QEQLVESGGG VVQPGRSLRL SCAASGFIFS SYGMHWVRQA PGKGLEWVAI IWYNGKKRDY  60
ADSVKGRFTI SRDNSKNTLY LQMNSLRAED TAVYYCARGL GYNWFDPWGQ GTLVTVSS    118

SEQ ID NO: 382         moltype = AA  length = 107
FEATURE                Location/Qualifiers
source                 1..107
                       mol_type = protein
                       organism = synthetic construct
SEQUENCE: 382
AIVLTQSPDF QSVTPKEKVT ITCRASQNIG SSLHWYQQKP DQSPKLLIKY ASQSFSGVPS  60
RFSGSGSGTD FTLTINSLEA EDAATYYCHQ SGSLPYTFGQ GTKLEIK                107

SEQ ID NO: 383         moltype = AA  length = 118
FEATURE                Location/Qualifiers
source                 1..118
                       mol_type = protein
                       organism = synthetic construct
SEQUENCE: 383
QGKLVESGGG VVQPGRSLRL SCVASGFTFS GYGMHWVRQV PNKGLEWVAI IYYDGKNKYY  60
ADSVKGRFTI SRDNSKNMLY LQMNSLRVED TAVYYCVRGP GYNWFDPWGQ GTLVTVSS    118
```

```
SEQ ID NO: 384          moltype = AA  length = 107
FEATURE                 Location/Qualifiers
source                  1..107
                        mol_type = protein
                        organism = synthetic construct
SEQUENCE: 384
EIVLTQSPDF QSVTPKEKVT ITCRASQNIG SSLHWYQQKP DQSPKLLIKL TSQSFSGVPS  60
RFSGSGSGTD FTLTINSLEA EDAATYYCHQ SSSLPYTFGQ GTKLEIK                107

SEQ ID NO: 385          moltype = AA  length = 118
FEATURE                 Location/Qualifiers
source                  1..118
                        mol_type = protein
                        organism = synthetic construct
SEQUENCE: 385
QGKLVESGGG VVQPGRSLRL SCVASGFTFS GYGMHWVRQA PNKGLEWVAI IYYDGKNKYY  60
ADSVKGRFTI SRDNSKNMLY LQMNSLRVED TAVYYCVRGP GYNWFDPWGQ GTLVTVSS    118

SEQ ID NO: 386          moltype = AA  length = 107
FEATURE                 Location/Qualifiers
source                  1..107
                        mol_type = protein
                        organism = synthetic construct
SEQUENCE: 386
EIVLTQSPDF QSVTPKEKVT ITCRASQNIG SSLHWYQQKP DQSPKLLIKH TSQSFSGVPS  60
RFSGSGSGTA FTLTINSLEA EDAATYYCHQ SSSLPYTFGQ GTKLEIK                107

SEQ ID NO: 387          moltype = AA  length = 118
FEATURE                 Location/Qualifiers
source                  1..118
                        mol_type = protein
                        organism = synthetic construct
SEQUENCE: 387
QEQLVESGGG VVQPGRSLRL SCAASGFTFR SYGMHWVRQA PGKGLEWVAI IWYDGKNKYY  60
ADSVKGRFTI SRDNSKNTLY LQMNSLRVED TAVYYCARGL GYNWFDPWGQ GTLVTVTS    118

SEQ ID NO: 388          moltype = AA  length = 107
FEATURE                 Location/Qualifiers
source                  1..107
                        mol_type = protein
                        organism = synthetic construct
SEQUENCE: 388
EIVLTQSPDF QSVTPKEKVT ITCRASQSIG SSLHWYQQKP DQSPKLLIKY ASQTFSGVPS  60
RFSGSGSGTD FTLTINSLEV EDAATYYCHQ SSSLPNTFGQ GTKLEIK                107

SEQ ID NO: 389          moltype = AA  length = 118
FEATURE                 Location/Qualifiers
source                  1..118
                        mol_type = protein
                        organism = synthetic construct
SEQUENCE: 389
QVKLVESGGG VVQPGRSLRL SCVASGFTFS GYGMHWVRQA PGKGLEWVAI IYYDGKNKYY  60
VDSVKGRFTI SRDNSKNTLY LQLNSLRAED TAVYYCVRGP GYNWFDLWGQ GTLVTVAS    118

SEQ ID NO: 390          moltype = AA  length = 107
FEATURE                 Location/Qualifiers
source                  1..107
                        mol_type = protein
                        organism = synthetic construct
SEQUENCE: 390
EIVLTQSPDF QSVTPKEKVT ITCRASQSIG SSLHWYQQKP DQSPKLLIKY ASQSFSGVPS  60
RFSGSGSGTD FTLTINSLEA EDAATYYCHQ SSSLPYTFGQ GTKLEIK                107

SEQ ID NO: 391          moltype = AA  length = 118
FEATURE                 Location/Qualifiers
source                  1..118
                        mol_type = protein
                        organism = synthetic construct
SEQUENCE: 391
QEQLVESGGG VVQPGRSLRL SCAASGFTFR SYGMHWVRQA PGKGLEWVAI IWYDGKNKYY  60
ADSVKGRFTI SRDNSKNTLY LQMNSLRAED TAVYYCARGL GYNWFDPWGQ GTLVTVSS    118

SEQ ID NO: 392          moltype = AA  length = 107
FEATURE                 Location/Qualifiers
source                  1..107
                        mol_type = protein
                        organism = synthetic construct
SEQUENCE: 392
```

```
EIVLTQSPDF QSVTPKEKVT ITCRASQSIG SSLHWYQQKP DQSPKLLIKY GSQSFSGVPS  60
RFSGSGSGTD FTLTINSLEA EDAATYYCHQ SSSLPYTFGQ GTKLEIK               107

SEQ ID NO: 393          moltype = AA  length = 118
FEATURE                 Location/Qualifiers
source                  1..118
                        mol_type = protein
                        organism = synthetic construct
SEQUENCE: 393
QEQLVESGGG VVQPGRSLRL SCAASGFIFS SYGMHWVRQA PGKGLEWVAI IWYNGKKRDY  60
ADSVKGRFTI SRDNSKNTLY LQMNSLRAED TAVYYCARGL GYNWFDPWGQ GTLVTVSS    118

SEQ ID NO: 394          moltype = AA  length = 107
FEATURE                 Location/Qualifiers
source                  1..107
                        mol_type = protein
                        organism = synthetic construct
SEQUENCE: 394
EIVLTQSPDF QSVTPKDKVT ITCRASQSIG SSLHWYQQKP DQSPKLLIKY ASQSFSGVPS  60
RFSGSGSGTD FTLTINSLEA EDAATYYCHQ SSTLPYTFGQ GTKLEIK               107

SEQ ID NO: 395          moltype = AA  length = 118
FEATURE                 Location/Qualifiers
source                  1..118
                        mol_type = protein
                        organism = synthetic construct
SEQUENCE: 395
QVKLVESGGG VVQPGRSLRL SCVASGFTFS GYGMHWVRQA PGKGLEWVAI IYYDGKNKYY  60
VDSVKGRFTI SRDNSKNTLY LQLNSLRAED TAVYYCVRGP GYNWFDHWGQ GTLVTVAS    118

SEQ ID NO: 396          moltype = AA  length = 107
FEATURE                 Location/Qualifiers
source                  1..107
                        mol_type = protein
                        organism = synthetic construct
SEQUENCE: 396
EIVLTQSPDF QSVTPKEKVT ITCRASQSIG SSLHWYQQKP DQSPKLLIKY ASQSFSGVPS  60
RFSGSGSGTD FTLTINSLEA EDAATYYCHQ SSSLPYTFGQ GTKLEIK               107

SEQ ID NO: 397          moltype = AA  length = 118
FEATURE                 Location/Qualifiers
source                  1..118
                        mol_type = protein
                        organism = synthetic construct
SEQUENCE: 397
QEQLVESGGG VVQPGRSLRL SCAASGFTFR SYGMHWVRQA PGKGLEWVAI IWYDGKNKYY  60
ADSVKGRFTI SRDNSKNTLY LQMNSLRAED TAVYYCARGL GYNWFDPWGQ GTLVTVSS    118

SEQ ID NO: 398          moltype = AA  length = 107
FEATURE                 Location/Qualifiers
source                  1..107
                        mol_type = protein
                        organism = synthetic construct
SEQUENCE: 398
EIVLTQSPDF QSVTPKEKVT ITCRASQSIG SSLHWYQQKP DQSPKLLIKY ASQSFSGVPS  60
RFSGSGSGTD FTLTINSLEA EDAATYYCHQ SSSLPYTFGQ GTKLEIK               107

SEQ ID NO: 399          moltype = AA  length = 126
FEATURE                 Location/Qualifiers
source                  1..126
                        mol_type = protein
                        organism = synthetic construct
SEQUENCE: 399
QVQLVESGGG VVQPGRSLRL SCAASGFTFS TYGMHWVRQA PGKGLEWVAV LWSDGRSKYY  60
ADSVQGRFTI SRDNSKNTLF LQMSSLRAED TAVYYCAREP YYDFWSGYYT GYMDVWGKGT  120
TVTVSS                                                            126

SEQ ID NO: 400          moltype = AA  length = 107
FEATURE                 Location/Qualifiers
source                  1..107
                        mol_type = protein
                        organism = synthetic construct
SEQUENCE: 400
DIQMTQSPSS LSASVGDRVT ITCRASQGIR NDLGWYQQKP GKAPKRLIYA ASSLQGGVPS  60
RFSGSGSGTE FTLTISSLQP EDFATYYCLQ HNSYPRTFGQ GTKVEIK               107

SEQ ID NO: 401          moltype = AA  length = 120
FEATURE                 Location/Qualifiers
source                  1..120
```

```
                        mol_type = protein
                        organism = synthetic construct
SEQUENCE: 401
EVQILESGGG LVQPGGSLRL SCVASGFTFR SYVMSWVRRA PGRGLEWVSG ISASGGNTYY  60
ADSVKGRFTI SRDNSKNTLF LQMNGLRAED TAVYYCAKLF SYYYYFMDVW GKGTTVTVSS  120

SEQ ID NO: 402          moltype = AA  length = 106
FEATURE                 Location/Qualifiers
source                  1..106
                        mol_type = protein
                        organism = synthetic construct
SEQUENCE: 402
SYELTQPLSV SVALGQTARI TCGGNNIGSK DVHWYQQKPG QAPVLVIYRD SNRPSGIPER  60
FSGSNSGNTA TLTISGAQAG DEADYYCQVW DRRTAVFGGG TQLTAL                 106

SEQ ID NO: 403          moltype = AA  length = 120
FEATURE                 Location/Qualifiers
source                  1..120
                        mol_type = protein
                        organism = synthetic construct
SEQUENCE: 403
EVQILESGGG LVQPGGSLRL SCVASGFTFR SYVMSWVRRA PGRGLEWVSG ISTSGGNTYY  60
ADSVKGRFTI SRDNSKNTLF LQMNGLRAED TAVYYCAKLF SYYYYFMDVW GKGTTVTVSS  120

SEQ ID NO: 404          moltype = AA  length = 106
FEATURE                 Location/Qualifiers
source                  1..106
                        mol_type = protein
                        organism = synthetic construct
SEQUENCE: 404
SYELTQPLSV SVALGQTARI TCGGNNIGSK DVHWYQQKPG QAPVLVIYRD SNRPSGIPER  60
FSGSNSGNTA TLTISGAQAG DEADYYCQVW DRRTAVFGGG TQLTAL                 106

SEQ ID NO: 405          moltype = AA  length = 124
FEATURE                 Location/Qualifiers
source                  1..124
                        mol_type = protein
                        organism = synthetic construct
SEQUENCE: 405
QVTLKESGPV LVKPTETLTL TCTVSGFSLS NARMGVSWIR QPPGKALEWL TLIFSIDEKS  60
YSTSLKSRLT ISQDTSKSQV VLTVTNMDPV DTVTYFCERI ETGPYYYYYY MDVWGKGTTV  120
TVSS                                                               124

SEQ ID NO: 406          moltype = AA  length = 110
FEATURE                 Location/Qualifiers
source                  1..110
                        mol_type = protein
                        organism = synthetic construct
SEQUENCE: 406
QSVLTQPPSA SGTPGQRVTI SCSGSSSNIG SNTVNWYQQL PGTAPKLLIY SNNQRPSGVP  60
DRFSGSKSGT SASLAISGLQ SEDEADYYCA AWDDSLNGPV FGGGTQLTAL             110

SEQ ID NO: 407          moltype = AA  length = 124
FEATURE                 Location/Qualifiers
source                  1..124
                        mol_type = protein
                        organism = synthetic construct
SEQUENCE: 407
QVTLKESGPV LVKPTETLTL TCTVSGFSLS NSRMGVSWLR QPPGKALEWL IFIFSIDEKS  60
YSTSLKSRLT ISQDTSKSQV VLTMTNMDPV DTVTYFCERI ETGPYYYYYY MDVWGKGTTV  120
TVSS                                                               124

SEQ ID NO: 408          moltype = AA  length = 110
FEATURE                 Location/Qualifiers
source                  1..110
                        mol_type = protein
                        organism = synthetic construct
SEQUENCE: 408
QSVLTQPPSA SGTPGQRVTI SCSGNSSNIG SNTVNWYQQL PGTAPKLLIY SNNQRPSGVP  60
DRFSGSKSGT SASLAISGLQ SEDEADYYCA AWDDSLNGPV FGGGTQLTAL             110

SEQ ID NO: 409          moltype = AA  length = 125
FEATURE                 Location/Qualifiers
source                  1..125
                        mol_type = protein
                        organism = synthetic construct
SEQUENCE: 409
QVQVQQSGPG LVKPSQTLSL TCAISGDSVS SKYASWNWIR QSPSRGLEWL GRTYYRSKWY  60
NDFAVSVKSR ITINADTSKN QFSLHLSSVT PEDTAIYFCA REANGRGYFY YMDVWGKGTT  120
```

```
VTVSS                                                        125

SEQ ID NO: 410          moltype = AA  length = 107
FEATURE                 Location/Qualifiers
source                  1..107
                        mol_type = protein
                        organism = synthetic construct
SEQUENCE: 410
EIVLTQSPDF QSVTPKEKVT ITCRASQSIG SSLHWYQQKP DQSPKLLIKY ASQSISGVPS  60
RFSGSGSGTV FTLTINSLEA EDAAAYFCHQ SSGSPHTFGG GTKVEIK             107

SEQ ID NO: 411          moltype = AA  length = 125
FEATURE                 Location/Qualifiers
source                  1..125
                        mol_type = protein
                        organism = synthetic construct
SEQUENCE: 411
QVQLQQSGPG LVKPSQTLSL TCAISGDSVS SNYASWNWIR QSPSRGLEWL GRTYYRSKWY  60
NDFAVSVKSR VTINADTSKN QFSLHLSSVT PEDTAIYFCA REANGRGYFY YMDVWGKGTT  120
VTVSS                                                        125

SEQ ID NO: 412          moltype = AA  length = 107
FEATURE                 Location/Qualifiers
source                  1..107
                        mol_type = protein
                        organism = synthetic construct
SEQUENCE: 412
EIVLTQSPDF QSVTPKEKVT ITCRASQSIG SSLHWYQQKP VQSPKLLIKY ASQSISGVPS  60
RFSGSGSGTV FTLTINSLEA EDAAAYFCHQ SSGSPHTFGG GTKVEIK             107

SEQ ID NO: 413          moltype = AA  length = 125
FEATURE                 Location/Qualifiers
source                  1..125
                        mol_type = protein
                        organism = synthetic construct
SEQUENCE: 413
QVQLQQSGPG LVKPSQTLSL TCAISGDSVS SNYASWNWIR QSPSRGLEWL GRTYYRSKWY  60
NDFAVSVRSR VTINADTSKN QFSLHLSSVT PEDTAIYFCA REANGRGYFY YMDVWGKGTT  120
VTVSS                                                        125

SEQ ID NO: 414          moltype = AA  length = 107
FEATURE                 Location/Qualifiers
source                  1..107
                        mol_type = protein
                        organism = synthetic construct
SEQUENCE: 414
EIVLTQSPDF QSVTPKEKVT ITCRASQSIG SSLHWYQQKP DQSPKLLIKY ASQSISGVPS  60
RFSGSGSGTV FTLTINSLEA EDAAAYFCHQ SSGSPHTFGG GTKVEIK             107

SEQ ID NO: 415          moltype = AA  length = 125
FEATURE                 Location/Qualifiers
source                  1..125
                        mol_type = protein
                        organism = synthetic construct
SEQUENCE: 415
EVQLLESGGG LVQPGGSLRL SCAASGFTFS NYAMNWVRQA PGKGLEWVSV ISNSGGTRLY  60
VDSVKGRFTI SRDNSKNTLY LQMSSLRAAD TAVYYCAKDA AAALYYYYFY YMDVWGKGTT  120
VTVSS                                                        125

SEQ ID NO: 416          moltype = AA  length = 107
FEATURE                 Location/Qualifiers
source                  1..107
                        mol_type = protein
                        organism = synthetic construct
SEQUENCE: 416
EIVLTQSPDF QSVTPKEKVT ITCRASQSIG SSLHWYQQKP DQSPKLLIKY ASQSFSGVPS  60
RFSGSGSGTD FTLTINSLEA EDAATYYCHQ SSSLPYTFGQ GTKLEIK             107

SEQ ID NO: 417          moltype = AA  length = 120
FEATURE                 Location/Qualifiers
source                  1..120
                        mol_type = protein
                        organism = synthetic construct
SEQUENCE: 417
EVLLLESGGG LVQPGGSLRL SCAASGFTFR SSSMTWVRQA PGKGLEWVSG IRGSGGRTYD  60
AESVKGRFTI SRDISKNTLY LQMNSVRAED TAEYYCAKLY DYYNDYMDVW GKGTTVTVSS  120

SEQ ID NO: 418          moltype = AA  length = 106
FEATURE                 Location/Qualifiers
```

```
source                  1..106
                        mol_type = protein
                        organism = synthetic construct
SEQUENCE: 418
SYELTQPLSV SVALGQTARI TCGGNNIGSK NVHWYQQKPG QAPVLVIYRD SNRPSGIPER  60
FSGSNSGNTA TLTISRAQAG DEADYYCQVW DSSTAVFGGG TQLTAL                106

SEQ ID NO: 419          moltype = AA  length = 120
FEATURE                 Location/Qualifiers
source                  1..120
                        mol_type = protein
                        organism = synthetic construct
SEQUENCE: 419
EVQLLESGGG LVQPGGSLRL SCVASGFTFR SSSMAWVRQA PGKGLEWVSG IRGSGGRTYD  60
AESVKGRFII SRDTSKNTLY LQMNSLRGED TAEYFCAKLY DYYNDYMDVW GKGTTVTVSS  120

SEQ ID NO: 420          moltype = AA  length = 106
FEATURE                 Location/Qualifiers
source                  1..106
                        mol_type = protein
                        organism = synthetic construct
SEQUENCE: 420
SYELTQPLSV SVALGQTARI TCGGNNIGSK NVHWYQQKPG QAPVLVIYRD SNRPSGIPER  60
FSGSNSGNTA TLTISRAQAG DEADYYCQVW DSSTAVFGGG TQLTAL                106

SEQ ID NO: 421          moltype = AA  length = 120
FEATURE                 Location/Qualifiers
source                  1..120
                        mol_type = protein
                        organism = synthetic construct
SEQUENCE: 421
EVQLLESGGG FMQPGGSLRL SCAVSGFTFR TSSMAWVRQA PGKGLEWVSG IRGSGGRTYD  60
AESVKGRFTI SRDISKNTLY LQMNNLRAED TAEYYCAKLY DYYNDFMDVW GKGTTVIVSA  120

SEQ ID NO: 422          moltype = AA  length = 106
FEATURE                 Location/Qualifiers
source                  1..106
                        mol_type = protein
                        organism = synthetic construct
SEQUENCE: 422
SYELTQPLSV SVALGQTARI TCGGNNIGSK NVHWYQQKPG QAPVLVIYRD SNRPSGIPER  60
FSGSNSGNTA TLTISRAQAG DEADYYCQVW DSSTAVFGGG TQLTAL                106

SEQ ID NO: 423          moltype = AA  length = 120
FEATURE                 Location/Qualifiers
source                  1..120
                        mol_type = protein
                        organism = synthetic construct
SEQUENCE: 423
EVRLLESGGG LVQPGGSLRL SCAASGFTFR SSSMAWVRQD PGKGLEWVTG IRGSGGRTYD  60
ADSVKGRFTI SRDNSKNTLY LQMNSLRAED TAEYYCAKLY DYYNDYMDVW GKGTTVTVSS  120

SEQ ID NO: 424          moltype = AA  length = 106
FEATURE                 Location/Qualifiers
source                  1..106
                        mol_type = protein
                        organism = synthetic construct
SEQUENCE: 424
SYELTQPLSV SVALGQTARI TCGGNNIGSK NVHWYQQKPG QAPVLVIYRD SNRPSGIPER  60
FSGSNSGNTA TLTISRAQAG DEADYYCQVW DSSTAVFGGG TQLTAL                106

SEQ ID NO: 425          moltype = AA  length = 119
FEATURE                 Location/Qualifiers
source                  1..119
                        mol_type = protein
                        organism = synthetic construct
SEQUENCE: 425
EVQLLESGGG LVQPGGSLRL SCTPSGITFN NYAMTWVRQA PGKGLEWVSG ISVSGGSTYY  60
ADSVMGRFTI SRDSSKTLYL QMNSLRAEDT AVYYCAKFHS HYYYYMDVWG KGTTVTVSS   119

SEQ ID NO: 426          moltype = AA  length = 106
FEATURE                 Location/Qualifiers
source                  1..106
                        mol_type = protein
                        organism = synthetic construct
SEQUENCE: 426
SYELTQPLSV SVALGQTARI TCGGNNIGSK DVHWYQQKPG QAPVLVIYRD SNRPSGIPER  60
FSGSNSGNTA TLTISRAQAG DEADYYCQVW DRRTAVFGGG TQLTAL                106
```

```
SEQ ID NO: 427          moltype = AA  length = 120
FEATURE                 Location/Qualifiers
source                  1..120
                        mol_type = protein
                        organism = synthetic construct
SEQUENCE: 427
EVQLLESGGG LVQPGGSLRL SCVASGFTFR SSSMTWVRQA PGKGLEWVSG IRGSGGRTYD  60
AESVKGRFTI SRDNSKNTLY LQMNSLRAED TAEYYCAKLY DYYNDYMDVW GKGTTVTVSS  120

SEQ ID NO: 428          moltype = AA  length = 106
FEATURE                 Location/Qualifiers
source                  1..106
                        mol_type = protein
                        organism = synthetic construct
SEQUENCE: 428
SYELTQPLSV SVALGQTARI TCGGNNIGSK NVHWYQQKPG QAPVLVIYRD SNRPSGIPER  60
FSGSNSGNTA TLTISRAQAG DEADYYCQVW DSSTAVFGGG TQLTAL                 106

SEQ ID NO: 429          moltype = AA  length = 120
FEATURE                 Location/Qualifiers
source                  1..120
                        mol_type = protein
                        organism = synthetic construct
SEQUENCE: 429
EVQLLESGGG LVQPGGSLRL SCAASGFTFR SSSMTWVRQA PGKGLEWVSG IRGSGGRTYD  60
AESVKGRFTI SRDNSKNTLY LQMNSLRAED TAEYFCAKLY DYYNDYMDVW GKGTTVTVSS  120

SEQ ID NO: 430          moltype = AA  length = 106
FEATURE                 Location/Qualifiers
source                  1..106
                        mol_type = protein
                        organism = synthetic construct
SEQUENCE: 430
SYELTQPLSV SVALGQTARI TCGGNNIGSK NVHWYQQKPG QAPVLVIYRD SNRPSGIPER  60
FSGSNSGNTA TLTISRAQAG DEADYYCQVW DSSTAVFGGG TQLTAL                 106

SEQ ID NO: 431          moltype = AA  length = 125
FEATURE                 Location/Qualifiers
source                  1..125
                        mol_type = protein
                        organism = synthetic construct
SEQUENCE: 431
QVQLQQSGPG LVKPSQTLSL TCAISGDSVS SNYASWNWIR QSPSRGLEWL GRTYYRSKWY  60
IDFAVSVKSR LTINADTSKN QFSLHLRSVT PEDTAIYFCA REANGRGYFY YMDVWGKGTT  120
VTVSS                                                              125

SEQ ID NO: 432          moltype = AA  length = 107
FEATURE                 Location/Qualifiers
source                  1..107
                        mol_type = protein
                        organism = synthetic construct
SEQUENCE: 432
EIVLTQSPDF QSVTPKEKVT ITCRASQSIG SSLHWYQQKP DQSPKLLIKY ASQSISGVPS  60
RFSGSGSGTV FTLTINSLEA EDAAAYFCHQ SSGSPHTFGG GTKVEIK                107

SEQ ID NO: 433          moltype = AA  length = 125
FEATURE                 Location/Qualifiers
source                  1..125
                        mol_type = protein
                        organism = synthetic construct
SEQUENCE: 433
QVQLQQSGPG LVKPSQTLSL TCAISGDSIS SNYASWNWIR QSPSRGLEWL GRTYYRSKWY  60
NDFAVSVKSR IIINPDTSRN QFSLHLNSVT PEDTAIYYCA REANGRGYFY YMDVWGKGTT  120
VTVSS                                                              125

SEQ ID NO: 434          moltype = AA  length = 107
FEATURE                 Location/Qualifiers
source                  1..107
                        mol_type = protein
                        organism = synthetic construct
SEQUENCE: 434
EIVLTQSPDF QSVTPKEKVT ITCRASQSIG SSLHWYQQKP DQSPKLLIKY ASQSISGVPS  60
RFSGRGSGTD FTLTINSLEA EDAAAYFCHQ SSGSPHTFGG GTKVEIK                107

SEQ ID NO: 435          moltype = AA  length = 117
FEATURE                 Location/Qualifiers
source                  1..117
                        mol_type = protein
                        organism = synthetic construct
```

```
SEQUENCE: 435
QVQLVQSGSE VKKPGASVKV SCKASGYTFT GYYIHWVRQA PGQGLEWMGW INPNSGRTNY  60
AQNFQGRVTM TRDTSITTAH MELTRLTSDD TAVYYCARLE LLVFDYWGQG TLVTVSS     117

SEQ ID NO: 436          moltype = AA  length = 107
FEATURE                 Location/Qualifiers
source                  1..107
                        mol_type = protein
                        organism = synthetic construct
SEQUENCE: 436
DIQMTQSPSS LSASVGDRVT ITCRASQTIY NYLNWYQQKP GKAPQVLIYA ASNLQSGVPS  60
IFSGSGSGTD FTLTITNLQP EDFATYYCQQ TYSIPFTFGG GTKVEIK               107

SEQ ID NO: 437          moltype = AA  length = 117
FEATURE                 Location/Qualifiers
source                  1..117
                        mol_type = protein
                        organism = synthetic construct
SEQUENCE: 437
QVQLVQSGSE VKKPGASVKV SCKASGYTFT GYYIHWVRQA PGQGLEWMGW INPNSGRTNY  60
AQNFQGRVTM TRDTSITTAH MELTRLTSDD TAVYYCARLE LLVFDYWGQG TLVTVSS     117

SEQ ID NO: 438          moltype = AA  length = 108
FEATURE                 Location/Qualifiers
source                  1..108
                        mol_type = protein
                        organism = synthetic construct
SEQUENCE: 438
ETVMTQSPAT LSVSPGERVT LSCRASQSVS SYLAWYQQKP GQTPRLLIYG ASTRATGIPA  60
RFSGSGSGTE FTLTISSLQS EDFAVYYCQQ YNNWPPWTFG QGTKVEIK              108

SEQ ID NO: 439          moltype = AA  length = 122
FEATURE                 Location/Qualifiers
source                  1..122
                        mol_type = protein
                        organism = synthetic construct
SEQUENCE: 439
EIQLVESGGG LVQPGESLKL SCAGSGFTFS VSAMHWVRQA SGKGLEWVGR IRNKANSYAT  60
AYDASVKGRF TLSRDDSRNT AYLQMNSLKT EDTAVYYCSS YYYLSGTYYN YWGQGTLVTV  120
SS                                                                122

SEQ ID NO: 440          moltype = AA  length = 107
FEATURE                 Location/Qualifiers
source                  1..107
                        mol_type = protein
                        organism = synthetic construct
SEQUENCE: 440
DIQMTQSPSS LSASVGDRVT ITCRASQVIR NDLGWYQQKP GKAPKRLIHS ASSLQGGVPS  60
RFSGSGSGTE FTLTISSLQP EDFATYYCQQ HNVNPCTFGQ GTKLEIK               107

SEQ ID NO: 441          moltype = AA  length = 122
FEATURE                 Location/Qualifiers
source                  1..122
                        mol_type = protein
                        organism = synthetic construct
SEQUENCE: 441
EIQLVESGGG LVQPGESLKL SCAGSGFTFS VSAMHWVRQA SGKGLEWVGR IRNKANSYAT  60
AYAASVKGRF TLSRDDSKNT AYLQMDSLKT EDTAVYYCSS YYYLSGTYYN YWGQGTLVTV  120
SS                                                                122

SEQ ID NO: 442          moltype = AA  length = 107
FEATURE                 Location/Qualifiers
source                  1..107
                        mol_type = protein
                        organism = synthetic construct
SEQUENCE: 442
DIQMTQSPSS LSASVGDRVT ITCRASQVIR NDLGWYQQKP GKAPKRLIHS ASSLQGGVPS  60
RFSGSGSGTE FTLTISSLQP EDFATYYCQQ HNVNPCTFGQ GTKLEIK               107

SEQ ID NO: 443          moltype = AA  length = 122
FEATURE                 Location/Qualifiers
source                  1..122
                        mol_type = protein
                        organism = synthetic construct
SEQUENCE: 443
EIQLVESGGG LVQPGESLKL SCAGSGFTFS VSAMHWVRQA SGKGLEWVGR IRNKANSYAT  60
AYAASVKGRF TLSRDDSKNT AYLQMNSLKT EDTAVYYCSS YYYLSGTYYN YWGQGTLVTV  120
SS                                                                122
```

```
SEQ ID NO: 444          moltype = AA  length = 107
FEATURE                 Location/Qualifiers
source                  1..107
                        mol_type = protein
                        organism = synthetic construct
SEQUENCE: 444
DIQMTQSPSS LSASVGDRVT ITCRASQVIR NDLGWYQQKP GKAPKRLIHS ASSLQGGVPS  60
RFSGSGSGTE FTLTISSLQP EDFATYYCQQ HNVNPCTFGQ GTKLEIK               107

SEQ ID NO: 445          moltype = AA  length = 122
FEATURE                 Location/Qualifiers
source                  1..122
                        mol_type = protein
                        organism = synthetic construct
SEQUENCE: 445
EVQLVESGGG LVQPGESLKL SCTASGFTFS VSAIHWVRQA SGKGLEWVGR IRSKANSYAT  60
AYVASVKGRF TLSRDDSKNT AYLQMNSLKT EDTAVYYCSS YYFVSGTYYN HWGQGTLVTV  120
SS                                                                122

SEQ ID NO: 446          moltype = AA  length = 107
FEATURE                 Location/Qualifiers
source                  1..107
                        mol_type = protein
                        organism = synthetic construct
SEQUENCE: 446
DIQMTQSPSS LSASVGDRVT ITCRASQGIR YDLGWYQQKP GRAPKRLIHS VSSLQSGVPS  60
RFSGSGSGTE FTLTISSLQP EDFATYYCLQ HNVNPCTFGQ GTKLEIK               107

SEQ ID NO: 447          moltype = AA  length = 117
FEATURE                 Location/Qualifiers
source                  1..117
                        mol_type = protein
                        organism = synthetic construct
SEQUENCE: 447
QVQLVQSGAE VKKPGASVRV SCKASGYTFT GYYMHWVRQA PGQGLEWMGW IYPNSGRTNY  60
AQKFQGRVTM TRDTSISTAY MELTRLISDD TAVYYCARLW DLYFDYWGQG TLVTVSS     117

SEQ ID NO: 448          moltype = AA  length = 107
FEATURE                 Location/Qualifiers
source                  1..107
                        mol_type = protein
                        organism = synthetic construct
SEQUENCE: 448
DIQLTQSPSF LSASVGDRVT ITCRASQGIS SYLAWYQQKP GKAPKLLIYA ASTLQSGVPS  60
RFSGSGSGTE FTLTISSLQP EDFATYYCQQ LNSYPWTFGQ GTKVEIK               107

SEQ ID NO: 449          moltype = AA  length = 124
FEATURE                 Location/Qualifiers
source                  1..124
                        mol_type = protein
                        organism = synthetic construct
SEQUENCE: 449
QVQLVQSGSE LKKPGASVKV SCKASGYTFT KYAMNWVRQA PGQGLEWMGW INTNTGNPTY  60
AQGFTGRFVF SLDASVTTAY LQISSLKAED TAVYYCAREG HYDFWGGFYY FDYWGQGTLV  120
TVSS                                                              124

SEQ ID NO: 450          moltype = AA  length = 107
FEATURE                 Location/Qualifiers
source                  1..107
                        mol_type = protein
                        organism = synthetic construct
SEQUENCE: 450
EIMLTQSPAT LSLSPGERGT LSCRASQSVS SYLAWYQQKP GQAPRLVIYD VSNRATGIPA  60
RFSGSGSGTD FILTIGSLEP EDFAVYYCQQ RSNWPLTFGG GTKVEIK               107

SEQ ID NO: 451          moltype = AA  length = 121
FEATURE                 Location/Qualifiers
source                  1..121
                        mol_type = protein
                        organism = synthetic construct
SEQUENCE: 451
EVQLVESGGG LVQPGGSLRL SCAASGIPFS TYSMNWVRQA PGKGLEWVSY ISGSSRTIYY  60
ADSVKGRFTI SRDNAKKLLF LQMNSLRDED TAVYYCAREG DYYDSSGWAY WGQGTLVTVS  120
S                                                                 121

SEQ ID NO: 452          moltype = AA  length = 107
FEATURE                 Location/Qualifiers
source                  1..107
                        mol_type = protein
```

```
                         organism = synthetic construct
SEQUENCE: 452
DIQMTQSPSS LSASVGDRVT ITCRASQNIY KYLNWYEQKP GRAPKLLIYT TSNLQSGVPS  60
RFSGSGSGTA FTLIISSLQP EDFATYYCQQ SYGSPYTFGQ GTKLEIK               107

SEQ ID NO: 453           moltype = AA  length = 117
FEATURE                  Location/Qualifiers
source                   1..117
                         mol_type = protein
                         organism = synthetic construct
SEQUENCE: 453
QVQLVQSGAA MKKPGASVKV SCKASGSTFT GYYLHWVRQA PGQGLEWMGW IYLNSGRTKY  60
AQKFQGRVTM TRDTSINTAH MELSRLTFDD TAVYYCVRVL ELIFDYWGQG TLVTVSS     117

SEQ ID NO: 454           moltype = AA  length = 107
FEATURE                  Location/Qualifiers
source                   1..107
                         mol_type = protein
                         organism = synthetic construct
SEQUENCE: 454
DIQLTQSPSF LSASVGDRVT ITCRASQGIS SYLAWYQQKP GKAPKLLIYA ASTLQSGVPS  60
RFSGSGSGTE FTLTISSLQP EDFATYYCQQ LNSYPWTFGQ GTKVEIK               107

SEQ ID NO: 455           moltype = AA  length = 117
FEATURE                  Location/Qualifiers
source                   1..117
                         mol_type = protein
                         organism = synthetic construct
SEQUENCE: 455
QVQLVQSGAA MKKPGASVKV SCKASGSTFT GYYLHWVRQA PGQGLEWMGW IYLNSGRTKY  60
AQKFQGRVTM TRDTSISTAH MELSRLTFDD TAVYYCARVL ELIFDYWGQG TLVTVSS     117

SEQ ID NO: 456           moltype = AA  length = 108
FEATURE                  Location/Qualifiers
source                   1..108
                         mol_type = protein
                         organism = synthetic construct
SEQUENCE: 456
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYGSSPYTFG QGTKLEIK              108

SEQ ID NO: 457           moltype = AA  length = 117
FEATURE                  Location/Qualifiers
source                   1..117
                         mol_type = protein
                         organism = synthetic construct
SEQUENCE: 457
QVQLVQSGAE VKKPGASVKV SCKASGYTFT GYYMHWVRQA PGQGLEWMGW IYPNSGRTNY  60
AQKFQGRVTM TRDTSISTAY MELTRLISDD TAVYYCARLW DLYFDYWGQG TLVTVSS     117

SEQ ID NO: 458           moltype = AA  length = 107
FEATURE                  Location/Qualifiers
source                   1..107
                         mol_type = protein
                         organism = synthetic construct
SEQUENCE: 458
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SYSTPFTFGP GTKVDIK               107

SEQ ID NO: 459           moltype = AA  length = 117
FEATURE                  Location/Qualifiers
source                   1..117
                         mol_type = protein
                         organism = synthetic construct
SEQUENCE: 459
QVQLVQSGAE VKKPGASVRV SCKASGYTFT GYYMHWVRQA PGQGLEWMGW IYPNSGRTNY  60
AQKFQGRVTM TRDTSISTAY MELTRLISDD TAVYYCARLW DLYFDYWGQG TLVTVSS     117

SEQ ID NO: 460           moltype = AA  length = 113
FEATURE                  Location/Qualifiers
source                   1..113
                         mol_type = protein
                         organism = synthetic construct
SEQUENCE: 460
DIVMTQSPDS LAVSLGERAT INCKSSQSVL YSSNNKNYLA WYQQKPGQPP KLLIYWASTR  60
ESGVPDRFSG SGSGTDFTLT ISSLQAEDVA VYYCQQYYST PYTFGQGTKL EIK        113

SEQ ID NO: 461           moltype = AA  length = 117
FEATURE                  Location/Qualifiers
```

```
source                  1..117
                        mol_type = protein
                        organism = synthetic construct
SEQUENCE: 461
QVQLVQSGAE VKKPGASVRV SCKASGYTFT GYYMHWVRQA PGQGLEWMGW IYPNSGRTNY  60
AQKFQGRVTM TRDTSISTAY MELTRLISDD TAVYYCARLW DLYFDYWGQG TLVTVSS     117

SEQ ID NO: 462          moltype = AA  length = 112
FEATURE                 Location/Qualifiers
source                  1..112
                        mol_type = protein
                        organism = synthetic construct
SEQUENCE: 462
DIVMTQSPLS LPVTPGEPAS ISCRSSQSLL HYNGNNYLDW YLQKPGQSPH LLIYLGSNRA  60
SGVPDRFSGS GSGTDFTLKI IRVEAEDVGI YYCMQGLQSP YTFGQGTKLE IK          112

SEQ ID NO: 463          moltype = AA  length = 117
FEATURE                 Location/Qualifiers
source                  1..117
                        mol_type = protein
                        organism = synthetic construct
SEQUENCE: 463
QVQLVQSETE VKKPGASVRV SCKASGYTFT GYYVHWVRQA PGQGLEWMGW INPKSGRTSY  60
SQKFQDRVTM TRDTSISTVY MELSRLRSDD TAVYYCARIL ELIFDYWGQG TLVTVSS     117

SEQ ID NO: 464          moltype = AA  length = 106
FEATURE                 Location/Qualifiers
source                  1..106
                        mol_type = protein
                        organism = synthetic construct
SEQUENCE: 464
EIVLTQSPDF QSVTPKEKVT ITCRASQSIG SSLHWYQQKP DQSPKLLIKY ASQSFSGVPS  60
RFSGSGSGTD FTLTINSLEA EDAATYYCHQ SSSLPTFGPG TKVDIK                 106

SEQ ID NO: 465          moltype = AA  length = 123
FEATURE                 Location/Qualifiers
source                  1..123
                        mol_type = protein
                        organism = synthetic construct
SEQUENCE: 465
QVHLVQSGAE VKKPGASVRV SCKASGYTFT GYYIHWLRQA PGQGLEWLGW INPNSGGTNY  60
SQKFRGRVTM TRDTSISTAY MELSRLRSDD TAVYYCARDK VWEQQLVGGF DYWGQGTLVT  120
VSS                                                                123

SEQ ID NO: 466          moltype = AA  length = 113
FEATURE                 Location/Qualifiers
source                  1..113
                        mol_type = protein
                        organism = synthetic construct
SEQUENCE: 466
DIVMTQSPDS LAVSLGERAT INCKSSQSVL YRSHKKNYLA WYQQKPGQPP KLLIYWTSTR  60
DSGVPDRFSG SGSGTDFTLT ISSLQTEDVA LYYCQQYYTT PFTFGPGTKV DIK         113

SEQ ID NO: 467          moltype = AA  length = 120
FEATURE                 Location/Qualifiers
source                  1..120
                        mol_type = protein
                        organism = synthetic construct
SEQUENCE: 467
EVQLLESGGG LVQPGGSLRL SCAASGFTFS SYAMSWVRQA PGKGLEWVSA ISGSSGRTYY  60
TDSVKGRFTI SRDNSKNTLS LQMNSLRAED TAVYYCAKKY SYYYYYMDVW GKGTTVTVSS  120

SEQ ID NO: 468          moltype = AA  length = 106
FEATURE                 Location/Qualifiers
source                  1..106
                        mol_type = protein
                        organism = synthetic construct
SEQUENCE: 468
SYELTQPLSV SVALGQTAKI TCGGNNIGSK NVHWYQQKPG QAPVLVIYRD SNRPSGIPER  60
FSGSNSGNTA TLTISRAQAG DEADYYCQVW DSSTAVFGGG TQLTAL                 106

SEQ ID NO: 469          moltype = AA  length = 120
FEATURE                 Location/Qualifiers
source                  1..120
                        mol_type = protein
                        organism = synthetic construct
SEQUENCE: 469
EVQLLESGGG LGQPGGSLRL SCAASGFTFS NYAMSWVRQA PGKGLEWVSV ISGSGGDKNY  60
ADSVKGRFTI SRDNSKNTLY LQMNSLRAED TAVYYCAKKY SYYYYYMDVW GKGTTVTVSS  120
```

```
SEQ ID NO: 470          moltype = AA  length = 106
FEATURE                 Location/Qualifiers
source                  1..106
                        mol_type = protein
                        organism = synthetic construct
SEQUENCE: 470
SYELTQPLSV SVALGQTARI TCGGNNIGSK DVHWYQQKPG QAPVLVIYRD SNRPSGIPER  60
FSGSNSGNTA TLTISSAQAG DEADYYCQVW DSRTAVFGGG TQLTAL                 106

SEQ ID NO: 471          moltype = AA  length = 126
FEATURE                 Location/Qualifiers
source                  1..126
                        mol_type = protein
                        organism = synthetic construct
SEQUENCE: 471
EVKLVESGGG VVRPGGSLRL SCAASGFTFD DYGMSWVRQA PGKGLEWVSG ISWNGGSTGY  60
ADSVKGRFTI SRDNAKNSLY LQMNSLRAED TALYHCARDG VPVVKRRYYY YYMDVWGKGT  120
TVTVSS                                                             126

SEQ ID NO: 472          moltype = AA  length = 107
FEATURE                 Location/Qualifiers
source                  1..107
                        mol_type = protein
                        organism = synthetic construct
SEQUENCE: 472
EIVLTQSPDF QSVTPKEKVT ITCRASQSIG SSLHWYQQKP DQSPKLLIKY ASQSFSGVPS  60
RFSGRGSGTD FTLTINSLEA EDAATYYCHQ SGSLPQTFGQ GTKVEIK                107

SEQ ID NO: 473          moltype = AA  length = 126
FEATURE                 Location/Qualifiers
source                  1..126
                        mol_type = protein
                        organism = synthetic construct
SEQUENCE: 473
EVQLVESGGG VVRPGGSLRL SCAASGFTFD DYGMSWVRQA PGKGLEWVSG ISWNGGSTGY  60
ADSVKGRFTI SRDNAKNSLY LQMNSLRAED TALYHCARDG VPVVKRRYYY YYMDVWGKGT  120
TVTVSS                                                             126

SEQ ID NO: 474          moltype = AA  length = 107
FEATURE                 Location/Qualifiers
source                  1..107
                        mol_type = protein
                        organism = synthetic construct
SEQUENCE: 474
EIVLTQSPDF QSVTPKEKVT ITCRASQSIG SSLHWYQQKP DQSPKLLIKY ASQSFSGVPS  60
RFSGSGSGTD FTLTINSLEA EDAATYYCHQ SASLPQTFGQ GTKVEIK                107

SEQ ID NO: 475          moltype = AA  length = 120
FEATURE                 Location/Qualifiers
source                  1..120
                        mol_type = protein
                        organism = synthetic construct
SEQUENCE: 475
EVQLLESGGN LGQPGGSLRL SCAVSGFTFS SYTMSWVRQA PGKGLEWVSA ISGSGGRTYY  60
ADSVKGRFTI SRDNSKNTLY LQMKSLRAED TAVYYCAKKF SYYYYYMDVW GKGTTVTVSS  120

SEQ ID NO: 476          moltype = AA  length = 106
FEATURE                 Location/Qualifiers
source                  1..106
                        mol_type = protein
                        organism = synthetic construct
SEQUENCE: 476
SYELTQPLSV SVALGQTARI TCGGNNIGSK DVHWYQQKPG QAPVLVIYRD SNRPSGIPER  60
FSGSNSGNTA TLTISSAQAG DEADYYCQVW DSNTAVFGGG TQLTAL                 106

SEQ ID NO: 477          moltype = AA  length = 120
FEATURE                 Location/Qualifiers
source                  1..120
                        mol_type = protein
                        organism = synthetic construct
SEQUENCE: 477
EVQLLESGGG LVQPGGSRRL SCAASGFTFS SFAMSWVRQA PGKGLEWVSV ISSRGDNTNY  60
ADSVKGRFTI SRDNSKNTLY LQMNSLRAED TAVYYCAKKY SYYYYYMDVW GKGTTVTVSS  120

SEQ ID NO: 478          moltype = AA  length = 106
FEATURE                 Location/Qualifiers
source                  1..106
                        mol_type = protein
```

```
                         organism = synthetic construct
SEQUENCE: 478
SYELTQPLSV SVALGQTARI TCGGNNIGSK NVHWHQQKPG QAPVLVIYRE SNRPSGIPER  60
FSGSNSGNTA TLTSSRAQAG DEADYYCQVW DSSTAVFGGG TQLTAL                 106

SEQ ID NO: 479           moltype = AA  length = 126
FEATURE                  Location/Qualifiers
source                   1..126
                         mol_type = protein
                         organism = synthetic construct
SEQUENCE: 479
EVQLVESGGG VVRPGGSLRL SCAASGFTFD DYGMSWVRQA PGKGLEWVSG ISWNGGSTGY  60
ADSVKGRFTI SRDNAKNSLY LQMNSLRAED TALYHCARDG VPVVKRRYYY YYMDVWGKGT  120
TVTVSS                                                             126

SEQ ID NO: 480           moltype = AA  length = 107
FEATURE                  Location/Qualifiers
source                   1..107
                         mol_type = protein
                         organism = synthetic construct
SEQUENCE: 480
EIVLTQSPDF QSVTPKEKIT ITCRASQSIG SSLHWYQQKP DQSPKLLIKY ASQSFSGVPS  60
RFSGSGSGTD FTLTINSLEA EDAATYYCHQ SASLPQTFGQ GTKVEIK                107

SEQ ID NO: 481           moltype = AA  length = 120
FEATURE                  Location/Qualifiers
source                   1..120
                         mol_type = protein
                         organism = synthetic construct
SEQUENCE: 481
EVQLLESGGG LVQPGGSRRL SCAASGFTFS SYALSWVRQA PGKGLEWVSV INTRGDSTSY  60
ADSVKGRFTI SRDNSKNTLY LQMNSLRAED TAVYYCAKKY SYYYYYMDVW GKGTTVTVSS  120

SEQ ID NO: 482           moltype = AA  length = 106
FEATURE                  Location/Qualifiers
source                   1..106
                         mol_type = protein
                         organism = synthetic construct
SEQUENCE: 482
SYELTQPLSV SVALGQTARI TCGGNNIGSK DVHWYQQKPG QAPVLVIYRD SNRPSGIPER  60
FSGSNSGNTA TLTISRAQAG DEADYYCQVW DSRTAVFGGG TQLTAL                 106

SEQ ID NO: 483           moltype = AA  length = 120
FEATURE                  Location/Qualifiers
source                   1..120
                         mol_type = protein
                         organism = synthetic construct
SEQUENCE: 483
EVQLLESGGG LVQPGGSRRL SCAASGFTFS TYAMSWVRQA PGKGLEWVSV INGRGDDTNY  60
ADSVKGRFTI SRDNSKNILF LQMNSLRAED TAVYYCAKKY SYYYYYMDVW GKGTTVTVSS  120

SEQ ID NO: 484           moltype = AA  length = 106
FEATURE                  Location/Qualifiers
source                   1..106
                         mol_type = protein
                         organism = synthetic construct
SEQUENCE: 484
SYELTQPLSV SVALGQTARI TCGGNNIGSK DVHWYQQKPG QAPVLVIYRD SNRPSGIPER  60
FSGSNSGNTA TLTISRAQAG DEADYYCQVW DSRTAVFGGG TQLTAL                 106

SEQ ID NO: 485           moltype = AA  length = 120
FEATURE                  Location/Qualifiers
source                   1..120
                         mol_type = protein
                         organism = synthetic construct
SEQUENCE: 485
EVQLLESGGD LVQPGGSLRL SCAASGFTFS RNAVSWVRQA PGRGLEWVST ISGRGDKTNY  60
VDSVKGRFTI SRDNSKNTLY LQMNSLRAED TAVYYCTKMF SYYYYYMDVW GKGTTVTVSS  120

SEQ ID NO: 486           moltype = AA  length = 106
FEATURE                  Location/Qualifiers
source                   1..106
                         mol_type = protein
                         organism = synthetic construct
SEQUENCE: 486
SYELTQPLSV SVALGQTARI TCGGNNIGSK DVHWYQQKPG QAPVLVIYRD SNRPSGIPER  60
FSGSNSGNTA TLTISRAQAG DEADYYCQVW DSSTAVFGGG TQLTAL                 106

SEQ ID NO: 487           moltype = AA  length = 120
```

```
FEATURE                Location/Qualifiers
source                 1..120
                       mol_type = protein
                       organism = synthetic construct
SEQUENCE: 487
EVQLLESGGG LVQPGGSLRL SCAASGFTFS SSVMSWVRQG PGKGLEWVSA IRGSGVYTYY  60
ADSVKGRFTI SRDNSKNTLY LQMNSLRAED TAVYYCAKKY SYYYYYMDVW GKGTTVTVSS  120

SEQ ID NO: 488         moltype = AA  length = 106
FEATURE                Location/Qualifiers
source                 1..106
                       mol_type = protein
                       organism = synthetic construct
SEQUENCE: 488
PYELTQPLSV SVALGQTARI TCGGNNIGSK DVHWYQQKPG QAPVLVIYRD SNRPSGIPER  60
FSGSNSGNTA TLTISRAQAG DEADYYCQVW DSSTAVFGGG TQLTAL                 106

SEQ ID NO: 489         moltype = AA  length = 120
FEATURE                Location/Qualifiers
source                 1..120
                       mol_type = protein
                       organism = synthetic construct
SEQUENCE: 489
EVQLLESGGG LVQPGGSLRL SCAASGITFS SYAMSWVRQA PGKGLEWVST ISGNGGTLYY  60
TDSVKGRFTI SRDNSKNTLY LQMNSLRAED TAVYYCAKKY SYYYYYMDVW GKGTTVTVSS  120

SEQ ID NO: 490         moltype = AA  length = 106
FEATURE                Location/Qualifiers
source                 1..106
                       mol_type = protein
                       organism = synthetic construct
SEQUENCE: 490
SYELTQPLSV SVALGQTARI TCGGNNIGSK NVHWYQQKPG QAPVLVIYRD SNRPSGIPER  60
FSGSNSGNTA TLTISRAQAG DEADYYCQVW DSSTAVFGGG TQLTAL                 106

SEQ ID NO: 491         moltype = AA  length = 120
FEATURE                Location/Qualifiers
source                 1..120
                       mol_type = protein
                       organism = synthetic construct
SEQUENCE: 491
EVQLLESGGG LVQPGGSLRL SCAASGFTFS SYAMSWVRQA PGKGLEWVSA ISGSGGTTYY  60
TDSVKGRFTI SRDNSKNTLY LQMNSLRAED TAVYYCAKKY SYYYYYMDVW GKGTTVTVSS  120

SEQ ID NO: 492         moltype = AA  length = 106
FEATURE                Location/Qualifiers
source                 1..106
                       mol_type = protein
                       organism = synthetic construct
SEQUENCE: 492
SYELTQPLSV SVALGQTARI TCGGNNIGSK NVHWYQQKPG QAPVLVIYRD SNRPSGIPER  60
FSGSNSGNTA TLTISRAQAG DEADYYCQVW DSSTAVFGGG TQLTAL                 106

SEQ ID NO: 493         moltype = AA  length = 122
FEATURE                Location/Qualifiers
source                 1..122
                       mol_type = protein
                       organism = synthetic construct
SEQUENCE: 493
EVQLLESGGG LVQPGGSLRL SCAASGFTFS SYAMNWVRQA PGKGLEWVSI ISGGRRDDIT  60
YYAASVKGRF TISRDNSKNT LYLQMNSLRA EDTAVYYCAK MYNYYYYYID VWGKGTTVTV  120
SS                                                                 122

SEQ ID NO: 494         moltype = AA  length = 106
FEATURE                Location/Qualifiers
source                 1..106
                       mol_type = protein
                       organism = synthetic construct
SEQUENCE: 494
SYELTQPLSV SVALGQTAKI TCGGNNIGSK DVHWYQQKPG QAPVLVIYRD SNRPSGIPER  60
FSGSNSGNTA TLTISRAQAG DEADYYCQVW DSNTAVFGGG TQLTAL                 106

SEQ ID NO: 495         moltype = AA  length = 120
FEATURE                Location/Qualifiers
source                 1..120
                       mol_type = protein
                       organism = synthetic construct
SEQUENCE: 495
EGQLLESGGG LVQPGGSLRL SCAASGFTFS RYAMSWIRQA PGKGLEWVSV INGSGGDKNY  60
```

```
ADSVKGRFTI SRDNSKNSLY LLMNGLRVED TAIYFCAKKF SYYYYYMDVW GKGTTVTVSS  120

SEQ ID NO: 496          moltype = AA  length = 106
FEATURE                 Location/Qualifiers
source                  1..106
                        mol_type = protein
                        organism = synthetic construct
SEQUENCE: 496
SYELTQPLSV SVALGQTARI TCGGNNIGGK DVHWYQQKPG QAPVLVIYRD SNRPSGIPER  60
FSGSNSGNTA TLTISRAQAG DEADYYCQVW DSRTAVFGGG TQLTAL                 106

SEQ ID NO: 497          moltype = AA  length = 120
FEATURE                 Location/Qualifiers
source                  1..120
                        mol_type = protein
                        organism = synthetic construct
SEQUENCE: 497
EVQLLESGGG LVQPGGSRRL SCAASGFTFR SYAMSWVRQA PGKGLEWVSV ISIRGDSTSY  60
ADSVKGRFTI SRDNSKNTLY LQMNSLRAED TAVYYCAKKY SYYYYYMDVW GKGTTVTVSS  120

SEQ ID NO: 498          moltype = AA  length = 106
FEATURE                 Location/Qualifiers
source                  1..106
                        mol_type = protein
                        organism = synthetic construct
SEQUENCE: 498
SYELTQPLSV SVALGQTARI TCGGNNIGSK DVHWYQQKPG QAPVLVIYRD SNRPSGIPER  60
FSGSNSGNTA TLTISRAQAG DEADYYCQVW DSRTAVFGGG TQLTAL                 106

SEQ ID NO: 499          moltype = AA  length = 120
FEATURE                 Location/Qualifiers
source                  1..120
                        mol_type = protein
                        organism = synthetic construct
SEQUENCE: 499
EVQLLESGGG LVQPGGSLRL SCAASGFTFS RYAMSWVRQA PGRGLEWVST ISGSGGRTYY  60
VDSVKGRFTI SRDNSKNTLY LQMNSLRAED TAVYYCAKMF SYYYYYMDVW GKGTTVTVSS  120

SEQ ID NO: 500          moltype = AA  length = 109
FEATURE                 Location/Qualifiers
source                  1..109
                        mol_type = protein
                        organism = synthetic construct
SEQUENCE: 500
EIVMTQSPAT LSLSPGKRAT LSCRASQSVS TTYLSWYLQK PGQAPRLLIY GASTRATGIP  60
ARFSGSGSGT DFTLTISSLQ PEDFAVYYCQ QDYNLPPYTF GQGTKLEIK              109

SEQ ID NO: 501          moltype = AA  length = 120
FEATURE                 Location/Qualifiers
source                  1..120
                        mol_type = protein
                        organism = synthetic construct
SEQUENCE: 501
EVQLLESGGG LVQPGGSRRL SCAASGFTFS SYAMSWVRQA PGKGLEWVSV ISGRGDNTNY  60
ADSVKGRFTI SRENSKNMLY LQMNSLRAED TAVYYCAKKY SYYYYYMDVW GKGTTVTVSS  120

SEQ ID NO: 502          moltype = AA  length = 106
FEATURE                 Location/Qualifiers
source                  1..106
                        mol_type = protein
                        organism = synthetic construct
SEQUENCE: 502
SYELTQPLSV SVALGQTARI TCGGNNIGSK DVHWYQQKPG QAPVLVIYRD SNRPSGIPER  60
FSGSNSGNTA TLTISRAQAG DEADYYCQVW DSRTAVFGGG TQLTAL                 106

SEQ ID NO: 503          moltype = AA  length = 120
FEATURE                 Location/Qualifiers
source                  1..120
                        mol_type = protein
                        organism = synthetic construct
SEQUENCE: 503
EGQLLESGGG LVQPGGSLRL SCAASGFTFS RYAMSWIRQA PGKGLEWVSV INGSGGDKNY  60
ADSVRGRFTI SRDNSKNSLY LLMNGLRVED TAIYFCAKKF SYYYYYMDVW GKGTTVTVSS  120

SEQ ID NO: 504          moltype = AA  length = 106
FEATURE                 Location/Qualifiers
source                  1..106
                        mol_type = protein
                        organism = synthetic construct
```

```
SEQUENCE: 504
SYELTQPLSV SVALGQTARI TCGGNNIGGK DVHWYQQKPG QAPVLVIYRD SNRPSGIPER  60
FSGSNSGNTA TLTISRAQAG DEADYYCQVW DSRTAVFGGG TQLTAL                106

SEQ ID NO: 505          moltype = AA  length = 122
FEATURE                 Location/Qualifiers
source                  1..122
                        mol_type = protein
                        organism = synthetic construct
SEQUENCE: 505
EVHLLESGGG LVQPGGSLRL SCAASGFTFS SYAMNWVRQA PGKGLEWISI ISGGRRSGIT  60
YYAASVKGRF TISRDNSKNT LDLQMNSLRA EDTAVYYCAK MYNYYYYYID VWGKGTTVTV  120
SS                                                                122

SEQ ID NO: 506          moltype = AA  length = 106
FEATURE                 Location/Qualifiers
source                  1..106
                        mol_type = protein
                        organism = synthetic construct
SEQUENCE: 506
SYELTQPLSV SVALGQTARI TCGGNNIGSK DVHWYQQKPG QAPVLVIYRD SNRPSGIPER  60
FSGSNSGNTA TLTISRAQAG DEADYYCQVW DSNTAVFGGG TQLTAL                106

SEQ ID NO: 507          moltype = AA  length = 120
FEATURE                 Location/Qualifiers
source                  1..120
                        mol_type = protein
                        organism = synthetic construct
SEQUENCE: 507
EVQLLESGGG LVQPGGSRRL SCAASGFTFS SYAMSWVRQA PGKGLEWVSV ISGRGDNTNY  60
ADSVKGRFTI SRENSKNILY LQMNSLRAED TAVYYCAKKY SYYYYYMDVW GKGTTVTVSS  120

SEQ ID NO: 508          moltype = AA  length = 106
FEATURE                 Location/Qualifiers
source                  1..106
                        mol_type = protein
                        organism = synthetic construct
SEQUENCE: 508
SYELTQPLSV SVALGQTARI TCGGNNIGSK DVHWYQQKPG QAPVLVIYRD SNRPSGIPER  60
FSGSNSGNTA TLTISRAQAG DEADYYCQVW DSRTAVFGGG TQLTAL                106

SEQ ID NO: 509          moltype = AA  length = 120
FEATURE                 Location/Qualifiers
source                  1..120
                        mol_type = protein
                        organism = synthetic construct
SEQUENCE: 509
EVQLLESGGG LVQPGGSLRL SCAASGFSFS SFALSWVRQA PGKGLEWVSV ISGNGGNKNY  60
ADSVKGRFTI SRDNSKNTLY LQMNSLRAED TAVYYCAKKY SYYYYYMDVW GKGTTVTVSS  120

SEQ ID NO: 510          moltype = AA  length = 106
FEATURE                 Location/Qualifiers
source                  1..106
                        mol_type = protein
                        organism = synthetic construct
SEQUENCE: 510
SYELTQPLSV SVALGQTARI TCGGNNIGGK DVHWYQQKPG QAPVLVIYRD SNRPSGIPER  60
FSGSNSGNTA TLTISRAQAG DEADYYCQVW DSRAAVFGGG TQLTAL                106

SEQ ID NO: 511          moltype = AA  length = 120
FEATURE                 Location/Qualifiers
source                  1..120
                        mol_type = protein
                        organism = synthetic construct
SEQUENCE: 511
EVQLLESGGG LVQPGGSLRL SCAASGFTFN SYAMSWVRQA PGRGLEWVSA ISGRKSTTYY  60
ADSVKGRFTI SRDNSKNTLY LQMNSLRAED TAVYYCAKLW NYYYYYMDVW GKGTTVTVSS  120

SEQ ID NO: 512          moltype = AA  length = 106
FEATURE                 Location/Qualifiers
source                  1..106
                        mol_type = protein
                        organism = synthetic construct
SEQUENCE: 512
SYELTQPLSV SVALGQTARI TCGGNNIGSK DVHWYQQKPG QAPVLVIYRD SNRPSGIPER  60
FSGSNSGNTA TLTISRAQAG DEADYYCQVW DSSTAVFGGG TQLTAL                106

SEQ ID NO: 513          moltype = AA  length = 120
FEATURE                 Location/Qualifiers
```

```
source                  1..120
                        mol_type = protein
                        organism = synthetic construct
SEQUENCE: 513
EVHLLESGGG MVQPGGSRRL SCAASGFSFR NSAMSWVRQA PGKGLEWVSV IDGRGTTSNY  60
ADSVKGRFTI SRDNSKNTLY LQMNSLRAED TAVYYCAKKY SYYYYYMDVW GKGTTVTVSS  120

SEQ ID NO: 514          moltype = AA  length = 106
FEATURE                 Location/Qualifiers
source                  1..106
                        mol_type = protein
                        organism = synthetic construct
SEQUENCE: 514
SYELTQPLSV SVALGQTARI TCGGNNIGSK DVHWYQQKPG QAPVLVIYRD SNRPSGIPER  60
FSGSNSGNTA TLTISRAQAG DEADYYCQVW DSRTAVFGGG THLTAL                106

SEQ ID NO: 515          moltype = AA  length = 122
FEATURE                 Location/Qualifiers
source                  1..122
                        mol_type = protein
                        organism = synthetic construct
SEQUENCE: 515
EVQLLESGGG SVQPGGSLRL SCAASGFTFS SYAMNWVRQA PGKGLEWISI ISGGRRTGIT  60
YYAASVKGRF TISRDNSKNT LYLQMNSLRA EDTAVYYCAK MYNYYYYYID VWGKGTTVTV  120
SS                                                                122

SEQ ID NO: 516          moltype = AA  length = 106
FEATURE                 Location/Qualifiers
source                  1..106
                        mol_type = protein
                        organism = synthetic construct
SEQUENCE: 516
SYELTQPLSV SVALGQTARI TCGGNNIGSK DVHWYQQKPG QAPVLVIYRD SNRPSGIPER  60
FSGSNSGNTA TLTISRAQAG DEADYYCQVW DSNTAVFGGG TQLTAL                106

SEQ ID NO: 517          moltype = AA  length = 120
FEATURE                 Location/Qualifiers
source                  1..120
                        mol_type = protein
                        organism = synthetic construct
SEQUENCE: 517
ELQLLESGGG LVQPGGSLRL SCAASGFTFS SYAMSWVRQA PGKGLEWVSV ISGNGGNKNH  60
ADSVKGRFTI SRDNSKNTLY LQMNSLRAED TAVYYCAKKY SYYYYYMDVW GKGTTVTVSS  120

SEQ ID NO: 518          moltype = AA  length = 106
FEATURE                 Location/Qualifiers
source                  1..106
                        mol_type = protein
                        organism = synthetic construct
SEQUENCE: 518
SYELTQPLSV SVALGQTARI TCGGNNIGSK DVHWYQQKPG QAPVLVIYRD SNRPSGIPER  60
FSGSNSGNTA TLTISRAQAG DEADYYCQVW DSRTAVFGGG TQLTAL                106

SEQ ID NO: 519          moltype = AA  length = 124
FEATURE                 Location/Qualifiers
source                  1..124
                        mol_type = protein
                        organism = synthetic construct
SEQUENCE: 519
QVQLVESGGG VVQPGRSLRL SCAASGFTFR SYGMHWVRQA PGKGLEWVTI IWYDGSKKYY  60
ADSVRGRFTI SRDNSKNMLY LQMNSLRAED TAVYYCASQE FNWNDGGFYY MDVWGKGTTV  120
TVSS                                                              124

SEQ ID NO: 520          moltype = AA  length = 107
FEATURE                 Location/Qualifiers
source                  1..107
                        mol_type = protein
                        organism = synthetic construct
SEQUENCE: 520
DIQLTQSPSF LSASVGDRVT ITCRASQDIS SYLHWCQQKP GKAPKLLIYG ASTLQSGVPS  60
RFSGSGSGKE FTLTISSLQP EDFATYYCQQ LDNYPPTFGG GTKVEIK               107

SEQ ID NO: 521          moltype = AA  length = 120
FEATURE                 Location/Qualifiers
source                  1..120
                        mol_type = protein
                        organism = synthetic construct
SEQUENCE: 521
EVQLLESGGG LVQPGGSRRL SCAASGFTFS SYAMSWVRQA PGKGLEWVSV INTRGDITSY  60
```

```
ADSVKGRFTI SRDNSKNTLY LQMNSLRAED TAVYYCAKKY SYYYYYMDVW GKGTTVTVSS  120

SEQ ID NO: 522          moltype = AA  length = 106
FEATURE                 Location/Qualifiers
source                  1..106
                        mol_type = protein
                        organism = synthetic construct
SEQUENCE: 522
SYELTQPLSV SVALGQTARI TCGGNNIGSK NVHWHQQKPG QAPVLVIYRE SNRPSGIPER  60
FSGSNSGNTA TLTSSRAQAG DEADYYCQVW DSSTAVFGGG TQLTAL                 106

SEQ ID NO: 523          moltype = AA  length = 120
FEATURE                 Location/Qualifiers
source                  1..120
                        mol_type = protein
                        organism = synthetic construct
SEQUENCE: 523
EGQLLESGGG LVQPGGSLRL SCAASGFTFS RYAMSWIRQA PGKGLEWVSV INGSGGDKNY  60
ADSVKGRFTI SRDNSKNSLY LLMNGLRVED TAIYFCAKKF SYYYYYMDVW GKGTSVTVSS  120

SEQ ID NO: 524          moltype = AA  length = 106
FEATURE                 Location/Qualifiers
source                  1..106
                        mol_type = protein
                        organism = synthetic construct
SEQUENCE: 524
SYELTQPLSV SVALGQTARI TCGGNNIGSK NVHWHQQKPG QAPVLVIYRE SNRPSGIPGR  60
FSGSNSGNTA TLTSSRAQAG DEADYYCQVW DSSTAVFGGG TQLTAL                 106

SEQ ID NO: 525          moltype = AA  length = 120
FEATURE                 Location/Qualifiers
source                  1..120
                        mol_type = protein
                        organism = synthetic construct
SEQUENCE: 525
EVQLLESGGG LVQPGGSLRL SCAASGFTFS SYAMSWVRQA PGKGLEWVSA ITGSGRTTYF  60
VDSVKGRFTI SRDNSKNTLY LQMNSLRAED TAVYYCAKKF SYYYYYMDVW GKGTTVTVSS  120

SEQ ID NO: 526          moltype = AA  length = 106
FEATURE                 Location/Qualifiers
source                  1..106
                        mol_type = protein
                        organism = synthetic construct
SEQUENCE: 526
SYELTQPLSV SVALGQTARI TCGGNNIGSK DVHWYQQKPG QAPVLVIYRD SNRPSGIPER  60
FSGSNSGNTA TLTISRAQAG DEADYYCQVW DRKIAVFGGG TQLTAL                 106

SEQ ID NO: 527          moltype = AA  length = 120
FEATURE                 Location/Qualifiers
source                  1..120
                        mol_type = protein
                        organism = synthetic construct
SEQUENCE: 527
EVQLLESGGG LVQPGGSLRL SCAASGFTFS SYAMSWVRQA PGKGLEWVSV ISGSGGNKNY  60
ADSVKGRFTI SRDNSKNTLY LQMNSLRAED TAVYYCAKKF SYYYYYMDVW GKGTTVTVSS  120

SEQ ID NO: 528          moltype = AA  length = 106
FEATURE                 Location/Qualifiers
source                  1..106
                        mol_type = protein
                        organism = synthetic construct
SEQUENCE: 528
SYELTQPLSV SVALGQTARI TCGGNNIGSK DVHWYQQKPG QAPVLVIYRD SNRPSGIPER  60
FSGSNSGNTA TLTISRAQAG DEADYYCQVW DSRTAVFGGG TQLTAL                 106

SEQ ID NO: 529          moltype = AA  length = 120
FEATURE                 Location/Qualifiers
source                  1..120
                        mol_type = protein
                        organism = synthetic construct
SEQUENCE: 529
EVQLLESGGG LVQPGGSRRL SCAASGFTFS SYAMSWVRQA PGKGLEWVSV INTRGDSTSY  60
ADSVKGRFTI SRDNSKNTLY LQMNSLRAED TAVYYCAKKY SYYYYYMDVW GKGTTVTVSS  120

SEQ ID NO: 530          moltype = AA  length = 106
FEATURE                 Location/Qualifiers
source                  1..106
                        mol_type = protein
                        organism = synthetic construct
```

```
SEQUENCE: 530
SYELTQPLSV SVALGQTARI TCGGNNIGSK DVHWYQQKPG QAPVLVIYRD SNRPSGIPER  60
FSGSNSGNTA TLTISRAQAG DEADYYCQVW DSRTAVFGGG TQLTAL                106

SEQ ID NO: 531         moltype = AA  length = 120
FEATURE                Location/Qualifiers
source                 1..120
                       mol_type = protein
                       organism = synthetic construct
SEQUENCE: 531
EVQLLESGGG LVQPGGSRRL SCAASGFTFR TYAMSWVRQA PGKGLEWVSV INGRGDDTNY  60
ADSVKGRFTI SRDNSKNILF LQMNSLRAED TAVYYCAKKY SYYYYYMDVW GKGTTVTVSS  120

SEQ ID NO: 532         moltype = AA  length = 106
FEATURE                Location/Qualifiers
source                 1..106
                       mol_type = protein
                       organism = synthetic construct
SEQUENCE: 532
SYELTQPLSV SVALGQTARI TCGGNNIGSK DVHWYQQKPG QAPVLVIYRD SNRPSGIPER  60
FSGSNSGNTA TLTISRAQAG DEADYYCQVW DSRTAVFGGG TQLTAL                106

SEQ ID NO: 533         moltype = AA  length = 120
FEATURE                Location/Qualifiers
source                 1..120
                       mol_type = protein
                       organism = synthetic construct
SEQUENCE: 533
EVQLLESGGG LVQPGGSLRL SCAASGFTFS SFAMSWVRQA PGKGLEWVSV ISGNGDKKNY  60
ADSVKGRFTI SRDNSKNTLY LQMNSLRAED TAVYYCAKKY SYYYYYMDVW GKGTTVTVSS  120

SEQ ID NO: 534         moltype = AA  length = 106
FEATURE                Location/Qualifiers
source                 1..106
                       mol_type = protein
                       organism = synthetic construct
SEQUENCE: 534
SYELTQPLSV SVALGQTARI TCGGNNIGSK DVHWYQQKPG QAPVLVIYRD SNRPSGIPER  60
FSGSNSGNTA TLTISRAQAG DEADYYCQVW DSRTAVFGGG TQLTAL                106

SEQ ID NO: 535         moltype = AA  length = 120
FEATURE                Location/Qualifiers
source                 1..120
                       mol_type = protein
                       organism = synthetic construct
SEQUENCE: 535
EGQLLESGGG LVQPGGSLRL SCAASGFTFS RYAMSWIRQA PGKGLEWVSV IDGSGGDKNY  60
ADSVKGRFTI SRDNSKNSLY LLMNGLRVED TAIYFCAKKF SYYYYYMDVW GKGTSVTVSS  120

SEQ ID NO: 536         moltype = AA  length = 106
FEATURE                Location/Qualifiers
source                 1..106
                       mol_type = protein
                       organism = synthetic construct
SEQUENCE: 536
SYELTQPLSV SVALGQTARI TCGGNNIGGK DVHWYQQKPG QAPVLVIYRD SNRPSGIPER  60
FSGSNSGNTA TLTISRAQAG DEADYYCQVW DSRTAVFGGG TQLTAL                106

SEQ ID NO: 537         moltype = AA  length = 120
FEATURE                Location/Qualifiers
source                 1..120
                       mol_type = protein
                       organism = synthetic construct
SEQUENCE: 537
EVQLLESGGG LLQPGGSRRL SCAATEFTFR SYAMSWVRQS PGKGLEWVSV ISGRGDNTYY  60
ADSVKGRFTI SRDNSKNTLY LQMNSLRAED TAVYYCAKMY SYYYYYMDVW GKGTTVTVSS  120

SEQ ID NO: 538         moltype = AA  length = 106
FEATURE                Location/Qualifiers
source                 1..106
                       mol_type = protein
                       organism = synthetic construct
SEQUENCE: 538
SYELTQPLSV SVALGQTARI TCGGNNIGSK NVHWHQQKPG QAPVLVIYRE SNRPSGIPER  60
FSGSNSGNTA TLTSSRAQAG DEADYYCQVW DSSTAVFGGG TQLTAL                106

SEQ ID NO: 539         moltype = AA  length = 124
FEATURE                Location/Qualifiers
source                 1..124
```

```
                        mol_type = protein
                        organism = synthetic construct
SEQUENCE: 539
QVQLVESGGG VVQPGRSLRL SCAASGFTFR SYGMHWVRQA PGKGLEWVAI IWYDGSKKYY  60
ADSVKGRFTI SRDNSKNILY LQMNSLRAED TAVYYCARQE FNWNDGGYYY MDVWGKGTTV  120
TVSS                                                              124

SEQ ID NO: 540          moltype = AA  length = 107
FEATURE                 Location/Qualifiers
source                  1..107
                        mol_type = protein
                        organism = synthetic construct
SEQUENCE: 540
DIQLTQSPSF LSASVGDRVT ITCRASQGIS SYLDWCQQKP GKAPKLLIYA ASTLQSGVPS  60
RFSGSGSGTE FTLTISSLQP EDFATYYCQQ LDNYPPTFGG GTKVEIK               107

SEQ ID NO: 541          moltype = AA  length = 119
FEATURE                 Location/Qualifiers
source                  1..119
                        mol_type = protein
                        organism = synthetic construct
SEQUENCE: 541
QVQLVESGGG VVQPGRSLRL SCVASGFTFR SFGMHWVRQA PGKGLEWVVV ISNDGSHKYY  60
VESVKGRFTI SRDNSKNTLY LQMNSLRPED TAVYYCARRD YYGSGMDVWG KGTTVTVSS   119

SEQ ID NO: 542          moltype = AA  length = 108
FEATURE                 Location/Qualifiers
source                  1..108
                        mol_type = protein
                        organism = synthetic construct
SEQUENCE: 542
SYELTQPPSV SVSPGQTARI TCSGDALPKK YAYWYQQKSG QAPVLVIYED RKRPSGIPER  60
FSGSSSGTMA TLTISGAQVE DEADYYCYST DSSGNHAVFG GGTQLTAL              108

SEQ ID NO: 543          moltype = AA  length = 119
FEATURE                 Location/Qualifiers
source                  1..119
                        mol_type = protein
                        organism = synthetic construct
SEQUENCE: 543
QVQLVESGGG VVQPGRSLRL SCVASGFTFR SYGMHWVRQA PGKGLEWVVV ISNDGSHKYY  60
VESVKGRFTI SRDNSKNTLY LQMNSLRAED TAVYYCARRD YYGSGMDVWG KGTTVTVSS   119

SEQ ID NO: 544          moltype = AA  length = 108
FEATURE                 Location/Qualifiers
source                  1..108
                        mol_type = protein
                        organism = synthetic construct
SEQUENCE: 544
SYELTQPPSV SVSPGQTARI TCSGDALPKK YAYWYQQKSG QAPVLVIYED RKRPSGIPER  60
FSGSSSGTMA TLTISGAQVE DEADYYCYST DSSGNHAVFG GGTQLTAL              108

SEQ ID NO: 545          moltype = AA  length = 117
FEATURE                 Location/Qualifiers
source                  1..117
                        mol_type = protein
                        organism = synthetic construct
SEQUENCE: 545
QVQVVQSGAE VKNPGASVKV SCKASGYTFT GYYMHWVRQA PGQGLEWMGW IYPNSGRTNY  60
AQKFQGRVTM TRDTSISTAY MELSRLRSDD TAVYYCARLE QLVFDYWGQG TLVTVSS     117

SEQ ID NO: 546          moltype = AA  length = 108
FEATURE                 Location/Qualifiers
source                  1..108
                        mol_type = protein
                        organism = synthetic construct
SEQUENCE: 546
EIVLTQSPGT LSLSPGERAT LSCRASQSVS SSYLAWYQQK PGQGPRLLIY GASSRATGIP  60
DRFSGSGSGT DFTLTISRLE PEDFAVYYCQ QYGSSPITFG QGTRLEIK              108

SEQ ID NO: 547          moltype = AA  length = 117
FEATURE                 Location/Qualifiers
source                  1..117
                        mol_type = protein
                        organism = synthetic construct
SEQUENCE: 547
QVQVVQSGAE VKKPGASVKV SCKTSGYTFT DYYIHWVRQA PGQGLEWMGW IYPKSGRTDN  60
AQNFKGRVAM TRDTSINTAY LELNRLRSDD TAIYYCARLE ELVFDYWGQG TLVTVSS     117
```

```
SEQ ID NO: 548          moltype = AA  length = 107
FEATURE                 Location/Qualifiers
source                  1..107
                        mol_type = protein
                        organism = synthetic construct
SEQUENCE: 548
DIQMTQSPSS VSASVGDRVT ITCRASQVIS RWLAWYQLKP GKAPKLLIYE ASSLQSWVPS  60
RFSGSGSGTD FTLTISSLQP EDFATYYCQQ ANSFPWTFGQ GTKVEIK                107

SEQ ID NO: 549          moltype = AA  length = 117
FEATURE                 Location/Qualifiers
source                  1..117
                        mol_type = protein
                        organism = synthetic construct
SEQUENCE: 549
QVQVVQSGAE VKKPGASVKV SCKTSGYTFT DQYIHWVRQA PGQGLEWMGW IYPKSGRTDN  60
AQKFKGRVAM TRDTSINTAY MELSSLRSDD TATYYCARLE ELVFDYWGQG TLVTVSS     117

SEQ ID NO: 550          moltype = AA  length = 106
FEATURE                 Location/Qualifiers
source                  1..106
                        mol_type = protein
                        organism = synthetic construct
SEQUENCE: 550
DIQMTQSPST LSASVGDRVT ITCRASQSIS SWLAWYQQKP GKAPKLLIYK ASSLESGVPS  60
RFSGSGSGTE FTLTISSLQP DDFATYYCQQ YNSYSTFGQG TKLEIK                 106

SEQ ID NO: 551          moltype = AA  length = 453
FEATURE                 Location/Qualifiers
source                  1..453
                        mol_type = protein
                        organism = synthetic construct
SEQUENCE: 551
QAQLVQSGSE LKKPGASVKV SCKASGYTFT KHSMNWVRYA PGQGLEWMGW INTNTGNPTY  60
AQRFTGRFVF SLDTSVTTAY LQISSLKAED TAVYYCAREG DYDFWSGFFN FDYWGRGTLV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
AAGGPSVFLF PPKPKDTLMI SRTPEVTCVV VDVSHEDPEV KFNWYVDGVE VHNAKTKPRE  300
EQYNSTYRVV SVLTVLHQDW LNGKEYKCKV SNKALPAPIE KTISKAKGQP RRPRVYTLPP  360
SREEMTKNQV SLVCLVKGFY PSDIAVEWES NGQPENNYKT TPPVLDSDGS FFLYSVLTVD  420
KSRWQQGNVF SCSVMHEALH NHYTQKSLSL SPG                               453

SEQ ID NO: 552          moltype = AA  length = 214
FEATURE                 Location/Qualifiers
source                  1..214
                        mol_type = protein
                        organism = synthetic construct
SEQUENCE: 552
DIQMTQSPSS LSASVGDRVT ITCRASQGIR NDLGWYQRKP GDAPKRLIYA ASSLQSGVPS  60
RFSGSGSGAE FTLTISSLQP EDFATYYCLQ HNSYPRTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 553          moltype = AA  length = 449
FEATURE                 Location/Qualifiers
source                  1..449
                        mol_type = protein
                        organism = synthetic construct
SEQUENCE: 553
EVQLVESGGG LVQPGGSLRL SCAASGFTLS SYTMNWVRYA PGKGLEWVSY ISSSSRTIYY  60
SDRVKGRFSI SRDNAKNSLY LQMNSLRDED TALYYCARED YYDSSGFDNW GRGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPRRPR VYTLPPSREE  360
MTKNQVSLVC LVKGFYPSDI AVEWESNGQP ENNYKTTPPV LDSDGSFFLY SVLTVDKSRW  420
QQGNVFSCSV MHEALHNHYT QKSLSLSPG                                    449

SEQ ID NO: 554          moltype = AA  length = 214
FEATURE                 Location/Qualifiers
source                  1..214
                        mol_type = protein
                        organism = synthetic construct
SEQUENCE: 554
DIRMTQSPSS FSASTGDRVT ITCRASQGIS SYLAWYQRKP GDAPKLLIYT ASTLQSGVPS  60
RFSGSGSGTD FTLTIRSLQS EDFATYYCQQ YYSYPRTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214
```

```
SEQ ID NO: 555          moltype = AA  length = 453
FEATURE                 Location/Qualifiers
source                  1..453
                        mol_type = protein
                        organism = synthetic construct
SEQUENCE: 555
QVQLVQSGAE VKKPGASVKV SCKASGYTFT SYDINWVRYA TGQGLEWMGW MNPKSGKTGY  60
AQKFQGRITM TRNTPISTVY MDLSSLRSED TAVYYCAREG HYDFWTGYYS FDYWGRGTLV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
AAGGPSVFLF PPKPKDTLMI SRTPEVTCVV VDVSHEDPEV KFNWYVDGVE VHNAKTKPRE  300
EQYNSTYRVV SVLTVLHQDW LNGKEYKCKV SNKALPAPIE KTISKAKGQP RRPRVYTLPP  360
SREEMTKNQV SLVCLVKGFY PSDIAVEWES NGQPENNYKT TPPVLDSDGS FFLYSVLTVD  420
KSRWQQGNVF SCSVMHEALH NHYTQKSLSL SPG                               453

SEQ ID NO: 556          moltype = AA  length = 214
FEATURE                 Location/Qualifiers
source                  1..214
                        mol_type = protein
                        organism = synthetic construct
SEQUENCE: 556
DIQMTQSPSS LSASVGDRVT ITCRASQGIR NDLGWYQRTP GDAPKRLIYA ASSLQSGVPS  60
RFSGSGSGTE FTLTISSLQP EDFATYYCLQ HYSYPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 557          moltype = AA  length = 447
FEATURE                 Location/Qualifiers
source                  1..447
                        mol_type = protein
                        organism = synthetic construct
SEQUENCE: 557
QVQLVESGGG VVQPGRSLRL SCAASGFTFS GYGMHWVRYA PGKGLDWVAI IYYNGNNKYY  60
ADRVKGRFTI SRDNSKNTLY LQMNSLRAED TAVYYCARGG GYNWFDPWGR GTLVIVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPRRPRVY TLPPSREEMT  360
KNQVSLVCLV KGFYPSDIAV EWESNGQPEN NYKTTPPVLD SDGSFFLYSV LTVDKSRWQQ  420
GNVFSCSVMH EALHNHYTQK SLSLSPG                                      447

SEQ ID NO: 558          moltype = AA  length = 214
FEATURE                 Location/Qualifiers
source                  1..214
                        mol_type = protein
                        organism = synthetic construct
SEQUENCE: 558
DIQMTQSPSS LSASVGDRVT ITCRPSQSIS NYLNWYQRKP GDAPKLLIYA ASSLQSGVPS  60
RFSGSGSGTD FTLTISSLQP EDFATYYCQQ SYSTPFTFGR GTRLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 559          moltype = AA  length = 455
FEATURE                 Location/Qualifiers
source                  1..455
                        mol_type = protein
                        organism = synthetic construct
SEQUENCE: 559
EVQLVESGGD LVQPGRSLRL SCAASGFTFD DCVIHWVRYA PGKGLEWVSG ITWNSGRIGY  60
ADRVKGRFTI SRDNAKNSLY LQMNSLRVED TALYYCAKEG NYDFWSTYYR GYFDLWGRGT  120
LVTVSSASTK GPSVFPLAPS SKSTSGGTAA LGCLVKDYFP EPVTVSWNSG ALTSGVHTFP  180
AVLQSSGLYS LSSVVTVPSS SLGTQTYICN VNHKPSNTKV DKKVEPKSCD KTHTCPPCPA  240
PEAAGGPSVF LFPPKPKDTL MISRTPEVTC VVVDVSHEDP EVKFNWYVDG VEVHNAKTKP  300
REEQYNSTYR VVSVLTVLHQ DWLNGKEYKC KVSNKALPAP IEKTISKAKG QPRRPRVYTL  360
PPSREEMTKN QVSLVCLVKG FYPSDIAVEW ESNGQPENNY KTTPPVLDSD GSFFLYSVLT  420
VDKSRWQQGN VFSCSVMHEA LHNHYTQKSL SLSPG                             455

SEQ ID NO: 560          moltype = AA  length = 214
FEATURE                 Location/Qualifiers
source                  1..214
                        mol_type = protein
                        organism = synthetic construct
SEQUENCE: 560
DIQMTQSPSS LSASVGDRVT ITCRASQGIR NDLGWYQRKP GDAPKRLIYA ASSLQGGVPL  60
RFSGSGSGTE FTLTISSLQP EDFATYYCLQ HNSYPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 561          moltype = AA  length = 450
```

```
FEATURE                Location/Qualifiers
source                 1..450
                       mol_type = protein
                       organism = synthetic construct
SEQUENCE: 561
EVQLVDSGGG LVQPGGSLRL SCSGSGFTFS SYWMSWVRYA PGKGLEWVAN IKQDGSQKYY  60
VDRVKGRFTI SRDNVKNSLY LQMNSLRVED TAVYYCARDE SSSWYWYFDL WGRGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPEAAG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPRRP RVYTLPPSRE  360
EMTKNQVSLV CLVKGFYPSD IAVEWESNGQ PENNYKTTPP VLDSDGSFFL YSVLTVDKSR  420
WQQGNVFSCS VMHEALHNHY TQKSLSLSPG                                  450

SEQ ID NO: 562         moltype = AA  length = 214
FEATURE                Location/Qualifiers
source                 1..214
                       mol_type = protein
                       organism = synthetic construct
SEQUENCE: 562
DIQMTQSPST LSASVGDRVT LTCRASQNIV KWLAWYQRKP GDAPKLLIYK ASSLESGVPS  60
WFSGSGSGTE FTLTINSLQP DDFATYYCQQ YYTYSRTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 563         moltype =   length =
SEQUENCE: 563
000

SEQ ID NO: 564         moltype = AA  length = 219
FEATURE                Location/Qualifiers
source                 1..219
                       mol_type = protein
                       organism = synthetic construct
SEQUENCE: 564
RIVVTQTPLS SPVTLGQPAS ISCRSSQRFV HSDGNTYLSW LQDRPGQPPR LLIYKISNRI  60
SGVPDRFSGS GAGTDFKLKI SRVEAEDVGI YYCMQATQFP YTFGQGTKLE IKRTVAAPSV  120
FIFPPSDKQL KSGTARVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 565         moltype = AA  length = 447
FEATURE                Location/Qualifiers
source                 1..447
                       mol_type = protein
                       organism = synthetic construct
SEQUENCE: 565
QGQLVESGGG VVQPGRSLRL SCEASGFTFR SYGMHWVRYP PGKGLEWVAI IWYDGGKKYY  60
GDRVKGRFTI SRDNPKNTLY LQMNSLRPED TAVYYCMAYD YSNGFDIWGR GTMVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPRRPRVY TLPPSREEMT  360
KNQVSLVCLV KGFYPSDIAV EWESNGQPEN NYKTTPPVLD SDGSFFLYSV LTVDKSRWQQ  420
GNVFSCSVMH EALHNHYTQK SLSLSPG                                     447

SEQ ID NO: 566         moltype = AA  length = 219
FEATURE                Location/Qualifiers
source                 1..219
                       mol_type = protein
                       organism = synthetic construct
SEQUENCE: 566
DIVMTQTPLS SPVTLGQPAS ISCRSSQSFV HSDGSTYLSW LQRRPGDPPR LLIYKISNRF  60
SGVPDRFSGR GAGTDFTLKI SRVEAEDVGI YYCMQNTQFP YTFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 567         moltype = AA  length = 450
FEATURE                Location/Qualifiers
source                 1..450
                       mol_type = protein
                       organism = synthetic construct
SEQUENCE: 567
QVQLVQSGAE VKKPGASVKV SCKASGYTVT GYYMHWVRYA PGQGLEWMGW INPNSGGTNF  60
AQRFQGRVTM TRDTSISTFY MDLNRLRSDD TAVYYCARGG APVSYWFFDL WGRGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPEAAG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPRRP RVYTLPPSRE  360
EMTKNQVSLV CLVKGFYPSD IAVEWESNGQ PENNYKTTPP VLDSDGSFFL YSVLTVDKSR  420
```

```
WQQGNVFSCS VMHEALHNHY TQKSLSLSPG                          450

SEQ ID NO: 568         moltype = AA  length = 214
FEATURE                Location/Qualifiers
source                 1..214
                       mol_type = protein
                       organism = synthetic construct
SEQUENCE: 568
DIQMTQSPSS LSASVGDRVT ITCRASQSIS RYLNWYQRKP GDAPKVLIYN TSSLKSGVPS  60
RFSGSGSGTD FTLTISSLQP EDFGTFYCQQ SHSTPFTFGP GTKVDIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                      214

SEQ ID NO: 569         moltype = AA  length = 447
FEATURE                Location/Qualifiers
source                 1..447
                       mol_type = protein
                       organism = synthetic construct
SEQUENCE: 569
QGQLVESGGG VVQPGRSLRL SCAASGFTFR GFGMHWVRYA PGKGLEWVAI IYYDGKNKYY  60
ADRVKGRFTI SRDNSKNTLY LQMNSLRAED TAVYYCAKGG GYNWFDPWGR GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPRRPRVY TLPPSREEMT  360
KNQVSLVCLV KGFYPSDIAV EWESNGQPEN NYKTTPPVLD SDGSFFLYSV LTVDKSRWQQ  420
GNVFSCSVMH EALHNHYTQK SLSLSPG                             447

SEQ ID NO: 570         moltype = AA  length = 214
FEATURE                Location/Qualifiers
source                 1..214
                       mol_type = protein
                       organism = synthetic construct
SEQUENCE: 570
DIQMTQSPSS LSASVGDRVT ITCRASQSIS TYLNWYQRKP GDAPKLLIYS ASSLQSGVPS  60
RFSGSGSGTD FTLTISNLQP EDFAIYYCQR SYSPPFTFGP GTKLDIRRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                      214

SEQ ID NO: 571         moltype = AA  length = 455
FEATURE                Location/Qualifiers
source                 1..455
                       mol_type = protein
                       organism = synthetic construct
SEQUENCE: 571
EVQLVESGGV LVKTGGSLRL SCVASGFSFK KAWMNWVRYA PGKGLEWVGR IKRNSDGGAA  60
DYAARVKDRF TLSRDDSKNT LYLQMNSLKT EDTAVYYCTT LDSSSWYVGY YYMDVWGRGT  120
TVTVSSASTK GPSVFPLAPS SKSTSGGTAA LGCLVKDYFP EPVTVSWNSG ALTSGVHTFP  180
AVLQSSGLYS LSSVVTVPSS SLGTQTYICN VNHKPSNTKV DKKVEPKSCD KTHTCPPCPA  240
PEAAGGPSVF LFPPKPKDTL MISRTPEVTC VVVDVSHEDP EVKFNWYVDG VEVHNAKTKP  300
REEQYNSTYR VVSVLTVLHQ DWLNGKEYKC KVSNKALPAP IEKTISKAKG QPRRPRVYTL  360
PPSREEMTKN QVSLVCLVKG FYPSDIAVEW ESNGQPENNY KTTPPVLDSD GSFFLYSVLT  420
VDKSRWQQGN VFSCSVMHEA LHNHYTQKSL SLSPG                     455

SEQ ID NO: 572         moltype = AA  length = 214
FEATURE                Location/Qualifiers
source                 1..214
                       mol_type = protein
                       organism = synthetic construct
SEQUENCE: 572
DIHMTQSPSS VSASLGDRVT FTCRASQNIN NWLAWYQRKP GDAPKLLIYT ASSLQSGVPS  60
RFSGSGSGTD FTLTISSLQP DDFATYYCQQ AHSLPITFGQ GTRLGIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                      214

SEQ ID NO: 573         moltype = AA  length = 455
FEATURE                Location/Qualifiers
source                 1..455
                       mol_type = protein
                       organism = synthetic construct
SEQUENCE: 573
EVQLVESGGG LVKTGGSHRL SCVASGFSFK KAWMNWVRYA PGKGLEWVGR IKRNSDGGTT  60
DYAARVKGRF ILSRDDSKNT LYLQMNSLKT EDTAVYYCTT LDSSSWYVGY YYMDVWGRGT  120
TVTVSSASTK GPSVFPLAPS SKSTSGGTAA LGCLVKDYFP EPVTVSWNSG ALTSGVHTFP  180
AVLQSSGLYS LSSVVTVPSS SLGTQTYICN VNHKPSNTKV DKKVEPKSCD KTHTCPPCPA  240
PEAAGGPSVF LFPPKPKDTL MISRTPEVTC VVVDVSHEDP EVKFNWYVDG VEVHNAKTKP  300
REEQYNSTYR VVSVLTVLHQ DWLNGKEYKC KVSNKALPAP IEKTISKAKG QPRRPRVYTL  360
PPSREEMTKN QVSLVCLVKG FYPSDIAVEW ESNGQPENNY KTTPPVLDSD GSFFLYSVLT  420
VDKSRWQQGN VFSCSVMHEA LHNHYTQKSL SLSPG                     455
```

```
SEQ ID NO: 574          moltype = AA  length = 214
FEATURE                 Location/Qualifiers
source                  1..214
                        mol_type = protein
                        organism = synthetic construct
SEQUENCE: 574
DIQMTQSPSS VSASVGDRVT ITCRASQDIN NWLAWYQRKP GDAPKILIYT ASNLQSGVPS  60
RFSGSGSGTD FTLTISSLQP EDFATYFCQQ AHSLPITFGQ GTRLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 575          moltype = AA  length = 455
FEATURE                 Location/Qualifiers
source                  1..455
                        mol_type = protein
                        organism = synthetic construct
SEQUENCE: 575
EVQLVESGGG LVKTGGSLRL SCVASGFSFK KAWMNWVRYA PGKGLEWVGR IKRNTDGGPA  60
DYAARVKGRF TLSRDDSKKT LYLQMNSLKT EDTAVYYCTT LDSSSWYVGY YYMDVWGRGT  120
TVTVSSASTK GPSVFPLAPS SKSTSGGTAA LGCLVKDYFP EPVTVSWNSG ALTSGVHTFP  180
AVLQSSGLYS LSSVVTVPSS SLGTQTYICN VNHKPSNTKV DKKVEPKSCD KTHTCPPCPA  240
PEAAGGPSVF LFPPKPKDTL MISRTPEVTC VVVDVSHEDP EVKFNWYVDG VEVHNAKTKP  300
REEQYNSTYR VVSVLTVLHQ DWLNGKEYKC KVSNKALPAP IEKTISKAKG QPRRPRVYTL  360
PPSREEMTKN QVSLVCLVKG FYPSDIAVEW ESNGQPENNY KTTPPVLDSD GSFFLYSVLT  420
VDKSRWQQGN VFSCSVMHEA LHNHYTQKSL SLSPG                             455

SEQ ID NO: 576          moltype = AA  length = 214
FEATURE                 Location/Qualifiers
source                  1..214
                        mol_type = protein
                        organism = synthetic construct
SEQUENCE: 576
DIQMTQSPSS VSASVGDRVI ITCRASQDIN NWLAWYLRRP GDAPKLLIYA ASSLQSGVPS  60
RFSGSGSGTD FTLTIGSLQP EDFATYYCQQ AHSLPITFGQ GTRLEIQRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 577          moltype = AA  length = 455
FEATURE                 Location/Qualifiers
source                  1..455
                        mol_type = protein
                        organism = synthetic construct
SEQUENCE: 577
EVQLVESGGG LVKTGGSLRL SCVASGFSFK KAWMNWVRYA PGKGLEWVGR IKRNTDGGTA  60
DYAARVKGRF TLSRDDSKKT LFLQMNSLKT EDTAVYYCTT LDSSSYYVGY YYMDVWGRGT  120
TVTVSSASTK GPSVFPLAPS SKSTSGGTAA LGCLVKDYFP EPVTVSWNSG ALTSGVHTFP  180
AVLQSSGLYS LSSVVTVPSS SLGTQTYICN VNHKPSNTKV DKKVEPKSCD KTHTCPPCPA  240
PEAAGGPSVF LFPPKPKDTL MISRTPEVTC VVVDVSHEDP EVKFNWYVDG VEVHNAKTKP  300
REEQYNSTYR VVSVLTVLHQ DWLNGKEYKC KVSNKALPAP IEKTISKAKG QPRRPRVYTL  360
PPSREEMTKN QVSLVCLVKG FYPSDIAVEW ESNGQPENNY KTTPPVLDSD GSFFLYSVLT  420
VDKSRWQQGN VFSCSVMHEA LHNHYTQKSL SLSPG                             455

SEQ ID NO: 578          moltype = AA  length = 214
FEATURE                 Location/Qualifiers
source                  1..214
                        mol_type = protein
                        organism = synthetic construct
SEQUENCE: 578
DIQMTQSPSS VSASVGDRVT ITCRASQDIN NWLAWYQRKP GDAPKLLIYT ASSLQSGVPS  60
RFSGSGSGTD FTLTIGSLQP EDFATYYCQQ AHSLPITFGQ GTRLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 579          moltype = AA  length = 450
FEATURE                 Location/Qualifiers
source                  1..450
                        mol_type = protein
                        organism = synthetic construct
SEQUENCE: 579
QVQLVQSGAE VKKPGASVKV SCKASGYTFT SHWMHWVRKA PGQGLEWIGE FNPSNGRTNY  60
NEEFKSKATM TVDTSTNTAY MELSSLRSED TAVYYCASRD YDYDGRYFDY WGQGTLVTVS  120
SASTKGPSVF PLAPSSKSTS GGTAALGCLV ADYFPEPVTV SWNSGALTSG VHTFPAVLQS  180
SGLYSLSSVV TVPSSSLGTQ TYICNVNHKP SNTKVDEKVE PKSCDKTHTC PPCPAPEAAG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRE  360
EMTDNQVSLT CLVKGFYPSD IAVEWESNGQ PENNYKTTPP VLMSDGSFFL ASKLTVDKSR  420
WQQGNVFSCS VMHEALHNHY TQKSLSLSPG                                   450
```

```
SEQ ID NO: 580         moltype = AA  length = 213
FEATURE                Location/Qualifiers
source                 1..213
                       mol_type = protein
                       organism = synthetic construct
SEQUENCE: 580
EIVMTQSPGT LSVSPGKRAT LSCRASQSVS SNLAWYQRKP GDGPRLLIYS TSTRATGIPA  60
RFSGSGSGTE FTLTISSLQS EDSAVYYCQH YNNWPHFGQG TRLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 581         moltype = AA  length = 453
FEATURE                Location/Qualifiers
source                 1..453
                       mol_type = protein
                       organism = synthetic construct
SEQUENCE: 581
EVQLVESGGG LVQPGRSLRL SCAASGFTFD DYTMHWVRYA PGKGLEWVSG ISWNSGSIGY  60
ADRVKGRFTI SRDNAKNSLY LQMNSLRAED TALYYCAKDS SGYGYYYYYS MDVWGRGTTV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
AAGGPSVFLF PPKPKDTLMI SRTPEVTCVV VDVSHEDPEV KFNWYVDGVE VHNAKTKPRE  300
EQYNSTYRVV SVLTVLHQDW LNGKEYKCKV SNKALPAPIE KTISKAKGQP RRPRVYTLPP  360
SREEMTKNQV SLVCLVKGFY PSDIAVEWES NGQPENNYKT TPPVLDSDGS FFLYSVLTVD  420
KSRWQQGNVF SCSVMHEALH NHYTQKSLSL SPG                               453

SEQ ID NO: 582         moltype = AA  length = 213
FEATURE                Location/Qualifiers
source                 1..213
                       mol_type = protein
                       organism = synthetic construct
SEQUENCE: 582
EIVMTQSPAT LSVSPGERAT LSCRASQSVS SNLAWYQRKP GDAPRLLIYG ASTRATGIPA  60
RFSGSGSGTE FTLTISSLQS EDFAVYYCQL YYNWPHFGQG TRLAIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 583         moltype = AA  length = 452
FEATURE                Location/Qualifiers
source                 1..452
                       mol_type = protein
                       organism = synthetic construct
SEQUENCE: 583
QVQLVESGGG VVQPGRSLRL SCAASGFTFS TYGMHWVRYA PGKGLEWVAV IWYDGSHKYY  60
ADRVKGRFTI SRDNSKKTLY LQMNSLRAED TGIYYCARTG ISGNMSYFYF DHWGRGILVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR RPRVYTLPPS  360
REEMTKNQVS LVCLVKGFYP SDIAVEWESN GQPENNYKTT PPVLDSDGSF FLYSVLTVDK  420
SRWQQGNVFS CSVMHEALHN HYTQKSLSLS PG                                452

SEQ ID NO: 584         moltype = AA  length = 219
FEATURE                Location/Qualifiers
source                 1..219
                       mol_type = protein
                       organism = synthetic construct
SEQUENCE: 584
DIVMTQSPDS LAVSLGERAT INCKSSQSVL YSSKNRNYLA WYQRKQGDPP KMFIYWASTR  60
ESGVPDRFSG SGSGTDFTLT ISSLQAEDVA VYYCQQYYGP VTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 585         moltype = AA  length = 366
FEATURE                Location/Qualifiers
source                 1..366
                       mol_type = protein
                       organism = synthetic construct
SEQUENCE: 585
LRSDDTAVYY CARGVRGNYY YYYMDVWGRG TTVTVSSAST KGPSVFPLAP SSKSTSGGTA  60
ALGCLVKDYF PEPVTVSWNS GALTSGVHTF PAVLQSSGLY SLSSVVTVPS SSLGTQTYIC  120
NVNHKPSNTK VDKKVEPKSC DKTHTCPPCP APEAAGGPSV FLFPPKPKDT LMISRTPEVT  180
CVVVDVSHED PEVKFNWYVD GVEVHNAKTK PREEQYNSTY RVVSVLTVLH QDWLNGKEYK  240
CKVSNKALPA PIEKTISKAK GQPRRPRVYT LPPSREEMTK NQVSLVCLVK GFYPSDIAVE  300
WESNGQPENN YKTTPPVLDS DGSFFLYSVL TVDKSRWQQG NVFSCSVMHE ALHNHYTQKS  360
LSLSPG                                                             366

SEQ ID NO: 586         moltype = AA  length = 214
FEATURE                Location/Qualifiers
```

```
source                  1..214
                        mol_type = protein
                        organism = synthetic construct
SEQUENCE: 586
EIVLTQSPDF QSVTPKEKVT ITCRASQSIG SKLHWYQRKP DDSPKLLIKY ASQSFSGVPS  60
RFSGSGSGTD FNLTINSLEA EDAATFYCHQ SSGLPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                            214

SEQ ID NO: 587          moltype = AA  length = 453
FEATURE                 Location/Qualifiers
source                  1..453
                        mol_type = protein
                        organism = synthetic construct
SEQUENCE: 587
EVNLVESGGG LVQPGRSLRL SCAASGFTFD DYTMHWVRYV PGKGLEWVSN ISWNSGSLGY  60
ADRVKGRFTI SRDNAKDSLY LQMNSLRVED TALYYCAKDS SGYGHYNSYY MDVWGRGTTV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
AAGGPSVFLF PPKPKDTLMI SRTPEVTCVV VDVSHEDPEV KFNWYVDGVE VHNAKTKPRE  300
EQYNSTYRVV SVLTVLHQDW LNGKEYKCKV SNKALPAPIE KTISKAKGQP RRPRVYTLPP  360
SREEMTKNQV SLVCLVKGFY PSDIAVEWES NGQPENNYKT TPPVLDSDGS FFLYSVLTVD  420
KSRWQQGNVF SCSVMHEALH NHYTQKSLSL SPG                             453

SEQ ID NO: 588          moltype = AA  length = 214
FEATURE                 Location/Qualifiers
source                  1..214
                        mol_type = protein
                        organism = synthetic construct
SEQUENCE: 588
DIQMTQSPSS LSASVGDRVT ITCRASQSIR NYLNWYQRKP GDAPKVLIYS ASSLQSGVPS  60
RFSGSGSGTD FTLTISSLQP EDFASFYCQQ TYSTPITFGQ GTRLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                            214

SEQ ID NO: 589          moltype = AA  length = 450
FEATURE                 Location/Qualifiers
source                  1..450
                        mol_type = protein
                        organism = synthetic construct
SEQUENCE: 589
QVQLVQSGAE VKKPGASVKV SCKASGYTFT SHWMHWVRKA PGQGLEWIGE FNPSNGRTNY  60
NEEFKSKATM TVDTSTNTAY MELSSLRSED TAVYYCASRD YDYDGRYFDY WGQGTLVTVS  120
SASTKGPSVF PLAPSSKSTS GGTAALGCLV ADYFPEPVTV SWNSGALTSG VHTFPAVLQS  180
SGLYSLSSVV TVPSSSLGTQ TYICNVNHKP SNTKVDEKVE PKSCDKTHTC PPCPAPEAAG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRE  360
EMTDNQVSLT CLVKGFYPSD IAVEWESNGQ PENNYKTTPP VLMSDGSFFL ASKLTVDKSR  420
WQQGNVFSCS VMHEALHNHY TQKSLSLSPG                                 450

SEQ ID NO: 590          moltype = AA  length = 213
FEATURE                 Location/Qualifiers
source                  1..213
                        mol_type = protein
                        organism = synthetic construct
SEQUENCE: 590
RIQMTQSPSS LSASVGDRVT ITCSASSSVT YMYWYQDKPG KAPKLLIYDT SNLASGVPSR  60
FSGSGSGTDY TFTISSLQPE DIATYYCQQW SSHIFTFGQG TKVEIKRTVA APSVFIFPPS  120
DKQLKSGTAR VVCLLNNFYP REAKVQWKVD NALQSGNSQE SVTEQDSKDS TYSLSSTLTL  180
SKADYEKHKV YACEVTHQGL SSPVTKSFNR GEC                             213

SEQ ID NO: 591          moltype = AA  length = 450
FEATURE                 Location/Qualifiers
source                  1..450
                        mol_type = protein
                        organism = synthetic construct
SEQUENCE: 591
QVQLVQSGAE VKKPGASVKV SCKASGYTFT SHWMHWVRYA PGQGLEWIGE FNPSNGRTNY  60
NEKFKSKATM TVDTSTNTAY MELSSLRSED TAVYYCASRD YDYDGRYFDY WGRGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPEAAG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPRRP RVYTLPPSRE  360
EMTKNQVSLV CLVKGFYPSD IAVEWESNGQ PENNYKTTPP VLDSDGSFFL YSVLTVDKSR  420
WQQGNVFSCS VMHEALHNHY TQKSLSLSPG                                 450

SEQ ID NO: 592          moltype = AA  length = 213
FEATURE                 Location/Qualifiers
source                  1..213
```

```
                        mol_type = protein
                        organism = synthetic construct
SEQUENCE: 592
DIQMTQSPSS LSASVGDRVT ITCSASSSVT YMYWYQRKPG DAPKLLIYDT SNLASGVPSR  60
FSGSGSGTDY TFTISSLQPE DIATYYCQQW SSHIFTFGQG TKVEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                              213
```

CD3 T-CELL ENGAGERS AND METHODS OF USE

CROSS-REFERENCE TO RELATED APPLICATIONS

Priority is claimed to U.S. Provisional Patent Application No. 63/321,745 filed on 20 Mar. 2022, which is hereby incorporated by reference in its entirety.

SEQUENCE LISTING

The instant application contains a Sequence Listing which has been submitted in XML format via the USPTO electronic filing system and is hereby incorporated by reference in its entirety. Said XML copy, created on 28 Mar. 2023, is named 27050028WO01SEQL.xml and is 585,728_bytes in size.

TECHNICAL FIELD OF THE INVENTION

This disclosure generally relates to the fields of medicine and immunology. More specifically, this disclosure relates to anti-CD3 antibodies and their use in the manufacture of bispecific antibodies for the treatment of hyperproliferative and autoimmune disorders.

BACKGROUND OF THE INVENTION

CD3 T cell engagers bridge the gap between cancer and the immune system by redirecting T cells to tumor targets, regardless of their specificity. But with hundreds of bispecific CD3 T cell engagers in development, there are only two approved molecules on the market.

The intensity of T cell activation is a key predictor of safety and efficacy and is, in part, determined by the affinity and epitope of the CD3-binding arm. CD3-binders that strongly activate T cells can trigger dose-limiting toxicities, including cytokine release syndrome. On the other hand, CD3-binders that weakly activate T cells can lack potency. The result is a narrow therapeutic window for T cell engager development.

In addition, a unique combination of CD3- and tumor-binding arms are needed for each cancer type to allow for the binding of two targets, at the same time, with the right three-dimensional geometry.

CD3 T cell engager discovery has been limited because diverse panels of parental antibodies are hard to produce, and the pairing of parental antibodies is hard to perfect. Accordingly, alternatives to the CD3 T cell engagers presently in development are necessary.

BRIEF SUMMARY OF THE INVENTION

The present disclosure relates to CD3 T-cell engagers, some of which are specific for human CD3 and some of which are cross-reactive with CD3 of a non-human mammal (e.g., a cynomolgus monkey). The disclosure also relates to compositions of matter, articles of manufacture, and methods of use of the CD3 T-cell engagers in the treatment of hyperproliferative disorders, autoimmune disorders, and other conditions.

A collection of two hundred and seventy five anti-CD3 antibodies annotated by non-internal designation numbers 42-55, 63-91, 93-185, and 187-325 are disclosed herein and are described in SEQ ID NOs: 1-550. Amino acid sequences of the heavy chain variable regions of these antibodies are set forth in odd numbered sequences of SEQ ID NOs: 1-550 disclosed herein. Amino acid sequences of the light chain variable regions of these antibodies are set forth in even numbered sequences of SEQ ID NOs: 1-550 disclosed herein. As one of skill in the art will appreciate, the four sequences pertaining to any particular antibody will be separated by sequences pertaining to other antibodies. For example, the SEQ ID NOs assigned to the first antibody (designated 42) are SEQ ID NOs: 1 and 2 the SEQ ID NOs assigned to the second antibody (designated 43) are SEQ ID NOs: 3 and 4 and so on all the way to the two hundred and seventy-fifth antibody (designated 325), which is assigned SEQ ID NOs: 549 and 550.

In some embodiments, the anti-CD3 antibody, or an antigen-binding fragment thereof, comprises (a) a heavy chain variable region comprising residues 31-35 for CDR-H1, residues 50-65 for CDR-H2, and residues 95-102 for CDR-H3; and (b) a light chain variable region comprising residues 24-34 for CDR-L1, residues 50-56 for CDR-L2, and residues 89-97 for CDR-L3; wherein the CDR numbering is according to Kabat.

In some embodiments, the anti-CD3 antibody or antigen-binding fragment thereof comprises: (a) a heavy chain variable region comprising residues 26-32 for CDR-H1, residues 52-56 for CDR-H2, and residues 95-102 for CDR-H3; and (b) a light chain variable region comprising residues 24-34 for CDR-L1, residues 50-56 of SEQ ID NO: 62 for CDR-L2, and residues 89-97 of SEQ ID NO: 62 for CDR-L3; wherein the CDR numbering is according to Chothia.

In some embodiments, the anti-CD3 antibody or antigen-binding fragment thereof comprises: (a) a heavy chain variable region comprising residues 30-35 for CDR-H1, residues 47-58 for CDR-H2, and residues 93-101 for CDR-H3; and (b) a light chain variable region comprising residues 30-36 for CDR-L1, residues 46-55 for CDR-L2, and residues 89-96 for CDR-L3; wherein the CDR numbering is according to MacCallum.

In some embodiments, the anti-CD3 antibody or antigen-binding fragment thereof comprises a heavy chain variable region having an amino acid sequence that is at least 60%, 70%, 80%, 85%, 90%, 95%, 96%, 97%, 98% or 99% identical to one of the heavy chain variable region sequences explicitly disclosed in SEQ ID NOs: 1-550 and a light chain variable region having an amino acid sequence that is at least 60%, 70%, 80%, 85%, 90%, 95%, 96%, 97%, 98% or 99% identical to one of the light chain variable region sequences explicitly disclosed in SEQ ID NOs: 1-550.

In some embodiments, antibodies are specific for human CD3. In some embodiments, the antibodies cross-react against both human CD3 and CD3 of a non-human mammal (e.g., cynomolgus monkey).

In some embodiments, the anti-CD3 antibody or antigen-binding fragment thereof comprises at least one amino acid substitution. In particular embodiments, the at least one amino acid substitution is a conservative substitution. In some embodiments, the at least one amino acid substitution is a substitution of an amino acid for a non-genetically encoded amino acid or a synthetic amino acid.

In some embodiments, the anti-CD3 antibody is a bispecific antibody comprising a first binding arm and a second binding arm, wherein the first binding arm binds to at least one CD3 molecule and further comprises: (a) a heavy chain having an amino acid sequence selected from the group consisting of SEQ ID NOs: 551, 553, 555, 557, 561, 563, 565, 567, 569, 571, 573, 575, 577, 579, 581, 583, 585, and 587; and (b) a light chain having an amino acid sequence selected from the group consisting of SEQ ID NOs: 552, 554, 556, 558, 157, 564, 566, 568, 570, 572, 574, 576, 578, 580, 582, 584, 586, and 588; and wherein the second binding arm binds to at least one EGFR molecule and further comprises: (c) a heavy chain having an amino acid sequence selected from the group consisting of SEQ ID NOs: 589 and 591; and (d) a light chain having an amino acid sequence selected from the group consisting of SEQ ID NOs: 590 and 592.

In some embodiments, the antibody or antigen-binding fragment thereof is conjugated to an immunomodulator, a cytokine, a cytotoxic agent, a chemotherapeutic agent, a diagnostic agent, or a drug.

In some embodiments, the antibody or antigen-binding fragment thereof is formulated as a pharmaceutical composition. In some embodiments, the pharmaceutical composition may comprise one or more pharmaceutically acceptable carriers, diluents, or excipients. In particular embodiments, the antibody or antigen-binding fragment thereof may be conjugated to an immunomodulator, a cytokine, a cytotoxic agent, a chemotherapeutic agent, a diagnostic agent, or a drug prior to formulation.

The instant disclosure also encompasses isolated nucleic acids encoding part or all of the anti-CD3 antibodies and antigen-binding fragments thereof disclosed herein. In some embodiments, the foregoing nucleic acids may be incorporated into an expression vector. In some embodiments, the foregoing nucleic acids may be incorporated into a host cell, or first incorporated into an expression vector and then into a host cell. The instant disclosure also includes methods of manufacturing the anti-CD3 antibodies and antigen-binding fragments thereof disclosed herein using the aforementioned nucleic acids, expression vectors, and host cells. In particular embodiments, the methods comprise cultivating a host cell under conditions such that the antibody is expressed and recovered.

The inventions disclosed herein also encompass methods of treating an hyperproliferative or autoimmune disorder comprising administering to a patient a therapeutically effective amount of an anti-CD3 antibody or antigen-binding fragment thereof. Prior to administration, the antibody or antigen-binding fragment thereof may be formulated as a conjugate (for example, conjugated to a drug) or as a pharmaceutical composition.

The instant disclosure also encompasses articles of manufacture useful for treating a hyperproliferative or autoimmune disorder comprising a receptacle comprising an anti-CD3 antibody or antigen-binding fragment thereof, or antibody conjugate, or pharmaceutical composition, as well as instructional materials for using the same.

The foregoing is a summary and thus contains, by necessity, simplifications, generalizations, and omissions of detail; consequently, those skilled in the art will appreciate that the summary is illustrative only and is not intended to be in any way limiting. Other aspects, features, and advantages of the subject matter described herein will become apparent in the teachings set forth herein. The summary is provided to introduce a selection of concepts in a simplified form that are further described below in the Detailed Description of the Invention. This summary is not intended to identify key features or essential features of the claimed subject matter, nor is it intended to be used as an aid in determining the scope of the claimed subject matter.

DETAILED DESCRIPTION OF THE INVENTION

Figure 1:
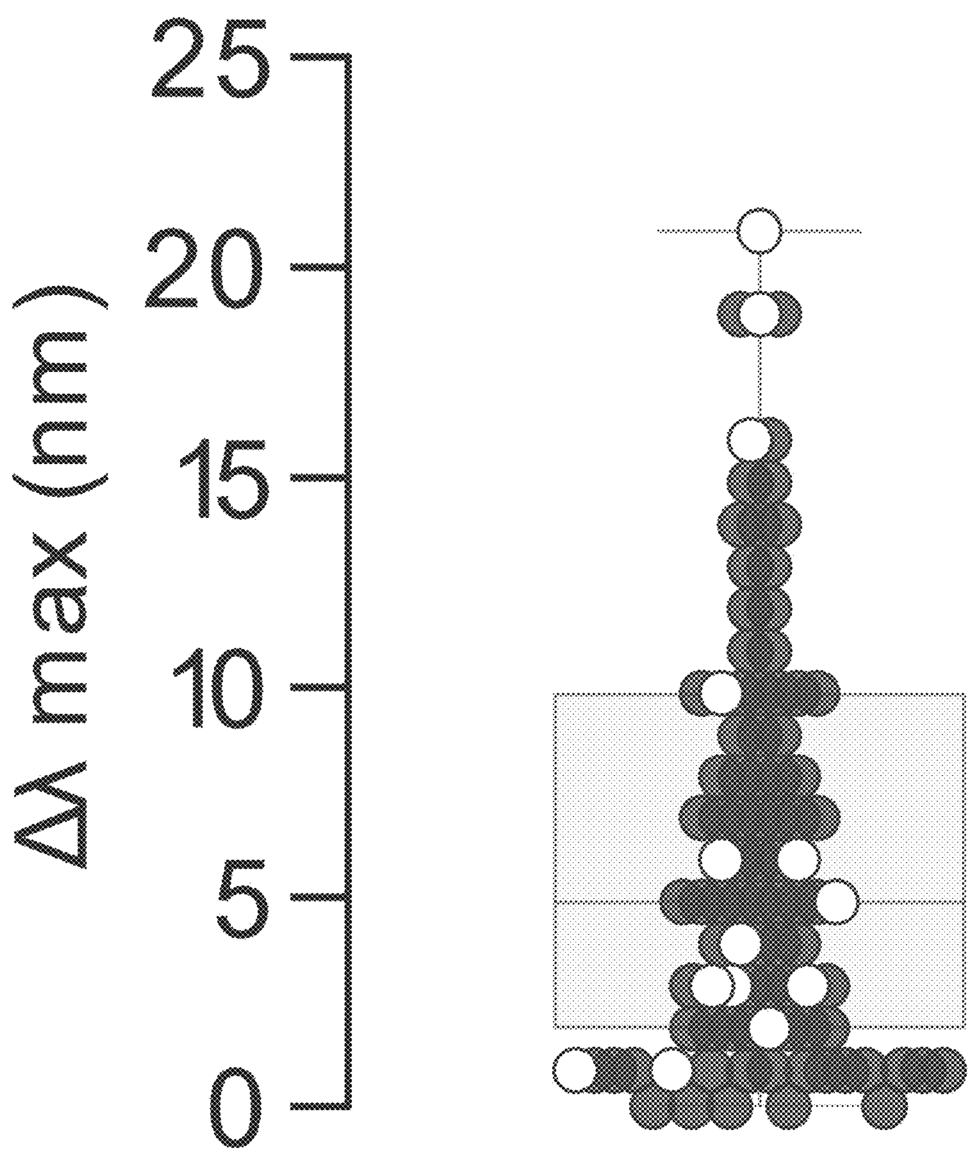
FIG. 1 is a self-association plot. Most of the anti-CD3 antibodies in accordance with the inventions disclosed herein demonstrate low self-association as shown by a very small increases in wavelengths of maximum absorbance, which is one indication that these antibodies possess favorable biophysical properties.

While the present invention may be embodied in many different forms, disclosed herein are specific illustrative embodiments thereof that exemplify the principles of inventions described herein. It should be emphasized that the inventions described herein are not limited to the specific embodiments illustrated. Moreover, any section headings used herein are for organizational purposes only and are not to be construed as limiting the subject matter described.

Unless otherwise defined herein, scientific, and technical terms used in connection with the present invention shall have the meanings that are commonly understood by those of ordinary skill in the art. Further, unless otherwise required by context, singular terms shall include pluralities and plural terms shall include the singular. More specifically, as used in this specification and the appended claims, the singular forms "a," "an" and "the" include plural referents unless the context clearly dictates otherwise. Thus, for example, reference to "a protein" includes a plurality of proteins; reference to "a cell" includes mixtures of cells, and the like. In addition, ranges provided in the specification and appended claims include both end points and all points between the end points. Therefore, a range of 1.0 to 2.0 includes 1.0, 2.0, and all points between 1.0 and 2.0.

Generally, nomenclature used in connection with, and techniques of, cell and tissue culture, molecular biology, immunology, microbiology, genetics and protein and nucleic acid chemistry and hybridization described herein are those well-known and commonly used in the art. The methods and techniques of the present invention are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art, or as described herein. The nomenclature used in connection with, and the laboratory procedures and techniques of, analytical chemistry, synthetic organic chemistry, and medicinal and pharmaceutical chemistry described herein are those well-known and commonly used in the art.

Exemplary Embodiments of the Invention

In particular embodiments, the inventions disclosed herein encompass an antibody or antigen-binding fragment thereof that binds to human CD3, wherein the antibody or antigen-binding fragment thereof comprises:

(a) three CDRs of a heavy chain variable region set forth as SEQ ID NO: 1 and three CDRs of a light chain variable region set forth as SEQ ID NO: 2; or (b) three CDRs of a heavy chain variable region set forth as SEQ ID NO: 3 and three CDRs of a light chain variable region set forth as SEQ ID NO: 4; or (c) three CDRs of a heavy chain variable region set forth as SEQ ID NO: 5 and three CDRs of a light chain variable region set forth as SEQ ID NO: 6; or (d) three CDRs of a heavy chain variable region set forth as SEQ ID NO: 7 and three CDRs of a light chain variable region set forth as SEQ ID NO: 8; or (e) three CDRs of a heavy chain variable region set forth as SEQ ID NO: 9 and three CDRs of a light chain variable region set forth as SEQ ID NO: 10; or (f) three CDRs of a heavy chain variable region set forth as SEQ ID NO: 11 and three CDRs of a light chain variable region set forth as SEQ ID NO: 12; or (g) three CDRs of a heavy chain variable region set forth as SEQ ID NO: 13 and three CDRs of a light chain variable region set forth as SEQ ID NO: 14; or (h) three CDRs of a heavy chain variable region set forth as SEQ ID NO: 15 and three CDRs of a light chain variable region set forth as SEQ ID NO: 16; or (i) three CDRs of a heavy chain variable region set forth as SEQ ID NO:17 and three CDRs of a light chain variable region set forth as SEQ ID NO: 18; or (j) three CDRs of a heavy chain variable region set forth as SEQ ID NO: 19 and three CDRs of a light chain variable region set forth as SEQ ID NO: 20; or (k) three CDRs of a heavy chain variable region set forth as SEQ ID NO: 21 and three CDRs of a light chain variable region set forth as SEQ ID NO: 22; or (l) three CDRs of a heavy chain variable region set forth as SEQ ID NO: 23 and three CDRs of a light chain variable region set forth as SEQ ID NO: 24; or (m) three CDRs of a heavy chain variable region set forth as SEQ ID NO: 25 and three CDRs of a light chain variable region set forth as SEQ ID NO: 26; or (n) three CDRs of a heavy chain variable region set forth as SEQ ID NO: 27 and three CDRs of a light chain variable region set forth as SEQ ID NO: 28; or (o) three CDRs of a heavy chain variable region set forth as SEQ ID NO: 29 and three CDRs of a light chain variable region set forth as SEQ ID NO: 30; or (p) three CDRs of a heavy chain variable region set forth as SEQ ID NO: 31 and three CDRs of a light chain variable region set forth as SEQ ID NO: 32; or (q) three CDRs of a heavy chain variable region set forth as SEQ ID NO: 33 and three CDRs of a light chain variable region set forth as SEQ ID NO: 34; or (r) three CDRs of a heavy chain variable region set forth as SEQ ID NO: 35 and three CDRs of a light chain variable region set forth as SEQ ID NO: 36; or (s) three CDRs of a heavy chain variable region set forth as SEQ ID NO: 37 and three CDRs of a light chain variable region set forth as SEQ ID NO: 38; or (t) three CDRs of a heavy chain variable region set forth as SEQ ID NO: 39 and three CDRs of a light chain variable region set forth as SEQ ID NO: 40; or (u) three CDRs of a heavy chain variable region set forth as SEQ ID NO: 41 and three CDRs of a light chain variable region set forth as SEQ ID NO: 42; or (v) three CDRs of a heavy chain variable region set forth as SEQ ID NO: 43 and three CDRs of a light chain variable region set forth as SEQ ID NO: 44; or (w) three CDRs of a heavy chain variable region set forth as SEQ ID NO: 45 and three CDRs of a light chain variable region set forth as SEQ ID NO: 46; or (x) three CDRs of a heavy chain variable region set forth as SEQ ID NO: 47 and three CDRs of a light chain variable region set forth as SEQ ID NO: 48; or (y) three CDRs of a heavy chain variable region set forth as SEQ ID NO: 49 and three CDRs of a light chain variable region set forth as SEQ ID NO: 50; or (z) three CDRs of a heavy chain variable region set forth as SEQ ID NO: 51 and three CDRs of a light chain variable region set forth as SEQ ID NO: 52; or (a-i) three CDRs of a heavy chain variable region set forth as SEQ ID NO: 53 and three CDRs of a light chain variable region set forth as SEQ ID NO: 54; or (b-i) three CDRs of a heavy chain variable region set forth as SEQ ID NO: 55 and three CDRs of a light chain variable region set forth as SEQ ID NO: 56; or (c-i) three CDRs of a heavy chain variable region set forth as SEQ ID NO: 57 and three CDRs of a light chain variable region set forth as SEQ ID NO: 58; or (d-i) three CDRs of a heavy chain variable region set forth as SEQ ID NO: 59 and three CDRs of a light chain variable region set forth as SEQ ID NO: 60; or (e-i) three CDRs of a heavy chain variable region set forth as SEQ ID NO: 61 and three CDRs of a light chain variable region set forth as SEQ ID NO: 62; or (f-i) three CDRs of a heavy chain variable region set forth as SEQ ID NO: 63 and three CDRs of a light chain variable region set forth as SEQ ID NO: 64; or (g-i) three CDRs of a heavy chain variable region set forth as SEQ ID NO: 65 and three CDRs of a light chain variable region set forth as SEQ ID NO: 66; or (h-i) three CDRs of a heavy chain variable region set forth as SEQ ID NO: 67 and three CDRs of a light chain variable region set forth as SEQ ID NO: 68; or (i-i) three CDRs of a heavy chain variable region set forth as SEQ ID NO: 69 and three CDRs of a light chain variable region set forth as SEQ ID NO: 70; or (j-i) three CDRs of a heavy chain variable region set forth as SEQ ID NO: 71 and three CDRs of a light chain variable region set forth as SEQ ID NO: 72; or (k-i) three CDRs of a heavy chain variable region set forth as SEQ ID NO: 73 and three CDRs of a light chain variable region set forth as SEQ ID NO: 74; or (l-i) three CDRs of a heavy chain variable region set forth as SEQ ID NO: 75 and three CDRs of a light chain variable region set forth as SEQ ID NO: 76; or (m-i) three CDRs of a heavy chain variable region set forth as SEQ ID NO: 77 and three CDRs of a light chain variable region set forth as SEQ ID NO: 78; or (n-i) three CDRs of a heavy chain variable region set forth as SEQ ID NO: 79 and three CDRs of a light chain variable region set forth as SEQ ID NO: 80; or (o-i) three CDRs of a heavy chain variable region set forth as SEQ ID NO: 81 and three CDRs of a light chain variable region set forth as SEQ ID NO: 82; or (p-i) three CDRs of a heavy chain variable region set forth as SEQ ID NO: 83 and three CDRs of a light chain variable region set forth as SEQ ID NO: 84; or (q-i) three CDRs of a heavy chain variable region set forth as SEQ ID NO: 85 and three CDRs of a light chain variable region set forth as SEQ ID NO: 86; or (r-i) three CDRs of a heavy chain variable region set forth as SEQ ID NO: 87 and three CDRs of a light chain variable region set forth as SEQ ID NO: 88; or (s-i) three CDRs of a heavy chain variable region set forth as SEQ ID NO: 89 and three CDRs of a light chain variable region set forth as SEQ ID NO: 90; or
(t-i) three CDRs of a heavy chain variable region set forth as SEQ ID NO: 91 and three CDRs of a light chain variable region set forth as SEQ ID NO: 92; or
(u-i) three CDRs of a heavy chain variable region set forth as SEQ ID NO: 93 and three CDRs of a light chain variable region set forth as SEQ ID NO: 94; or
(v-i) three CDRs of a heavy chain variable region set forth as SEQ ID NO: 95 and three CDRs of a light chain variable region set forth as SEQ ID NO: 96; or
(w-i) three CDRs of a heavy chain variable region set forth as SEQ ID NO: 97 and three CDRs of a light chain variable region set forth as SEQ ID NO: 98; or
(x-i) three CDRs of a heavy chain variable region set forth as SEQ ID NO: 99 and three CDRs of a light chain variable region set forth as SEQ ID NO: 100; or
(y-i) three CDRs of a heavy chain variable region set forth as SEQ ID NO: 101 and three CDRs of a light chain variable region set forth as SEQ ID NO: 102; or
(z-i) three CDRs of a heavy chain variable region set forth as SEQ ID NO: 103 and three CDRs of a light chain variable region set forth as SEQ ID NO: 104; or
(a-ii) three CDRs of a heavy chain variable region set forth as SEQ ID NO: 105 and three CDRs of a light chain variable region set forth as SEQ ID NO: 106; or
(b-ii) three CDRs of a heavy chain variable region set forth as SEQ ID NO: 107 and three CDRs of a light chain variable region set forth as SEQ ID NO: 108; or
(c-ii) three CDRs of a heavy chain variable region set forth as SEQ ID NO: 109 and three CDRs of a light chain variable region set forth as SEQ ID NO: 110; or
(d-ii) three CDRs of a heavy chain variable region set forth as SEQ ID NO: 111 and three CDRs of a light chain variable region set forth as SEQ ID NO: 112; or
(e-ii) three CDRs of a heavy chain variable region set forth as SEQ ID NO: 113 and three CDRs of a light chain variable region set forth as SEQ ID NO: 114; or
(f-ii) three CDRs of a heavy chain variable region set forth as SEQ ID NO: 115 and three CDRs of a light chain variable region set forth as SEQ ID NO: 116; or
(g-ii) three CDRs of a heavy chain variable region set forth as SEQ ID NO: 117 and three CDRs of a light chain variable region set forth as SEQ ID NO: 118; or
(h-ii) three CDRs of a heavy chain variable region set forth as SEQ ID NO: 119 and three CDRs of a light chain variable region set forth as SEQ ID NO: 120; or
(i-ii) three CDRs of a heavy chain variable region set forth as SEQ ID NO:121 and three CDRs of a light chain variable region set forth as SEQ ID NO: 122; or
(j-ii) three CDRs of a heavy chain variable region set forth as SEQ ID NO: 123 and three CDRs of a light chain variable region set forth as SEQ ID NO: 124; or
(k-ii) three CDRs of a heavy chain variable region set forth as SEQ ID NO: 125 and three CDRs of a light chain variable region set forth as SEQ ID NO: 126; or
(l-ii) three CDRs of a heavy chain variable region set forth as SEQ ID NO: 127 and three CDRs of a light chain variable region set forth as SEQ ID NO: 128; or
(m-ii) three CDRs of a heavy chain variable region set forth as SEQ ID NO: 129 and three CDRs of a light chain variable region set forth as SEQ ID NO: 130; or
(n-ii) three CDRs of a heavy chain variable region set forth as SEQ ID NO: 131 and three CDRs of a light chain variable region set forth as SEQ ID NO: 132; or
(o-ii) three CDRs of a heavy chain variable region set forth as SEQ ID NO: 133 and three CDRs of a light chain variable region set forth as SEQ ID NO: 134; or
(p-ii) three CDRs of a heavy chain variable region set forth as SEQ ID NO: 135 and three CDRs of a light chain variable region set forth as SEQ ID NO: 136; or
(q-ii) three CDRs of a heavy chain variable region set forth as SEQ ID NO: 137 and three CDRs of a light chain variable region set forth as SEQ ID NO: 138; or
(r-ii) three CDRs of a heavy chain variable region set forth as SEQ ID NO: 139 and three CDRs of a light chain variable region set forth as SEQ ID NO: 140; or
(s-ii) three CDRs of a heavy chain variable region set forth as SEQ ID NO: 141 and three CDRs of a light chain variable region set forth as SEQ ID NO: 142; or
(t-ii) three CDRs of a heavy chain variable region set forth as SEQ ID NO: 143 and three CDRs of a light chain variable region set forth as SEQ ID NO: 144; or
(u-ii) three CDRs of a heavy chain variable region set forth as SEQ ID NO: 145 and three CDRs of a light chain variable region set forth as SEQ ID NO: 146; or
(v-ii) three CDRs of a heavy chain variable region set forth as SEQ ID NO: 147 and three CDRs of a light chain variable region set forth as SEQ ID NO: 148; or
(w-ii) three CDRs of a heavy chain variable region set forth as SEQ ID NO: 149 and three CDRs of a light chain variable region set forth as SEQ ID NO: 150; or
(x-ii) three CDRs of a heavy chain variable region set forth as SEQ ID NO: 151 and three CDRs of a light chain variable region set forth as SEQ ID NO: 152; or
(y-ii) three CDRs of a heavy chain variable region set forth as SEQ ID NO: 153 and three CDRs of a light chain variable region set forth as SEQ ID NO: 154; or
(z-ii) three CDRs of a heavy chain variable region set forth as SEQ ID NO: 155 and three CDRs of a light chain variable region set forth as SEQ ID NO: 156; or
(a-iii) three CDRs of a heavy chain variable region set forth as SEQ ID NO: 157 and three CDRs of a light chain variable region set forth as SEQ ID NO: 158; or
(b-iii) three CDRs of a heavy chain variable region set forth as SEQ ID NO: 159 and three CDRs of a light chain variable region set forth as SEQ ID NO: 160; or
(c-iii) three CDRs of a heavy chain variable region set forth as SEQ ID NO: 161 and three CDRs of a light chain variable region set forth as SEQ ID NO: 162; or
(d-iii) three CDRs of a heavy chain variable region set forth as SEQ ID NO: 163 and three CDRs of a light chain variable region set forth as SEQ ID NO: 164; or
(e-iii) three CDRs of a heavy chain variable region set forth as SEQ ID NO: 165 and three CDRs of a light chain variable region set forth as SEQ ID NO: 166; or
(f-iii) three CDRs of a heavy chain variable region set forth as SEQ ID NO: 167 and three CDRs of a light chain variable region set forth as SEQ ID NO: 168; or
(g-iii) three CDRs of a heavy chain variable region set forth as SEQ ID NO: 169 and three CDRs of a light chain variable region set forth as SEQ ID NO: 170; or
(h-iii) three CDRs of a heavy chain variable region set forth as SEQ ID NO: 171 and three CDRs of a light chain variable region set forth as SEQ ID NO: 172; or
(i-iii) three CDRs of a heavy chain variable region set forth as SEQ ID NO: 173 and three CDRs of a light chain variable region set forth as SEQ ID NO: 174; or
(j-iii) three CDRs of a heavy chain variable region set forth as SEQ ID NO: 175 and three CDRs of a light chain variable region set forth as SEQ ID NO: 176; or (k-iii) three CDRs of a heavy chain variable region set forth as SEQ ID NO: 177 and three CDRs of a light chain variable region set forth as SEQ ID NO: 178; or (l-iii) three CDRs of a heavy chain variable region set forth as SEQ ID NO: 179 and three CDRs of a light chain variable region set forth as SEQ ID NO: 180; or (m-iii) three CDRs of a heavy chain variable region set forth as SEQ ID NO: 181 and three CDRs of a light chain variable region set forth as SEQ ID NO: 182; or (n-iii) three CDRs of a heavy chain variable region set forth as SEQ ID NO: 183 and three CDRs of a light chain variable region set forth as SEQ ID NO: 184; or (o-iii) three CDRs of a heavy chain variable region set forth as SEQ ID NO: 185 and three CDRs of a light chain variable region set forth as SEQ ID NO: 186; or (p-iii) three CDRs of a heavy chain variable region set forth as SEQ ID NO: 187 and three CDRs of a light chain variable region set forth as SEQ ID NO: 188; or (q-iii) three CDRs of a heavy chain variable region set forth as SEQ ID NO: 189 and three CDRs of a light chain variable region set forth as SEQ ID NO: 190; or (r-iii) three CDRs of a heavy chain variable region set forth as SEQ ID NO: 191 and three CDRs of a light chain variable region set forth as SEQ ID NO: 192; or (s-iii) three CDRs of a heavy chain variable region set forth as SEQ ID NO: 193 and three CDRs of a light chain variable region set forth as SEQ ID NO: 194; or (t-iii) three CDRs of a heavy chain variable region set forth as SEQ ID NO: 195 and three CDRs of a light chain variable region set forth as SEQ ID NO: 196; or (u-iii) three CDRs of a heavy chain variable region set forth as SEQ ID NO: 197 and three CDRs of a light chain variable region set forth as SEQ ID NO: 198; or (v-iii) three CDRs of a heavy chain variable region set forth as SEQ ID NO: 199 and three CDRs of a light chain variable region set forth as SEQ ID NO: 200; or (w-iii) three CDRs of a heavy chain variable region set forth as SEQ ID NO: 201 and three CDRs of a light chain variable region set forth as SEQ ID NO: 202; or (x-iii) three CDRs of a heavy chain variable region set forth as SEQ ID NO: 203 and three CDRs of a light chain variable region set forth as SEQ ID NO: 204; or (y-iii) three CDRs of a heavy chain variable region set forth as SEQ ID NO: 205 and three CDRs of a light chain variable region set forth as SEQ ID NO: 206; or (z-iii) three CDRs of a heavy chain variable region set forth as SEQ ID NO: 207 and three CDRs of a light chain variable region set forth as SEQ ID NO: 208; or (a-iv) three CDRs of a heavy chain variable region set forth as SEQ ID NO: 209 and three CDRs of a light chain variable region set forth as SEQ ID NO: 210; or (b-iv) three CDRs of a heavy chain variable region set forth as SEQ ID NO: 211 and three CDRs of a light chain variable region set forth as SEQ ID NO: 212; or (c-iv) three CDRs of a heavy chain variable region set forth as SEQ ID NO: 213 and three CDRs of a light chain variable region set forth as SEQ ID NO: 214; or (d-iv) three CDRs of a heavy chain variable region set forth as SEQ ID NO: 215 and three CDRs of a light chain variable region set forth as SEQ ID NO: 216; or (e-iv) three CDRs of a heavy chain variable region set forth as SEQ ID NO: 217 and three CDRs of a light chain variable region set forth as SEQ ID NO: 218; or (f-iv) three CDRs of a heavy chain variable region set forth as SEQ ID NO: 219 and three CDRs of a light chain variable region set forth as SEQ ID NO: 220; or (g-iv) three CDRs of a heavy chain variable region set forth as SEQ ID NO: 221 and three CDRs of a light chain variable region set forth as SEQ ID NO: 222; or (h-iv) three CDRs of a heavy chain variable region set forth as SEQ ID NO: 223 and three CDRs of a light chain variable region set forth as SEQ ID NO: 224; or (i-iv) three CDRs of a heavy chain variable region set forth as SEQ ID NO: 225 and three CDRs of a light chain variable region set forth as SEQ ID NO: 226; or (j-iv) three CDRs of a heavy chain variable region set forth as SEQ ID NO: 227 and three CDRs of a light chain variable region set forth as SEQ ID NO: 228; or (k-iv) three CDRs of a heavy chain variable region set forth as SEQ ID NO: 229 and three CDRs of a light chain variable region set forth as SEQ ID NO: 230; or (l-iv) three CDRs of a heavy chain variable region set forth as SEQ ID NO: 231 and three CDRs of a light chain variable region set forth as SEQ ID NO: 232; or (m-iv) three CDRs of a heavy chain variable region set forth as SEQ ID NO: 233 and three CDRs of a light chain variable region set forth as SEQ ID NO: 234; or (n-iv) three CDRs of a heavy chain variable region set forth as SEQ ID NO: 235 and three CDRs of a light chain variable region set forth as SEQ ID NO: 236; or (o-iv) three CDRs of a heavy chain variable region set forth as SEQ ID NO: 237 and three CDRs of a light chain variable region set forth as SEQ ID NO: 238; or (p-iv) three CDRs of a heavy chain variable region set forth as SEQ ID NO: 239 and three CDRs of a light chain variable region set forth as SEQ ID NO: 240; or (q-iv) three CDRs of a heavy chain variable region set forth as SEQ ID NO: 241 and three CDRs of a light chain variable region set forth as SEQ ID NO: 242; or (r-iv) three CDRs of a heavy chain variable region set forth as SEQ ID NO: 243 and three CDRs of a light chain variable region set forth as SEQ ID NO: 244; or (s-iv) three CDRs of a heavy chain variable region set forth as SEQ ID NO: 245 and three CDRs of a light chain variable region set forth as SEQ ID NO: 246; or (t-iv) three CDRs of a heavy chain variable region set forth as SEQ ID NO: 247 and three CDRs of a light chain variable region set forth as SEQ ID NO: 248; or (u-iv) three CDRs of a heavy chain variable region set forth as SEQ ID NO: 249 and three CDRs of a light chain variable region set forth as SEQ ID NO: 250; or (v-iv) three CDRs of a heavy chain variable region set forth as SEQ ID NO: 251 and three CDRs of a light chain variable region set forth as SEQ ID NO: 252; or (w-iv) three CDRs of a heavy chain variable region set forth as SEQ ID NO: 253 and three CDRs of a light chain variable region set forth as SEQ ID NO: 254; or (x-iv) three CDRs of a heavy chain variable region set forth as SEQ ID NO: 255 and three CDRs of a light chain variable region set forth as SEQ ID NO: 256; or (y-iv) three CDRs of a heavy chain variable region set forth as SEQ ID NO: 257 and three CDRs of a light chain variable region set forth as SEQ ID NO: 258; or (z-iv) three CDRs of a heavy chain variable region set forth as SEQ ID NO: 259 and three CDRs of a light chain variable region set forth as SEQ ID NO: 260; or (a-v) three CDRs of a heavy chain variable region set forth as SEQ ID NO: 261 and three CDRs of a light chain variable region set forth as SEQ ID NO: 262; or (b-v) three CDRs of a heavy chain variable region set forth as SEQ ID NO: 263 and three CDRs of a light chain variable region set forth as SEQ ID NO: 264; or (c-v) three CDRs of a heavy chain variable region set forth as SEQ ID NO: 265 and three CDRs of a light chain variable region set forth as SEQ ID NO: 266; or (d-v) three CDRs of a heavy chain variable region set forth as SEQ ID NO: 267 and three CDRs of a light chain variable region set forth as SEQ ID NO: 268; or (e-v) three CDRs of a heavy chain variable region set forth as SEQ ID NO: 269 and three CDRs of a light chain variable region set forth as SEQ ID NO: 270; or (f-v) three CDRs of a heavy chain variable region set forth as SEQ ID NO: 271 and three CDRs of a light chain variable region set forth as SEQ ID NO: 272; or (g-v) three CDRs of a heavy chain variable region set forth as SEQ ID NO: 273 and three CDRs of a light chain variable region set forth as SEQ ID NO: 274; or (h-v) three CDRs of a heavy chain variable region set forth as SEQ ID NO: 275 and three CDRs of a light chain variable region set forth as SEQ ID NO: 276; or (i-v) three CDRs of a heavy chain variable region set forth as SEQ ID NO: 277 and three CDRs of a light chain variable region set forth as SEQ ID NO: 278; or (j-v) three CDRs of a heavy chain variable region set forth as SEQ ID NO: 279 and three CDRs of a light chain variable region set forth as SEQ ID NO: 280; or (k-v) three CDRs of a heavy chain variable region set forth as SEQ ID NO: 281 and three CDRs of a light chain variable region set forth as SEQ ID NO: 282; or (l-v) three CDRs of a heavy chain variable region set forth as SEQ ID NO: 283 and three CDRs of a light chain variable region set forth as SEQ ID NO: 284; or (m-v) three CDRs of a heavy chain variable region set forth as SEQ ID NO: 285 and three CDRs of a light chain variable region set forth as SEQ ID NO: 286; or (n-v) three CDRs of a heavy chain variable region set forth as SEQ ID NO: 287 and three CDRs of a light chain variable region set forth as SEQ ID NO: 288; or (o-v) three CDRs of a heavy chain variable region set forth as SEQ ID NO: 289 and three CDRs of a light chain variable region set forth as SEQ ID NO: 290; or (p-v) three CDRs of a heavy chain variable region set forth as SEQ ID NO: 291 and three CDRs of a light chain variable region set forth as SEQ ID NO: 292; or (q-v) three CDRs of a heavy chain variable region set forth as SEQ ID NO: 293 and three CDRs of a light chain variable region set forth as SEQ ID NO: 294; or (r-v) three CDRs of a heavy chain variable region set forth as SEQ ID NO: 295 and three CDRs of a light chain variable region set forth as SEQ ID NO: 296; or (s-v) three CDRs of a heavy chain variable region set forth as SEQ ID NO: 297 and three CDRs of a light chain variable region set forth as SEQ ID NO: 298; or (t-v) three CDRs of a heavy chain variable region set forth as SEQ ID NO: 299 and three CDRs of a light chain variable region set forth as SEQ ID NO: 300; or (u-v) three CDRs of a heavy chain variable region set forth as SEQ ID NO: 301 and three CDRs of a light chain variable region set forth as SEQ ID NO: 302; or (v-v) three CDRs of a heavy chain variable region set forth as SEQ ID NO: 303 and three CDRs of a light chain variable region set forth as SEQ ID NO: 304; or (w-v) three CDRs of a heavy chain variable region set forth as SEQ ID NO: 305 and three CDRs of a light chain variable region set forth as SEQ ID NO: 306; or (x-v) three CDRs of a heavy chain variable region set forth as SEQ ID NO: 307 and three CDRs of a light chain variable region set forth as SEQ ID NO: 308; or (y-v) three CDRs of a heavy chain variable region set forth as SEQ ID NO: 309 and three CDRs of a light chain variable region set forth as SEQ ID NO: 310; or (z-v) three CDRs of a heavy chain variable region set forth as SEQ ID NO: 311 and three CDRs of a light chain variable region set forth as SEQ ID NO: 312; or (a-vi) three CDRs of a heavy chain variable region set forth as SEQ ID NO: 313 and three CDRs of a light chain variable region set forth as SEQ ID NO: 314; or (b-vi) three CDRs of a heavy chain variable region set forth as SEQ ID NO: 315 and three CDRs of a light chain variable region set forth as SEQ ID NO: 316; or (c-vi) three CDRs of a heavy chain variable region set forth as SEQ ID NO: 317 and three CDRs of a light chain variable region set forth as SEQ ID NO: 318; or (d-vi) three CDRs of a heavy chain variable region set forth as SEQ ID NO: 319 and three CDRs of a light chain variable region set forth as SEQ ID NO: 320; or (e-vi) three CDRs of a heavy chain variable region set forth as SEQ ID NO: 321 and three CDRs of a light chain variable region set forth as SEQ ID NO: 322; or (f-vi) three CDRs of a heavy chain variable region set forth as SEQ ID NO: 323 and three CDRs of a light chain variable region set forth as SEQ ID NO: 324; or (g-vi) three CDRs of a heavy chain variable region set forth as SEQ ID NO: 325 and three CDRs of a light chain variable region set forth as SEQ ID NO: 326; or (h-vi) three CDRs of a heavy chain variable region set forth as SEQ ID NO: 327 and three CDRs of a light chain variable region set forth as SEQ ID NO: 328; or (i-vi) three CDRs of a heavy chain variable region set forth as SEQ ID NO: 329 and three CDRs of a light chain variable region set forth as SEQ ID NO: 330; or (j-vi) three CDRs of a heavy chain variable region set forth as SEQ ID NO: 331 and three CDRs of a light chain variable region set forth as SEQ ID NO: 332; or (k-vi) three CDRs of a heavy chain variable region set forth as SEQ ID NO: 333 and three CDRs of a light chain variable region set forth as SEQ ID NO: 334; or (l-vi) three CDRs of a heavy chain variable region set forth as SEQ ID NO: 335 and three CDRs of a light chain variable region set forth as SEQ ID NO: 336; or (m-vi) three CDRs of a heavy chain variable region set forth as SEQ ID NO: 337 and three CDRs of a light chain variable region set forth as SEQ ID NO: 338; or (n-vi) three CDRs of a heavy chain variable region set forth as SEQ ID NO: 339 and three CDRs of a light chain variable region set forth as SEQ ID NO: 340; or (o-vi) three CDRs of a heavy chain variable region set forth as SEQ ID NO: 341 and three CDRs of a light chain variable region set forth as SEQ ID NO: 342; or (p-vi) three CDRs of a heavy chain variable region set forth as SEQ ID NO: 343 and three CDRs of a light chain variable region set forth as SEQ ID NO: 344; or (q-vi) three CDRs of a heavy chain variable region set forth as SEQ ID NO: 345 and three CDRs of a light chain variable region set forth as SEQ ID NO: 346; or (r-vi) three CDRs of a heavy chain variable region set forth as SEQ ID NO: 347 and three CDRs of a light chain variable region set forth as SEQ ID NO: 348; or (s-vi) three CDRs of a heavy chain variable region set forth as SEQ ID NO: 349 and three CDRs of a light chain variable region set forth as SEQ ID NO: 350; or (t-vi) three CDRs of a heavy chain variable region set forth as SEQ ID NO: 351 and three CDRs of a light chain variable region set forth as SEQ ID NO: 352; or (u-vi) three CDRs of a heavy chain variable region set forth as SEQ ID NO: 353 and three CDRs of a light chain variable region set forth as SEQ ID NO: 354; or (v-vi) three CDRs of a heavy chain variable region set forth as SEQ ID NO: 355 and three CDRs of a light chain variable region set forth as SEQ ID NO: 356; or (w-vi) three CDRs of a heavy chain variable region set forth as SEQ ID NO: 357 and three CDRs of a light chain variable region set forth as SEQ ID NO: 358; or (x-vi) three CDRs of a heavy chain variable region set forth as SEQ ID NO: 359 and three CDRs of a light chain variable region set forth as SEQ ID NO: 360; or (y-vi) three CDRs of a heavy chain variable region set forth as SEQ ID NO: 361 and three CDRs of a light chain variable region set forth as SEQ ID NO: 362; or (z-vi) three CDRs of a heavy chain variable region set forth as SEQ ID NO: 363 and three CDRs of a light chain variable region set forth as SEQ ID NO: 364; or (a-vii) three CDRs of a heavy chain variable region set forth as SEQ ID NO: 365 and three CDRs of a light chain variable region set forth as SEQ ID NO: 366; or (b-vii) three CDRs of a heavy chain variable region set forth as SEQ ID NO: 367 and three CDRs of a light chain variable region set forth as SEQ ID NO: 368; or (c-vii) three CDRs of a heavy chain variable region set forth as SEQ ID NO: 369 and three CDRs of a light chain variable region set forth as SEQ ID NO: 370; or (d-vii) three CDRs of a heavy chain variable region set forth as SEQ ID NO: 371 and three CDRs of a light chain variable region set forth as SEQ ID NO: 372; or (e-vii) three CDRs of a heavy chain variable region set forth as SEQ ID NO: 373 and three CDRs of a light chain variable region set forth as SEQ ID NO: 374; or (f-vii) three CDRs of a heavy chain variable region set forth as SEQ ID NO: 375 and three CDRs of a light chain variable region set forth as SEQ ID NO: 376; or (g-vii) three CDRs of a heavy chain variable region set forth as SEQ ID NO: 377 and three CDRs of a light chain variable region set forth as SEQ ID NO: 378; or (h-vii) three CDRs of a heavy chain variable region set forth as SEQ ID NO: 379 and three CDRs of a light chain variable region set forth as SEQ ID NO: 380; or (i-vii) three CDRs of a heavy chain variable region set forth as SEQ ID NO: 381 and three CDRs of a light chain variable region set forth as SEQ ID NO: 382; or (j-vii) three CDRs of a heavy chain variable region set forth as SEQ ID NO: 383 and three CDRs of a light chain variable region set forth as SEQ ID NO: 384; or (k-vii) three CDRs of a heavy chain variable region set forth as SEQ ID NO: 385 and three CDRs of a light chain variable region set forth as SEQ ID NO: 386; or (l-vii) three CDRs of a heavy chain variable region set forth as SEQ ID NO: 387 and three CDRs of a light chain variable region set forth as SEQ ID NO: 388; or (m-vii) three CDRs of a heavy chain variable region set forth as SEQ ID NO: 389 and three CDRs of a light chain variable region set forth as SEQ ID NO: 390; or (n-vii) three CDRs of a heavy chain variable region set forth as SEQ ID NO: 391 and three CDRs of a light chain variable region set forth as SEQ ID NO: 392; or (o-vii) three CDRs of a heavy chain variable region set forth as SEQ ID NO: 393 and three CDRs of a light chain variable region set forth as SEQ ID NO: 394; or (p-vii) three CDRs of a heavy chain variable region set forth as SEQ ID NO: 395 and three CDRs of a light chain variable region set forth as SEQ ID NO: 396; or (q-vii) three CDRs of a heavy chain variable region set forth as SEQ ID NO: 397 and three CDRs of a light chain variable region set forth as SEQ ID NO: 398; or (r-vii) three CDRs of a heavy chain variable region set forth as SEQ ID NO: 399 and three CDRs of a light chain variable region set forth as SEQ ID NO: 400; or (s-vii) three CDRs of a heavy chain variable region set forth as SEQ ID NO: 401 and three CDRs of a light chain variable region set forth as SEQ ID NO: 402; or (t-vii) three CDRs of a heavy chain variable region set forth as SEQ ID NO: 403 and three CDRs of a light chain variable region set forth as SEQ ID NO: 404; or (u-vii) three CDRs of a heavy chain variable region set forth as SEQ ID NO: 405 and three CDRs of a light chain variable region set forth as SEQ ID NO: 406; or (v-vii) three CDRs of a heavy chain variable region set forth as SEQ ID NO: 407 and three CDRs of a light chain variable region set forth as SEQ ID NO: 408; or (w-vii) three CDRs of a heavy chain variable region set forth as SEQ ID NO: 409 and three CDRs of a light chain variable region set forth as SEQ ID NO: 410; or (x-vii) three CDRs of a heavy chain variable region set forth as SEQ ID NO: 411 and three CDRs of a light chain variable region set forth as SEQ ID NO: 412; or (y-vii) three CDRs of a heavy chain variable region set forth as SEQ ID NO: 413 and three CDRs of a light chain variable region set forth as SEQ ID NO: 414; or (z-vii) three CDRs of a heavy chain variable region set forth as SEQ ID NO: 415 and three CDRs of a light chain variable region set forth as SEQ ID NO: 416; or (a-viii) three CDRs of a heavy chain variable region set forth as SEQ ID NO: 417 and three CDRs of a light chain variable region set forth as SEQ ID NO: 418; or (b-viii) three CDRs of a heavy chain variable region set forth as SEQ ID NO: 419 and three CDRs of a light chain variable region set forth as SEQ ID NO: 420; or (c-viii) three CDRs of a heavy chain variable region set forth as SEQ ID NO: 421 and three CDRs of a light chain variable region set forth as SEQ ID NO: 422; or (d-viii) three CDRs of a heavy chain variable region set forth as SEQ ID NO: 423 and three CDRs of a light chain variable region set forth as SEQ ID NO: 424; or (e-viii) three CDRs of a heavy chain variable region set forth as SEQ ID NO: 425 and three CDRs of a light chain variable region set forth as SEQ ID NO: 426; or (f-viii) three CDRs of a heavy chain variable region set forth as SEQ ID NO: 427 and three CDRs of a light chain variable region set forth as SEQ ID NO: 428; or (g-viii) three CDRs of a heavy chain variable region set forth as SEQ ID NO: 429 and three CDRs of a light chain variable region set forth as SEQ ID NO: 430; or (h-viii) three CDRs of a heavy chain variable region set forth as SEQ ID NO: 431 and three CDRs of a light chain variable region set forth as SEQ ID NO: 432; or (i-viii) three CDRs of a heavy chain variable region set forth as SEQ ID NO: 433 and three CDRs of a light chain variable region set forth as SEQ ID NO: 434; or (j-viii) three CDRs of a heavy chain variable region set forth as SEQ ID NO: 435 and three CDRs of a light chain variable region set forth as SEQ ID NO: 436; or (k-viii) three CDRs of a heavy chain variable region set forth as SEQ ID NO: 437 and three CDRs of a light chain variable region set forth as SEQ ID NO: 438; or (l-viii) three CDRs of a heavy chain variable region set forth as SEQ ID NO: 439 and three CDRs of a light chain variable region set forth as SEQ ID NO: 440; or (m-viii) three CDRs of a heavy chain variable region set forth as SEQ ID NO: 441 and three CDRs of a light chain variable region set forth as SEQ ID NO: 442; or (n-viii) three CDRs of a heavy chain variable region set forth as SEQ ID NO: 443 and three CDRs of a light chain variable region set forth as SEQ ID NO: 444; or (o-viii) three CDRs of a heavy chain variable region set forth as SEQ ID NO: 445 and three CDRs of a light chain variable region set forth as SEQ ID NO: 446; or (p-viii) three CDRs of a heavy chain variable region set forth as SEQ ID NO: 447 and three CDRs of a light chain variable region set forth as SEQ ID NO: 448; or (q-viii) three CDRs of a heavy chain variable region set forth as SEQ ID NO: 449 and three CDRs of a light chain variable region set forth as SEQ ID NO: 450; or (r-viii) three CDRs of a heavy chain variable region set forth as SEQ ID NO: 451 and three CDRs of a light chain variable region set forth as SEQ ID NO: 452; or (s-viii) three CDRs of a heavy chain variable region set forth as SEQ ID NO: 453 and three CDRs of a light chain variable region set forth as SEQ ID NO: 454; or (t-viii) three CDRs of a heavy chain variable region set forth as SEQ ID NO: 455 and three CDRs of a light chain variable region set forth as SEQ ID NO: 456; or (u-viii) three CDRs of a heavy chain variable region set forth as SEQ ID NO: 457 and three CDRs of a light chain variable region set forth as SEQ ID NO: 458; or (v-viii) three CDRs of a heavy chain variable region set forth as SEQ ID NO: 459 and three CDRs of a light chain variable region set forth as SEQ ID NO: 460; or (w-viii) three CDRs of a heavy chain variable region set forth as SEQ ID NO: 461 and three CDRs of a light chain variable region set forth as SEQ ID NO: 462; or (x-viii) three CDRs of a heavy chain variable region set forth as SEQ ID NO: 463 and three CDRs of a light chain variable region set forth as SEQ ID NO: 464; or (y-vii) three CDRs of a heavy chain variable region set forth as SEQ ID NO: 465 and three CDRs of a light chain variable region set forth as SEQ ID NO: 466; or (z-viii) three CDRs of a heavy chain variable region set forth as SEQ ID NO: 467 and three CDRs of a light chain variable region set forth as SEQ ID NO: 468; or (a-vix) three CDRs of a heavy chain variable region set forth as SEQ ID NO: 469 and three CDRs of a light chain variable region set forth as SEQ ID NO: 470; or (b-vix) three CDRs of a heavy chain variable region set forth as SEQ ID NO: 471 and three CDRs of a light chain variable region set forth as SEQ ID NO: 472; or (c-vix) three CDRs of a heavy chain variable region set forth as SEQ ID NO: 473 and three CDRs of a light chain variable region set forth as SEQ ID NO: 474; or (d-vix) three CDRs of a heavy chain variable region set forth as SEQ ID NO: 475 and three CDRs of a light chain variable region set forth as SEQ ID NO: 476; or (e-vix) three CDRs of a heavy chain variable region set forth as SEQ ID NO: 477 and three CDRs of a light chain variable region set forth as SEQ ID NO: 478; or (f-vix) three CDRs of a heavy chain variable region set forth as SEQ ID NO: 479 and three CDRs of a light chain variable region set forth as SEQ ID NO: 480; or (g-vix) three CDRs of a heavy chain variable region set forth as SEQ ID NO: 481 and three CDRs of a light chain variable region set forth as SEQ ID NO: 482; or (h-vix) three CDRs of a heavy chain variable region set forth as SEQ ID NO: 483 and three CDRs of a light chain variable region set forth as SEQ ID NO: 484; or (i-vix) three CDRs of a heavy chain variable region set forth as SEQ ID NO: 485 and three CDRs of a light chain variable region set forth as SEQ ID NO: 486; or (j-vix) three CDRs of a heavy chain variable region set forth as SEQ ID NO: 487 and three CDRs of a light chain variable region set forth as SEQ ID NO: 488; or (k-vix) three CDRs of a heavy chain variable region set forth as SEQ ID NO: 489 and three CDRs of a light chain variable region set forth as SEQ ID NO: 490; or (l-vix) three CDRs of a heavy chain variable region set forth as SEQ ID NO: 491 and three CDRs of a light chain variable region set forth as SEQ ID NO: 492; or (m-vix) three CDRs of a heavy chain variable region set forth as SEQ ID NO: 493 and three CDRs of a light chain variable region set forth as SEQ ID NO: 494; or (n-vix) three CDRs of a heavy chain variable region set forth as SEQ ID NO: 495 and three CDRs of a light chain variable region set forth as SEQ ID NO: 496; or (o-vix) three CDRs of a heavy chain variable region set forth as SEQ ID NO: 497 and three CDRs of a light chain variable region set forth as SEQ ID NO: 498; or (p-vix) three CDRs of a heavy chain variable region set forth as SEQ ID NO: 499 and three CDRs of a light chain variable region set forth as SEQ ID NO: 500; or (q-vix) three CDRs of a heavy chain variable region set forth as SEQ ID NO: 501 and three CDRs of a light chain variable region set forth as SEQ ID NO: 502; or (r-vix) three CDRs of a heavy chain variable region set forth as SEQ ID NO: 503 and three CDRs of a light chain variable region set forth as SEQ ID NO: 504; or (s-vix) three CDRs of a heavy chain variable region set forth as SEQ ID NO: 505 and three CDRs of a light chain variable region set forth as SEQ ID NO: 506; or (t-vix) three CDRs of a heavy chain variable region set forth as SEQ ID NO: 507 and three CDRs of a light chain variable region set forth as SEQ ID NO: 508; or (u-vix) three CDRs of a heavy chain variable region set forth as SEQ ID NO: 509 and three CDRs of a light chain variable region set forth as SEQ ID NO: 510; or (v-vix) three CDRs of a heavy chain variable region set forth as SEQ ID NO: 511 and three CDRs of a light chain variable region set forth as SEQ ID NO: 512; or (w-vix) three CDRs of a heavy chain variable region set forth as SEQ ID NO: 513 and three CDRs of a light chain variable region set forth as SEQ ID NO: 514; or (x-ix) three CDRs of a heavy chain variable region set forth as SEQ ID NO: 515 and three CDRs of a light chain variable region set forth as SEQ ID NO: 516; or (y-ix) three CDRs of a heavy chain variable region set forth as SEQ ID NO: 517 and three CDRs of a light chain variable region set forth as SEQ ID NO: 518; or (z-ix) three CDRs of a heavy chain variable region set forth as SEQ ID NO: 519 and three CDRs of a light chain variable region set forth as SEQ ID NO: 520; or (a-x) three CDRs of a heavy chain variable region set forth as SEQ ID NO: 521 and three CDRs of a light chain variable region set forth as SEQ ID NO: 522; or (b-x) three CDRs of a heavy chain variable region set forth as SEQ ID NO: 523 and three CDRs of a light chain variable region set forth as SEQ ID NO: 524; or (c-x) three CDRs of a heavy chain variable region set forth as SEQ ID NO: 525 and three CDRs of a light chain variable region set forth as SEQ ID NO: 526; or (d-x) three CDRs of a heavy chain variable region set forth as SEQ ID NO: 527 and three CDRs of a light chain variable region set forth as SEQ ID NO: 528; or (e-x) three CDRs of a heavy chain variable region set forth as SEQ ID NO: 529 and three CDRs of a light chain variable region set forth as SEQ ID NO: 530; or (f-x) three CDRs of a heavy chain variable region set forth as SEQ ID NO: 531 and three CDRs of a light chain variable region set forth as SEQ ID NO: 532; or (g-x) three CDRs of a heavy chain variable region set forth as SEQ ID NO: 533 and three CDRs of a light chain variable region set forth as SEQ ID NO: 534; or (h-x) three CDRs of a heavy chain variable region set forth as SEQ ID NO: 535 and three CDRs of a light chain variable region set forth as SEQ ID NO: 536; or (i-x) three CDRs of a heavy chain variable region set forth as SEQ ID NO: 537 and three CDRs of a light chain variable region set forth as SEQ ID NO: 538; or (j-x) three CDRs of a heavy chain variable region set forth as SEQ ID NO: 539 and three CDRs of a light chain variable region set forth as SEQ ID NO: 540; or (k-x) three CDRs of a heavy chain variable region set forth as SEQ ID NO: 541 and three CDRs of a light chain variable region set forth as SEQ ID NO: 542; or (l-x) three CDRs of a heavy chain variable region set forth as SEQ ID NO: 543 and three CDRs of a light chain variable region set forth as SEQ ID NO: 544; or (m-x) three CDRs of a heavy chain variable region set forth as SEQ ID NO: 545 and three CDRs of a light chain variable region set forth as SEQ ID NO: 546; or (n-x) three CDRs of a heavy chain variable region set forth as SEQ ID NO: 547 and three CDRs of a light chain variable region set forth as SEQ ID NO: 548; or (o-x) three CDRs of a heavy chain variable region set forth as SEQ ID NO: 549 and three CDRs of a light chain variable region set forth as SEQ ID NO: 550.

In particular embodiments, the inventions disclosed herein encompass an antibody or antigen-binding fragment thereof, wherein the antibody or fragment thereof comprises: (a) CDR-H1 comprising residues 31-35, CDR-H2 comprising residues 50-65, and CDR-H3 comprising residues 95-102 of the heavy chain variable region ($V_H$); and (b) CDR-L1 comprising residues 24-34, CDR-L2 comprising residues 50-56, and CDR-L3 comprising residues 89-97 of the light chain variable region ($V_L$), wherein the CDR numbering is according to Kabat.

In particular embodiments, the inventions disclosed herein encompass an antibody or antigen-binding fragment thereof, wherein the antibody or fragment thereof comprises: (a) CDR-H1 comprising residues 26-32, CDR-H2 comprising residues 52-56, and CDR-H3 comprising residues 95-102 of the $V_H$; and (b) CDR-L1 comprising residues 24-34, CDR-L2 comprising residues 50-56, and CDR-L3 comprising residues 89-97 of the $V_L$, wherein the CDR numbering is according to Chothia.

In particular embodiments, the inventions disclosed herein encompass an antibody or antigen-binding fragment thereof, wherein the antibody or fragment thereof comprises: (a) CDR-H1 comprising residues 30-35, CDR-H2 comprising residues 47-58, and CDR-H3 comprising residues 93-101 of the $V_H$; and (b) CDR-L1 comprising residues 30-36, CDR-L2 comprising residues 46-55, and CDR-L3 comprising the residues 89-96 of the $V_L$, wherein the CDR numbering is according to MacCallum.

In particular embodiments, the inventions disclosed herein encompass an antibody or antigen-binding fragment thereof, which comprises a heavy chain variable region having an amino acid sequence that is at least 60% identical (e.g., at least 70%, at least 80%, at least 85%, at least 90%, at least 95%, at least 98%, at least 99%, or 100% identical) to a heavy chain variable region sequence comprising three CDRs of the heavy chain variable region set forth in odd-numbered SEQ ID NOs: 1-550 and a light chain variable region having an amino acid sequence that is at least 60% identical (e.g., at least 70%, at least 80%, at least 85%, at least 90%, at least 95%, at least 98%, at least 99%, or 100% identical) to one of the light chain variable region sequences comprising three CDRs of a corresponding light chain variable region set forth in even-numbered SEQ ID NOs: 1-550.

In particular embodiments, the inventions disclosed herein encompass an antibody or antigen-binding fragment thereof, wherein the antibody or fragment thereof comprises (a) a heavy chain variable region set forth as any one of odd-numbered sequence set forth in SEQ ID NOs 1-550 and (b) a light chain variable region set forth as the corresponding even numbered sequence set forth in SEQ ID NOs 1-550 (e.g., SEQ ID NOs: 1 and 2, 3 and 4, etc.).

In some embodiments, the inventions disclosed herein encompass a bispecific antibody that is capable of binding to both CD3 and a tumor antigen. In some embodiments, the tumor antigen is epidermal growth factor receptor (EGFR). In some embodiments, the antibody comprises a first binding arm and a second binding arm, wherein the first binding arm binds to at least one CD3 molecule and further comprises: (a) a heavy chain having an amino acid sequence selected from the group consisting of SEQ ID NOs: 551, 553, 555, 557, 561, 563, 565, 567, 569, 571, 573, 575, 577, 579, 581, 583, 585, and 587; and (b) a light chain having an amino acid sequence selected from the group consisting of SEQ ID NOs: 552, 554, 556, 558, 157, 564, 566, 568, 570, 572, 574, 576, 578, 580, 582, 584, 586, and 588; and wherein the second binding arm binds to at least one EGFR molecule and further comprises: (c) a heavy chain having an amino acid sequence selected from the group consisting of SEQ ID NOs: 589 and 591; and (d) a light chain having an amino acid sequence selected from the group consisting of SEQ ID NOs: 590 and 592.

In particular embodiments, the inventions disclosed herein encompass an antibody or antigen-binding fragment thereof described in the preceding paragraphs of this section that comprises at least one amino acid substitution in a framework region or constant region. In particular embodiments, the at least one amino acid substitution is a conservative substitution. In particular embodiments, the at least one amino acid substitution is a substitution of an amino acid for a non-genetically encoded amino acid or a synthetic amino acid.

In particular embodiments, the inventions disclosed herein encompass an antibody or antigen-binding fragment thereof described in the preceding paragraphs of this section that is conjugated to an immunomodulator, a cytokine, a cytotoxic agent, a chemotherapeutic agent, a diagnostic agent, or a drug.

In particular embodiments, the inventions disclosed herein encompass an antibody conjugate comprising an antibody or antigen-binding fragment thereof described in the preceding paragraphs of this section that is conjugated to an immunomodulator, a cytokine, a cytotoxic agent, a chemotherapeutic agent, a diagnostic agent, or a drug.

In particular embodiments, the inventions disclosed herein encompass a pharmaceutical composition comprising an antibody or antigen-binding fragment thereof described in the preceding paragraphs of this section or an antibody conjugate comprising the same, and one or more pharmaceutically acceptable carriers, diluents, or excipients.

In particular embodiments, the inventions disclosed herein encompass a nucleic acid encoding a heavy chain variable region or a light chain variable region having an amino acid sequence that is identical to the heavy chain variable region set forth in odd-numbered SEQ ID NOs: 1-550 or the light chain variable region set forth in even-numbered SEQ ID NOs: 1-550.

In particular embodiments, the inventions disclosed herein encompass a vector comprising at least one of (a) a nucleic acid encoding a heavy chain variable region having an amino acid sequence that is identical to the heavy chain variable region set forth in odd-numbered SEQ ID NOs: 1-550; and (b) a nucleic acid encoding a light chain variable region having an amino acid sequence that is identical to the light chain variable region set forth in even-numbered SEQ ID NOs: 1-550. In some embodiments, the vector may comprise (a) and (b).

In particular embodiments, the inventions disclosed herein encompass a host cell comprising at least one of (a) a nucleic acid encoding a heavy chain variable region having an amino acid sequence that is identical to the heavy chain variable region set forth in odd-numbered SEQ ID NOs: 1-550; and (b) a nucleic acid encoding a light chain variable region having an amino acid sequence that is identical to the light chain variable region set forth in even-numbered SEQ ID NOs: 1-550.

In particular embodiments, the inventions disclosed herein encompass a host cell comprising a first vector comprising a nucleic acid encoding a heavy chain variable region having an amino acid sequence that is identical to the heavy chain variable region set forth in odd-numbered SEQ ID NOs: 1-550 and a second vector comprising a nucleic acid encoding a light chain variable region having an amino acid sequence that is identical to the light chain variable region set forth in even-numbered SEQ ID NOs: 1-550. In particular embodiments, the inventions disclosed herein encompass a host cell comprising a vector comprising nucleic acid encoding a heavy chain variable region having an amino acid sequence that is identical to the heavy chain variable region set forth in odd-numbered SEQ ID NOs: 1-550 and a nucleic acid encoding a light chain variable region having an amino acid sequence that is identical to the light chain variable region set forth in even-numbered SEQ ID NOs: 1-550.

In particular embodiments, the inventions disclosed herein encompass a process for producing an antibody or antigen-binding fragment thereof described in the preceding paragraphs of this section comprising (a) cultivating the host cell described in the preceding paragraphs under conditions such that the antibody or antigen-binding fragment thereof is expressed; and (b) recovering the expressed antibody or antigen-binding fragment thereof.

In particular embodiments, the inventions disclosed herein encompass an article of manufacture useful for diagnosing or treating a comprising a receptacle comprising the antibody or antigen-binding fragment thereof described in the preceding paragraphs of this section, or an antibody conjugate comprising the same, or a pharmaceutical composition comprising the same and instructional materials for using the same to treat or diagnose a hyperproliferative or autoimmune disorder.

In particular embodiments, the inventions disclosed herein encompass a method of preventing or treating an a hyperproliferative or autoimmune disorder comprising administering to a patient a therapeutically effective amount of the antibody or antigen-binding fragment thereof described in the preceding paragraphs of this section, or an antibody conjugate comprising the same, or a pharmaceutical composition comprising the same.

In particular embodiments, the inventions disclosed herein encompass a method of treating a hyperproliferative or autoimmune disorder comprising: (a) contacting a sample obtained from a patient with an antibody or antigen-binding fragment thereof described in the preceding paragraphs of this section, which is conjugated to a detectable agent; (b) detecting specific binding of the antibody or antigen-binding fragment thereof to a T cell present in the sample; and (c) administering to the patient a therapeutically effective amount of an antibody or antigen-binding fragment thereof described in the preceding paragraphs of this section or a pharmaceutical composition comprising the same. In some embodiments, the antibody or antigen-binding fragment thereof of step (a) is the same as the antibody or antigen-binding fragment thereof of step (c). In other embodiments, the antibody or antigen-binding fragment thereof of step (a) is different from the antibody or antigen-binding fragment thereof of step (c) (e.g., the antibody used in step (c) is a bispecific antibody).

In particular embodiments, the inventions disclosed herein encompass an antibody or antigen-binding fragment thereof described in the preceding paragraphs of this section or a pharmaceutical composition comprising the same for use in the diagnosis or treatment of a hyperproliferative or autoimmune disorder or one or more symptoms thereof.

In particular embodiments, the inventions disclosed herein encompass an antibody or antigen-binding fragment thereof described in the preceding paragraphs of this section or a pharmaceutical composition comprising the same for use in the manufacture of a medicament for diagnosis or treatment of a hyperproliferative or autoimmune disorder or one or more symptoms thereof.

Anti-CD3 Antibodies

The present disclosure is directed to anti-CD3 antibodies and their use in the diagnosis and treatment of a hyperproliferative or autoimmune disorder and symptoms thereof. As used herein, the term "antibody" or "immunoglobulin" are used interchangeably and in the broadest sense and cover both intact molecules and immunologically-reactive fragments thereof. These terms cover, for example, synthetic antibodies, monoclonal antibodies, oligoclonal or polyclonal antibodies, multiclonal antibodies, recombinantly produced antibodies, intrabodies, bispecific antibodies, multi-specific antibodies, bispecific antibodies, monovalent antibodies, multivalent antibodies, human antibodies, humanized antibodies, chimeric antibodies, CDR-grafted antibodies, primatized antibodies, Fab fragments, F(ab') fragments, $F(ab')_2$ fragments, F(ab)c fragments, single-chain FvFcs (scFvFc), single-chain Fvs (scFv), and any other immunologically-reactive/antigen-binding fragments thereof.

As used herein, the term "anti-CD3 antibody(ies)" describes antibodies that specifically recognize, bind to, or otherwise associate with a CD3 molecule from at least one mammalian species. As used herein terms, "specifically recognize", "bind", and "binds" are intended to mean, unless indicated otherwise, the ability of a protein or molecule to form a chemical bond or attractive interaction with another protein or molecule, which results in proximity of the two proteins or molecules as determined by common methods known in the art.

Antibodies are grouped into five distinct classes that can be distinguished biochemically and depending on the amino acid sequence of the constant domain of their heavy chains, can readily be assigned to the appropriate class. For historical reasons, the major classes of intact antibodies are termed IgA, IgD, IgE, IgG, and IgM. In humans, the IgG and IgA classes may be further divided into recognized subclasses (isotypes), i.e., IgG1, IgG2, IgG3, IgG4, IgA1, and IgA2 depending on structure and certain biochemical properties. It will be appreciated that the IgG isotypes in humans are named in order of their abundance in serum with IgG1 being the most abundant.

While all five classes of antibodies (i.e., IgA, IgD, IgE, IgG, and IgM) and all isotypes (i.e., IgG1, IgG2, IgG3, IgG4, IgA1, and IgA2), as well as variations thereof, are within the scope of the present disclosure, preferred embodiments belonging to the IgG class are discussed in some detail solely for the purposes of illustration. It will be understood that such disclosure is, however, merely demonstrative of exemplary compositions and methods and is not in any way limiting.

In this respect, human IgG immunoglobulins comprise two identical light polypeptide chains of molecular weight approximately 23,000 Daltons, and two identical heavy chains of molecular weight 53,000-70,000 depending on the isotype. Heavy-chain constant domains that correspond to the different classes of antibodies are denoted by the corresponding lower case Greek letter α, δ, ε, γ, and μ, respectively. The light chains of the antibodies from any vertebrate species can be assigned to one of two clearly distinct types, called kappa (κ) and lambda (λ), based on the amino acid sequences of their constant domains. Those skilled in the art will appreciate that the subunit structures and three-dimensional configurations of different classes of immunoglobulins are well known.

The four chains are joined by disulfide bonds in a "Y" configuration wherein the light chains bracket the heavy chains starting at the mouth of the "Y" and continuing through the variable region to the dual ends of the "Y". Each light chain is linked to a heavy chain by one covalent disulfide bond while two disulfide linkages in the hinge region join the heavy chains. The respective heavy and light chains also have regularly spaced intrachain disulfide bridges the number of which may vary based on the isotype of IgG.

Each heavy chain has at one end a variable region ($V_H$) followed by a number of constant regions. Each light chain has a variable region at one end ($V_L$) and a constant region at its other end; the constant region of the light chain is aligned with the first constant region of the heavy chain, and the light chain variable region is aligned with the variable region of the heavy chain. The variable regions of both the light ($V_L$) and heavy ($V_H$) chain portions determine antigen recognition and specificity. Conversely, the constant regions of the light chain ($C_L$) and the heavy chain ($C_H$ 1, $C_H$2 or $C_H$3) confer and regulate important biological properties such as secretion, transplacental mobility, circulation half-life, complement binding, and the like. By convention, the numbering of the constant region regions increases as they become more distal from the antigen binding site or amino-terminus of the antibody. Thus, the amino or N-terminus of the antibody comprises the variable region and the carboxy or C-terminus comprises the constant region. Thus, the $C_H$3 and $C_L$ regions actually comprise the carboxy-terminus of the heavy and light chain, respectively.

Portions of the variable regions of both the heavy chain and light chain differ extensively in sequence among immunoglobulins and these hypervariable sites largely define the binding and specificity of a particular antibody. These hypervariable sites manifest themselves in three segments, known as complementarity determining regions (CDRs). The more highly conserved portions of variable regions flanking the CDRs are termed framework regions (FRs). More specifically, in naturally occurring monomeric IgG antibodies, the six CDRs present on each arm of the antibody are short, non-contiguous sequences of amino acids that are specifically positioned to form the antigen-binding site as the antibody assumes its three-dimensional configuration in vivo or in vitro. CDRs encompass amino acid residues identified using any sequence or structure-based method or nomenclature system known in the art and as described below.

By way of example, CDRs may be defined using the nomenclature described by Kabat et al. (1991, NIH Publication 91-3242, National Technical Information Service, Springfield, Va.), specifically, residues 31-35 (CDR-H1), 50-65 (CDR-H2), and 95-102 (CDR-H3) in the heavy chain variable region and residues 24-34 (CDR-L1), 50-56 (CDR-L2), and 89-97 (CDR-L3) in the light chain variable region.

By way of example, CDRs may also be defined using the nomenclature described by Chothia et al. (*J. Mol. Biol.* 196:901-917 (1987); *Nature* 342, pp. 877-883 (1989)), specifically, residues 26-32 (CDR-H1), 52-56 (CDR-H2), and 95-102 (CDR-H3) in the heavy chain variable region and residues 23-34 (CDR-L1), 50-56 (CDR-L2), and 89-97 (CDR-L3) in the light chain variable region.

By way of example, CDRs may also be defined using the nomenclature described by MacCallum et al. (*J. Mol. Biol.* 262:732-745 (1996), specifically, residues 30-35 (CDR-H1), 47-58 (CDR-H2), and 93-101 (CDR-H3) in the heavy chain variable region and residues 30-36 (CDR-L1), 46-55 (CDR-L2), and 89-96 (CDR-L3) in the light chain variable region.

CDRs vary considerably from antibody to antibody (and by definition will not exhibit homology with the Kabat consensus sequences). Maximal alignment of framework residues frequently requires the insertion of spacer residues in the numbering system, to be used for the Fv region. In addition, the identity of certain individual residues at any given Kabat site number may vary from antibody chain to antibody chain due to interspecies or allelic divergence.

One skilled in the art could readily define, identify derive and/or enumerate the CDRs as defined by Kabat et al., Chothia et al., or MacCallum et al. for each respective antibody heavy and light chain sequence set forth herein. Accordingly, each of the subject CDRs and antibodies comprising CDRs defined by all such nomenclature are expressly included within the scope of the instant disclosure.

The framework regions comprise the remainder of the heavy and light chain variable regions and are thus comprised of a non-contiguous sequence between about 100-120 amino acids in length. For example, using the nomenclature of Kabat et al., framework region 1 corresponds to the region of the variable region encompassing amino acids 1-30; framework region 2 corresponds to the region of the variable region encompassing amino acids 36-49; framework region 3 corresponds to the region of the variable region encompassing amino acids 66-94, and framework region 4 corresponds to the region of the variable region from amino acids 103 to the end of the variable region. Similarly, using the definition of CDRs by Chothia et al. or McCallum et al., the framework region boundaries are separated by the respective CDR termini as described above.

The framework regions show less inter-molecular variability in amino acid sequence and largely adopt a β-sheet conformation and the CDRs form loops which connect, and in some cases form part of, the β-sheet structure. Thus, these framework regions act to form a scaffold that provides for positioning the six CDRs in correct orientation by inter-chain, non-covalent interactions. The antigen-binding site formed by the positioned CDRs defines a surface complementary to the epitope on the immunoreactive antigen. This complementary surface promotes the non-covalent binding of the antibody to the immunoreactive antigen epitope.

All or part of the heavy and light chain variable regions may be recombined or engineered using standard recombinant and expression techniques to provide improve one or more properties of the resultant antibody. That is, the heavy or light chain variable region from a first antibody (or any portion thereof) may be mixed and matched with any selected portion of the heavy or light chain variable region from a second antibody. For example, in one embodiment, the entire light chain variable region comprising the three light chain CDRs of a first antibody may be paired with the entire heavy chain variable region comprising the three heavy chain CDRs of a second antibody. Moreover, in other embodiments, individual heavy and light chain CDRs derived from various antibodies may be mixed and matched to provide the desired antibody having optimized characteristics. Thus, an exemplary antibody may comprise three light chain CDRs from a first antibody, two heavy chain CDRs derived from a second antibody and a third heavy chain CDR from a third antibody.

With the aforementioned structural considerations in mind, those skilled in the art will appreciate that the antibodies of the present invention may comprise any one of a number of functional embodiments. In this respect, compatible antibodies may comprise any immunoreactive antibody (as the term is defined herein) that provides the desired physiological response in a subject. While any of the disclosed antibodies may be used in conjunction with the present teachings, certain embodiments of the invention will comprise chimeric, humanized, or human monoclonal antibodies or immunoreactive fragments thereof. Yet other embodiments may, for example, comprise homogeneous or heterogeneous multimeric constructs, Fc variants and conjugated or glycosylationally-altered antibodies. Moreover, it will be understood that such configurations are not mutually exclusive and that compatible individual antibodies may comprise one or more of the functional aspects disclosed herein. For example, a compatible antibody may comprise a single chain diabody with humanized variable regions or a fully human full length antibody with Fc modifications that alter the glycosylation pattern to modulate serum half-life. Other exemplary embodiments are readily apparent to those skilled in the art and may easily be discernable as being within the scope of the invention.

Antibodies produced by naive libraries (either natural or synthetic) can be of moderate affinity ($K_a$ of about $10^6$ to $10^7$ $M^{-1}$), but affinity maturation can also be mimicked in vitro by constructing and reselecting from secondary libraries as described in the art. For example, mutations can be introduced at random in vitro by using error-prone polymerase.

Additionally, affinity maturation can be performed by randomly mutating one or more CDRs, e.g., using PCR with primers carrying random sequence spanning the CDR of interest, in selected individual Fv clones and screening for higher affinity clones. Another approach is to recombine the $V_H$ or $V_L$ regions selected by phage display with repertoires of naturally occurring variable region variants obtained from unimmunized donors and screen for higher affinity in several rounds of chain reshuffling. This technique allows the production of antibodies and antibody fragments with a dissociation constant $K_d$ ($k_{off}/k_{on}$) of about $10^{-9}$ M or less.

Regardless of the type of antibody (e.g., chimeric, humanized, etc.), those skilled in the art will appreciate that immunoreactive or antigen-binding fragments of the same may also be used. In the broadest sense, an antibody fragment comprises at least a portion of an intact antibody (e.g., a naturally occurring immunoglobulin). More particularly the term "fragment" refers to a part or portion of an antibody or antibody chain comprising fewer amino acid residues than an intact or complete antibody or antibody chain. As used herein, the term "antigen-binding fragment" refers to a polypeptide fragment of an immunoglobulin or antibody that binds antigen or competes with intact antibody (i.e., with the intact antibody from which they were derived) for antigen binding (i.e., specific binding). As used herein, antigen-binding fragments included an antibody light chain ($V_L$), an antibody heavy chain ($V_H$), a single chain antibody (scFv), a $F(ab')_2$ fragment, a Fab fragment, an Fd fragment, an Fv fragment, single region antibody fragments, diabodies, linear antibodies, single-chain antibody molecules and multispecific antibodies formed from antibody fragments.

Those skilled in the art will also appreciate that antibody fragments can be obtained via chemical or enzymatic treatment of an intact or complete modulator (e.g., antibody or antibody chain) or by recombinant means. In this regard, while various antibody fragments are defined in terms of the digestion of an intact antibody, one of skill will appreciate that such fragments may be synthesized de novo either chemically or by using recombinant DNA methodology.

By way of example, papain digestion of antibodies produces two identical antigen-binding fragments, called Fab fragments, each with a single antigen-binding site, and a residual Fc fragment, whose name reflects its ability to crystallize readily. Pepsin treatment yields an $F(ab')_2$ fragment that has two antigen-binding sites and is still capable of cross-linking antigen. The Fab fragment also contains the constant region of the light chain and the first constant region ($C_H1$) of the heavy chain. Fab' fragments differ from Fab fragments by the addition of a few residues at the carboxy terminus of the heavy-chain $C_H$ 1 region including one or more cysteines from the antibody hinge region. Fab'-SH is the designation herein for Fab' in which the cysteine residue(s) of the constant regions bear at least one free thiol group. $F(ab')_2$ antibody fragments originally were produced as pairs of Fab' fragments that have hinge cysteines between them. Other chemical couplings of antibody fragments are also known.

By way of further example, an Fv fragment is an antibody fragment that contains a complete antigen recognition and binding site. This region is made up of a dimer of one heavy and one light chain variable region in tight association, which can be covalent in nature, for example in scFv. It is in this configuration that the three CDRs of each variable region interact to define an antigen binding site on the surface of the $V_H$-$V_L$ dimer. Collectively, the six CDRs or a subset thereof confer antigen binding specificity to the antibody. However, even a single variable region (or half of an Fv comprising only three CDRs specific for an antigen) has the ability to recognize and bind antigen, although usually at a lower affinity than the entire binding site.

In some embodiments an anti-CD3 antibody fragment, for example, is one that comprises the Fc region, retains at least one of the biological functions normally associated with the Fc region when present in an intact antibody, such as FcRn binding, antibody half-life modulation, ADCC function and complement binding. In one embodiment, an antibody fragment is a monovalent antibody that has an in vivo half-life substantially similar to an intact antibody. For example, such an antibody fragment may comprise on antigen binding arm linked to an Fc sequence capable of conferring in vivo stability to the fragment.

In addition to various modifications, substitutions, additions, or deletions to the variable or binding regions of anti-CD3 antibodies disclosed herein, those skilled in the art will appreciate that selected embodiments may also comprise substitutions or modifications of the constant region (i.e., the Fc region). More particularly, it is contemplated that anti-CD3 antibodies disclosed herein may contain one or more additional amino acid residue substitutions, mutations and/or modifications, which result in a compound with preferred characteristics including, but not limited to: altered pharmacokinetics, increased serum half-life, increase binding affinity, reduced immunogenicity, increased production, altered Fc ligand binding, enhanced or reduced ADCC or CDC activity, altered glycosylation and/or disulfide bonds, and modified binding specificity.

As used herein, the term "Fc region" defines a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. A functional Fc region possesses an effector function of a native sequence Fc region. Exemplary effector functions include C1q binding; CDC; Fc receptor binding; ADCC; phagocytosis; down regulation of cell surface receptors (e.g., B cell receptor; BCR), etc. Such effector functions generally require the Fc region to be combined with a binding region (e.g., an antibody variable region) and can be assessed using various assays as disclosed, for example, in definitions herein.

As used herein, the term "Fc receptor" or FcR, describes a receptor that binds to the Fc region of an antibody. In some embodiments, an FcR is a native human FcR. In some embodiments, an FcR is one that binds an IgG antibody (a gamma receptor) and includes receptors of the FcβRI, Fc.RII, and FcβRIII subclasses, including allelic variants and alternatively spliced forms of those receptors. Fcγll receptors include FcβRIIA (an activating receptor) and FcγRIIB (an inhibiting receptor), which have similar amino acid sequences that differ primarily in the cytoplasmic regions thereof.

Activating receptor Fey RIIA contains an immunoreceptor tyrosine-based activation motif (ITAM) in its cytoplasmic region. Inhibiting receptor FyRIIB contains an immunoreceptor tyrosine-based inhibition motif (ITIM) in its cytoplasmic region. Methods of measuring binding to FcRn are known in the art.

As used herein, "complement dependent cytotoxicity" or CDC refers to the lysing of a target cell in the presence of complement. The complement activation pathway is initiated by the binding of the first component of the complement system (C1 q) to a molecule, an antibody for example, complexed with a cognate antigen. To assess complement activation, a CDC assay may be performed. Further, antibody-dependent cell-mediated cytotoxicity or ADCC refers to a form of cytotoxicity in which secreted Ig bound onto Fc receptors (FcRs) present on certain cytotoxic cells (e.g., Natural Killer (NK) cells, neutrophils, and macrophages) enables these cytotoxic effector cells to bind specifically to an antigen-bearing target cell and subsequently kill the target cell with cytotoxins. Lysis of the target cell is extracellular, requires direct cell-to-cell contact, and does not involve complement.

Variants of anti-CD3 antibodies disclosed herein that have altered FcR binding affinity or ADCC activity are those that have either enhanced or diminished FcR binding activity and/or ADCC activity compared to a parent or unmodified antibody or to a modulator comprising a native sequence Fc region. A variant antibody that displays increased binding to an FcR binds at least one FcR with better affinity than the parent or unmodified antibody or to a modulator comprising a native sequence Fc region. A variant antibody that displays decreased binding to an FcR, binds at least one FcR with worse affinity than the parent or unmodified antibody or to a modulator comprising a native sequence Fc region. Such variants which display decreased binding to an FcR may possess little or no appreciable binding to an FcR, e.g., 0-20% binding to the FcR compared to a native sequence IgG Fc region, e.g., as determined by techniques well known in the art. In some embodiments, the anti-CD3 antibodies disclosed herein have enhanced ADCC activities.

As to FcRn, anti-CD3 antibodies disclosed herein can also encompass Fc variants with modifications to the constant region that provide half-lives (e.g., serum half-lives) in a mammal, preferably a human, of greater than 5 days, greater than 10 days, greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the antibodies (or Fc containing molecules) of the present invention in a mammal, preferably a human, results in a higher serum titer of antibodies or antibody fragments in the mammal, and thus, reduces the frequency of the administration of antibodies or antibody fragments and/or reduces the concentration of antibodies or antibody fragments to be administered. Antibodies having increased in vivo half-lives can be generated by techniques known to those of skill in the art. For example, antibodies with increased in vivo half-lives can be generated by modifying (e.g., substituting, deleting, or adding) amino acid residues identified as involved in the interaction between the Fc region and the FcRn receptor. Binding to human FcRn in vivo and serum half-life of human FcRn high affinity binding polypeptides can be assayed, e.g., in transgenic mice or transfected human cell lines expressing human FcRn, or in primates to which the polypeptides with a variant Fc region are administered.

Variants of anti-CD3 antibodies disclosed herein can encompass an Fc region with modifications that improve their half-lives (e.g., serum half-lives) in a human. Studies have shown that some Fc mutation that enhances FcRn binding results in increased binding to rheumatoid factor (RF), whereas some Fc mutation combinations enhance FcRn binding and prolong antibody half-life without increased binding to RF, e.g., N434A/Y436T/Q438R/S440E (ACT1), N434A/Y436V/Q438R/S440E (ACT2), M428L/N434A/Y436T/Q438R/S440E (ACT3), M428L/N434A/Y436V/Q438R/S440E (ACT4), M428L/N434A/Q438R/S440E (ACT5) (positions numbered according to EU Index numbering).

In still other embodiments, glycosylation patterns or compositions of the anti-CD3 antibodies disclosed herein may be modified. More particularly, preferred embodiments may comprise one or more engineered glycoforms, i.e., an altered glycosylation pattern or altered carbohydrate composition that is covalently attached to a molecule comprising an Fc region. Engineered glycoforms may be useful for a variety of purposes, including but not limited to enhancing or reducing effector function, increasing the affinity of the antibody for a target antigen, or facilitating production of the antibody. In cases where reduced effector function is desired, it will be appreciated that the antibody may be engineered to express in an aglycosylated form. Such carbohydrate modifications can be accomplished by, for example, altering one or more sites of glycosylation within the antibody sequence. That is, one or more amino acid substitutions can be made that result in elimination of one or more variable region framework glycosylation sites to thereby eliminate glycosylation at that site. Conversely, enhanced effector functions or improved binding may be imparted to the Fc containing molecule by engineering in one or more additional glycosylation sites.

Additionally, or alternatively, an Fc variant can be made that has an altered glycosylation composition, such as a hypofucosylated antibody having reduced amounts of fucosyl residues or an antibody having increased bisecting GlcNAc structures. These and similar altered glycosylation patterns have been demonstrated to increase the ADCC ability of antibodies. Engineered glycoforms may be generated by any method known to one skilled in the art, for example by using engineered or variant expression strains, by co-expression with one or more enzymes (for example N-acetylglucosaminyltransferase III (GnTIII)), by expressing a molecule comprising an Fc region in various organisms or cell lines from various organisms or by modifying carbohydrate(s) after the molecule comprising Fc region has been expressed.

In some embodiments, variants of the anti-CD3 antibodies described herein have reduced fucosylation. In some embodiments, such variants comprise an Fc region comprising N-glycoside-linked sugar chains bound to the Fc region, wherein the sugar chains do not contain fucose. In some embodiments, such variants have increased ADCC activities, compared to the same antibodies comprising N-glycoside-linked sugar chains that comprise fucose.

Provided herein are anti-CD3 antibodies having internal designation numbers 42-55, 63-91, 93-185, and 187-325 as described in the following paragraphs. In some embodiments, provided herein are anti-CD3 antibodies or antigen-binding fragments thereof that comprise the $V_H$ and/or the $V_L$ of any one of antibodies identified by internal designation numbers 42-55, 63-91, 93-185, and 187-325. In some embodiments, provided herein are anti-CD3 antibodies or antigen-binding fragments thereof that comprise a $V_H$ domain having at least 80%, at least 85%, at least 90%, at least 95%, at least 98%, at least 99%, or 100% identity to the $V_H$ domain of any one of the foregoing antibodies or a $V_L$ domain having at least 80%, at least 85%, at least 90%, at least 95%, at least 98%, at least 99%, or 100% identity to the $V_L$ domain of any one of the foregoing. Preferably homologous $V_H$ and $V_L$ domains correspond to those of the same antibody (e.g., SEQ ID NOs: 1 and 2 describe the $V_H$ and $V_L$ domains of mAb 42, SEQ ID NOs: 3 and 4 describe the $V_H$ and $V_L$ domains of mAb 43, etc.).

In some embodiments, provided herein are anti-CD3 antibodies or antigen-binding fragments thereof that comprise a $V_H$ domain comprising the same three CDRs as comprised in the $V_H$ domain of any one of antibodies identified by internal designation numbers 42-55, 63-91, 93-185, and 187-325 and/or comprises a $V_L$ domain comprising the same three CDRs as the $V_L$ domain of any one of antibodies 42-55, 63-91, 93-185, and 187-325, wherein the CDRs are defined by Kabat, Chothia, or MacCallum numbering.

The amino acid sequences of the antibodies described in the foregoing paragraphs are provided below:

```
mAb 42 VH
                                          (SEQ ID NO: 1)
QAQLVQSGSELKKPGASVKVSCKASGYTFTKHSMNWVRQA

PGQGLEWMGWINTNTGNPTYAQGFTGRFVFSLDTSVTTAY

LQISSLKAEDTAVYYCAREGDYDFWSGFFNFDYWGQGTLV

TVSS

mAb 42 VL
                                          (SEQ ID NO: 2)
DIQMTQSPSSLSASVGDRVTITCRASQGIRNDLGWYQQKP

GKAPKRLIYAASSLQSGVPSRFSGSGSGAEFTLTISSLQP

EDFATYYCLQHNSYPRTFGQGTKVEIK

mAb 43 VH
                                          (SEQ ID NO: 3)
QAQLVQSGSELKKPGASVKVSCKASGYTFTKHSMNWVRQA

PGQGLEWMGWINTNTGNPMYAQGFTGRFVFSLDTSVTTAY

LQISSLKAEDTAVYYCAREGDYDFWSGFFNFDYWGQGTLV

TVSS

mAb 43 VL
                                          (SEQ ID NO: 4)
DIQMTQSPSSLSASVGDRVTITCRASQGIRNDLGWYQQKP

GKAPKRLIYAASSLQSGVPSRFSGSGSGTEFTLTISSLQP

EDFATYYCLQHNSYPRTFGQGTKVEIK

mAb 44 VH
                                          (SEQ ID NO: 5)
QAQLVQSGSELKKPGASVKVSCKASGYTFTRHAMNWVRQA

PGQGLEWMGWINTNTGNPTYAQGFTGRFVFSLDTSVSTAY

LKISSLKAEDTAVYYCVREGDYDFWSGFFNFDYWGQGTLV

TVSS

mAb 44 VL
                                          (SEQ ID NO: 6)
DIQMTQSPSSLSASVGDRVTITCRASQGIRNDLGWFQQKP

GKAPTRLIYAASSLQSGVPSRFSGSGSGAEFTLTISSLQP

EDFATYYCLQHNSYPRTFGQGTKVEIK

mAb 45 VH
                                          (SEQ ID NO: 7)
QAQLVQSGSELKKPGASVKVSCKASGYTFTKHSMNWVRQA

PGQGLEWMGWINTNTGNPMYGQGFTGRFVFSLDTSMTTTY

LQISSLKAEDTAIYYCAREGDYDLWRGFFNFDYWGQGTLV

TVSS

mAb 45 VL
                                          (SEQ ID NO: 8)
DIQMTQSPSSLSASVGDRVTITCRASQGIRNDLGWYQQKP

GKAPKRLIYAASSLQSGVPSRFSGSGSGAEFTLTISSLQP

EDFATYYCLQHNSYPRTFGQGTKVEIK
```

-continued mAb 46 VH (SEQ ID NO: 9)
EGQLVESGGGLVQPGGSLRLSCVASGFTLSSYTLNWVRQA

PGKGLEWVSYISSTSRTIYYSDSVKGRFTISRDNAKNSLY

LQMNSLRDEDTALYYCAREDYYDSSGFDYWGQGTLVTVSS mAb 46 VL (SEQ ID NO: 10)
AIRMTQSPSSFSASTGDRVTITCRASQGISSYLAWYQQKP

GKAPKLLIYTASTLQSGVPSRFSGSGSGTDFTLTIRSLQS

EDFATYYCQQYYSYPRTFGQGTKVEIK mAb 47 VH (SEQ ID NO: 11)
QAQLVQSGSELKKPGASVKVSCKASGYTFTKHSMNWVRQA

PGQGLEWMGWINTNTGNPTYAQGFTGRFVFSLDTSVTTAY

LQISSLKAEDTAVYYCAREGDYDFWSGFFNFDYWGQGTLV

TVSS mAb 47 VL (SEQ ID NO: 12)
DIQMTQSPSSLSASVGDRVTITCRASQGIRNDLGWYQQKP

GKAPKRLIYAASSLQSGVPSRFSGSGSGTEFTLTISSLQP

EDFATYYCLQHNSYPRTFGQGTKVEIK mAb 48 VH (SEQ ID NO: 13)
QVQLVQSGAEVKKPGASVKVSCKASGYTFTGYYIHWVRQA

PGQGLEWMGWINPKSGNRNYAQKFQGRVTMTRDTSIDTAY

MELTRLRSDDTAVYYCARIEQLVFDYWGQGTLVTVSS mAb 48 VL (SEQ ID NO: 14)
DIVMTQSPDSLAVSLGERATINCKSSQSVLYSSNNKNYLA

WYQQKPGQPPKLLIYWASTRESGVPDRFSGSGSGTDFTLT

ISSLQAEDVAVYYCQQYYSTPYTFGQGTKLEIK mAb 49 VH (SEQ ID NO: 15)
EVQLVESGGGLVPPGGSLRLSCVASGFTLRSYTMNWVRQA

PGQGLEWISYISSTSRTIYYSDSVKGRFTISRDNAKNSLY

LQVNSLRDEDTALYYCAREDYYDSSGFDCWGQGTLVTVSS mAb 49 VL (SEQ ID NO: 16)
AIRMTQSPSSFSASTGDRVTITCRASQGIFNYLAWYQQKP

GKAPKLLIYSTSTLQSGVPSRFSGSGSGTDFTLTIRGLQS

EDLATYYCQQYYSFPRTFGQGTKVDIK mAb 50 VH (SEQ ID NO: 17)
QAQLVQSGSELKKPGASVKVSCKASGYTFTRHAMNWVRQA

PGQGLEWMGWINTNTGNPTYAQGFTGRFVFSLDTSVTTAY

LQISSLKAEDTAVYYCAREGDYDFWSGFFNFDYWGQGTLV

TVSS mAb 50 VL (SEQ ID NO: 18)
DIQMTQSPSSLSASVGDRVTITCRASQGIRNDLGWFQQKP

-continued

GKAPTRLIYAASSLQSGVPSRFSGSGSGAEFTLTISSLQP

EDFATYYCLQHNSYPRTFGQGTKVEIK mAb 51 VH (SEQ ID NO: 19)
EVQLVESGGGLVQPGGSLRLSCAASGFTLSSYTMNWVRQA

PGKGLEWVSYISSSSRTIYYSDSVKGRFSISRDNAKNSLY

LQMNSLRDEDTALYYCAREDYYDSSGFDNWGQGTLVTVSS mAb 51 VL (SEQ ID NO: 20)
AIRMTQSPSSFSASTGDRVTITCRASQGISSYLAWYQQKP

GKAPKLLIYTASTLQSGVPSRFSGSGSGTDFTLTIRSLQS

EDFATYYCQQYYSYPRTFGQGTKVEIK mAb 52 VH (SEQ ID NO: 21)
QVQLVQSGAEVKKPGASVKVSCKASGYTFTSHDINWVRQA

TGQGLEWMGWLNPNSGKTGYAQKFQGRVTMARDTSMYTAD

MELSSLRFEDTAVYYCARVGHYDMWPGFFSFDYWGQGTLV

TVSS mAb 52 VL (SEQ ID NO: 22)
DIQMTQSPSSLSASVGDRIIITCRASQDIRNDLGWYQQKP

GKAPKRLIYAASSLQSGVPSRFSGSRSGTEFTLTISSLHP

EDFATYYCLQHRSYPYTFGQGTNLEIK mAb 53 VH (SEQ ID NO: 23)
QVQLVQSGAEVKKPGASVKVSCKASGYTFTSYDINWVRQA

TGQGLEWMGWMNPKSGKTGYAQKFQGRITMTRNTPISTVY

MDLSSLRSEDTAVYYCAREGHYDFWTGYYSFDYWGQGTLV

TVSS mAb 53 VL (SEQ ID NO: 24)
DIQMTQSPSSLSASVGDRVTITCRASQGIRNDLGWYQQTP

GKAPKRLIYAASSLQSGVPSRFSGSGSGTEFTLTISSLQP

EDFATYYCLQHYSYPYTFGQGTKLEIK mAb 54 VH (SEQ ID NO: 25)
EVQLEESGGGLVQPGGSLRLSCAASGFTFSRYSMNWVRQA

PGKGLEWFSYISSSSRTIYYADSVKGRFTMSRDNAKNSLY

LQMNSLRDEDTAVYFCARGDYYDSEGMDVWGKGTTVTVSS mAb 54 VL (SEQ ID NO: 26)
DIQMTQSPSTLSASVGDRVTITCRASQTITTWLAWYQQKP

GKAPKLLIYKASTLESGVPSRFSGSGSGTEFTLTISSLQP

DDFATYHCQQYKTFSYTFGQGTKLDIK mAb 55 VH (SEQ ID NO: 27)
QVQLEQSGAEVKKPGASVKVSCKTSGYIFANYDINWVRQA

TGQGLEWMGWMNPKSGKAGYAQKFQGRVTMTSNTPINTAY

MELSSLRSEDTAVYYCAREGHYDFWRGFYSFDYWGQGILV

TVSS

-continued mAb 55 VL (SEQ ID NO: 28)

DIQMTQSPSSLSASVGDRVTITCRASQGIRNDLGWYQQKP

GKAPKRLIYTASSLQSGVPSRFSGSGSGTEFTLTISSLQP

EDFATYFCLQYNTYPYTFGQGTKLEIK mAb 63 VH (SEQ ID NO: 29)

QVQLVQSGAEVRKPGASVKVSCKASGYTFTGNHMHWVRQA

PGQGLEWMGWINPKSGRTNFAQNFQGRVTMTRDTSISTAF

MELSRLRSDDTAVYYCARMGDLLLFDFWGQGTLVTVSS mAb 63 VL (SEQ ID NO: 30)

DIVMTQSPDSLAVSLGERATINCKSSQSVLYSSNNKNYLA

WYQQKPGQPPKLLIYWASTRESGVPDRFSGSGSGTDFTLT

ISSLQAEDVAVYYCQQYYSTPLTFGGGTKVEIK mAb 64 VH (SEQ ID NO: 31)

QVQLMPSGAEVKEPGASVKVSCKASGYTFTGYYMHWVRQA

PGQGLEWMGWINPNSGRTSYAKNFQGRVTMTRDTSISTAY

MELSRLRSDDTAVYYCARIEQLVFDYWGQGTLVTVSS mAb 64 VL (SEQ ID NO: 32)

DIVMTQSPLSLPVTPGEPASISCRSSQSLLHSNGYNYLDW

YLQKPGQSPQLLIYLGSNRASGVPDRFSGSGSGTDFTLKI

SRVEAEDVGVYYCMQALQTPLTFGGGTKVEIK mAb 65 VH (SEQ ID NO: 33)

QVQLVESGGGVVQPGRSLRLSCAASGFTFSGYGMHWVRQA

PGKGLDWVAIIYYNGNNKYYADSVKGRFTISRDNSKNTLY

LQMNSLRAEDTAVYYCARGGGYNWFDPWGQGTLVIVSS mAb 65 VL (SEQ ID NO: 34)

DIQMTQSPSSLSASVGDRVTITCRPSQSISNYLNWYQQKP

GKAPKLLIYAASSLQSGVPSRFSGSGSGTDFTLTISSLQP

EDFATYYCQQSYSTPFTFGRGTRLEIK mAb 66 VH (SEQ ID NO: 35)

QVQLVQSGAEVKKPGASVKVSCKASGYTVTGYYMHWVRQA

PGQGLEWMGWINPNSGGTNFAQNFQGRVTMTRDTSISTFY

MDLSRLRSDDTAVYYCARGGAPVSYWFFDLWGRGTLVTVS

S mAb 66 VL (SEQ ID NO: 36)

DIQMTQSPSSLSASVGDRVTITCRASQSISRYLNWYQQKP

GKAPKVLIYNTSSLKSGVPSRFSGSGSGTDFTLTISSLQP

EDFATLYCQQSHSTPFTFGPGTKVDIK mAb 67 VH (SEQ ID NO: 37)

EVQLVESGGDLVQPGRSLRLSCAASGFTFDDCVIHWVRQA

PGKGLEWVSGITWNSGRIGYADSVKGRFTISRDNAKNSLY

-continued

LQMNSLRVEDTALYYCAKEGNYDFWSTYYRGYFDLWGRGT

LVTVSS mAb 67 VL (SEQ ID NO: 38)

DIQMTQSPSSLSASVGDRVTITCRASQGIRNDLGWYQQKP

GIAPKRLIYAASSLQGGVPLRFSGSGSGTEFTLTISSLQP

EDFATYYCLQHNSYPYTFGQGTKLEIK mAb 68 VH (SEQ ID NO: 39)

EVQLVDSGGGLVQPGGSLRLSCSGSGFTFSSYWMSWVRQA

PGKGLEWVANIKQDGSQKYYVDSVKGRFTISRDNVKNSLY

LQMNSLRVEDTAVYYCARDESSSWYWYFDLWGRGTLVTVS

S mAb 68 VL (SEQ ID NO: 40)

DIQMTQSPSTLSASVGDRVTLTCRASQNIVKWLAWYQQKP

GKAPKLLIYKASSLESGVPSWFSGSGSGTEFTLTINSLQP

DDFATYYCQQYYTYSRTFGQGTKVEIK mAb 69 VH (SEQ ID NO: 41)

QMLLVESGGGVVQPGRSLTLSCAASGFTFRSYGMHWVRQA

PGRGLEWVAIIWYDGSTEYYADSVKGRFTISRANSKNMLY

LQMNSLRAEDTAVYYCAAFDYTNSFDIWGQGTMVTVSS mAb 69 VL (SEQ ID NO: 42)

DIVVTQTPLSSPVTLGQPASISCRSSQRFVHSDGNTYLSW

LQQRPGQPPRLLIYKISNRISGVPDRFSGSGAGTDFKLKI

SRVEAEDVGIYYCMQATQFPYTFGQGTKLEIK mAb 70 VH (SEQ ID NO: 43)

QGQLVESGGGVVQPGRSLRLSCEASGFTFRSYGMHWVRQP

PGKGLEWVAIIWYDGGKKYYGDSVKGRFTISRDNPKNTLY

LQMNSLRPEDTAVYYCMAYDYSNGFDIWGQGTMVTVSS mAb 70 VL (SEQ ID NO: 44)

DIVMTQTPLSSPVTLGQPASISCRSSQSFVHSDGSTYLSW

LQQRPGQPPRLLIYKISNRFSGVPDRFSGRGAGTDFTLKI

SRVEAEDVGIYYCMQNTQFPYTFGQGTKLEIK mAb 71 VH (SEQ ID NO: 45)

QVQLVQSGAEVRKPGASVKVSCKASGYTFTKYDVNWVRQA

PGQGLEWMGWMNSNNGNIGYAQKFQGRVTMTRKTSISTAY

MELSSLRSEDTAVYYCAREGHYDFWRGFYNFDYWGQGTLV

TVSS mAb 71 VL (SEQ ID NO: 46)

DIQMTQSPSSLSASVGDRVTITCRASQDIKNDLGWYQQKP

GKAPKRLIYAASSLQSGVPSRFSGSGSGTEFTLTISSLQP

EDFATYYCLQHNFYPITFGQGTRLEIK

-continued mAb 72 VH
(SEQ ID NO: 47)
EVQLVDSGGGLVQPGGSLRLSCAASGFTFSSYWMSWVRQA
PGKGLEWVANIKQDGSEKYYVDSVKGRFTISRDNVKNSLS
LEMNSLRAEDTALYYCARDESSSWYWYFDLWGRGTLVTVS
S mAb 72 VL
(SEQ ID NO: 48)
DIQMTQSPSTLSASVGDRVTITCRASQSISKWLAWYQQKP
GKAPKLLIYKASSLENGVPSRFSGSGSGTEFTLTISSLQP
DDFATYYCQQYSSYSRTFGQGTKVEIK mAb 73 VH
(SEQ ID NO: 49)
EVELVESGGGLVQPGRSLRLSCAASGFTFDDKVMHWVRQA
PGKGLEWVSCINWNSGHIGYADSVKGRFTISRDNARTSLY
LQMNSLRPEDTALYYCVREGNYDFWSGYYRGFFDLWGRGT
LVTVSS mAb 73 VL
(SEQ ID NO: 50)
DIQMTQSPSSLSASVGDRVTITCRASQGIRNDLGWYQQKP
GKAPKRLIYAASSLQGGVPSRFSGSGSGTEFTLTISSLQP
EDFATYYCLQHTSYPFTFGQGTKLEIK mAb 74 VH
(SEQ ID NO: 51)
EVQLVESGGGLVQPGRSLRLSCAASGFTFADYVMHWVRQA
PGKGLEWVSGINWNNARIGYVGSVKGRFTISRDNAKNSLY
LQMTSLRVEDTALYHCVREGNFDFWSAYYRGFLDLWGRGT
LVTVSS mAb 74 VL
(SEQ ID NO: 52)
DIQMTQSPSSLSASVGDRVTITCRASQGIRSDLGWYQQKP
GKAPKRLIYGASSLQGGVPSRFSGSGSGTEFTLTISSLQP
EDFATYYCLQHNSYPYTFGQGTKLEIK mAb 75 VH
(SEQ ID NO: 53)
QVQLVQSGAEVKKPGASVRVSCKASGYTFTGNYIHWVRLA
PGQGLEWMGWINPKSGRTQFVQKFQGRVTMTRDTSITTVY
MELSRLRSDDTAVYYCARLGDLLNFDYWGQGTLVTVSS mAb 75 VL
(SEQ ID NO: 54)
DIQMTQSPSSLSASVGDRVTITCQASQDISNYLNWYQQKP
GKAPKLLIYDASNLETGVPSRFSGSGSGTDFTFTISSLQP
EDIATYYCQQYDNLPLTFGGGTKVEIK mAb 76 VH
(SEQ ID NO: 55)
QVHLVQSGAEVKKPGASVKVSCKASGHTFTGFYVHWARQA
PGQGLEWMGWIYSNSGRTSYSQKFQGRVAMTRDTSISTIY
MDLSRLRSDDTAVYYCARLEQLVFDFWGQGTLVTVSS mAb 76 VL
(SEQ ID NO: 56)
EIVMTQSPATLSVSPGERATLSCRASQSVSSNLAWYQQKP
GQAPRLLIYGASTRATGIPARFSGSGSGTEFTLTISSLQS
EDFAVYYCQQYNNWWTFGQGTKVEIK mAb 77 VH
(SEQ ID NO: 57)
EVQLVESGGGLVQPGGSLRLSCAASGFTFSNYWMSWVRQA
PGKGLEWVANIKQDGSEKYYVDSVRGRFTISRDNAKKSLY
LQMNSLRAEDTAVYYCARDNSNYAYWYFDIWGRGTLVTVS
S mAb 77 VL
(SEQ ID NO: 58)
DIQMTQSPSTLSVSVGDRVTITC58RASQSIRKWLA
WYQQKPGKAPKLLIFKASSLESGVPSRFSGSGSGTEFTLT
ISSLQPDDFATYYCQQYDTYSRTFGQGTKVEIK mAb 78 VH
(SEQ ID NO: 59)
EVQLVESGGGLVQPGGSLRLSCAASGFTFSSYWMSWVRQA
PGKGLEWVANIKQDGSEKYYVDSVKGRFTISRDNAKNSLY
LQMNSLRAEDTAVYYCARDNSPSFYWYFDLWGRGTLVTVS
S mAb 78 VL
(SEQ ID NO: 60)
DIQMTQSPSTLSASVGDRVTITCRASQSLSRWLAWYQQKP
GKAPKLLIYKASSLESGVPSRFSGSGSGTEFTLTISSLQP
DDFATYYCQQYYTYSRTFGQGTKVEIK mAb 79 VH
(SEQ ID NO: 61)
QVQLVQSGAEVKKPGASVKVSCKASGYIVTGYYMHWVRQA
PGHGLEWMGWINPNSGGTNFAQNFQGRVTMTRDTSISTFY
MDLNRLTSDDTAVYYCARGGAPVSYWFFDLWGRGTLVTVS
S mAb 79 VL
(SEQ ID NO: 62)
DIQMTQSPSSLSASVGDRVTITCRASQNINSYLNWYHQKP
GKAPKVLIYNTSTLKSGVPSRFSGSGSGTYFTLTISSLQP
EDFATFYCQQSHSTPFTFGPGTKVDIK mAb 80 VH
(SEQ ID NO: 63)
QVQLVQSGAEVKKPGASVKVSCKASGYTFAGYYLHWVRQA
PGQGLEWMGWINPNSGRTESAQKFQGRVTLTRDTSITTAY
MALSRLRSDDTAIYYCTRLEQLVFDYWGQGTLVTVSS mAb 80 VL
(SEQ ID NO: 64)
EIVLTQSPDFQSVTPKEKVTITCRASQSIGSSLHWYQQKP
DQSPKLLIKYASQSFSGVPSRFSGSGSGTDFTLTINSLEA
EDAATYYCHQSSSLPTFGQGTKVEIK mAb 81 VH (SEQ ID NO: 65)

QVQLAESGGGVVQPGRSLRLSCAASGFTFSGYGMHWVRQA

PGKGLDWVAIIYYDGKNKYYADSVKGRFTISRDNSKNTLY

LQMNSLRAEDTAVYYCARGGGYNWFDPWGQGTLVTVSS mAb 81 VL (SEQ ID NO: 66)

DIQMTQSPSSLSASVGDRVTITCRPSQTISNYLNWYQQDP

GKAPKLLIYAASSLQSGVPSRFSGSGSGTDFTLTISSLQP

EDFATYYCQQSYSTPITFGRGTRLEIK mAb 82 VH (SEQ ID NO: 67)

QVHLVQSGAEVKKPGASVKVSCKASGHTFTGYYVHWARQA

PGQGLEWMGWIYSNSGRTSYSQKFQGRVAMTRDTSISTIY

MDLSRLRSDDTAVYYCARLEQLVFDFWGQGTLVTVSS mAb 82 VL (SEQ ID NO: 68)

DIQMTQSPSSLSASVGDRVTITCQASQDISNYLNWYQQKP

GKAPKLLIYDASNLETGVPSRFSGSGSGTDFTFTISSLQP

EDIATYYCQQYDNLPLFTFGPGTKVDIK mAb 83 VH (SEQ ID NO: 69)

QVQLVESGGGVVQPGRSLRLSCAASGFTFSGYGMHWVRQA

PGKGLDWVAIIYYNGNNKYYADSVKGRFTISRDNSKNTLY

LQMNSLRAEDTAVYYCARGGGYNWFDPWGQGTLVIVSS mAb 83 VL (SEQ ID NO: 70)

DIQMTQSPSSLSASVGDRVTITCRPSQIIINYLNWYQQKP

GKAPKLLIYAASSLQSGVPSRFSGSGSGTDFTLTISSLQP

EDFATYYCQQSYSTPFTFGRGTRLEIK mAb 84 VH (SEQ ID NO: 71)

QVHLVQSGAEVKKPGASVKVSCKASGHSFTGYYVHWARQA

PGQGLEWMGWIYSNSGRTSYAQKFQGRVTMTRDTSISTTY

MELSRLRSDDTAVYYCARLDQLVFDYWGQGTLVTVSS mAb 84 VL (SEQ ID NO: 72)

DIQMTQSPSSLSASVGDRVTITCQASQDISNYLNWYQQKP

GKAPKLLIYDASNLETGVPSRFSGSGSGTDFTFTISSLQP

EDIATYYCQQYDNLPLTFGGGTKVEIK mAb 85 VH (SEQ ID NO: 73)

QVQLVQSGAEVKKPGASVKVSCKASGYTVTGYYMHWVRQA

PGQGLEWMGWINPNSGGTNFAQNFQGRVTMTRDTSISTFY

MDLNRLRSDDTAVYYCARGGAPVSYWFFDLWGRGTLVTVS

S mAb 85 VL (SEQ ID NO: 74)

DIQMTQSPSSLSASVGDRVTITCRASQSISRYLNWYQQKP

GKAPKVLIYNTSSLKSGVPSRFSGSGSGTDFTLTISSLQP

EDFGTFYCQQSHSTPFTFGPGTKVDIK mAb 86 VH (SEQ ID NO: 75)

QVQLAESGGGVVQPGRSLRLSCEASGFTFSGYGMHWVRQA

PGKGLDWVAIIYYDGKNKYYADSVKGRFTISRDNSKNTLY

LQMNSLRAEDTAVYYCARGGGYNWFDPWGQGTLVTVSS mAb 86 VL (SEQ ID NO: 76)

DIQMTQSPSSLSASVGDRVTITCRPSQTISKYLNWYQQKP

GKAPKLLIYAASSLQSGVPSRFSGSGSGTDFTLTISSLQP

EDFATYYCQQSYITPITFGRGTRLEIK mAb 87 VH (SEQ ID NO: 77)

QVQLVQSGAEMKKPGASVKVSCKASGYTFTDYYLHWVRRA

PGHGLEWMGWIYPKSGRRNYAQHFQGRVTMTRDTSINTAY

MELSSLRSDDSAVYFCVRLEQLVFDYWGQGTLVTVSS mAb 87 VL (SEQ ID NO: 78)

EIVLTQSPGTLSLSPGERATLSCRASQSVSSSYLAWYQQK

PGQAPRLLIYGASSRATGIPDRFSGSGSGTDFTLTISRLE

PEDFAVYYCQQYGSSPLTFGGGTKVEIK mAb 88 VH (SEQ ID NO: 79)

QVHLVQSGAEVKKPGASVKVSCKASGHTFTGYYVHWARQA

PGQGLEWMGWIYSNSGRTSYSQKFQGRVAMTRDTSINTIY

MDLSRLRSDDTAVYYCARLEQLVFDFWGQGTLVTVSS mAb 88 VL (SEQ ID NO: 80)

EIVMTQSPATLSVSPGERATLSCRASQSVSSNLAWYQQKP

GQAPRLLIYGASTRATGIPARFSGSGSGTEFTLTISSLQS

EDFAVYYCQQYNNWWTFGQGTKVEIK mAb 89 VH (SEQ ID NO: 81)

QVQLVQSGAEVKKPGASVKVSCKASGYTFAGYYLHWVRQA

PGQGLEWMGWINPNSGRTESAQKFQGRVTLTRDTSITTAY

MALSRLRSDDTAIYYCTRLEQLVFDYWGQGTLVTVSS mAb 89 VL (SEQ ID NO: 82)

DIQMTQSPSSLSASVGDRVTITCRASQGISNYLAWFQQKP

GKAPKSLIYAASSLQSGVPSKFSGSGSGTDFTLTISSLQP

EDFATYYCQQYNSYPITFGQGTRLEIK mAb 90 VH (SEQ ID NO: 83)

EVQLVESGGGLVQPGGSLKLSCAASGFTFSGSAMHWVRQA

SGKGLEWVGRIRTKPNSYATSYAASVKDRFTISRDDSKNT

AYLQMNSLKTEDTAVYYCIRGELEPWGQGTLVTVSS

-continued mAb 90 VL (SEQ ID NO: 84)
DIVMTQSPDSLAVSLGERATINCKSSQSVLYRSNNKNYLA
WYQQKPGQPPKLFIYWASTRESGVPDRFSGSGSGTDFTLT
ISSLQAEDVAVYYCQQFYTTPWTFGQGTKVEIK mAb 91 VH (SEQ ID NO: 85)
QVQLVQSGAEVKKPGASVKVSCKASGYTFTGYYIHWVRQA
PGQGLEWMGWINPKSGNTVYAQRFQGRVTMTRDTSISTAY
MDLSRLKSDDTAVYYCARLEQLVFDYWGQGALVTVSS mAb 91 VL (SEQ ID NO: 86)
DIVMTQSPDSLAVSLGERATINCKSSQSVLYSSNNKNYLA
WYQQKPGQPPKLLIYWASTRESGVPDRFSGSGSGTDFTLT
ISSLQAEDVAVYYCQQYYSTITFGQGTRLEIK mAb 93 VH (SEQ ID NO: 87)
QVQLVESGGGVVQPGRSLRLSCAASGFTFRGYGMHWVRQA
PGKGLEWVAIIYYNGNNKYYADSVKGRFTISRDNSKNTLY
LQMNSLRAEDTAVYYCARGGGYNWFDPWGQGTLVTVSS mAb 93 VL (SEQ ID NO: 88)
DIQMTQSPSSLSASVGDRVTITCRASQSISNYLNWYQQEP
GKAPKLLIYTASSLQSGVPSRFSGSGSGTAFTLTISSLQP
EDFAIYYCQRSSSPPFTFGPGTKLDIK mAb 94 VH (SEQ ID NO: 89)
QVHLVESGGGVVQPGRSLRLSCSASGFTFSGYGMHWVRQA
PGKGLEWVALIYFDGRNKYYADSVKGRFTISRDNSKNTLY
LQMNSLRAEDTAVYYCARGGGYNWFDPWGQGTLVTVSS mAb 94 VL (SEQ ID NO: 90)
DIQMTQSPSSLSASVGDRVTITCRASQSISNYLNWYQQKP
GKAPKLLIYLASSLQSGVPSRFSGSGSGTDFTLTINSLQP
EDFASYYCQLSYSSPFTFGPGTKVDVN mAb 95 VH (SEQ ID NO: 91)
QAHLVESGGGVVQPGRSLRLSCSASGFTFSGYGMHWVRQA
PGKGLEWVALIYFDGRNKYYADSVKGRFTISRDNSKNTLY
LQMNSLRAEDTAVYYCARGGGYNWFDPWGQGTLVTVSS mAb 95 VL (SEQ ID NO: 92)
DIQMTQSPSSLSASVGDRVTITCRASQSINNYLSWYQQKP
GKAPKLLIYLASNLQSGVPSRFSGSGSGTDFTLTISSLQP
EDFATYYCQLSYRSPFTFGPGTKVDVK mAb 96 VH (SEQ ID NO: 93)
QAHLVESGGGVVQPGRSLRLSCSASGFTFSGYGMHWVRQA
PGKGLEWVSLIYFDGRNKYYADSVKGRFTISRDNSKNTLY
LQMNSLRAEDTAVYYCARGGGYNWFDPWGQGTLVTVSS -continued mAb 96 VL (SEQ ID NO: 94)
DIQMTQSPSSLSASVGDRVTITCRASQSINNYLSWYQQKP
GKAPKLLIYLASNLQSGVPSRFSGNGSGTDFTLTISSLQP
EDFATYYCQLSYRSPFTFGPGTKVDVK mAb 97 VH (SEQ ID NO: 95)
QGQLVESGGGVVQPGRSLRLSCAASGFTFRGYGMHWVRQA
PGKGLEWVAIIYYDGKNKYYADSVKGRFTISRDNSKNTLY
LQMNNLRVEDTAVYYCARGGGYNWFDPWGQGTLVTVSS mAb 97 VL (SEQ ID NO: 96)
DIQMTQSPSSLSASIGDRVTITCRASQSISNYLNWYQQKP
GKAPKLLIYSASSLQSGVPSRFSGSGSGTDFTLTISNLQP
EDFAIYYCQRSYSPPFTFGPGTKLDIR mAb 98 VH (SEQ ID NO: 97)
QVHLVESGGDVVQPGRSLRLSCSASGFTFSGYGMHWVRQA
PGKGLEWVALIYFDGRNKYYADSVKGRFTISRDNSKNTLY
LQMNSLRAEDTAVYYCARGGGYNWFDPWGQGTLVTVSS mAb 98 VL (SEQ ID NO: 98)
DIQMTQSPSSLSASVGDRVTITCRASQSINNYLNWYQQKP
GKAPKLLIYLASSLQSGVPSRFSGSGSGTDFTLTISSLQP
EDLATYYCQLSYSSPFTFGPGTKVDVK mAb 99 VH (SEQ ID NO: 99)
QGQLVESGGGVVQPGRSLRLSCAASGFTFRGFGMHWVRQA
PGKGLEWVAIIYYDGKNKYYADSVKGRFTISRDNSKNTLY
LQMNSLRAEDTAVYYCAKGGGYNWFDPWGQGTLVTVSS mAb 99 VL (SEQ ID NO: 100)
DIQMTQSPSSLSASVGDRVTITCRASQSISTYLNWYQQKP
GKAPKLLIYSASSLQSGVPSRFSGSGSGTDFTLTISNLQP
EDFAIYYCQRSYSPPFTFGPGTKLDIR mAb 100 VH (SEQ ID NO: 101)
QVQLVESGGGVVQPGRSLRLSCVASGFTFRGYGMHWVRQA
PGKGLEWVAIIYYDGKNKYYADSVKGRFTISRDNSKNTLY
LQMNSLRVEDTALYYCARGGGYNWFDPWGQGTLVTVSS mAb 100 VL (SEQ ID NO: 102)
DIQMTQSPSSLSASVGDRVTITCRASQSISTYLNWYQQKP
GKAPKLLIYTASSLQSGVPSRFSGSGSGTVFTLTISSLQP
EDFAIYYCQRSYSPPFTFGPGTRLDIK mAb 101 VH (SEQ ID NO: 103)
QGQLVESGGGVVQPGRSLRLSCAASGFTFRGFGMHWVRQA
PGKGLEWVAIIYYDGKNKYYADSVKGRFTISRDNSKNMLY
LQMNSLRAEDTAVYYCAKGGGYNWFDPWGQGTLVTVSS -continued mAb 101 VL (SEQ ID NO: 104)

DIQMTQSPSSLSASVGDRVTITCRASQSISTYLNWYQQKP

GKAPKLLIYSASSLQSGVPSRFSGSGSGTDFTLTISNLQP

EDFAIYYCQRSYSPPFTFGPGTKLDIR mAb 102 VH (SEQ ID NO: 105)

QVQLVESGGGVVQPGRSLRLSCAASGFSFRSYGMHWVRQA

PGKGLEWVSVISYDGGNKYYADSVKGRFTISRDNSKNTLF

LQMKSLRAEDTALYYCAKGGGTYWRGLFEYWGQGTLVTVS

S mAb 102 VL (SEQ ID NO: 106)

DIQLTQSPSFLSASVGDRVTITCRASQGISSYLAWYQKKP

GKAPKLLIYAASTLHSGVPSRFSGGGSGTAFTLTISSLQP

EDFATYYCQQLNNYPFTFGPGTKVDIK mAb 103 VH (SEQ ID NO: 107)

QVQLVQSGAEVMKPGASVKVSCKASGYTFTDFYIHWVRQA

PGQGLEWMGWINPKSGNTRFAQKFQGRVTMTRDTSIATSY

MELSRLRSDDTAVFYCARMGDLLALDYWGQGTLVTVSS mAb 103 VL (SEQ ID NO: 108)

EIVLTQSPATLSLSPGERATLSCRASQSVSSYLAWYQQKP

GQAPRLLIYDASNRATGIPARFSGSGSGTDFTLTISSLEP

EDFAVYYCQQRSNWYTFGQGTKLEIK mAb 104 VH (SEQ ID NO: 109)

QVQLVQSGAEVKKPGASVKVSCKASGYTFTDFYIHWVRQA

PGQGLEWMGWINPKSGNTRFAQRFQGRVTMTRDTSITTSY

MELSRLRSDDTAVFYCARMGDLLALDYWGQGTLVTVSS mAb 104 VL (SEQ ID NO: 110)

EIVLTQSPGTLSLSPGERATLSCRASQSVSSSYLAWYQQK

PGQAPRLLIYGASSRATGIPDRFSGSGSGTDFTLTISRLE

PEDFAVYYCQQYGSSPRTFGQGTKVEIK mAb 105 VH (SEQ ID NO: 111)

QVQLQESGPGLVKPSATLSLTCTVSGGSISTYYWSWIRQS

PGKGLEWIGYISYSVNTNPSLKSRVTISVDKSKNQLSLNL

RSATGADTAVYYCARGGLYGGNAGRFDLWGQGTLVTVSS mAb 105 VL (SEQ ID NO: 112)

EIVLTQSPGTLSLSPGERATLSCRASQSVINNYVAWYQQK

PGQAPSLIITGVSRRATGIPDRFIGSGSGTDFILIISRLE

PEDFAVYCCQQYGNSPWTFGQGTRVEIK mAb 106 VH (SEQ ID NO: 113)

QVQLVESGGGVVQPGRSLRLSCAASGFTFRSYGMHWVRQA

PGKGLEWVAIIWYNGNKKDYVDSVKGRFTISRDNSKNTLY

LQMNSLRAEDTALYYCARGPGYNWFDPWGQGTLVTVSS mAb 106 VL (SEQ ID NO: 114)

DIQMTQSPPSLSASVGDRVTITCRASQRISSYLNWYQQKP

GKAPKLLIYAASSLQSGVPSRFSGSGSGTDFTLTISSLQP

EDFATYYCQQSDSFPLTFGGGTKVEII mAb 107 VH (SEQ ID NO: 115)

QVQLQESGPGLVKPSETLSLTCTVSGGSISSYCWSWIRQP

PGKGLEWIGYIYNIGSTNFNPSLKSRVTISVDTSKNQFSL

KLNSVTAADTAVYYCARGGLYSGNGGRFDPWGRGTLVTVS

S mAb 107 VL (SEQ ID NO: 116)

EIVLTQSPGTLSLSPGQTATLSCRASQGVRSNYLAWYQQK

PGQAPRLLIYGASSRATGIPVRFSGSGSGTGFTLTMSRLE

PEDFAVYYCQQYGSSPWTFGQGSKVEIK mAb 108 VH (SEQ ID NO: 117)

QVQLVESGGGVVQPGRSLRLSCAASGFTFSSYGMHWVRQA

PGKGLEWVAVIWYDGSNKYYEDSVKGRFTISRDNSKNTLH

LQMNSLRVEDTAVYYCARGLEFDYWGQGTLVTVSS mAb 108 VL (SEQ ID NO: 118)

DIVMTQTPLSSPVTLGQPASISCRSSQSLVHSDGITYLNW

LQQRPGQPPRLLIYKISNRFSGVPDRFSGSGSGTDFTLKI

SRVEAEDVGVYYCMQATQFPWTFGQGTKVEIK mAb 109 VH (SEQ ID NO: 119)

QVQLVESGGGVVQPGRSLRLSCVASGFPFRSYGMHWVRQA

PGKGLEWVAFIWYDGSNKYYADSVRGRFTISRDNFKKMVY

LQMNSLRAEDTAVYYCARDLAGIYAFDVWGQGTVVTVSS mAb 109 VL (SEQ ID NO: 120)

EIVMTQSPATLSVSPGERATLSCRASQSVSSNLAWYQQKP

GQAPRLLIYGASTRATGIPARFSGSGSGTEFTLTVSSLQS

EDFAIYYCQQYNNWRPLTFGGGTKVEIK mAb 110 VH (SEQ ID NO: 121)

QVQLVESGGGVVQPGRSLRLSCAASGFTFRSYGMHWVRQA

PGKGLEWVAIIWYNGNKKDYVDSVKGRFTISRDNSKNMLY

LQMNSLRAEDTALYYCARGPGYNWFDPWGQGTLVTVSS

-continued mAb 110 VL (SEQ ID NO: 122)

DIQMTQSPPSLSASVGDRVTITCRASQRISSYLNWYQQRP

GKAPKLLIYAASSLQSGVPSRFSGSGSGTDFTLTISSLQP

EDFATYYCQQTDSFPLTFGGGTKVEII mAb 111 VH (SEQ ID NO: 123)

EVQLVESGGVLVKTGGSLRLSCVASGFSFKKAWMNWVRQA

PGKGLEWVGRIKRNSDGGAADYAAPVKDRFTLSRDDSKNT

LYLQMNSLKTEDTAVYYCTTLDSSSWYVGYYYMDVWGKGT

TVTVSS mAb 111 VL (SEQ ID NO: 124)

DIHMTQSPSSVSASLGDRVTFTCRASQNINNWLAWYQQKP

GKAPKLLIYTASSLQSGVPSRFSGSGSGTDFTLTISSLQP

DDFATYYCQQAHSLPITFGQGTRLGIK mAb 112 VH (SEQ ID NO: 125)

EVQLVESGGGLVKTGGSHRLSCVASGFSFKKAWMNWVRQA

PGKGLEWVGRIKRNSDGGTTDYAAPVKGRFILSRDDSKNT

LYLQMNSLKTEDTAVYYCTTLDSSSWYVGYYYMDVWGKGT

TVTVSS mAb 112 VL (SEQ ID NO: 126)

DIQMTQSPSSVSASVGDRVTITCRASQDINNWLAWYQQKP

GKAPKILIYTASNLQSGVPSRFSGSGSGTDFTLTISSLQP

EDFATYFCQQAHSLPITFGQGTRLEIK mAb 113 VH (SEQ ID NO: 127)

EVQLVESGGGLVKTGGSLRLSCVASGFSFKKAWMNWVRQA

PGKGLEWVGRIKRNTDGGTTDYAAPVKGRFTLSRDDSKNT

LYLQMNSLKTEDTAVYYCTTLDSSSWYVGYYYMDVWGKGT

TVTVSS mAb 113 VL (SEQ ID NO: 128)

DIQMTQSPSSVSASVGDRVTITCRASQDINNWLAWYQQKP

GKAPKILIYTASSLQSGVPSRFSGSGSGTDFTLTISSLQP

EDFATYYCQQAHSLPITFGQGTRLEIK mAb 114 VH (SEQ ID NO: 129)

EVQLVESGGGLVKTGGSLRLSCVASGFSFKKAWMNWVRQA

PGKGLEWVGRIKRNTDGGPADYAAPVKGRFTLSRDDSKKT

LYLQMNSLKTEDTAVYYCTTLDSSSWYVGYYYMDVWGKGT

TVTVSS mAb 114 VL (SEQ ID NO: 130)

DIQMTQSPSSVSASVGDRVIITCRASQDINNWLAWYLQRP

GKAPKLLIYAASSLQSGVPSRFSGSGSGTDFTLTIGSLQP

EDFATYYCQQAHSLPITFGQGTRLEIQ

-continued mAb 115 VH (SEQ ID NO: 131)

EVQLVESGGGLVKTGGSHRLSCVASGFSFKKAWMNWVRQA

PGKGLEWVGRIKRNSDGGTTDYAAPVKGRFILSRDDSKNT

LYLQMNSLKTEDTAVYYCTTLDSSSWYVGYYYMDVWGKGT

TVTVSS mAb 115 VL (SEQ ID NO: 132)

DIQMTQSPSSVSASVGDRVTITCRASQDINNWLAWYQQKP

GKAPKILIYTASNLQSGVPSRFSGSGSGTDFTLTISSLQP

EDFATYFCQQAHGLPITFGQGTRLEIK mAb 116 VH (SEQ ID NO: 133)

EVQLVESGGGLVKTGGSLRLSCVASGFSFKKAWMNWVRQA

PGKGLEWVGRIKRNSDGGTTDYAAPVKGRFTLSRDDSKNT

LYLQMNSLKTEDTAVYYCTTLDSSSWYVGYYYMDVWGKGT

TVTVSS mAb 116 VL (SEQ ID NO: 134)

DIQMTQSPFSVSASVGDRVTITCRASQDINNWLAWYQQKP

GKAPKILIYTASSLQSGVPSRFSGSGSGTDFTLTISSLQP

EDFATYYCQQAHSLPITFGQGTRLEIK mAb 117 VH (SEQ ID NO: 135)

EVQLVESGGGLVKTGGSLRLSCVASGFSFKKAWMNWVRQA

PGKGLEWVGRIKRNTDGGTTDYAAPVKGRFTLSRDDSKNT

LYLQMNSLKTEDTAVYYCTTLDSSSLYVGYYYMDVWGKGT

TVTVSS mAb 117 VL (SEQ ID NO: 136)

DIQMTQSPSSVSASVGDRVTITCRASQDINNWLAWYQQKP

GKAPKLLIYTASSLQSGVPSRFSGSGSGTDFTLTISSLQP

EDFATYYCQQAHSLPITFGQGTRLEIK mAb 118 VH (SEQ ID NO: 137)

EVQLVESGGGLVQPGRSLRLSCAASGFTFDDYTMHWVRQA

PGKGLEWVSGISWNSGSIGYADSVKGRFTISRDNAKNSLY

LQMNSLRAEDTALYYCSKDSSGYGYYLNYSLDVWGKGTTV

TVSS mAb 118 VL (SEQ ID NO: 138)

EIVMTQSPATLSVSPGERATLSCRASQSVSSNLAWYQQKP

GQAPRLLIYGASTRATGIPARFSGSGSGTEFTLTISSLQS

EDFAVYYCQQYNNWPHFGQGTRLEIK mAb 119 VH (SEQ ID NO: 139)

EVQLVESGGGLVQPGRSLRLSCAASGFTFDDYTMHWVRQA

PGKGLEWVSGISWNSGSIGYADSVKGRFTISRDNAKNSLY

LQMNSLRAEDTALYYCSKDSSGYGYYLNYSLDVWGKGTTV

TVSS mAb 119 VL (SEQ ID NO: 140)

EIVMTQSPATLSVSPGERATLSCRASQSVSNLAWYQQKPG

QAPRLLIYGASTRATGIPARFSGSGSGTEFTLTISSLQSE

DFAVYYCQQYNNWPHFGQGTRLQIK mAb 120 VH (SEQ ID NO: 141)

EVQLVESGGGLVKTGGSLRLSCVASGFSFKKAWMNWVRQA

PGKGLEWVGRIKRNTDGGTADYAAPVKGRFTLSRDDSKKT

LFLQMNSLKTEDTAVYYCTTLDSSSYYVGYYYMDVWGKGT

TVTVSS mAb 120 VL (SEQ ID NO: 142)

DIQMTQSPSSVSASVGDRVTITCRASQDINNWLAWYQQKP

GKAPKLLIYTASSLQSGVPSRFSGSGSGTDFTLTIGSLQP

EDFATYYCQQAHSLPITFGQGTRLEIK mAb 121 VH (SEQ ID NO: 143)

EVQLVESGGGLVQPGRSLRLSCATSGFTFADYTMHWVRQA

PGKGLEWVSGISWNSGSIDYADSVKGRFTISRDNAKKSLY

LQMNSLRAEDTALYFCAKDSSGYGHYYFYYLDVWGKGTTV

TVSS mAb 121 VL (SEQ ID NO: 144)

EIVMTQSPGTLSVSPGKRATLSCRASQSVSSNLAWYQQKP

GQGPRLLIYSTSTRATGIPARFSGSGSGTEFTLTISSLQS

EDSAVYYCQHYNNWPHFGQGTRLEIK mAb 122 VH (SEQ ID NO: 145)

EVQLVESGGGLVKTGGSLRLSCVASGFSFKKAWMNWVRQA

PGKGLEWVGRIKRNTDGGTADYAAPVKGRFTLSRDDSKKT

LYLQMNSLKTEDTAVYYCTTLDSSSRYVGYYYMDVWGKGT

TVTVSS mAb 122 VL (SEQ ID NO: 146)

DIQMTQSPSSVSASVGDRVIITCRASQDINNWLAWYQQKP

GKVPKLLIYTASSLQSGVPSRFSGSGSGTDFTLTIGSLQP

EDFATYYCQQAHSLPITFGQGTRLEIK mAb 123 VH (SEQ ID NO: 147)

DVQLVESGGGTVKTGGSLRLSCVASGFSFKKAWMNWVRQA

PGKGLEWVGRIKKNSDDGTADYAAPVKGRFTISRDDSKRT

LFLQMNSLQTEDTAVYYCTTLDSSSWFVGYYYMDVWGKGT

TVTVSS mAb 123 VL (SEQ ID NO: 148)

DIQMTQSPSSVSASVGDRVIITCRASQDINNWLAWYQQKP

GKAPKLLIYTASSLQSGVPSRFSGSGSVSDFTLTIDSLQP

EDFATYYCQQAHSLPITFGQGTRLEIK mAb 124 VH (SEQ ID NO: 149)

EVQVVESGGDLVQPGGSLRLSCAASGFTFSTYAMTWVRQA

PGKGLEWISTISGSGHNTYYADSVKGRFTISRGNSKNTLF

LQMNSLRAEDTAVYYCAKENCGGDCLYYMDVWGKGTTVTV

SS mAb 124 VL (SEQ ID NO: 150)

DIQMTQSPSSLSASVGDRVTITCRASQSISNYLNWYQQKS

GKAPKLLIYFASSLQSGVPSRFGGSGAGTDFTLTISSLQP

EDFATYSCQQSYSTPLTFGGGTKVEIK mAb 125 VH (SEQ ID NO: 151)

EVQLVESGGGLVKTGGSLRLSCVASGFSFKKAWMNWVRQA

PGKGLEWVGRIKRNTDGGTADYAAPVKGRFTLSRDDSKKT

LYLQMNSLKTEDTAVYYCTTLDSSSRYVGYYYMDVWGKGT

TVTVSS mAb 125 VL (SEQ ID NO: 152)

DIQMTQSPSSVSASVGDRVIITCRASQDINNWLAWYQQKP

GKVPKLLIYTASSLQSGVPSRFSGSGSGTDFTLTIGTLQP

EDFATYYCQQAHSLPITFGQGTRLDIK mAb 126 VH (SEQ ID NO: 153)

EVQLVESGGGLVQPGRSLRLSCAASGFTFNDYTMHWVRQV

PGKGLEWVSGISWNSGSIDYADSVKGRFTISRDNAKNSLY

LQMNSLRAEDTALYYCAKDSSGYGYYYYYYMDVWGKGTTV

TVSS mAb 126 VL (SEQ ID NO: 154)

EIVMTQSPATLSVSPGERATLSCRASQSVSINLAWYQQKP

GQAPRLLIYGASTRATGIPARFSGSGSGTEFTLTISSLQS

EDFAVYYCQLYHNWPHFGQGTRLEIK mAb 127 VH (SEQ ID NO: 155)

EVQLVESGGGLVKTGGSHRLSCVASGFSFKKAWMNWVRQA

PGKGLEWVGRIKRNSDGGTTDYAAPVKGRFILSRDDSKNT

LYLQMNSLKTEDTAVYYCTTLDSSSWYVGYYYMDVWGKGT

TVTVSS mAb 127 VL (SEQ ID NO: 156)

DIQMTQSPSSVSASVGDRVTITCRASQDINNWLAWYQQKP

GKAPKILIYTASNLQSGVPSRFSGSGSGTDFTLTISTLQP

EDFATYFCQQAHGLPITFGQGTRLEIK mAb 128 VH (SEQ ID NO: 157)

EVQLVESGGGLVQPGRSLRLSCAASGFTFDDYTMHWVRQA

PGKGLEWVSGISWNSGSIGYADSVKGRFTISRDNAKNSLY

LQMNSLRAEDTALYYCAKDSSGYGYYYYYSMDVWGKGTTV

TVSS

-continued mAb 128 VL (SEQ ID NO: 158)
EIVMTQSPATLSVSPGERATLSCRASQSVSSNLAWYQQKP
GQAPRLLIYGASTRATGIPARFSGSGSGTEFTLTISSLQS
EDFAVYYCQLYYNWPHFGQGTRLAIK mAb 129 VH (SEQ ID NO: 159)
EVQLVESGGDLVKTGGSLRLSCVASGFSFKKAWMNWVRQA
PGKGLEWVGRIKRNTDGGATDYAAPVKDRFTLSRDDSKNT
LYLQMNSLKTEDTAVYYCTTLDSSSWYVGYYYMDVWGKGT
TVTVSS mAb 129 VL (SEQ ID NO: 160)
DIHMTQSPSSVSASLGDRVTFTCRASQDINNWLAWYQQKP
GKAPRLLIYTASSLQSGVPSRFSGSGSGTDFTLTISSLQP
DDFATYYCQQAHSLPITFGQGTRLGIE mAb 130 VH (SEQ ID NO: 161)
EVQLVESGGGLVKTGGSLRLSCVASGFSFKKAWMNWVRQA
PGKGLEWVGRIKRNSDGGATDYAAPVKDRFTLSRDDSKNT
LYLQMNSLKTEDTAVYYCTTLDSSSWYVGYYYMDVWGKGT
TVTVSS mAb 130 VL (SEQ ID NO: 162)
DIHMTQSPSSVSASLGDRVTFTCRASQDINNWLAWYQQRP
GKAPKLLIYTASSLQSGVPSRFSGSGSGTDFTLTISSLQP
EDFATYYCQQAHSLPITFGQGTRLGIK mAb 131 VH (SEQ ID NO: 163)
EVQLVESGGGLVKTGGSLRISCVASGFSFKKAWMNWVRQA
PGKGLEWVGRIKRNTDGGTIDYAAPVKGRFSLSRDDSKNT
LFLQMNSLKTEDTAVYFCTTLDSSSYYVGYYYMDVWGKGT
TVTVSS mAb 131 VL (SEQ ID NO: 164)
DIHMTQSPSSVSASVGDRVTITCRASQDINNWLAWYQQKP
GKAPKLLIYTASSLQSGVPSRFSGSGSGTDFTLTISSLQP
EDFATYFCQQAHSLPITFGQGTRLGIK mAb 132 VH (SEQ ID NO: 165)
DVQLVESGGGTVKTGGSLRLSCVASGFSFKKAWMNWVRQA
PGKGLEWVGRIKKNSDGGTADYAAPVKGRFTISRDDSKKT
LYLQMNSLQTEDTAVYYCTTLDSSSWYVGYYYMDVWGKGT
TVTVSS mAb 132 VL (SEQ ID NO: 166)
DIQMTQSPSSVSASVGDRVIITCRASQDINNWLAWYQQKP
GIAPKLLIYTASSLQSGVPSRFSGSGSVSDFTLTIGSLQP
EDFATYYCQQAHSLPITFGQGTRLEIK mAb 133 VH (SEQ ID NO: 167)
EVQLVESGGGLVKTGGSLRLSCVASGFSFKKAWMSWVRQA
PGKGLEWVGRIKRNTDGGTADYAAPVKGRFTLSRDDSKKT
LFLQMNSLKTEDSAVYYCVTLDSSSYYVGYYYMDVWGKGT
TVTVSS mAb 133 VL (SEQ ID NO: 168)
DIQMTQSPSSVSASVGDRVSITCRASQDINNWLAWYQQKP
GKAPKLLIYTASSLQSGVPSRFSGSGSGTDFTLTIGSLQP
EDFATYYCQQAHSLPITFGQGTRLEIK mAb 134 VH (SEQ ID NO: 169)
EVQLVESGGGLVKTGGSLRLSCVASGFSFKKAWMNWVRQA
PGKGLEWVGRIKRNTDGGTADYAAPVKGRFTLSRDDSKKT
LFLQMNSLKTEDTAVYYCTTLDSSSWYVGYYYMDVWGKGT
TVTVSS mAb 134 VL (SEQ ID NO: 170)
DIQMTQSPSSVSASVGDRVIITCRASQDINNWLAWYQQKP
GKAPKLLIYTASSLQSGVPSRFSGSGSGTDFTLTIGSLQP
EDFATYYCQQAHSLPITFGQGTRLEIK mAb 135 VH (SEQ ID NO: 171)
EVQLVESGGGLVKTGGSLRLSCVASGFSFKKAWMNWVRQA
PGKGLEWVGRIKRNSDGGTTDYAAPVKGRFTLSRDDSKNT
LYLQMNSLKTEDTAVYYCTTLDSSSWYVGYYYMDVWGKGT
TVTVSS mAb 135 VL (SEQ ID NO: 172)
EIVLTQSPGTLSLSPGERATLSCRASQSVSSSYLAWYQQK
PGQAPRLLIYGASSRATGIPDRFSGSGSGTDFTLTISRLE
PEDFAVYYCQQYGSSPLTFGGGTKVEIK mAb 136 VH (SEQ ID NO: 173)
QVQLVESGGGVVQPGRSLRLSCAASGFTFSIYGMHWVRQA
PGKGLEWVAVIWHDGSNKYYADSVKGRFTISRDNSKNTLY
LQMNSLRAEDTAVYYCARTGITGTKAYFYFDYWGQGTLVT
VSS mAb 136 VL (SEQ ID NO: 174)
DIVMTQSPDSLAVSLGERATINCKSSQSVLYSSNNKNYLA
WYQQKPGRPPKLFIYWASNRESGVPDRFSGRGSGTDFTLT
ISSLQAEDVAVYYCQQYYSTVTFGGGTKVEIK mAb 137 VH (SEQ ID NO: 175)
QVQLVESGGGVVQPGRSLRLSCAASGFTFSTYGMHWVRQA
PGKGLEWVAVIWYDGSHKYYADSVKGRFTISRDNSKKTLY
LQMNSLRAEDTGIYYCARTGISGNMSYFYFDHWGQGILVT
VSS -continued mAb 137 VL (SEQ ID NO: 176)
DIVMTQSPDSLAVSLGERATINCKSSQSVLYSSKNRNYLA
WYQQKQGQPPKMFIYWASTRESGVPDRFSGSGSGTDFTLT
ISSLQAEDVAVYYCQQYYGPVTFGGGTKVEIK mAb 138 VH (SEQ ID NO: 177)
QVLLVQSGPEVKKPGASVKVSCKASGYTFTDYYLHWVRQA
PGQGLDWMGWINPKSGGTRNAQKFQGRVTMTRDTSISTAY
MDLTRLRSDDTAVYYCARVGGELLFDYWGQGTLVTVSS mAb 138 VL (SEQ ID NO: 178)
DIVMTQSPLSLSVTPGEPASISCRSSQSLLHSDGYNYLDW
FLQKPGQSPHLLIFLGSNRASGVPDRFSGSGSGTDFTLKI
SRVEAEDVGIYYCMQALQTPLTFGGGTKVEIK mAb 139 VH (SEQ ID NO: 179)
QVQLVESGGGVVQPGRSLRLSCAASGFTFSSYAMHWVRQA
PGKGLEWVAVIWFDGTNKYYTDSVRGRFTISRDNSKNTLY
LQMNSLRAEDTAVYYCATERGITETTRGFDYWGQGTLVTV
SS mAb 139 VL (SEQ ID NO: 180)
DIQMTQSPSSLSASVGDRVTITCRTSQGIGNDLDWYQQNP
GKAPKRLIYATSNLQSGVPSRFSGSGSGTEFTLTISGLQP
EDFTTYYCLRHNSYPYTFGQGTKLEIT mAb 140 VH (SEQ ID NO: 181)
QVQLVESGGGVVQPGRSLRLSCAASGFTFSTYGMHWVRQA
PGKGLEWVAVIWYDGSHKYYADSVKGRFTISRDNSKNTLY
LQMNSLRAEDTAVYYCARTGITGTTAYFYFDYWGQGTLVT
VSS mAb 140 VL (SEQ ID NO: 182)
DIVMTQSPDSLAVSLGERATINCKSSQSVLYSSKNKNYLA
WYQQKQGQPPKLFIYWASTRESGVPDRFSGSGSGTDFTLT
ISSLQAEDVAVYYCQQYYSTVTFGGGTKVEIK mAb 141 VH (SEQ ID NO: 183)
QVQLVQSGAEVKKPGASVKVSCKASGYTFTSYYIHWVRQA
PGQGLDWMGIINPSGGITGYAQKLQGRVTMTRDTSTTTVY
MELSSLRSDDTAVYYCARGVRGNYYYYYMDVWGKGTTVTV
SS mAb 141 VL (SEQ ID NO: 184)
EIVLTQSPDFQSVTPKEKVTITCRASQSIGSKLHWYQQKP
DQSPKLLIKYASQSFSGVPSRFSGSGSGTDFNLTINSLEA
EDAATFYCHQSSGLPYTFGQGTKLEIK mAb 142 VH (SEQ ID NO: 185)
QVQLVESGGGVVQPGRSLRLSCAASGFTFSSYGMHWVRQA
PGKGLEWVAVIWYDGSNKYYADSVKGRFTISRDNSKNTLY
LQMNSLRAEDTAVYYCARTGITGTTAYFYFDSWGQGTLVT
VSS mAb 142 VL (SEQ ID NO: 186)
DIVMTQSPDSLAVSLGERATINCKSSQSVLYSSKNKNYLA
WYQQKPGQTPKLLIYWASTRESGVPDRFSGSGSGTDFTLT
ISSLQAEDVALYYCQQYYSTVTFGGGTKVEIK mAb 143 VH (SEQ ID NO: 187)
QVQLMQSGSELEKPGASVKVSCKASGYTFTSFAINWVRQA
PGQGLEWMGWINTITGNPSYAQGFTGRFVFSLDTSVTTAF
LQINSLKTEDTAVYYCARYVTSSGKFDYWGQGTLVTVSS mAb 143 VL (SEQ ID NO: 188)
DIQMTQSPSSVSASVGDRVTITCRASRGISRWLDWYQQKP
GKAPKLLIYAASNLQGGVPSRFSGSGSGTDFTLTIRSLQP
EDFAIYYCQQAKTFPFTFGPGTKVDIK mAb 144 VH (SEQ ID NO: 189)
QVQLVESGGYVVQPGRSLRLSCAASGFTFSNFGMHWVRQA
PGKGLEWVAVIWYDGSHKYYADSVKGRFTISRDNSKNTLY
LQMNSLRAEDTAVYYCARTGITGTTAYFYFDYWGQGTLVT
VSS mAb 144 VL (SEQ ID NO: 190)
DIVMTQSPDSLAVSLGERATINCKSSQSVLYSSKNKNYLA
WYQQKQGQPPKLFIYWASTRESGVPDRFSGSGSGTDFTLT
IRSLQAEDVAVYYCQQYYGPVTFGGGTKVEIK mAb 145 VH (SEQ ID NO: 191)
QVQLVQSGAEVKKPGASVKVSCKASGYTFTNYYIHWVRQA
PGQGLDWMGIINPSGGITGYAQKFQGRVTMTRDTSTTTVY
MELSSLRSDDTAVYYCARGVRGNYYYYYMDVWGKGTTVTV
SS mAb 145 VL (SEQ ID NO: 192)
EIVLTQSPDFQSVTPKEKVTITCRASQSIGSKLHWYQQKP
DQSPKLLIKFASQSFSGVPSRFSGSGSGTDFNLTINSLEP
EDAATFYCHQSSGLPYTFGQGTKLEIK mAb 146 VH (SEQ ID NO: 193)
QVQLVESGGGVVQPGRSLRLSCAASGFTFITYGMHWVRQA
PGKGLEWVAVIWYDGSHKYYADSVKGRFTISRDNSKNMLY
LQMNSLRVEDTAVYYCARTGITGTTAYFYFDNWGQGTLVT
VSS -continued mAb 146 VL (SEQ ID NO: 194)

DIVMTQSPDSLAVSLGERATINCKSSQSVLYRSKNKNYLA

WYQQKQGQPPKMFISWASTRESGVPDRFSGSGSGTDFTLT

ISSLQAEDVAVYYCQQYYGPVTFGGGTKVEIK mAb 147 VH (SEQ ID NO: 195)

QVQLVQSGAEVKKPGASVKVSCKASGYTFTAYHTHWVRQA

PGQGLEWMGWIYPKSGRTTYTQKFQGRVTMTRDTSISTVY

MELSRLKSDDTAVYYCARVGALLFDYWGQGTLVTVSS mAb 147 VL (SEQ ID NO: 196)

DIVMTQSPDSLAVSLGERATINCKSSQSVLYSSNNKNYLA

WYQQKPGQPPKLLIYWASTRESGVPDRFSGSGSGTDFTLT

ISSLQAEDVAVYYCQQYYSTPLTFGGGTKVEIK mAb 148 VH (SEQ ID NO: 197)

QVQLVQSGAEVKKPGASVKVSCKASGYTFTAYHTHWVRQA

PGQGLEWMGWIYPKSGRTTYTQKFQGRVTMTRDTSISTVY

MELSRLKSDDTAVYYCARVGALLFDYWGQGTLVTVSS mAb 148 VL (SEQ ID NO: 198)

EIVLTQSPATLSLSPGERATLSCRASQSVSSYLAWYQQKP

GQAPRLLIYDASNRATGIPARFSGSGSGTDFTLTISSLEP

EDFAVYYCQQRSNWPFTFGPGTKVDIK mAb 149 VH (SEQ ID NO: 199)

QVQLVQSGAEVKKPGASVKVSCKASGYTFTAYHTHWVRQA

PGQGLEWMGWIYPKSGRTTYTQKFQGRVTMTRDTSISTVY

MELSRLKSDDTAVYYCARVGALLFDYWGQGTLVTVSS mAb 149 VL (SEQ ID NO: 200)

DIVMTQTPLSSPVTLGQPASISCRSSQSLVHSDGNTYLSW

LQQRPGQPPRLLIYKISNRFSGVPDRFSGSGAGTDFTLKI

SRVEAEDVGVYYCMQATQFPQTFGQGTKVEIK mAb 150 VH (SEQ ID NO: 201)

QVQLVQSGAEVKKPGASVKVSCKASGYTFTAYHTHWVRQA

PGQGLEWMGWIYPKSGRTTYTQKFQGRVTMTRDTSISTVY

MELSRLKSDDTAVYYCARVGALLFDYWGQGTLVTVSS mAb 150 VL (SEQ ID NO: 202)

EIVLTQSPATLSLSPGERATLSCRASQSVSSYLAWYQQKP

GQAPRLLIYDASNRATGIPARFSGSGSGTDFTLTISSLEP

EDFAVYYCQQRSNWPLTFGGGTKVEIK mAb 151 VH (SEQ ID NO: 203)

QVQLVQSGAEVKKPGASVKVSCKASGYTFTAYHTHWVRQA

PGQGLEWMGWIYPKSGRTTYTQKFQGRVTMTRDTSISTVY

MELSRLKSDDTAVYYCARVGALLFDYWGQGTLVTVSS

-continued mAb 151 VL (SEQ ID NO: 204)

DIQMTQSPSSLSASVGDRVTITCRASQGIRNDLGWYQQKP

GKAPKCLIYAASNLQSGVPSRFSGSGSGTEFTLTISSLQP

EDFATYYCLQHNSYPRTFGQGTKVDVK mAb 152 VH (SEQ ID NO: 205)

QVQLVQSGAEVKKPGASVKVSCKASGYTFTAYHTHWVRQA

PGQGLEWMGWIYPKSGRTTYTQKFQGRVTMTRDTSISTVY

MELSRLKSDDTAVYYCARVGALLFDYWGQGTLVTVSS mAb 152 VL (SEQ ID NO: 206)

EIVLTQSPGTLSLSPGERATLSCRASQSVSSSYLAWYQQK

PGQAPRLLIYGASSRATGIPDRFSGSGSGTDFTLTISRLE

PEDFAVYYCQQYGSSPPEYTFGQGTKLEIK mAb 153 VH (SEQ ID NO: 207)

QVQLVESGGGVVQPGRSLRLSCAASGFTFSTYGMHWVRQA

PGKGLEWVAVIWYDGSHKYYSDSVKGRFTISRDNSKNTLY

LQMNSLRVEDTAIYYCARTGITGTTAYFYFDSWGQGTLVT

VSS mAb 153 VL (SEQ ID NO: 208)

DIVMTQSPDSLAVSLGERATINCKSSQSVLYRSKNKNYLA

WYQQKQGQPPKLFIYWASTRESGVPDRFSGSGSGTDFTLT

ISSLQTEDVAIYYCQQYYGPVTFGGGTKVEIK mAb 154 VH (SEQ ID NO: 209)

QVQLMQSGSELEKPGASVKVSCKASGYTFTSFAINWVRQA

PGQGLEWMGWINTITGNPSYAQGFTGRFVFSLDTSVSTAF

LQINSLKTEDTAVYYCARYVTSSGKFDYWGQGTLVTVSS mAb 154 VL (SEQ ID NO: 210)

DIQMTQSPSSVSASVGDRVTITCRASRGISRWLDWYQQKP

GKAPKLLIYAASNLQGGVPSRFSGSGSGTDFTLTIRSLQP

EDFALYYCQQAKTFPFTFGPGTKVDIR mAb 155 VH (SEQ ID NO: 211)

EVQLVESGGGLVKTGGSLRLSCVASGFSFKKAWMNWVRQA

PGKGLEWVGRIKRNTDGGTADYAAPVKGRFTLSRDDSKKT

LFLQMNSLKTEDTAVYYCTTLDSSSYYVGYYYMDVWGKGT

TVTVSS mAb 155 VL (SEQ ID NO: 212)

DIQMTQSPSSVSASVGDRVIITCRASQDINNWLAWYQQKP

GKAPKLLIYTASSLQSGVPSRFSGSGSGTDFTLTIGSLQP

EDFATYYCQQAHSLPISFGQGTRLDIK mAb 156 VH (SEQ ID NO: 213)

EVQLVESGGGLVKTGGSLRLSCVASGFSFKKAWMNWVRQA

PGKGLEWVGRIKRNTDGGTADYAAPVKGRFTLSRDDSKKT

-continued

LFLQMNSLKTEDTAVYYCTTLDSSSYYVGYYYMDVWGKGT

TVTVSS mAb 156 VL (SEQ ID NO: 214)

DIQMTQSPSSVSASVGDRVIITCRASQDINNWLAWYQQKA

GKAPKLLIYTASSLQSGVPSRFSGSGSGTDFTLTIGSLQP

EDFATYYCQQAHSLPITFGQGTRLEIK mAb 157 VH (SEQ ID NO: 215)

EVQLVESGGGLVKTGGSLRLSCVASGFSFKKAWMNWVRQA

PGKGLEWVGRIKRTADGGATDYAAPVKGRFTLSRDDSKNT

LYLQMNSLKTEDTAVYYCTTLDSSSWYVGYYYMDVWGKGT

TVTVSS mAb 157 VL (SEQ ID NO: 216)

DIHMTQAPSSVSASVGDRVTFTCRASQDINNWLAWYQQKP

GKAPKLLIYTASSLQSGVPSRFSGSGSGTDFTLTISSLQP

EDFATYYCQQAHSLPITFGQGTRLGIK mAb 158 VH (SEQ ID NO: 217)

EVQLVESGGGLVQPGRSLRLSCAASGFTFADYTMHWVRQV

PGKGLEWVSGISWNSGSVDYADSVKGRFTISRDNAKKTLY

LQMNSLRAEDTALYYCAKDSSGYGHYYFYYLDVWGKGTTV

TVSS mAb 158 VL (SEQ ID NO: 218)

EIVMTQSPATLSVSPGERATLSCRATQSVSSNLAWYQQKP

GQAPRLLIYSTSTRATGIPARFSGSRSGTEFTLTISSLQS

EDSAVYYCQQYNNWPHFGQGTRLEIK mAb 159 VH (SEQ ID NO: 219)

EVQLVESGGGLVQPGRSLRLSCAASGFTFNGYTMHWVRQV

PGKGLEWVSGISWNSGSVGYADSVKGRFTISRDNAKNSLF

LQMNSLRAEDTALYYCAKDSSGYGHYYYYYMDVWGKGTTV

TVSS mAb 159 VL (SEQ ID NO: 220)

EIVMTQSPATLSVSPGERATLSCRASQSVRNNLAWYQQKP

GQAPRLLIYGASTRATGIPARFSGSGSGTEFTLTISSLQS

EDFALYYCQLYNNWPHFGQGTRLEIK mAb 160 VH (SEQ ID NO: 221)

EVQLVESGGGLVQPGRSLRLSCAVSGFTFNDYTMHWVRQV

PGKGLEWVSGISWNSGSIGYADSVKGRFTISRDNAKNSLY

LQMNSLRAEDTALYFCAKDSSGYGHYYYYYMDVWGRGTTV

TVSS

-continued mAb 160 VL (SEQ ID NO: 222)

EIVMTQSPATLSVSPGERATLSCRASQSVRKNLAWYQQKP

GQAPRLLIYGASTRATGIPARFSGSGSGTEFTLTISSLQS

EDFAVYYCQLYNNWPHFGQGTRLEIK mAb 161 VH (SEQ ID NO: 223)

EVQLVESGGGLVQPGRSLRLSCAASGITFADYTMHWVRQA

PGKGLEWVSGISWNSGSIDYADSVKGRFTISRDNAKKTLY

LQMNRLRAEDTALYYCAKDSSGYGHYYFYYLDVWGKGTTV

TVSS mAb 161 VL (SEQ ID NO: 224)

EIVMTQSPATLSVSPGERATLSCRASQSVSNNLAWYQQKP

GQAPRLLIYSTSTRATGIPARFSGSRSGTEFTLTISSLQS

EDSAVYYCQQYNNWPHFGQGTRLEIK mAb 162 VH (SEQ ID NO: 225)

EVQLVESGGGLVQPGRSLRLSCAASGFTFDNYAMHWVRQA

PGKGLEWVSGISWNSGSIGYADSVKGRFTISRDNAKNSLY

LELNSLRAEDTALYYCAKDSSGYGYYYNYYMDVWGKGTTV

TVSS mAb 162 VL (SEQ ID NO: 226)

EIVMTQSPATLSVSPGERATLSCRASQSVRSNLAWYQQKP

GQAPRLLIYGASTRATGIPAKFSGSGSGTEFTLTISSLQS

EDFAVYYCQYYYNWPHFGQGTRLEIK mAb 163 VH (SEQ ID NO: 227)

EVQLVESGGGLVKTGGSLRLSCVASGFSFKKAWMNWVRQV

PGKGLEWVGRIKRNTDGGTADYAAPVKGRFTLSRDDSKKT

LFLQMNSLKTEDTAVYYCTTLDSSSYYVGYYYMDVWGKGT

TVTVSS mAb 163 VL (SEQ ID NO: 228)

DIQMTQSPSSVSASVGDRVIITCRASQDINNWLAWYQQKP

GKAPKLLIYTASSLQSGVPSRFSGSGSGTDFTLTIGSLQP

EDFATYYCQQAHSLPITFGQGTRLEIK mAb 164 VH (SEQ ID NO: 229)

EVQLVESGGGLVKTGGSLRLSCVASGFSFKKAWMNWVRQA

PGKGLEWVGRIKRNTDGGTADYAAPVKGRFTLSRDDSKKT

LFLQMNSLKTEDTAVYYCTTLDSSSYYVGYYYMDVWGKGT

TVTVSS mAb 164 VL (SEQ ID NO: 230)

DIQMTQSPSSVSASVGDRVTITCRASQDIKNWLAWYQQKP

GKAPKLLIYTASSLQSGVPSRFSGSGSGTDFTLTIGSLQP

EDFATYYCQQAHSLPITFGQGTRLEIK

-continued mAb 165 VH
(SEQ ID NO: 231)
EVQLVESGGGLVKTGGSLRLSCVASGFSFKKAWMNWVRQA
PGKGLEWVGRIKRNTDGGTADYAAPVKGRFTLSRDDSKRT
LYLQMNSLKTEDTAVYYCTTLDSSSRYVGYYYMDVWGKGT
TVTVSS mAb 165 VL
(SEQ ID NO: 232)
DIQMTQSPSSVSASVGDRVIITCRASQDINNWLAWYQQKP
GKVPKLLIYTASSLQSGVPSRFSGSGSGTDFTLTIGSLQP
EDFATYYCQQAHSLPITFGQGTRLEIK mAb 166 VH
(SEQ ID NO: 233)
EVQLVESGGGLVKTGGSLRLSCVASGFSFKKAWMNWVRQA
PGRGLEWVGRIKRNTDGGTTDYAAPVKGRFTLSRDDSKNM
LYLQMNSLKTEDTAVYYCTTLDSSSLYVGYYYMDVWGKGT
TVTVSS mAb 166 VL
(SEQ ID NO: 234)
DIQMTQSPSSVSASVGDRVTITCRASQDINNWLAWYQQKP
GKAPKLLIYTASSLQSGVPSRFSGSGSGTDFTLTISSLQP
EDFATYFCQQAHSLPITFGQGTRLEIT mAb 167 VH
(SEQ ID NO: 235)
EVHLVESGGGLVQPGRSLRLSCAASGFTFDDYAMHWVRQA
PGKGLEWVSGISWNSGTIGYADSVKGRFTISRDNAKNSLY
LEMNSLRAEDTALYYCAKDSSGYGHYYHYYIDVWGTGTTV
TVSS mAb 167 VL
(SEQ ID NO: 236)
EIVMTQSPATLSVSPGGRATLSCRASQSVGSNLAWYQQKP
GQAPRLLIYDASTRATGIPARFRGSGSGTEFTLTISGLQS
EDFAVYYCQLYYNWPHFGQGTRLEIK mAb 168 VH
(SEQ ID NO: 237)
EVQLVQSGAEVKKPGESLKISCKGSGYIFTSYWIGWVRQM
PGKGLEWMGIIYPGDSDTRYSPSFQGQVTISADKSISTAY
LQWSSLKASDTAMYYCARRNYYYYMDVWGKGTTVTVSS mAb 168 VL
(SEQ ID NO: 238)
DIVMTQSPDSLAVSLGERATINCKSSQSVLYSSNNKNYLA
WYQQKPGQPPKLLIYWASTRESGVPDRFSGSGSGTDFTLT
ISSLQAEDVAVYYCQQYYSTPYTFGQGTKLEIK mAb 169 VH
(SEQ ID NO: 239)
EVQLVESGGGLVKTGGSLRLSCVASGFSFKKAWMNWVRQA
PGKGLEWVGRIKRNTDGGTADYAAPVKGRFTLSRDDSKKT
LFLQMNSLKTEDTAVYYCTTLDSSSYYVGYYYMDVWGKGT
TVTVSS -continued mAb 169 VL
(SEQ ID NO: 240)
DIQMTQSPSSVSASVGDRVIITCRASQDINNWLAWYQQKP
GKAPKLLIYTASSLQSGVPSRFSGSGSGTDFILTIGSLQP
EDFATYYCQQAHSLPITFGQGTRLEIK mAb 170 VH
(SEQ ID NO: 241)
EVQLVESGGGLVRPGRSLRLSCAASGFTFDDYTMHWVRQA
PGKGLEWVSGISWNSGSIGYADSVKGRFTISRDNAKNSLY
LQMNSLRAEDTALYYCSKDSSGYGYYLNYSLDVWGKGTTV
TVSS mAb 170 VL
(SEQ ID NO: 242)
EIVMTQSPATLSVSPGERATLSCRASLSVTSNLAWYQQKP
GQAPRLLIYGASTRATGVPARFSGSGSGTEFTLTISSLQS
EDFAVYYCQQYNNWPHFGQGTRLEIK mAb 171 VH
(SEQ ID NO: 243)
EVQLVESGGGLVQPGRSLRLSCAASGFTFADYTMHWVRQA
PGQGLEWVSGISWNSGSIDYADSVKGRFIISRDNAKKTLY
LQMNSLRAEDTALYYCAKDSSGYGHYYFYYLDVWGKGTTV
TVSS mAb 171 VL
(SEQ ID NO: 244)
EIVMTQSPATLSVSPGERATLSCRASQSVSSNLAWYQQKP
GQAPRLLIYSTSTRATGIPARFSGSRSGTEFTLTISSLQS
EDSAVYYCQQYNNWPHFGQGTRLEIK mAb 172 VH
(SEQ ID NO: 245)
EVQLVESGGGLVQPGRSLRLSCTTSGFTFDDYTMHWVRQV
PGKGLEWVSDISWNSGSVGYADSVKGRFTISRDNAKNSLY
LQMNSLRAEDTALYYCVKDSSGYGHYFHYYMDVWGKGTTV
TVSS mAb 172 VL
(SEQ ID NO: 246)
DIQMTQSPSSLSASVGDRVTITCRASQSISNYLNWYQVKP
GKAPKVLIYAASSLQSGVPSRFSGSGSGTDFTLTISSLQP
EDFVSYYCHQSYNAPITFGQGTRLESK mAb 173 VH
(SEQ ID NO: 247)
EVQLVESGGGLVQPGRSLRLSCAASGFTFDDYTMHWVRQV
PGKGLEWVSDISWNSGSVGYADSVKGRFTISRDNAKNSLY
LQMNSLRAEDTALYYCVKDSSGYGHYFHYYMDVWGKGTTV
TVSS mAb 173 VL
(SEQ ID NO: 248)
DIQMTQSPSSLSASVGDRVTITCRASQSISNYLNWYQVKP
GKAPKVLIYAASSLQSGVPSRFSGSGSGTDFTLTISSLQP
EDFVSYYCHQSYNTPITFGQGTRLEIK -continued mAb 174 VH
(SEQ ID NO: 249)
EVQLVESGGGLVQPGGSLRLSCAASGFTFSSNWMSWVRQA
PGKGLEWVANIKQDGSEKYSVDSVKGRFTISRDNAKNSLY
LQMNSLRAEDTAVYYCARDRSRNYYWYFDLWGRGTLVTVS
S mAb 174 VL
(SEQ ID NO: 250)
DIQMTQSPSTLSASVGDRVTITCRASQTISRWLAWYQQKP
GKAPKLLIYKASSLESGVPSRFSGSGSGTEFTLTISSLQP
DDFATYYCQQYNSYSRTFGQGTKVEIK mAb 175 VH
(SEQ ID NO: 251)
EVELVESGGGLVQPGGSLRLSCAASGFTFSSNWMSWVRQA
PGKGLEWVANIKQDGSEKYYVDSVKGRFTISRDNAKNSLY
LKMNSLRAEDTAVYYCARDCSSNWYWYFDLWGRGTLVTVS
S mAb 175 VL
(SEQ ID NO: 252)
DIQMTQSPSTLSASVGDRVTITCRASQSISRWLAWYQQKP
GKAPKLLIYKASSLESGVPSRFSGSGSGTEFILTISSLQP
DDFATYYCQQYNSYSRTFGQGTKVEIK mAb 176 VH
(SEQ ID NO: 253)
EVELVESGGGLVQPGRSLRLSCAASGFKFDDYTMHWVRLP
PGKGLEWVSGISWNSGTIDYGDSVKGRFTISRDNAKNSLY
LQMNSLRVEDTALYYCAKDTSGYGHYFYYYMDVWGKGTTV
TVSS mAb 176 VL
(SEQ ID NO: 254)
DIQMTQSPSSLSASIGDRVSITCRTSQIINNYLNWYQQKP
GKAPKVLIYSASSLQSGVPSRFSGSGSGTDFTLTINSLQP
EDFATYYCQQSYNFPITFGQGTRLELK mAb 177 VH
(SEQ ID NO: 255)
EVQLVESGGGLVQPGMSLRLSCAASGFTFDDYTMHWVRQS
PGKGLEWVAGISWNSGTIGYGDSMKGRFTISRDNAKNSLD
LQMNSLRVEDTALYYCAKDTSGYGHYYYYFMDVWGKGTTV
TVSS mAb 177 VL
(SEQ ID NO: 256)
DIQMTQSPSSLSASIGDRVSITCRTSQUINNYLNWYQQKP
GKAPKLLIYSASSLQSGVPSRFSGSGSGTDFTLTLSSLQP
EDFATYFCQQSYNFPITFGQGTRLELK mAb 178 VH
(SEQ ID NO: 257)
EVQLVESGGGLVQPGRSLRLSCAASGFTFDDYTMHWVRQA
PGKGLEWVSDISWNSGTIGYADSVKGRFTISRDNAKNSLY
LQMNSLRAEDTALYYCVKDSSGYGHYYKYYMDVWGKGTTV
TVSS mAb 178 VL
(SEQ ID NO: 258)
DIQMTQSPSSLSASVGDRVTITCRASQSISNYLNWYQQKA
GKVPKVLIYGSSSLQSGVPSRFSGSGSGTDFTLTISSLQP
EDFASYYCQQTYSSPLTFGGGTKVDFK mAb 179 VH
(SEQ ID NO: 259)
EVQLVESGGGLVQPGRSLRLSCAASGFTFDDYTMHWVRQT
PGKGLEWVSDISWNSGSIGYADSVKGRFTISRDNAKNTLY
LQMNSLRAEDTALYYCVKDSSGYGHYLYYYMDVWGKGTTV
TVSS mAb 179 VL
(SEQ ID NO: 260)
DIQMTQSPSSLSASVGDRVTITCRASQSIRNYLNWYQQSP
GRAPKLLIFSASSLQSGVPSRFSGSGSGTDFTLTISSLQP
EDFVTYYCQQRYSTPITFGQGTRLEIK mAb 180 VH
(SEQ ID NO: 261)
EVNLVESGGGLVQPGRSLRLSCAASGFTFDDYTMHWVRQV
PGKGLEWVSNISWNSGSLGYADSVKGRFTISRDNAKDSLY
LQMNSLRVEDTALYYCAKDSSGYGHYNSYYMDVWGKGTTV
TVSS mAb 180 VL
(SEQ ID NO: 262)
DIQMTQSPSSLSASVGDRVTITCRASQSIRNYLNWYQQKP
GKAPKVLIYSASSLQSGVPSRFSGSGSGTDFTLTISSLQP
EDFASFYCQQTYSTPITFGQGTRLEIK mAb 181 VH
(SEQ ID NO: 263)
QVQLVQSGADMKKPGASVKVSCKASGYTFTDYHIHWVRQA
PGQGLEWMGWINPKSGRTMFAQNFQDRVTMTRDTSISTAY
MELNRLRSDDSAVYYCARVTQLVFDHWGQGTLVTVSF mAb 181 VL
(SEQ ID NO: 264)
AIQMTQSPSSLSASVGDRVTITCRASQGIRNDLGWYQQKP
GKAPKLLIYAASSLQSGVPSRFSGSGSGTDFTLTISSLQP
EDFATYYCLQDYNYMYTFGQGTKLEIK mAb 182 VH
(SEQ ID NO: 265)
QVQLVQSGAGMKKPGASVRVSCKASGYNFIDYHIHWVRQA
PGQGLEWMGWINPKSGRTMSAQKFQGRVTMTRDTSITAAY
MELNRLRSDDSAIYYCARVTQLVFDHWGQGTLVTVSL mAb 182 VL
(SEQ ID NO: 266)
DIVMTQSPDSLAVSLGERATINCKSSQSVLYSSNNKNYLA
WYQQKPGQPPKLLIYWASTRESGVPDRFSGSGSGTDFTLT
ISSLQAEDVAVYYCQQYYSTPYTFGQGTKLEIK -continued mAb 183 VH (SEQ ID NO: 267)

QVQLVQSGAEVKKPGASVRVSCKSSGYTFTGYYIHWVRQA

PGQGLEWMGWINPKSGRTSYAEKFQGSITMTRDTSINTAY

MELTKLRSDDTAVYYCERMGELLLFDYWGQGTLVTVSS mAb 183 VL (SEQ ID NO: 268)

DIVMTQTPLSSPVTLGQPASISCRSSQSLVHSDGNTYLSW

LQQRPGQPPRLLIYKISNRFSGVPDRFSGSGAGTDFTLKI

SRVEAEDVGVYYCMQATQLYTFGQGTKLEIK mAb 184 VH (SEQ ID NO: 269)

QVQLVESGGGVVQPGRSLRLSCAASGFTFSDYGMHWVRQA

PGKGLEWVSVIWSDGLNKYYKDSVKGRFTISRDNSKNTLY

LQMNSLRAADTAVYYCARLYSGSHYHYFMDVWGKGTSVTV

SS mAb 184 VL (SEQ ID NO: 270)

DILLTQSPSFLSASVGDRVTITCRASQDISSSLAWYQQKP

KKAPDLLIYTASTLQSGVPSRFSGRGSGTEFTLTISNLQP

EDFATYYCQQLKNYPITFGQGTRLEIK mAb 185 VH (SEQ ID NO: 271)

QVQLVQSGSEVKKPGASVRVSCKASGYIFTGYHIHWVRQA

PGQGLEWMGWINPKSGRTSYAQNFQARVTMTRDTSINTIH

MELSRLRSDDTAIYYCMRVGEQLLFDFWGQGTLVTVSS mAb 185 VL (SEQ ID NO: 272)

DIQMTQSPSSLSASVGDRVTITCRASQSISSYLNWYQQKP

GKAPKLLIYAASSLQSGVPSRFSGSGSGTDFTLTISSLQP

EDFATYYCQQSYSTPLTFGGGTKVEIK mAb 187 VH (SEQ ID NO: 273)

EVQLLESGGGLVQPGGSLRLSCAASGFTFSSYAMNWVRQA

PGKGLEWVSAISSSGGRTYYADSVKGRFTISRDNSKNTLY

LQMNSLRAEDTAVYYCAKDSTSHPYMDVWGKGTTVTVSS mAb 187 VL (SEQ ID NO: 274)

AIQMTQSPSSLSASVGDRVTITCRASQGIRNDLGWYQQQP

GKAPKLLIYDASSLQSGVPSRFSGSGSGTVFTLTISSLQP

EDFATYFCLQDYNYPFTFGPGTKVDIK mAb 188 VH (SEQ ID NO: 275)

QVQLVESGGGVVQPGRSLRLSCAASGFTFSGYGMHWVRQA

PGKGLEWVAIIYYNGKKEYYADSVKGRFTISRDNSKNTLY

LQMNSLRAEDTAVYYCTRGEGYNWFDPWGQGTLVTVSS

-continued mAb 188 VL (SEQ ID NO: 276)

EIVMTQSPATLSVSPGERATLSCRASQSVSSNLAWYQQKP

GQAPRLLIYGASTRATGIPARFSGSGSGTEFTLTISSLQS

EDFAVYYCQQYNNWPLTFGGGTKVEIK mAb 189 VH (SEQ ID NO: 277)

QVQLVESGGGVVQPGRSLRLSCAASGFTFSGYGMHWVRQA

PGKGLEWVAIIYYDGKNKYYADSVKGRFTISRDNSKSTLY

LQMNSLGADDTAVYYCTRGKGYNWFDPWGQGTLVTVSS mAb 189 VL (SEQ ID NO: 278)

EIVMTQSPATLSVSPGERATLSCRASQSVSSNLAWYQQKP

GQAPRLLIYGASTRATGIPARFSGSGSGTEFTLTISSLQS

EDFAVYYCQQYNNWPLTFGGGTKVEIK mAb 190 VH (SEQ ID NO: 279)

QVQLVESGGGVVQPGRSLRLSCAASGFTFSGYGMHWVRQA

PGKGLEWVAIIYYNGKKEYYADSVKGRFTISRDNSKNTLY

LQMNSLRAEDTAVYYCTRGEGYNWFDPWGQGTLVTVSS mAb 190 VL (SEQ ID NO: 280)

EIVMTQSPATLSVSPGERATLSCRASQSVSSNLAWYQQKP

GQAPRLLIYGASTRATGIPARFSGSGSGTEFTLTISSLQS

EDFAVYYCKQYNNWPLTFGGGTKVEIK mAb 191 VH (SEQ ID NO: 281)

QVQLVESGGGVVQPGRSLRLSCAASGFTFSGYGMHWVRQA

PGKGLEWVAIIYYNGKKEYYADSVKGRFTISRDNSKNTLY

LQMNSLRAEDTAVYYCTRGEGYNWFDPWGQGTLVTVSS mAb 191 VL (SEQ ID NO: 282)

EIVMTQSPATLSVSPGERATLSCRASQSVSSNLAWYQQKP

GQAPRLLIYGASTRATGIPARFSGSGSGTDFTLTISSLQS

EHFAVYYCQQYTNWPLTFGGGTKVEIK mAb 192 VH (SEQ ID NO: 283)

QVQLVESGGGVVQPGRSLRLSCAASGFTFSGYGMHWVRQA

PGKGLEWVAIIYYNGKKEYYADSVKGRFTISRDNSKNTLY

LQMNSLRAEDTAVYYCTRGEGYNWFDPWGQGILVTVSS mAb 192 VL (SEQ ID NO: 284)

EIVMTQSPATLSVSPGERATLSCRASQSVSSNLAWYQQKP

GQAPRLLIYGASTRATGIPARFSGSGSGTEFTLTISSLQS

EDFAVYYCKQYKNWPLTFGGGTKVEIK mAb 193 VH (SEQ ID NO: 285

QVQLVESGGGVVQPGRSLRLSCAASGFTFSGYGMHWVRQA

PGKGLEWVAIIYYNGNNRKYADSVKGRFTISRDNSKNTVS

LQMNSLRVEDTAIYYCTRGDGYNWFVTWGQGTLVTVSS

-continued mAb 193 VL (SEQ ID NO: 286)

EIVMTQSPATLSVSPGERATLSCRASQSVSSNLAWYHQKP

GQAPRLLIYGASTRATGIPVRFSGSGSGTEFTLTISSLQS

DDFAVYYCQQYNNWPLTFGGGTKVEIK mAb 194 VH (SEQ ID NO: 287)

QEQLVESGGGVVQPGGSLRLSCAASGFIFSGYGMHWVRQA

PGKGLEWVAIIWYNGRKTYYAESVKGRFTISRDNSKNTLS

LQMNSLRVEDTAVYYCTAGQGYNWFDPWGQGTLVTVSS mAb 194 VL (SEQ ID NO: 288)

EIVMTQSPATLSVSPGERATLSCRASQSVSSNLAWYQQKP

GQAPRLLIYGASTRATGIPARFSGSGSGTEFTLTISSLQS

EDFAVYYCQQFNAWPLTFGGGTKMEIK mAb 195 VH (SEQ ID NO: 289)

QEQLVESGGGVVQSGRSLRLSCVASGFKFSGYGMHWVRQA

PGKGLEWVAIIYYDGKNKYYADSVKGRFTISRDNSKNTLY

LQMNSLRAEDTAVYYCTRGAGYNWFDSWGQGTLVTVSS mAb 195 VL (SEQ ID NO: 290)

EIVMTQSPATLSVSPGERATLSCRASQSVRNNLAWYQQKP

GQAPRLLIYGVSTRATAFPARFSGSGSGTEFTLTISSLQS

EDFAVYYCQQYNNWPLTFGGGTKVEIK mAb 196 VH (SEQ ID NO: 291)

QEQLVESGGGVVQSGRSLRLSCVASGFKFSGYGMHWVRQA

PGKGLEWVAIIYYDGKNKYYADSVKGRFTVSRDNSKNTLY

LQMNSLRAEDTAVYYCTRGAGYNWFDSWGQGTLVTVSS mAb 196 VL (SEQ ID NO: 292)

EIVMTQSPATLSVSPGERATLSCRASQSVRNNLAWYQQKP

GQAPRLLIYGVSTRATAFPARFSGSGSGTEFTLTISSLQS

EDFAVYYCQQYNNWPLTFGGGTKVEIK mAb 197 VH (SEQ ID NO: 293)

QVQLVESGGGVVQPGGSLRLSCAASGFTFSGYGMHWVRQA

PGKGLEWVAIIWYNGRKTYYAESVKGRFTISRDNSKNTLS

LQMNSLRVEDTAVYYCTTGQGYNWFDPWGQGTLVTVSS mAb 197 VL (SEQ ID NO: 294)

EIVMTQSPATLSVSPGERATLSCRASQSVSSNLAWYQQKP

GQAPRLLIYGASTRATGIPARFSGSGSGTEFTLTISSLQS

EDFAVYYCQQFNAWPLTFGGGTKMEIK mAb 198 VH (SEQ ID NO: 295)

QVQLVESGGGVVQPGGSLRLSCAASGFTFSGYGMHWVRQA

PGKGLEWVAIIWYNGRKTYYAESVKGRFTISRDNSKNTLS

LQMNSLRIEDTAVYYCTTGQGYNWFDPWGQGTLVTVSS

-continued mAb 198 VL (SEQ ID NO: 296)

EIVMTQSPATLSVSPGERATLSCRASQSVSSNLAWYQQKP

GQAPRLLIYGASTRATGIPARFSGSGSGTEFTLTISSLQS

EDFAVYYCQQFNAWPLTFGGGTKMEIK mAb 199 VH (SEQ ID NO: 297)

QVQLVESGGGVVQPGRSLRLSCAASGFTFSGYGMHWVRQA

PGKGLEWVAIIYYNGKKEYYADSVKGRFTIFRDNSKNTLY

LHMNSLRAEDTAVYYCTRGEGYNWFDPWGQGTLVTVSS mAb 199 VL (SEQ ID NO: 298)

EIVMTQSPATLSVSPGERATLSCRASQSVSRNLAWYQQKP

GQAPRLLIYGASTRATGIPARFSGSGSGTEFTLTISSLQS

EDFAVYYCQQYNNWPLTFGGGTKVEIK mAb 200 VH (SEQ ID NO: 299)

QVQLAESGGGVVQPGRSLRLSCAASGFTFSGYGMHWVRQA

PGKGLEWVAIIYYNGKKEYYADSVKGRFTISRDNSKNTLY

LQMNSLRAEDTAVYFCTRGEGYNWFDPWGQGTLVTVSS mAb 200 VL (SEQ ID NO: 300)

EIVMTQSPATLSVSPGERATLSCRASQSVSSNLAWYQQKP

GQAPRLLIYGASTRATGIPARFSGSGSGTEFTLTISSLQS

EDFAVYYCKQYKNWPLTFGGGTKVEIK mAb 201 VH (SEQ ID NO: 301)

QVQLVESGGGVVQPGRSLRLSCAASGFTFSGYGMHWVRQA

PGKGLEWVAIIYYNGKKEYYADSVKGRFTISRDNSKNTLY

LQMNSLRAEDTAVYYCTRGEGYNWFDPWGQGTLVTVSS mAb 201 VL (SEQ ID NO: 302)

EIVMTQSPATLSVSPGERATLSCRASQSVSSSLAWYQQKP

GQAPRLLIYGASTRATGIPARFSGSGSGTEFTLTISSLQS

EDFAVYYCQQYNNWPLTFGGGTKVEIK mAb 202 VH (SEQ ID NO: 303)

QVQLVESGGGVVQPGRSLRLSCAASGFTFSGYGMHWVRQA

PGKGLEWVAIIYYNGKKEYYADSVKGRFTISRDNSKNTLY

LQMNSLRAEDTAVYFCTRGEGYNWFDPWGQGTLVTVSS mAb 202 VL (SEQ ID NO: 304)

EIVMTQSPATLSVSPGERATLSCRASQSVSSNLAWYQQKP

GQAPRLLIYGASTRATGIPARFSGSGSGTEFTLTISSLQS

EDFAVYYCKQYKNWPLTFGGGTKVEIK mAb 203 VH (SEQ ID NO: 305)

QVQLVESGGGVVQPGGSLRLSCAASGFTFRGYGMHWVRQA

PGKGLEWVAIIYYNGRKTYYAESVKGRFTISRDNSKNTLS

LQMNSLRVEDTAVYYCTAGQGYNWFDPWGQGTLVTVSS

-continued mAb 203 VL (SEQ ID NO: 306)
EIVMTQSPATLSVSPGERATLSCRASQSVSSNLAWYQQKP
GQAPRLLIYGASTRATGIPARFSGSGSGTEFTLTISSLQS
EDFAVYYCQQFNAWPLTFGGGTKMEIK mAb 204 VH (SEQ ID NO: 307)
QVQLVESGGGVVQSGRSLRLSCAASGFTFSGYGMHWVRQA
PGKGLEWVAIVYYDGKNKYYADSVKGRFTISRDNSKNTLY
LQMNSLRAEDTAVYYCVRGEGYNWFDPWGQGTLVTVSS mAb 204 VL (SEQ ID NO: 308)
EIVMTQSPATLSVSPGERATLSCRASQSVSSNLAWYQQKP
GQVPRLLIYGASTRATGIPARFSGSGSGTQFTLTISSLQS
EDFAVYYCQQYNNWPLTFGGGTKVEIK mAb 205 VH (SEQ ID NO: 309)
QVQLVESGGGVVQPGKSLRLSCAASGFTFSGYGMHWVRQA
PGKGLEWVAIIYYNGKKEYYADSVKGRFTISRDNSKNTLY
LQMNSLRAEDTAVYYCTRGEGYNWFDPWGQGTLVTVSS mAb 205 VL (SEQ ID NO: 310)
EIVMTQSPATLSVSPGERATLSCRASQSVSSNLAWYQQKP
GQAPRLLIYGASTRATGIPARFSGSGSGTEFTLTISSLQS
EDFAVYYCKQYNNWPLTFGGGTKVEIK mAb 206 VH (SEQ ID NO: 311)
QVQLVESGGGVVQPGRSLRLSCAASGFTFSGYGMHWVRQA
PGKGLEWVAIIYYNGNNRKYADSVKGRFTISRDNSKNTVS
LQMNSLRVEDTAIYYCTRGDGYNWFVTWGQGTLVTVSS mAb 206 VL (SEQ ID NO: 312)
EIVMTQSPATLSVSPGERATLSCRASQSVSSNLAWYHQKP
GQAPRLLIYGASTRATGIPVRFSGSGSGTEFTLTISSLQS
EDFAVYYCQQYNNWPLTFGGGTKVEIK mAb 207 VH (SEQ ID NO: 313)
QVQLVESGGGVVQPGRSLRLSCAASGFTFSGYGMHWVRQA
PGKGLEWVAIIYYNGKKEYYADSVKGRFTISRDNSRNTLF
LQMNSLRAEDTAIYYCTRGEGYNWFDPWGQGTLVTVSS mAb 207 VL (SEQ ID NO: 314)
EIVMTQSPATLSVSPGERATLSCRASQSVSSNLAWYQQKP
GQAPRLLIYGASTRATGIPARFSGSGSGTEFTLTISSLLS
EDFAVYYCKQYNNWPLTFGGGTKVEIK mAb 208 VH (SEQ ID NO: 315)
QEQLVESGGGVVQPGRSLRLSCAASGFTFSSYGMHWVRQA
PGKGLEWVAIIWYNGKKKDYADSVKGRFTISRDNSKSTLY
LQMNSLRAEDTAVYYCARGLGYNWFDPWGQGTLVTVSS -continued mAb 208 VL (SEQ ID NO: 316)
EIVLTQSPDFQSVTPMEKVTIACRASQNIGSSLHWYQQKP
DQSPKLLIKYASQSFSGVPSRFSGSGSGTDFTLTINSLEA
EDAATYYCHQSSSFPNTFGQGTKLEIK mAb 209 VH (SEQ ID NO: 317)
QVQLVESGGGVVQPGRSLRLSCAASGFTFSGYGMHWVRQA
PGKGLEWVAIIYYNGKKEYYADSVKGRFTVSRDNSKNMLY
LQMNSLRAEDTAVYYCTRGEGYNWFDPWGQGTLVTVSS mAb 209 VL (SEQ ID NO: 318)
EIVMTQSPATLSVSPGERATLSCRASQTVSSNLAWYQQKP
GQAPRLLIYGASTRATGIPARFSGSGSGTEFTLTISSLQS
EDFAVYYCKQYNNRPLTFGGGTKVEIK mAb 210 VH (SEQ ID NO: 319)
QVQLVESGGGVVQPGRSLRLSCAASGFTFSGYGMHWVRQA
PGKGLEWLAIIYYNGNNRKYADSVKGRFTISRDNSKNTVS
LQMNSLRVEDTAMYYCTRGDGYNWFVTWGQGTLVTVSS mAb 210 VL (SEQ ID NO: 320)
EIVMTQSPATLSVSPGERAALSCRASQSVTSNLAWYHQKP
GQAPRLLIYGASTRATGIPVRFSGSGSGTEFTLTISSLQS
EDFAVYYCQQYNNWPLTFGGGTKVENK mAb 211 VH (SEQ ID NO: 321)
QVQLVESGGGVVQPGRSLRLSCAASGFTFSGYGMHWVRQA
PGKGLEWVAIIYYNGKREYYADSVKGRFTISRDNSKNTLY
LQMNSLRAEDTAVYYCTRGEGYNWFDPWGQGTLVTVSS mAb 211 VL (SEQ ID NO: 322)
EIVMTQSPATLSVSPGERATLSCRASQSVSSNLAWYQQKP
GQAPRLLIYGASTRATGIPARFSGSGSGTEFTLTISSLQS
EDFAVYYCKHYNNWPLTFGGGTKVEIK mAb 212 VH (SEQ ID NO: 323)
EVQLLESGGGLVQPGGSLRLSCAASGFTFSNYAMNWVRQA
PGKGLEWVSAISGSRSNTYYADSVKGRFTISRDNSKNTLY
LQMNSLRAEDTGVYYCAKGAYSKYPYYYYMDVWGKGTTVT
VSS mAb 212 VL (SEQ ID NO: 324)
EIVMTQSPATLSLSPGERATLSCRASQSVSSSYLSWYQQK
PGQAPRLLIYGASTRAIGIPARFSGSGSGTDFTLTISSLQ
AEDFAVYYCQQDDNLPWTFGQGTKVEIK mAb 213 VH (SEQ ID NO: 325)
QEQLVESGGGVVQPGGSLRLSCAASGFTFSGYGMHWVRQA
PGKGLEWVAIIWYNGRKTYYAESVKGRFTISRDNSKNTLS
LQMNSLRVEDTAVYYCTTGKGYNWFDPWGQGTLVTVSS -continued mAb 213 VL
(SEQ ID NO: 326)
EIVMTQSPATLSVSPGERATLSCRASQSVSSNLAWYQQKP
GQAPRLLIYGASTRATGIPARFSGSGSGTEFTLTISSLQS
EDFAVYYCQQFNAWPLTFGGGTKMEIK mAb 214 VH
(SEQ ID NO: 327)
EVQLLESGGGLVQPGGSLRLSCAASGFTFSNYAMNWVRQA
PGKGLEWVSAISGSRSNTYYADSVKGRFTISRDNSKNTLY
LQMNSLRAEDTAVYYCAKGAYSKYPYYYYMDVWGKGTTVT
VSS mAb 214 VL
(SEQ ID NO: 328)
EIVMTQSPATLSLSPGERATLSCRASQSVSSSYLSWYQQK
PGQAPRLLIYGASTRAIGIPARFSGSGSGTDFTLTISSLQ
AEDFAVYYCQQDDNLPWTFGQGTKVEIK mAb 215 VH
(SEQ ID NO: 329)
QVQLVESGGGVVQPGRSLRLSCAATGFTFSGYGMHWVRQA
PGKGLEWVAIIYYNGNNRKYADSVKGRFTISRDNSKNTVS
LQMNSLRVEDTAIYYCTRGDGYNWFVTWGQGTLVTVSS mAb 215 VL
(SEQ ID NO: 330)
EIVMTQSPATLSVSPGERATLSCRASQSVSSNLAWYRQK
PGQAPRLLIYGASTRATGIPVRFSGSGSGTEFTLTISSL
QSEDFAVYYCQQYNNWPLTFGGGTKVEIK mAb 216 VH
(SEQ ID NO: 331)
QVQLVESGGGVVQPGRSLRLSCAASGFTFSGYGMHWVRQA
PGKGLEWVAIIYYNGKKEYYADSVKGRFTISRDNSKNTLY
LQMNSLRAEDTAVYYCTRGEGYNWFDPWGQGTLVTVSS mAb 216 VL
(SEQ ID NO: 332)
EIVMTQSPATLSVSPGERATLSCRASQSVSSNLAWYQQKP
GQAPRLLIYGASTRATGIPARFSGSGSGTEFTLTISSLQS
EDFAVYYCKQYKNWPLTFGGGTKVEIK mAb 217 VH
(SEQ ID NO: 333)
QVQLVESGGGVVQPGRSLRLSCAASGFTFSGYGMHWVRQA
PGKGLEWVAIIYYNGKKEYYADSVKGRFTIFRDNSKNTVY
LQMKSLRAEDTAVYYCTRGEGYNWFDPWGQGTLVTVSS mAb 217 VL
(SEQ ID NO: 334)
EIVMTQSPATLSVSPGERATLSCRASQSVSSNLAWYQQKP
GQAPRLLIYGASTRATGIPARFSGSGSGTEFTLTISSLQS
EDFAVYYCQQYNNWPLTFGGGTKVEIK -continued mAb 218 VH
(SEQ ID NO: 335)
QVQLVESGGGVVQPGRSLRLSCAASGFTFSGYGMHWVRQA
PGKGLEWVAIIYYNGNNRKYADSVRGRFTISRDNSKNTVS
LQMNSLRVEDTAIYYCTRGDGYNWFVTWGQGTLVTVSS mAb 218 VL
(SEQ ID NO: 336)
EIVMTQSPATLSVSPGERATLSCRASQSVSSNLAWYYQKP
GQAPRLLIYGASTRATGIPVRFSGSGSGTEFTLTISSLQS
EDFAVYYCQQYNNWPLTFGGGTKVEIK mAb 219 VH
(SEQ ID NO: 337)
QEQLVESGGGVVQPGGSLRLSCAASGFMFSGYGMHWVRQA
PGKGLEWVAIIWYNGRKTYYTESVKGRFTISRDNSKNTLS
LQMNSLRVEDTAVYYCTAGQGYNWFDPWGQGTLVTVSS mAb 219 VL
(SEQ ID NO: 338)
EIVMTQSPATLSVSPGERATLSCRASQSVSSNLAWYQQKP
GQAPRLLIYGASTRATGIPARFSGSGSGTEFTLTISSLQS
EDFAVYYCQQFNAWPLTFGGGTKMEIK mAb 220 VH
(SEQ ID NO: 339)
QEQLVESGGGVVQPGGSLRLSCVASGFTFSGYGMHWVRQA
PGKGLEWVAIIWYNGRKTYYAESVKGRFTISRDNSKNTLS
LQMNSLRVEDTAVYYCTTGKGYNWFDPWGQGTLVTVSS mAb 220 VL
(SEQ ID NO: 340)
EIVMTQSPATLSVSPGERATLSCRASQSVSSNLAWYQQKP
GQAPRLLIYGASTRATGIPARFSGSGSGTEFTLTISSLQS
EDFAVYYCQQFNAWPLTFGGGTKMEIK mAb 221 VH
(SEQ ID NO: 341)
QVQLVESGGGVVQPGGSLRLSCAASGFTFSGYGMHWVRQA
PGKGLEWVAIIWYNGRKTYYAESVKGRFTISRDNSKNTLS
LQMNSLRVEDTAVYYCTAGQGYNWFDPWGQGTLVTVSS mAb 221 VL
(SEQ ID NO: 342)
EIVMTQSPATLSVSPGERATLSCRASQSVSSNLAWYQQKP
GQAPRLLIYGASTRATGIPARFSGSGSGTEFTLTISSLQS
EDFAVYYCQQFNAWPLTFGGGTKMEIK mAb 222 VH
(SEQ ID NO: 343)
QVQLVESGGGVVQPGRSLRLSCAASGFTFSGYGMHWVRQA
PGKGLEWVAIIYYNGKKEYYADSVKGRFTISRDNSKNTVY
LQMNSLRAEDTAVYYCTRGEGYNWFDPWGQGTLVTVSS mAb 222 VL
(SEQ ID NO: 344)
KIVMTQSPATLSVSPGERATLSCRASQSVSSNLAWYQQKP
GQAPRLLIYGASTRATGIPARFSGSGSGTEFTLTISSLQS
EDFAVYYCKQYNNWPLTFGGGTKVEIK -continued mAb 223 VH
(SEQ ID NO: 345)
QVQLVESGGGVVQPGRSLRLSCAASGFTFSGYGMHWVRQA
PGKGLEWVAIIYYNGNNRKYADSVKGRFTISRDNSKNMVS
LQMNSLRVEDTAIYYCTRGDGYNWFVTWGQGTLVTVSS mAb 223 VL
(SEQ ID NO: 346)
EIVMTQSPATLSVSPGEGATLSCRASQSVSSNLAWYHQKP
GQAPRLLIYGASTRATGIPVRFSGSGSGTEFTLTISSLQS
DDFAVYFCQQYNNWPLTFGGGTKVEIK mAb 224 VH
(SEQ ID NO: 347)
QVQLVESGGGVVQPGRSLRLSCAASGFTFSGYGMHWVRQA
PGKGLEWVAIIYYNGKKEYYADSVKGRFTISRDNSKNMLY
LQMNGLRAEDTAIYYCTRGEGYNWFDPWGQGTLVTVSS mAb 224 VL
(SEQ ID NO: 348)
EIVMTQSPATLSVSPGERTTLSCRASQSVSNNLAWYQQKP
GQAPRLLIYGASTRATGIPARFSGSGSGTEFTLTISSLQS
EDFAVYYCQQYNNWPLTFGGGTKVEIK mAb 225 VH
(SEQ ID NO: 349)
QEQLVESGGGVVQPGGSLRLSCAASGFKFSGYGMHWVRQA
PGKGLEWVAIIWYNGRKTYYAESVKGRFTISRDNSKNTLS
LQMNRLRVEDTAVYYCTAGQGYNWFDPWGQGTLVTVSS mAb 225 VL
(SEQ ID NO: 350)
EIVMTQSPATLSVSPGERATLSCRASQSVSSNLAWYQQKP
GQAPRLLIYGASTRATGIPARFSGSGSGTEFTLTISSLQS
EDFAVYYCQQFNAWPLTFGGGTKMEIK mAb 226 VH
(SEQ ID NO: 351)
QVQLVESGGGVVQPGRSLRLSCAASGFTFSGYGMHWVRQA
PGKGLEWVAIIYYNGNNRKYADSVKGRFTISRDNSKNTVS
LQMNSLRVEDTAIYYCTRGDGYNWFVTWGQGTLVTVSS mAb 226 VL
(SEQ ID NO: 352)
EIVMTQSPATLSVSPGERATLSCRASQSISSNLAWYHQKP
GQAPRLLIYGASTRATGIPVRFSGSGSGTEFTLTISSLQS
EDFALYYCQQYNNWPLTFGGGTKVEIK mAb 227 VH
(SEQ ID NO: 353)
QEQLVESGGGVVQPGRSLRLSCAASGFIFSSYGMHWVRQA
PGKGLEWVAIIWYNGKKRDYADSVKGRFTISRDNSKNTLY
LQMNSLRAEDTAVYYCARGLGYNWFDPWGQGTLVTVSS mAb 227 VL
(SEQ ID NO: 354)
EIVLTQSPDFQSVTPKEKVTITCRASQSIGSSLHWYQQKP
DQSPKLLIKYASQSFSGVPSRFSGSGSGTDFTLTINSLEA
EDAATYYCHQSSSLPYTFGQGTKLEIK mAb 228 VH
(SEQ ID NO: 355)
EVQLLESGGGLVQPGGSLRLSCAASGFTFSNYAMNWVRQA
PGKGLEWVSTISGSGGGKYYADSVKGRFTISRDNSKNTLY
LHMNSLRAEDTAVYYCAKDPVQDRYYFYYYYMDVWGKGTT
VTVSS mAb 228 VL
(SEQ ID NO: 356)
EIVLTQSPDFQSVTPKEKVTITCRASQSIGSSLHWYQQKP
DQSPKLLIKYASQSISGVPSRFSGSGSGTDFTLTINSLEA
EDAAAYYCHQSSSLPHTFGQGTKLEIK mAb 229 VH
(SEQ ID NO: 357)
QEQLVESGGGVVQPGRSLRLSCAASGFTFSSYGMHWVRQA
PGKGLEWVAIIYYNGKKKDYADSVKGRFTISRDNSKNTLY
LQMNSLRAEDTAVYYCARGLGYNWFDPWGQGTLVTVSS mAb 229 VL
(SEQ ID NO: 358)
EIVLTQSPDFQSVTPKEKVTITCRASQSIGSSLHWYQQKP
DQSPKLLIKYASQSFSGVPSRFSGSGSGTDFTLTINSLEA
EDAATYYCHQSSSLPYTFGQGTKLEIK mAb 230 VH
(SEQ ID NO: 359)
EVQLLESGGGLVQPGGSLRLSCAASGFTFSSYAMSWVRQA
PGKGLEWVSSISGSGGSRYYADSVKGRFTISRDNSKNTLY
LQMNSLRAEDTAVYYCAKDPVQDRYYFYYYYMDVWGKGTT
VTVSS mAb 230 VL
(SEQ ID NO: 360)
EIVLTQSPDFQSVTPKEKVTITCRASQSIGSSLHWYQQKP
DQSPKLLIKYASQSISGVPSRFSGSGSGTDFTLTINSLEA
EDAAAYYCHQSSSLPHTFGQGTKLEIK mAb 231 VH
(SEQ ID NO: 361)
QEQLVESGGGVVQPGRSLRLSCAASGFTFSSYGMHWVRQA
PGKGLEWVAIIYYNGKKKDYADSVKGRFTISRDNSKNTLY
LQMNSLRAEDTAVYYCVRGLGYNWFDPWGQGTLVTVSS mAb 231 VL
(SEQ ID NO: 362)
EIVLTQSPDFQSVTPKEKVTITCRASQSIGSSLHWYQQKP
DQSPKLLIKYASQSFSGVPSRFSGSGSGTDFTLTINSLEA
EDAATYYCHQSSNLPYTFGQGTKLEIK mAb 232 VH
(SEQ ID NO: 363)
QEQLVESGGGVVQPGRSLRLSCAASGFTFSSYGMHWVRQA
PGKGLEWVAIIWYNGRKKDYADSVKGRFTISRDNSKNTLY
LQMNSLRAEDTAVYYCARGLGYNWFDPWGQGTLVTVSS -continued mAb 232 VL (SEQ ID NO: 364)

EIVLTQSPDFQSVTPMEKVTIACRASQSIGSSLHWYQQKP

DQSPKLLIKYASQSFSGVPSRFSGSGSGTDFTLTINSLEA

EDAATYYCHQSSSLPYTFGQGTKLEIK mAb 233 VH (SEQ ID NO: 365)

QGKLVESGGGVVQPGRSLRLSCVASGFTFSGYGMHWVRQV

PNKGLEWVAIIYYDGKNKYYADSVKGRFTISRDNSKNMLY

LQMNSLRAEDTAVYYCVRGPGYNWFDPWGQGTLVTVSS mAb 233 VL (SEQ ID NO: 366)

EIVLTQSPDFQSVTPKEKVTITCRASQNIGSSLHWYQQKP

DQSPKLLIKLTSQSFSGVPSRFSGSGSGTDFTLTINSLEA

EDAATYYCHQSSSLPYTFGQGTKLEIK mAb 234 VH (SEQ ID NO: 367)

QEQLVESGGGVVQPGRSLRLSCAASGFIFSSYGMHWVRQA

PGKGLEWVAIIWYNGKKRDYADSVKGRFTISRDNSKNTLY

LQMNSLRVEDTAVYYCARGLGYNWFDSWGQGTLVTVSS mAb 234 VL (SEQ ID NO: 368)

EIVLTQSPDFQSVTPKEKVTITCRASQSIGSSLHWYQQKP

DQSPKLLIKYASQSFSGVPSRFSGSGSGTDFTLTINSLEA

EDAATYYCHQSSSLPYTFGQGTKLEIK mAb 235 VH (SEQ ID NO: 369)

QGKLVESGGGVVQPGRSLRLSCVASGFTFSGYGMHWVRQA

PNKGLEWVAIIYYDGKNKYYADSVKGRFTVSRDNSKNTLY

LQLNNLRAEDTAVYYCVRGPGYNWFDPWGQGTLVTVSS mAb 235 VL (SEQ ID NO: 370)

EIVLTQSPDFQSVTPKEKVTITCRASQNIGSSLHWYQQKP

DQSPKLFIKHASQSFSGVPSRFSGSGSGTDFTLTINSLEA

EDAATYYCHQSSSLPYTFGQGTKLEIK mAb 236 VH (SEQ ID NO: 371)

QVKLVESGGGVVQPGRSLRLSCVASGFTFSGYGMHWVRQA

PGKGLEWVAIIYYDGKNKYYADSAKGRFTVSRDNSKNTLY

LQLNSLRAEDTAVYYCVRGPGYNWFDSWGQGTLVTVSS mAb 236 VL (SEQ ID NO: 372)

EIVLTQSPDFQSVTPKEKVTITCRASQSIGSNLHWYQQKP

DQSPKLLIKYTSQSFSGVPSRFSGSGSGTDFTLTINSLEA

EDAATYYCHQSSSLPYTFGQGTKLEIK mAb 237 VH (SEQ ID NO: 373)

EVQLLESGGDLVQPGGSLRLTCAASGFTFRSYAMNWVRQA

PGKGLEWVSTISSRGDTTNYADSVKGRFTISRDTSKNTLY

LQMDNLRADDTAVYYCSKMFSYYYYYMDVWGKGTTVTVSS mAb 237 VL (SEQ ID NO: 374)

SYELTQPLSVSVALGQTARITCGGNNIGSKDVHWYQQKPG

QAPVLVIYRDSNRPSGIPERFSGSNSGNTATLTISRAQAG

DEADYYCQVWDSRTAVFGGGTQLTAL mAb 238 VH (SEQ ID NO: 375)

EVQLLESGGDLVQPGGSLRLTCAASGFTFRSYAMNWVRQA

PGKGLEWVSTISSRGDTTNYADSVKGRFTISRDTSKNTLY

LQMDNLRADDTAVYYCSKMFSYYYYYMDVWGKGTTVTVSS mAb 238 VL (SEQ ID NO: 376)

SYELTQPLSVSVALGQTARITCGGNNIGSKDVHWYQQKPG

QAPVLVIYRDSNRPSGIPERFSGSNSGNTATLTISRAQAG

DEADYYCQVWDSSTAVFGGGTQLTAL mAb 239 VH (SEQ ID NO: 377)

QEKLVESGGGVVQPGRSLRLSCVASGFTFSGFGMHWVRQA

PGKGLEWVAIIYYDGKNKYYADSVKGRFTISRDNSKNTLY

LQMNSLRAEDTAVYYCVRGPGYNWFDPWGQGTLVTVSS mAb 239 VL (SEQ ID NO: 378)

EIVLTQSPDFQSVTPKEKVTITCRASQSIGSSLHWYQQKP

DQSPKLLIKYASQSFSGVPSRFSGSGSGTDFTLTINSLEA

EDAATYYCHQSSSLPYTFGQGTKLEIK mAb 240 VH (SEQ ID NO: 379)

QGKLVESGGGVVQPGRSLRLSCVASGFTFSGYGMHWVRQA

PNKGLEWVAIIYYDGKNKYYADSVKGRFTISRDNSKNTLY

LQLNSLRAEDTAVYYCVRGPGYNWFDPWGQGTLVTVSS mAb 240 VL (SEQ ID NO: 380)

EIVLTQSPDFQSVTPKEKVTITCRASQNIGSSLHWYQQKP

DQSPKLLIKHASQSFSGVPSRFSGSGSGTDFTLTINSLEA

EDAATYYCHQSSSLPYTFGQGTKLEIK mAb 241 VH (SEQ ID NO: 381)

QEQLVESGGGVVQPGRSLRLSCAASGFIFSSYGMHWVRQA

PGKGLEWVAIIWYNGKKRDYADSVKGRFTISRDNSKNTLY

LQMNSLRAEDTAVYYCARGLGYNWFDPWGQGTLVTVSS mAb 241 VL (SEQ ID NO: 382)

AIVLTQSPDFQSVTPKEKVTITCRASQNIGSSLHWYQQKP

DQSPKLLIKYASQSFSGVPSRFSGSGSGTDFTLTINSLEA

EDAATYYCHQSGSLPYTFGQGTKLEIK mAb 242 VH (SEQ ID NO: 383)

QGKLVESGGGVVQPGRSLRLSCVASGFTFSGYGMHWVRQV

PNKGLEWVAIIYYDGKNKYYADSVKGRFTISRDNSKNMLY

LQMNSLRVEDTAVYYCVRGPGYNWFDPWGQGTLVTVSS

-continued mAb 242 VL (SEQ ID NO: 384)

EIVLTQSPDFQSVTPKEKVTITCRASQNIGSSLHWYQQKP

DQSPKLLIKLTSQSFSGVPSRFSGSGSGTDFTLTINSLEA

EDAATYYCHQSSSLPYTFGQGTKLEIK mAb 243 VH (SEQ ID NO: 385)

QGKLVESGGGVVQPGRSLRLSCVASGFTFSGYGMHWVRQA

PNKGLEWVAIIYYDGKNKYYADSVKGRFTISRDNSKNMLY

LQMNSLRVEDTAVYYCVRGPGYNWFDPWGQGTLVTVSS mAb 243 VL (SEQ ID NO: 386)

EIVLTQSPDFQSVTPKEKVTITCRASQNIGSSLHWYQQKP

DQSPKLLIKHTSQSFSGVPSRFSGSGSGTAFTLTINSLEA

EDAATYYCHQSSSLPYTFGQGTKLEIK mAb 244 VH (SEQ ID NO: 387)

QEQLVESGGGVVQPGRSLRLSCAASGFTFRSYGMHWVRQA

PGKGLEWVAIIWYDGKNKYYADSVKGRFTISRDNSKNTLY

LQMNSLRVEDTAVYYCARGLGYNWFDPWGQGTLVTVTS mAb 244 VL (SEQ ID NO: 388)

EIVLTQSPDFQSVTPKEKVTITCRASQSIGSSLHWYQQKP

DQSPKLLIKYASQTFSGVPSRFSGSGSGTDFTLTINSLEV

EDAATYYCHQSSSLPNTFGQGTKLEIK mAb 245 VH (SEQ ID NO: 389)

QVKLVESGGGVVQPGRSLRLSCVASGFTFSGYGMHWVRQA

PGKGLEWVAIIYYDGKNKYYVDSVKGRFTISRDNSKNTLY

LQLNSLRAEDTAVYYCVRGPGYNWFDLWGQGTLVTVAS mAb 245 VL (SEQ ID NO: 390)

EIVLTQSPDFQSVTPKEKVTITCRASQSIGSSLHWYQQKP

DQSPKLLIKYASQSFSGVPSRFSGSGSGTDFTLTINSLEA

EDAATYYCHQSSSLPYTFGQGTKLEIK mAb 246 VH (SEQ ID NO: 391)

QEQLVESGGGVVQPGRSLRLSCAASGFTFRSYGMHWVRQA

PGKGLEWVAIIWYDGKNKYYADSVKGRFTISRDNSKNTLY

LQMNSLRAEDTAVYYCARGLGYNWFDPWGQGTLVTVSS mAb 246 VL (SEQ ID NO: 392)

EIVLTQSPDFQSVTPKEKVTITCRASQSIGSSLHWYQQKP

DQSPKLLIKYGSQSFSGVPSRFSGSGSGTDFTLTINSLEA

EDAATYYCHQSSSLPYTFGQGTKLEIK mAb 247 VH (SEQ ID NO: 393)

QEQLVESGGGVVQPGRSLRLSCAASGFIFSSYGMHWVRQA

PGKGLEWVAIIWYNGKKRDYADSVKGRFTISRDNSKNTLY

LQMNSLRAEDTAVYYCARGLGYNWFDPWGQGTLVTVSS

-continued mAb 247 VL (SEQ ID NO: 394)

EIVLTQSPDFQSVTPKDKVTITCRASQSIGSSLHWYQQKP

DQSPKLLIKYASQSFSGVPSRFSGSGSGTDFTLTINSLEA

EDAATYYCHQSSTLPYTFGQGTKLEIK mAb 248 VH (SEQ ID NO: 395)

QVKLVESGGGVVQPGRSLRLSCVASGFTFSGYGMHWVRQA

PGKGLEWVAIIYYDGKNKYYVDSVKGRFTISRDNSKNTLY

LQLNSLRAEDTAVYYCVRGPGYNWFDHWGQGTLVTVAS mAb 248 VL (SEQ ID NO: 396)

EIVLTQSPDFQSVTPKEKVTITCRASQSIGSSLHWYQQKP

DQSPKLLIKYASQSFSGVPSRFSGSGSGTDFTLTINSLEA

EDAATYYCHQSSSLPYTFGQGTKLEIK mAb 249 VH (SEQ ID NO: 397)

QEQLVESGGGVVQPGRSLRLSCAASGFTFRSYGMHWVRQA

PGKGLEWVAIIWYDGKNKYYADSVKGRFTISRDNSKNTLY

LQMNSLRAEDTAVYYCARGLGYNWFDPWGQGTLVTVSS mAb 249 VL (SEQ ID NO: 398)

EIVLTQSPDFQSVTPKEKVTITCRASQSIGSSLHWYQQKP

DQSPKLLIKYASQSFSGVPSRFSGSGSGTDFTLTINSLEA

EDAATYYCHQSSSLPYTFGQGTKLEIK mAb 250 VH (SEQ ID NO: 399)

QVQLVESGGGVVQPGRSLRLSCAASGFTFSTYGMHWVRQA

PGKGLEWVAVLWSDGRSKYYADSVQGRFTISRDNSKNTLF

LQMSSLRAEDTAVYYCAREPYYDFWSGYYTGYMDVWGKGT

TVTVSS mAb 250 VL (SEQ ID NO: 400)

DIQMTQSPSSLSASVGDRVTITCRASQGIRNDLGWYQQKP

GKAPKRLIYAASSLQGGVPSRFSGSGSGTEFTLTISSLQP

EDFATYYCLQHNSYPRTFGQGTKVEIK mAb 251 VH (SEQ ID NO: 401)

EVQILESGGGLVQPGGSLRLSCVASGFTFRSYVMSWVRRA

PGRGLEWVSGISASGGNTYYADSVKGRFTISRDNSKNTLF

LQMNGLRAEDTAVYYCAKLFSYYYYFMDVWGKGTTVTVSS mAb 251 VL (SEQ ID NO: 402)

SYELTQPLSVSVALGQTARITCGGNNIGSKDVHWYQQKPG

QAPVLVIYRDSNRPSGIPERFSGSNSGNTATLTISGAQAG

DEADYYCQVWDRRTAVFGGGTQLTAL mAb 252 VH (SEQ ID NO: 403)

EVQILESGGGLVQPGGSLRLSCVASGFTFRSYVMSWVRRA

PGRGLEWVSGISTSGGNTYYADSVKGRFTISRDNSKNTLF

LQMNGLRAEDTAVYYCAKLFSYYYYFMDVWGKGTTVTVSS

-continued mAb 252 VL (SEQ ID NO: 404)
SYELTQPLSVSVALGQTARITCGGNNIGSKDVHWYQQKPG
QAPVLVIYRDSNRPSGIPERFSGSNSGNTATLTISGAQAG
DEADYYCQVWDRRTAVFGGGTQLTAL mAb 253 VH (SEQ ID NO: 405)
QVTLKESGPVLVKPTETLTLTCTVSGFSLSNARMGVSWIR
QPPGKALEWLTLIFSIDEKSYSTSLKSRLTISQDTSKSQV
VLTVTNMDPVDTVTYFCERIETGPYYYYYYMDVWGKGTTV
TVSS mAb 253 VL (SEQ ID NO: 406)
QSVLTQPPSASGTPGQRVTISCSGSSSNIGSNTVNWYQQL
PGTAPKLLIYSNNQRPSGVPDRFSGSKSGTSASLAISGLQ
SEDEADYYCAAWDDSLNGPVFGGGTQLTAL mAb 254 VH (SEQ ID NO: 407)
QVTLKESGPVLVKPTETLTLTCTVSGFSLSNSRMGVSWLR
QPPGKALEWLIFIFSIDEKSYSTSLKSRLTISQDTSKSQV
VLTMTNMDPVDTVTYFCERIETGPYYYYYYMDVWGKGTTV
TVSS mAb 254 VL (SEQ ID NO: 408)
QSVLTQPPSASGTPGQRVTISCSGNSSNIGSNTVNWYQQL
PGTAPKLLIYSNNQRPSGVPDRFSGSKSGTSASLAISGLQ
SEDEADYYCAAWDDSLNGPVFGGGTQLTAL mAb 255 VH (SEQ ID NO: 409)
QVQVQQSGPGLVKPSQTLSLTCAISGDSVSSKYASWNWIR
QSPSRGLEWLGRTYYRSKWYNDFAVSVKSRITINADTSKN
QFSLHLSSVTPEDTAIYFCAREANGRGYFYYMDVWGKGTT
VTVSS mAb 255 VL (SEQ ID NO: 410)
EIVLTQSPDFQSVTPKEKVTITCRASQSIGSSLHWYQQKP
DQSPKLLIKYASQSISGVPSRFSGSGSGTVFTLTINSLEA
EDAAAYFCHQSSGSPHTFGGGTKVEIK mAb 256 VH (SEQ ID NO: 411)
QVQLQQSGPGLVKPSQTLSLTCAISGDSVSSNYASWNWIR
QSPSRGLEWLGRTYYRSKWYNDFAVSVKSRVTINADTSKN
QFSLHLSSVTPEDTAIYFCAREANGRGYFYYMDVWGKGTT
VTVSS mAb 256 VL (SEQ ID NO: 412)
EIVLTQSPDFQSVTPKEKVTITCRASQSIGSSLHWYQQKP
VQSPKLLIKYASQSISGVPSRFSGSGSGTVFTLTINSLEA
EDAAAYFCHQSSGSPHTFGGGTKVEIK -continued mAb 257 VH (SEQ ID NO: 413)
QVQLQQSGPGLVKPSQTLSLTCAISGDSVSSNYASWNWIR
QSPSRGLEWLGRTYYRSKWYNDFAVSVRSRVTINADTSKN
QFSLHLSSVTPEDTAIYFCAREANGRGYFYYMDVWGKGTT
VTVSS mAb 257 VL (SEQ ID NO: 414)
EIVLTQSPDFQSVTPKEKVTITCRASQSIGSSLHWYQQKP
DQSPKLLIKYASQSISGVPSRFSGSGSGTVFTLTINSLEA
EDAAAYFCHQSSGSPHTFGGGTKVEIK mAb 258 VH (SEQ ID NO: 415)
EVQLLESGGGLVQPGGSLRLSCAASGFTFSNYAMNWVRQA
PGKGLEWVSVISNSGGTRLYVDSVKGRFTISRDNSKNTLY
LQMSSLRAADTAVYYCAKDAAAALYYYYFYYMDVWGKGTT
VTVSS mAb 258 VL (SEQ ID NO: 416)
EIVLTQSPDFQSVTPKEKVTITCRASQSIGSSLHWYQQKP
DQSPKLLIKYASQSFSGVPSRFSGSGSGTDFTLTINSLEA
EDAATYYCHQSSSLPYTFGQGTKLEIK mAb 259 VH (SEQ ID NO: 417)
EVLLLESGGGLVQPGGSLRLSCAASGFTFRSSSMTWVRQA
PGKGLEWVSGIRGSGGRTYDAESVKGRFTISRDISKNTLY
LQMNSVRAEDTAEYYCAKLYDYYNDYMDVWGKGTTVTVSS mAb 259 VL (SEQ ID NO: 418)
SYELTQPLSVSVALGQTARITCGGNNIGSKNVHWYQQKPG
QAPVLVIYRDSNRPSGIPERFSGSNSGNTATLTISRAQAG
DEADYYCQVWDSSTAVFGGGTQLTAL mAb 260 VH (SEQ ID NO: 419)
EVQLLESGGGLVQPGGSLRLSCVASGFTFRSSSMAWVRQA
PGKGLEWVSGIRGSGGRTYDAESVKGRFIISRDTSKNTLY
LQMNSLRGEDTAEYFCAKLYDYYNDYMDVWGKGTTVTVSS mAb 260 VL (SEQ ID NO: 420)
SYELTQPLSVSVALGQTARITCGGNNIGSKNVHWYQQKPG
QAPVLVIYRDSNRPSGIPERFSGSNSGNTATLTISRAQAG
DEADYYCQVWDSSTAVFGGGTQLTAL mAb 261 VH (SEQ ID NO: 421)
EVQLLESGGGFMQPGGSLRLSCAVSGFTFRTSSMAWVRQA
PGKGLEWVSGIRGSGGRTYDAESVKGRFTISRDISKNTLY
LQMNNLRAEDTAEYYCAKLYDYYNDFMDVWGKGTTVIVSA -continued mAb 261 VL (SEQ ID NO: 422)
SYELTQPLSVSVALGQTARITCGGNNIGSKNVHWYQQKPG
QAPVLVIYRDSNRPSGIPERFSGSNSGNTATLTISRAQAG
DEADYYCQVWDSSTAVFGGGTQLTAL mAb 262 VH (SEQ ID NO: 423)
EVRLLESGGGLVQPGGSLRLSCAASGFTFRSSSMAWVRQD
PGKGLEWVTGIRGSGGRTYDADSVKGRFTISRDNSKNTLY
LQMNSLRAEDTAEYYCAKLYDYYNDYMDVWGKGTTVTVSS mAb 262 VL (SEQ ID NO: 424)
SYELTQPLSVSVALGQTARITCGGNNIGSKNVHWYQQKPG
QAPVLVIYRDSNRPSGIPERFSGSNSGNTATLTISRAQAG
DEADYYCQVWDSSTAVFGGGTQLTAL mAb 263 VH (SEQ ID NO: 425)
EVQLLESGGGLVQPGGSLRLSCTPSGITFNNYAMTWVRQA
PGKGLEWVSGISVSGGSTYYADSVMGRFTISRDSSKTLYL
QMNSLRAEDTAVYYCAKFHSHYYYYMDVWGKGTTVTVSS mAb 263 VL (SEQ ID NO: 426)
SYELTQPLSVSVALGQTARITCGGNNIGSKDVHWYQQKPG
QAPVLVIYRDSNRPSGIPERFSGSNSGNTATLTISRAQAG
DEADYYCQVWDRRTAVFGGGTQLTAL mAb 264 VH (SEQ ID NO: 427)
EVQLLESGGGLVQPGGSLRLSCVASGFTFRSSSMTWVRQA
PGKGLEWVSGIRGSGGRTYDAESVKGRFTISRDNSKNTLY
LQMNSLRAEDTAEYYCAKLYDYYNDYMDVWGKGTTVTVSS mAb 264 VL (SEQ ID NO: 428)
SYELTQPLSVSVALGQTARITCGGNNIGSKNVHWYQQKPG
QAPVLVIYRDSNRPSGIPERFSGSNSGNTATLTISRAQAG
DEADYYCQVWDSSTAVFGGGTQLTAL mAb 265 VH (SEQ ID NO: 429)
EVQLLESGGGLVQPGGSLRLSCAASGFTFRSSSMTWVRQA
PGKGLEWVSGIRGSGGRTYDAESVKGRFTISRDNSKNTLY
LQMNSLRAEDTAEYFCAKLYDYYNDYMDVWGKGTTVTVSS mAb 265 VL (SEQ ID NO: 430)
SYELTQPLSVSVALGQTARITCGGNNIGSKNVHWYQQKPG
QAPVLVIYRDSNRPSGIPERFSGSNSGNTATLTISRAQAG
DEADYYCQVWDSSTAVFGGGTQLTAL mAb 266 VH (SEQ ID NO: 431)
QVQLQQSGPGLVKPSQTLSLTCAISGDSVSSNYASWNWIR
QSPSRGLEWLGRTYYRSKWYIDFAVSVKSRLTINADTSKN
QFSLHLRSVTPEDTAIYFCAREANGRGYFYYMDVWGKGTT
VTVSS mAb 266 VL (SEQ ID NO: 432)
EIVLTQSPDFQSVTPKEKVTITCRASQSIGSSLHWYQQKP
DQSPKLLIKYASQSISGVPSRFSGSGSGTVFTLTINSLEA
EDAAAYFCHQSSGSPHTFGGGTKVEIK mAb 267 VH (SEQ ID NO: 433)
QVQLQQSGPGLVKPSQTLSLTCAISGDSISSNYASWNWIR
QSPSRGLEWLGRTYYRSKWYNDFAVSVKSRIIINPDTSRN
QFSLHLNSVTPEDTAIYYCAREANGRGYFYYMDVWGKGTT
VTVSS mAb 267 VL (SEQ ID NO: 434)
EIVLTQSPDFQSVTPKEKVTITCRASQSIGSSLHWYQQKP
DQSPKLLIKYASQSISGVPSRFSGRGSGTDFTLTINSLEA
EDAAAYFCHQSSGSPHTFGGGTKVEIK mAb 268 VH (SEQ ID NO: 435)
QVQLVQSGSEVKKPGASVKVSCKASGYTFTGYYIHWVRQA
PGQGLEWMGWINPNSGRTNYAQNFQGRVTMTRDTSITTAH
MELTRLTSDDTAVYYCARLELLVFDYWGQGTLVTVSS mAb 268 VL (SEQ ID NO: 436)
DIQMTQSPSSLSASVGDRVTITCRASQTIYNYLNWYQQKP
GKAPQVLIYAASNLQSGVPSIFSGSGSGTDFTLTITNLQP
EDFATYYCQQTYSIPFTFGGGTKVEIK mAb 269 VH (SEQ ID NO: 437)
QVQLVQSGSEVKKPGASVKVSCKASGYTFTGYYIHWVRQA
PGQGLEWMGWINPNSGRTNYAQNFQGRVTMTRDTSITTAH
MELTRLTSDDTAVYYCARLELLVFDYWGQGTLVTVSS mAb 269 VL (SEQ ID NO: 438)
ETVMTQSPATLSVSPGERVTLSCRASQSVSSYLAWYQQKP
GQTPRLLIYGASTRATGIPARFSGSGSGTEFTLTISSLQS
EDFAVYYCQQYNNWPPWTFGQGTKVEIK mAb 270 VH (SEQ ID NO: 439)
EIQLVESGGGLVQPGESLKLSCAGSGFTFSVSAMHWVRQA
SGKGLEWVGRIRNKANSYATAYDASVKGRFTLSRDDSRNT
AYLQMNSLKTEDTAVYYCSSYYYLSGTYYNYWGQGTLVTV
SS mAb 270 VL (SEQ ID NO: 440)
DIQMTQSPSSLSASVGDRVTITCRASQVIRNDLGWYQQKP
GKAPKRLIHSASSLQGGVPSRFSGSGSGTEFTLTISSLQP
EDFATYYCQQHNVNPCTFGQGTKLEIK -continued mAb 271 VH (SEQ ID NO: 441)

EIQLVESGGGLVQPGESLKLSCAGSGFTFSVSAMHWVRQA

SGKGLEWVGRIRNKANSYATAYAASVKGRFTLSRDDSKNT

AYLQMDSLKTEDTAVYYCSSYYYLSGTYYNYWGQGTLVTV

SS mAb 271 VL (SEQ ID NO: 442)

DIQMTQSPSSLSASVGDRVTITCRASQVIRNDLGWYQQKP

GKAPKRLIHSASSLQGGVPSRFSGSGSGTEFTLTISSLQP

EDFATYYCQQHNVNPCTFGQGTKLEIK mAb 272 VH (SEQ ID NO: 443)

EIQLVESGGGLVQPGESLKLSCAGSGFTFSVSAMHWVRQA

SGKGLEWVGRIRNKANSYATAYAASVKGRFTLSRDDSKNT

AYLQMNSLKTEDTAVYYCSSYYYLSGTYYNYWGQGTLVTV

SS mAb 272 VL (SEQ ID NO: 444)

DIQMTQSPSSLSASVGDRVTITCRASQVIRNDLGWYQQKP

GKAPKRLIHSASSLQGGVPSRFSGSGSGTEFTLTISSLQP

EDFATYYCQQHNVNPCTFGQGTKLEIK mAb 273 VH (SEQ ID NO: 445)

EVQLVESGGGLVQPGESLKLSCTASGFTFSVSAIHWVRQA

SGKGLEWVGRIRSKANSYATAYVASVKGRFTLSRDDSKNT

AYLQMNSLKTEDTAVYYCSSYYFVSGTYYNHWGQGTLVTV

SS mAb 273 VL (SEQ ID NO: 446)

DIQMTQSPSSLSASVGDRVTITCRASQGIRYDLGWYQQKP

GRAPKRLIHSVSSLQSGVPSRFSGSGSGTEFTLTISSLQP

EDFATYYCLQHNVNPCTFGQGTKLEIK mAb 274 VH (SEQ ID NO: 447)

QVQLVQSGAEVKKPGASVRVSCKASGYTFTGYYMHWVRQA

PGQGLEWMGWIYPNSGRTNYAQKFQGRVTMTRDTSISTAY

MELTRLISDDTAVYYCARLWDLYFDYWGQGTLVTVSS mAb 274 VL (SEQ ID NO: 448)

DIQLTQSPSFLSASVGDRVTITCRASQGISSYLAWYQQKP

GKAPKLLIYAASTLQSGVPSRFSGSGSGTEFTLTISSLQP

EDFATYYCQQLNSYPWTFGQGTKVEIK mAb 275 VH (SEQ ID NO: 449)

QVQLVQSGSELKKPGASVKVSCKASGYTFTKYAMNWVRQA

PGQGLEWMGWINTNTGNPTYAQGFTGRFVFSLDASVTTAY

LQISSLKAEDTAVYYCAREGHYDFWGGFYYFDYWGQGTLV

TVSS mAb 275 VL (SEQ ID NO: 450)

EIMLTQSPATLSLSPGERGTLSCRASQSVSSYLAWYQQKP

GQAPRLVIYDVSNRATGIPARFSGSGSGTDFILTIGSLEP

EDFAVYYCQQRSNWPLTFGGGTKVEIK mAb 276 VH (SEQ ID NO: 451)

EVQLVESGGGLVQPGGSLRLSCAASGIPFSTYSMNWVRQA

PGKGLEWVSYISGSSRTIYYADSVKGRFTISRDNAKKLLF

LQMNSLRDEDTAVYYCAREGDYYDSSGWAYWGQGTLVTVS

S mAb 276 VL (SEQ ID NO: 452)

DIQMTQSPSSLSASVGDRVTITCRASQNIYKYLNWYEQKP

GRAPKLLIYTTSNLQSGVPSRFSGSGSGTAFTLIISSLQP

EDFATYYCQQSYGSPYTFGQGTKLEIK mAb 277 VH (SEQ ID NO: 453)

QVQLVQSGAAMKKPGASVKVSCKASGSTFTGYYLHWVRQA

PGQGLEWMGWIYLNSGRTKYAQKFQGRVTMTRDTSINTAH

MELSRLTFDDTAVYYCVRVLELIFDYWGQGTLVTVSS mAb 277 VL (SEQ ID NO: 454)

DIQLTQSPSFLSASVGDRVTITCRASQGISSYLAWYQQKP

GKAPKLLIYAASTLQSGVPSRFSGSGSGTEFTLTISSLQP

EDFATYYCQQLNSYPWTFGQGTKVEIK mAb 278 VH (SEQ ID NO: 455)

QVQLVQSGAAMKKPGASVKVSCKASGSTFTGYYLHWVRQA

PGQGLEWMGWIYLNSGRTKYAQKFQGRVTMTRDTSISTAH

MELSRLTFDDTAVYYCARVLELIFDYWGQGTLVTVSS mAb 278 VL (SEQ ID NO: 456)

EIVLTQSPGTLSLSPGERATLSCRASQSVSSSYLAWYQQK

PGQAPRLLIYGASSRATGIPDRFSGSGSGTDFTLTISRLE

PEDFAVYYCQQYGSSPYTFGQGTKLEIK mAb 279 VH (SEQ ID NO: 457)

QVQLVQSGAEVKKPGASVKVSCKASGYTFTGYYMHWVRQA

PGQGLEWMGWIYPNSGRTNYAQKFQGRVTMTRDTSISTAY

MELTRLISDDTAVYYCARLWDLYFDYWGQGTLVTVSS mAb 279 VL (SEQ ID NO: 458)

DIQMTQSPSSLSASVGDRVTITCRASQSISSYLNWYQQKP

GKAPKLLIYAASSLQSGVPSRFSGSGSGTDFTLTISSLQP

EDFATYYCQQSYSTPFTFGPGTKVDIK mAb 280 VH (SEQ ID NO: 459)

QVQLVQSGAEVKKPGASVRVSCKASGYTFTGYYMHWVRQA

PGQGLEWMGWIYPNSGRTNYAQKFQGRVTMTRDTSISTAY

MELTRLISDDTAVYYCARLWDLYFDYWGQGTLVTVSS

-continued mAb 280 VL
(SEQ ID NO: 460)
DIVMTQSPDSLAVSLGERATINCKSSQSVLYSSNNKNYLA
WYQQKPGQPPKLLIYWASTRESGVPDRFSGSGSGTDFTLT
ISSLQAEDVAVYYCQQYYSTPYTFGQGTKLEIK mAb 281 VH
(SEQ ID NO: 461)
QVQLVQSGAEVKKPGASVRVSCKASGYTFTGYYMHWVRQA
PGQGLEWMGWIYPNSGRTNYAQKFQGRVTMTRDTSISTAY
MELTRLISDDTAVYYCARLWDLYFDYWGQGTLVTVSS mAb 281 VL
(SEQ ID NO: 462)
DIVMTQSPLSLPVTPGEPASISCRSSQSLLHYNGNNYLDW
YLQKPGQSPHLLIYLGSNRASGVPDRFSGSGSGTDFTLKI
IRVEAEDVGIYYCMQGLQSPYTFGQGTKLEIK mAb 282 VH
(SEQ ID NO: 463)
QVQLVQSETEVKKPGASVRVSCKASGYTFTGYYVHWVRQA
PGQGLEWMGWINPKSGRTSYSQKFQDRVTMTRDTSISTVY
MELSRLRSDDTAVYYCARILELIFDYWGQGTLVTVSS mAb 282 VL
(SEQ ID NO: 464)
EIVLTQSPDFQSVTPKEKVTITCRASQSIGSSLHWYQQKP
DQSPKLLIKYASQSFSGVPSRFSGSGSGTDFTLTINSLEA
EDAATYYCHQSSSLPTFGPGTKVDIK mAb 283 VH
(SEQ ID NO: 465)
QVHLVQSGAEVKKPGASVRVSCKASGYTFTGYYIHWLRQA
PGQGLEWLGWINPNSGGTNYSQKFRGRVTMTRDTSISTAY
MELSRLRSDDTAVYYCARDKVWEQQLVGGFDYWGQGTLVT
VSS mAb 283 VL
(SEQ ID NO: 466)
DIVMTQSPDSLAVSLGERATINCKSSQSVLYRSHKKNYLA
WYQQKPGQPPKLLIYWTSTRDSGVPDRFSGSGSGTDFTLT
ISSLQTEDVALYYCQQYYTTPFTFGPGTKVDIK mAb 284 VH
(SEQ ID NO: 467)
EVQLLESGGGLVQPGGSLRLSCAASGFTFSSYAMSWVRQA
PGKGLEWVSAISGSSGRTYYTDSVKGRFTISRDNSKNTLS
LQMNSLRAEDTAVYYCAKKYSYYYYYMDVWGKGTTVTVSS mAb 284 VL
(SEQ ID NO: 468)
SYELTQPLSVSVALGQTAKITCGGNNIGSKNVHWYQQKPG
QAPVLVIYRDSNRPSGIPERFSGSNSGNTATLTISRAQAG
DEADYYCQVWDSSTAVFGGGTQLTAL mAb 285 VH
(SEQ ID NO: 469)
EVQLLESGGGLGQPGGSLRLSCAASGFTFSNYAMSWVRQA
PGKGLEWVSVISGSGGDKNYADSVKGRFTISRDNSKNTLY
LQMNSLRAEDTAVYYCAKKYSYYYYYMDVWGKGTTVTVSS mAb 285 VL
(SEQ ID NO: 470)
SYELTQPLSVSVALGQTARITCGGNNIGSKDVHWYQQKPG
QAPVLVIYRDSNRPSGIPERFSGSNSGNTATLTISSAQAG
DEADYYCQVWDSRTAVFGGGTQLTAL mAb 286 VH
(SEQ ID NO: 471)
EVKLVESGGGVVRPGGSLRLSCAASGFTFDDYGMSWVRQA
PGKGLEWVSGISWNGGSTGYADSVKGRFTISRDNAKNSLY
LQMNSLRAEDTALYHCARDGVPVVKRRYYYYYMDVWGKGT
TVTVSS mAb 286 VL
(SEQ ID NO: 472)
EIVLTQSPDFQSVTPKEKVTITCRASQSIGSSLHWYQQKP
DQSPKLLIKYASQSFSGVPSRFSGRGSGTDFTLTINSLEA
EDAATYYCHQSGSLPQTFGQGTKVEIK mAb 287 VH
(SEQ ID NO: 473)
EVQLVESGGGVVRPGGSLRLSCAASGFTFDDYGMSWVRQA
PGKGLEWVSGISWNGGSTGYADSVKGRFTISRDNAKNSLY
LQMNSLRAEDTALYHCARDGVPVVKRRYYYYYMDVWGKGT
TVTVSS mAb 287 VL
(SEQ ID NO: 474)
EIVLTQSPDFQSVTPKEKVTITCRASQSIGSSLHWYQQKP
DQSPKLLIKYASQSFSGVPSRFSGSGSGTDFTLTINSLEA
EDAATYYCHQSASLPQTFGQGTKVEIK mAb 288 VH
(SEQ ID NO: 475)
EVQLLESGGNLGQPGGSLRLSCAVSGFTFSSYTMSWVRQA
PGKGLEWVSAISGSGGRTYYADSVKGRFTISRDNSKNTLY
LQMKSLRAEDTAVYYCAKKFSYYYYYMDVWGKGTTVTVSS mAb 288 VL
(SEQ ID NO: 476)
SYELTQPLSVSVALGQTARITCGGNNIGSKDVHWYQQKPG
QAPVLVIYRDSNRPSGIPERFSGSNSGNTATLTISSAQAG
DEADYYCQVWDSNTAVFGGGTQLTAL mAb 289 VH
(SEQ ID NO: 477)
EVQLLESGGGLVQPGGSRRLSCAASGFTFSSFAMSWVRQA
PGKGLEWVSVISSRGDNTNYADSVKGRFTISRDNSKNTLY
LQMNSLRAEDTAVYYCAKKYSYYYYYMDVWGKGTTVTVSS mAb 289 VL
(SEQ ID NO: 478)
SYELTQPLSVSVALGQTARITCGGNNIGSKNVHWHQQKPG
QAPVLVIYRESNRPSGIPERFSGSNSGNTATLTSSRAQAG
DEADYYCQVWDSSTAVFGGGTQLTAL mAb 290 VH
(SEQ ID NO: 479)
EVQLVESGGGVVRPGGSLRLSCAASGFTFDDYGMSWVRQA
PGKGLEWVSGISWNGGSTGYADSVKGRFTISRDNAKNSLY
LQMNSLRAEDTALYHCARDGVPVVKRRYYYYYMDVWGKGT
TVTVSS mAb 290 VL
(SEQ ID NO: 480)
EIVLTQSPDFQSVTPKEKITITCRASQSIGSSLHWYQQKP
DQSPKLLIKYASQSFSGVPSRFSGSGSGTDFTLTINSLEA
EDAATYYCHQSASLPQTFGQGTKVEIK mAb 291 VH
(SEQ ID NO: 481)
EVQLLESGGGLVQPGGSRRLSCAASGFTFSSYALSWVRQA
PGKGLEWVSVINTRGDSTSYADSVKGRFTISRDNSKNTLY
LQMNSLRAEDTAVYYCAKKYSYYYYYMDVWGKGTTVTVSS mAb 291 VL
(SEQ ID NO: 482)
SYELTQPLSVSVALGQTARITCGGNNIGSKDVHWYQQKPG
QAPVLVIYRDSNRPSGIPERFSGSNSGNTATLTISRAQAG
DEADYYCQVWDSRTAVFGGGTQLTAL mAb 292 VH
(SEQ ID NO: 483)
EVQLLESGGGLVQPGGSRRLSCAASGFTFSTYAMSWVRQA
PGKGLEWVSVINGRGDDTNYADSVKGRFTISRDNSKNILF
LQMNSLRAEDTAVYYCAKKYSYYYYYMDVWGKGTTVTVSS mAb 292 VL
(SEQ ID NO: 484)
SYELTQPLSVSVALGQTARITCGGNNIGSKDVHWYQQKPG
QAPVLVIYRDSNRPSGIPERFSGSNSGNTATLTISRAQAG
DEADYYCQVWDSRTAVFGGGTQLTAL mAb 293 VH
(SEQ ID NO: 485)
EVQLLESGGDLVQPGGSLRLSCAASGFTFSRNAVSWVRQA
PGRGLEWVSTISGRGDKTNYVDSVKGRFTISRDNSKNTLY
LQMNSLRAEDTAVYYCTKMFSYYYYYMDVWGKGTTVTVSS mAb 293 VL
(SEQ ID NO: 486)
SYELTQPLSVSVALGQTARITCGGNNIGSKDVHWYQQKPG
QAPVLVIYRDSNRPSGIPERFSGSNSGNTATLTISRAQAG
DEADYYCQVWDSSTAVFGGGTQLTAL mAb 294 VH
(SEQ ID NO: 487)
EVQLLESGGGLVQPGGSLRLSCAASGFTFSSSVMSWVRQG
PGKGLEWVSAIRGSGVYTYYADSVKGRFTISRDNSKNTLY
LQMNSLRAEDTAVYYCAKKYSYYYYYMDVWGKGTTVTVSS mAb 294 VL
(SEQ ID NO: 488)
PYELTQPLSVSVALGQTARITCGGNNIGSKDVHWYQQKPG
QAPVLVIYRDSNRPSGIPERFSGSNSGNTATLTISRAQAG
DEADYYCQVWDSSTAVFGGGTQLTAL mAb 295 VH
(SEQ ID NO: 489)
EVQLLESGGGLVQPGGSLRLSCAASGITFSSYAMSWVRQA
PGKGLEWVSTISGNGGTLYYTDSVKGRFTISRDNSKNTLY
LQMNSLRAEDTAVYYCAKKYSYYYYYMDVWGKGTTVTVSS mAb 295 VL
(SEQ ID NO: 490)
SYELTQPLSVSVALGQTARITCGGNNIGSKNVHWYQQKPG
QAPVLVIYRDSNRPSGIPERFSGSNSGNTATLTISRAQAG
DEADYYCQVWDSSTAVFGGGTQLTAL mAb 296 VH
(SEQ ID NO: 491)
EVQLLESGGGLVQPGGSLRLSCAASGFTFSSYAMSWVRQA
PGKGLEWVSAISGSGGTTYYTDSVKGRFTISRDNSKNTLY
LQMNSLRAEDTAVYYCAKKYSYYYYYMDVWGKGTTVTVSS mAb 296 VL
(SEQ ID NO: 492)
SYELTQPLSVSVALGQTARITCGGNNIGSKNVHWYQQKPG
QAPVLVIYRDSNRPSGIPERFSGSNSGNTATLTISRAQAG
DEADYYCQVWDSSTAVFGGGTQLTAL mAb 297 VH
(SEQ ID NO: 493)
EVQLLESGGGLVQPGGSLRLSCAASGFTFSSYAMNWVRQA
PGKGLEWVSIISGGRRDDITYYAASVKGRFTISRDNSKNT
LYLQMNSLRAEDTAVYYCAKMYNYYYYYIDVWGKGTTVTV
SS mAb 297 VL
(SEQ ID NO: 494)
SYELTQPLSVSVALGQTAKITCGGNNIGSKDVHWYQQKPG
QAPVLVIYRDSNRPSGIPERFSGSNSGNTATLTISRAQAG
DEADYYCQVWDSNTAVFGGGTQLTAL mAb 298 VH
(SEQ ID NO: 495)
EGQLLESGGGLVQPGGSLRLSCAASGFTFSRYAMSWIRQA
PGKGLEWVSVINGSGGDKNYADSVKGRFTISRDNSKNSLY
LLMNGLRVEDTAIYFCAKKFSYYYYYMDVWGKGTTVTVSS mAb 298 VL
(SEQ ID NO: 496)
SYELTQPLSVSVALGQTARITCGGNNIGGKDVHWYQQKPG
QAPVLVIYRDSNRPSGIPERFSGSNSGNTATLTISRAQAG
DEADYYCQVWDSRTAVFGGGTQLTAL mAb 299 VH
(SEQ ID NO: 497)
EVQLLESGGGLVQPGGSRRLSCAASGFTFRSYAMSWVRQA
PGKGLEWVSVISIRGDSTSYADSVKGRFTISRDNSKNTLY
LQMNSLRAEDTAVYYCAKKYSYYYYYMDVWGKGTTVTVSS mAb 299 VL
(SEQ ID NO: 498)
SYELTQPLSVSVALGQTARITCGGNNIGSKDVHWYQQKPG
QAPVLVIYRDSNRPSGIPERFSGSNSGNTATLTISRAQAG
DEADYYCQVWDSRTAVFGGGTQLTAL mAb 300 VH
(SEQ ID NO: 499)
EVQLLESGGGLVQPGGSLRLSCAASGFTFSRYAMSWVRQA
PGRGLEWVSTISGSGGRTYYVDSVKGRFTISRDNSKNTLY
LQMNSLRAEDTAVYYCAKMFSYYYYYMDVWGKGTTVTVSS mAb 300 VL
(SEQ ID NO: 500)
EIVMTQSPATLSLSPGKRATLSCRASQSVSTTYLSWYLQK
PGQAPRLLIYGASTRATGIPARFSGSGSGTDFTLTISSLQ
PEDFAVYYCQQDYNLPPYTFGQGTKLEIK mAb 301 VH
(SEQ ID NO: 501)
EVQLLESGGGLVQPGGSRRLSCAASGFTFSSYAMSWVRQA
PGKGLEWVSVISGRGDNTNYADSVKGRFTISRENSKNMLY
LQMNSLRAEDTAVYYCAKKYSYYYYYMDVWGKGTTVTVSS mAb 301 VL
(SEQ ID NO: 502)
SYELTQPLSVSVALGQTARITCGGNNIGSKDVHWYQQKPG
QAPVLVIYRDSNRPSGIPERFSGSNSGNTATLTISRAQAG
DEADYYCQVWDSRTAVFGGGTQLTAL mAb 302 VH
(SEQ ID NO: 503)
EGQLLESGGGLVQPGGSLRLSCAASGFTFSRYAMSWIRQA
PGKGLEWVSVINGSGGDKNYADSVRGRFTISRDNSKNSLY
LLMNGLRVEDTAIYFCAKKFSYYYYYMDVWGKGTTVTVSS mAb 302 VL
(SEQ ID NO: 504)
SYELTQPLSVSVALGQTARITCGGNNIGGKDVHWYQQKPG
QAPVLVIYRDSNRPSGIPERFSGSNSGNTATLTISRAQAG
DEADYYCQVWDSRTAVFGGGTQLTAL mAb 303 VH
(SEQ ID NO: 505)
EVHLLESGGGLVQPGGSLRLSCAASGFTFSSYAMNWVRQA
PGKGLEWISIISGGRRSGITYYAASVKGRFTISRDNSKNT

LDLQMNSLRAEDTAVYYCAKMYNYYYYYIDVWGKGTTVTV
SS mAb 303 VL
(SEQ ID NO: 506)
SYELTQPLSVSVALGQTARITCGGNNIGSKDVHWYQQKPG
QAPVLVIYRDSNRPSGIPERFSGSNSGNTATLTISRAQAG
DEADYYCQVWDSNTAVFGGGTQLTAL mAb 304 VH
(SEQ ID NO: 507)
EVQLLESGGGLVQPGGSRRLSCAASGFTFSSYAMSWVRQA
PGKGLEWVSVISGRGDNTNYADSVKGRFTISRENSKNILY
LQMNSLRAEDTAVYYCAKKYSYYYYYMDVWGKGTTVTVSS mAb 304 VL
(SEQ ID NO: 508)
SYELTQPLSVSVALGQTARITCGGNNIGSKDVHWYQQKPG
QAPVLVIYRDSNRPSGIPERFSGSNSGNTATLTISRAQAG
DEADYYCQVWDSRTAVFGGGTQLTAL mAb 305 VH
(SEQ ID NO: 509)
EVQLLESGGGLVQPGGSLRLSCAASGFSFSSFALSWVRQA
PGKGLEWVSVISGNGGNKNYADSVKGRFTISRDNSKNTLY
LQMNSLRAEDTAVYYCAKKYSYYYYYMDVWGKGTTVTVSS mAb 305 VL
(SEQ ID NO: 510)
SYELTQPLSVSVALGQTARITCGGNNIGGKDVHWYQQKPG
QAPVLVIYRDSNRPSGIPERFSGSNSGNTATLTISRAQAG
DEADYYCQVWDSRAAVFGGGTQLTAL mAb 306 VH
(SEQ ID NO: 511)
EVQLLESGGGLVQPGGSLRLSCAASGFTFNSYAMSWVRQA
PGRGLEWVSAISGRKSTTYYADSVKGRFTISRDNSKNTLY
LQMNSLRAEDTAVYYCAKLWNYYYYYMDVWGKGTTVTVSS mAb 306 VL
(SEQ ID NO: 512)
SYELTQPLSVSVALGQTARITCGGNNIGSKDVHWYQQKPG
QAPVLVIYRDSNRPSGIPERFSGSNSGNTATLTISRAQAG
DEADYYCQVWDSSTAVFGGGTQLTAL mAb 307 VH
(SEQ ID NO: 513)
EVHLLESGGGMVQPGGSRRLSCAASGFSFRNSAMSWVRQA
PGKGLEWVSVIDGRGTTSNYADSVKGRFTISRDNSKNTLY
LQMNSLRAEDTAVYYCAKKYSYYYYYMDVWGKGTTVTVSS mAb 307 VL
(SEQ ID NO: 514)
SYELTQPLSVSVALGQTARITCGGNNIGSKDVHWYQQKPG
QAPVLVIYRDSNRPSGIPERFSGSNSGNTATLTISRAQAG
DEADYYCQVWDSRTAVFGGGTHLTAL

-continued mAb 308 VH
(SEQ ID NO: 515)
EVQLLESGGGSVQPGGSLRLSCAASGFTFSSYAMNWVRQAPGKGLEWISIISGGRRTGITYYAASVKGRFTISRDNSKNTLYLQMNSLRAEDTAVYYCAKMYNYYYYYIDVWGKGTTVTVSS mAb 308 VL
(SEQ ID NO: 516)
SYELTQPLSVSVALGQTARITCGGNNIGSKDVHWYQQKPGQAPVLVIYRDSNRPSGIPERFSGSNSGNTATLTISRAQAGDEADYYCQVWDSNTAVFGGGTQLTAL mAb 309 VH
(SEQ ID NO: 517)
ELQLLESGGGLVQPGGSLRLSCAASGFTFSSYAMSWVRQAPGKGLEWVSVISGNGGNKNHADSVKGRFTISRDNSKNTLYLQMNSLRAEDTAVYYCAKKYSYYYYYMDVWGKGTTVTVSS mAb 309 VL
(SEQ ID NO: 518)
SYELTQPLSVSVALGQTARITCGGNNIGSKDVHWYQQKPGQAPVLVIYRDSNRPSGIPERFSGSNSGNTATLTISRAQAGDEADYYCQVWDSRTAVFGGGTQLTAL mAb 310 VH
(SEQ ID NO: 519)
QVQLVESGGGVVQPGRSLRLSCAASGFTFRSYGMHWVRQAPGKGLEWVTIIWYDGSKKYYADSVRGRFTISRDNSKNMLYLQMNSLRAEDTAVYYCASQEFNWNDGGFYYMDVWGKGTTVTVSS mAb 310 VL
(SEQ ID NO: 520)
DIQLTQSPSFLSASVGDRVTITCRASQDISSYLHWCQQKPGKAPKLLIYGASTLQSGVPSRFSGSGSGKEFTLTISSLQPEDFATYYCQQLDNYPPTFGGGTKVEIK mAb 311 VH
(SEQ ID NO: 521)
EVQLLESGGGLVQPGGSRRLSCAASGFTFSSYAMSWVRQAPGKGLEWVSVINTRGDITSYADSVKGRFTISRDNSKNTLYLQMNSLRAEDTAVYYCAKKYSYYYYYMDVWGKGTTVTVSS mAb 311 VL
(SEQ ID NO: 522)
SYELTQPLSVSVALGQTARITCGGNNIGSKNVHWHQQKPGQAPVLVIYRESNRPSGIPERFSGSNSGNTATLTSSRAQAGDEADYYCQVWDSSTAVFGGGTQLTAL mAb 312 VH
(SEQ ID NO: 523)
EGQLLESGGGLVQPGGSLRLSCAASGFTFSRYAMSWIRQAPGKGLEWVSVINGSGGDKNYADSVKGRFTISRDNSKNSLYLLMNGLRVEDTAIYFCAKKFSYYYYYMDVWGKGTSVTVSS mAb 312 VL
(SEQ ID NO: 524)
SYELTQPLSVSVALGQTARITCGGNNIGSKNVHWHQQKPGQAPVLVIYRESNRPSGIPGRFSGSNSGNTATLTSSRAQAGDEADYYCQVWDSSTAVFGGGTQLTAL mAb 313 VH
(SEQ ID NO: 525)
EVQLLESGGGLVQPGGSLRLSCAASGFTFSSYAMSWVRQAPGKGLEWVSAITGSGRTTYFVDSVKGRFTISRDNSKNTLYLQMNSLRAEDTAVYYCAKKFSYYYYYMDVWGKGTTVTVSS mAb 313 VL
(SEQ ID NO: 526)
SYELTQPLSVSVALGQTARITCGGNNIGSKDVHWYQQKPGQAPVLVIYRDSNRPSGIPERFSGSNSGNTATLTISRAQAGDEADYYCQVWDRKIAVFGGGTQLTAL mAb 314 VH
(SEQ ID NO: 527)
EVQLLESGGGLVQPGGSLRLSCAASGFTFSSYAMSWVRQAPGKGLEWVSVISGSGGNKNYADSVKGRFTISRDNSKNTLYLQMNSLRAEDTAVYYCAKKFSYYYYYMDVWGKGTTVTVSS mAb 314 VL
(SEQ ID NO: 528)
SYELTQPLSVSVALGQTARITCGGNNIGSKDVHWYQQKPGQAPVLVIYRDSNRPSGIPERFSGSNSGNTATLTISRAQAGDEADYYCQVWDSRTAVFGGGTQLTAL mAb 315 VH
(SEQ ID NO: 529)
EVQLLESGGGLVQPGGSRRLSCAASGFTFSSYAMSWVRQAPGKGLEWVSVINTRGDSTSYADSVKGRFTISRDNSKNTLYLQMNSLRAEDTAVYYCAKKYSYYYYYMDVWGKGTTVTVSS mAb 315 VL
(SEQ ID NO: 530)
SYELTQPLSVSVALGQTARITCGGNNIGSKDVHWYQQKPGQAPVLVIYRDSNRPSGIPERFSGSNSGNTATLTISRAQAGDEADYYCQVWDSRTAVFGGGTQLTAL mAb 316 VH
(SEQ ID NO: 531)
EVQLLESGGGLVQPGGSRRLSCAASGFTFRTYAMSWVRQAPGKGLEWVSVINGRGDDTNYADSVKGRFTISRDNSKNILFLQMNSLRAEDTAVYYCAKKYSYYYYYMDVWGKGTTVTVSS mAb 316 VL
(SEQ ID NO: 532)
SYELTQPLSVSVALGQTARITCGGNNIGSKDVHWYQQKPGQAPVLVIYRDSNRPSGIPERFSGSNSGNTATLTISRAQAGDEADYYCQVWDSRTAVFGGGTQLTAL mAb 317 VH
(SEQ ID NO: 533)
EVQLLESGGGLVQPGGSLRLSCAASGFTFSSFAMSWVRQAPGKGLEWVSVISGNGDKKNYADSVKGRFTISRDNSKNTLYLQMNSLRAEDTAVYYCAKKYSYYYYYMDVWGKGTTVTVSS -continued mAb 317 VL (SEQ ID NO: 534)

SYELTQPLSVSVALGQTARITCGGNNIGSKDVHWYQQKPG

QAPVLVIYRDSNRPSGIPERFSGSNSGNTATLTISRAQAG

DEADYYCQVWDSRTAVFGGGTQLTAL mAb 318 VH (SEQ ID NO: 535)

EGQLLESGGGLVQPGGSLRLSCAASGFTFSRYAMSWIRQA

PGKGLEWVSVIDGSGGDKNYADSVKGRFTISRDNSKNSLY

LLMNGLRVEDTAIYFCAKKFSYYYYYMDVWGKGTSVTVSS mAb 318 VL (SEQ ID NO: 536)

SYELTQPLSVSVALGQTARITCGGNNIGGKDVHWYQQKPG

QAPVLVIYRDSNRPSGIPERFSGSNSGNTATLTISRAQAG

DEADYYCQVWDSRTAVFGGGTQLTAL mAb 319 VH (SEQ ID NO: 537)

EVQLLESGGGLLQPGGSRRLSCAATEFTFRSYAMSWVRQS

PGKGLEWVSVISGRGDNTYYADSVKGRFTISRDNSKNTLY

LQMNSLRAEDTAVYYCAKMYSYYYYYMDVWGKGTTVTVSS mAb 319 VL (SEQ ID NO: 538)

SYELTQPLSVSVALGQTARITCGGNNIGSKNVHWHQQKPG

QAPVLVIYRESNRPSGIPERFSGSNSGNTATLTSSRAQAG

DEADYYCQVWDSSTAVFGGGTQLTAL mAb 320 VH (SEQ ID NO: 539)

QVQLVESGGGVVQPGRSLRLSCAASGFTFRSYGMHWVRQA

PGKGLEWVAIIWYDGSKKYYADSVKGRFTISRDNSKNILY

LQMNSLRAEDTAVYYCARQEFNWNDGGYYYMDVWGKGTTV

TVSS mAb 320 VL (SEQ ID NO: 540)

DIQLTQSPSFLSASVGDRVTITCRASQGISSYLDWCQQKP

GKAPKLLIYAASTLQSGVPSRFSGSGSGTEFTLTISSLQP

EDFATYYCQQLDNYPPTFGGGTKVEIK mAb 321 VH (SEQ ID NO: 541)

QVQLVESGGGVVQPGRSLRLSCVASGFTFRSFGMHWVRQA

PGKGLEWVVVISNDGSHKYYVESVKGRFTISRDNSKNTLY

LQMNSLRPEDTAVYYCARRDYYGSGMDVWGKGTTVTVSS mAb 321 VL (SEQ ID NO: 542)

SYELTQPPSVSVSPGQTARITCSGDALPKKYAYWYQQKSG

QAPVLVIYEDRKRPSGIPERFSGSSSGTMATLTISGAQVE

DEADYYCYSTDSSGNHAVFGGGTQLTAL

-continued mAb 322 VH (SEQ ID NO: 543)

QVQLVESGGGVVQPGRSLRLSCVASGFTFRSYGMHWVRQA

PGKGLEWVVVISNDGSHKYYVESVKGRFTISRDNSKNTLY

LQMNSLRAEDTAVYYCARRDYYGSGMDVWGKGTTVTVSS mAb 322 VL (SEQ ID NO: 544)

SYELTQPPSVSVSPGQTARITCSGDALPKKYAYWYQQKSG

QAPVLVIYEDRKRPSGIPERFSGSSSGTMATLTISGAQVE

DEADYYCYSTDSSGNHAVFGGGTQLTAL mAb 323 VH (SEQ ID NO: 545)

QVQVVQSGAEVKNPGASVKVSCKASGYTFTGYYMHWVRQA

PGQGLEWMGWIYPNSGRTNYAQKFQGRVTMTRDTSISTAY

MELSRLRSDDTAVYYCARLEQLVFDYWGQGTLVTVSS mAb 323 VL (SEQ ID NO: 546)

EIVLTQSPGTLSLSPGERATLSCRASQSVSSSYLAWYQQK

PGQGPRLLIYGASSRATGIPDRFSGSGSGTDFTLTISRLE

PEDFAVYYCQQYGSSPITFGQGTRLEIK mAb 324 VH (SEQ ID NO: 547)

QVQVVQSGAEVKKPGASVKVSCKTSGYTFTDYYIHWVRQA

PGQGLEWMGWIYPKSGRTDNAQNFKGRVAMTRDTSINTAY

LELNRLRSDDTAIYYCARLEELVFDYWGQGTLVTVSS mAb 324 VL (SEQ ID NO: 548)

DIQMTQSPSSVSASVGDRVTITCRASQVISRWLAWYQLKP

GKAPKLLIYEASSLQSWVPSRFSGSGSGTDFTLTISSLQP

EDFATYYCQQANSFPWTFGQGTKVEIK mAb 325 VH (SEQ ID NO: 549)

QVQVVQSGAEVKKPGASVKVSCKTSGYTFTDQYIHWVRQA

PGQGLEWMGWIYPKSGRTDNAQKFKGRVAMTRDTSINTAY

MELSSLRSDDTATYYCARLEELVFDYWGQGTLVTVSS mAb 325 VL (SEQ ID NO: 550)

DIQMTQSPSTLSASVGDRVTITCRASQSISSWLAWYQQKP

GKAPKLLIYKASSLESGVPSRFSGSGSGTEFTLTISSLQP

DDFATYYCQQYNSYSTFGQGTKLEIK

Bispecific Antibodies (bsAbs)

Those skilled in the art will also appreciate that anti-CD3 antibodies disclosed herein may be monovalent or multivalent (e.g., bivalent, trivalent, etc.). As used herein, the term "valency" refers to the number of potential binding sites associated with an antibody. Each target binding site specifically binds one target molecule or specific position or locus on a target molecule. When an antibody of the instant invention comprises more than one target binding site (multivalent), each target binding site may specifically bind the same or different molecules (e.g., may bind to different ligands or different antigens, or different epitopes or positions on the same antigen). In some embodiments, anti-CD3 antibodies disclosed herein will be multivalent in that they comprise more than one binding site and the different binding sites specifically associate with more than a single position or epitope. In such cases, a first epitope may be on a CD3 molecule, while a second, different epitope may be present on, e.g., a hyperproliferative disorder or autoimmune disorder-related antigen (e.g., EGFR).

Bispecific antibodies generally fall into two categories: those that are IgG-like (in that they comprise a constant region) and those that are not. Traditional production of full-length bispecific antibodies is based on the co-expression of two immunoglobulin heavy chain-light chain pairs, where the two chains have different specificities. Examples of such antibodies possessing a CD3-targeting domain include catumaxomab (REMOVAB®) and mosunetuzumab-axgb (LUNSUMIO™). Other more sophisticated compatible multispecific constructs and methods of their fabrication are also known in the art. Examples of such antibodies possessing a CD3-targeting domain include the bispecific T-cell engager (BiTE®) blinatumomab (BLINCYTO®) and the IMMTAC® fusion protein tebentafusp-tebn (KIMMTRAK®) A non-exhaustive list of both types of bispecific antibodies, as well as a list of those currently undergoing clinical trials for the treatment of various hyperproliferative disorders is described in Wei et al., "Current landscape and future directions of bispecific antibodies in cancer immunotherapy", Front. Immunol., Vol. 13 (2022).

Bispecific antibodies have also been developed and evaluated for use in treating a range of autoimmune disorders depleting T or B cells, inhibiting T cell differentiation or activation, or the neutralizing proinflammatory cytokines. Examples of such antibodies possessing a CD3-targeting domain include TNB-383B, an anti-CD3× anti BCMA bispecific being investigated for treating systemic lupus erythematosus (SLE), and ONO-4685, an anti-CD3× anti-PD1 antibody being investigated for the treatment of psoriasis. See, e.g., Zhao, Q. "Bispecific Antibodies for Autoimmune and Inflammatory Diseases: Clinical Progress to Date." *BioDrugs* 34, 111-119 (2020).

In some embodiments, the antibodies in accordance with the inventions disclosed herein are bispecific in nature, i.e., an antibody that comprises a first binding arm and a second binding arm, wherein the first binding arm binds to at least one CD3 molecule and further comprises: (a) a heavy chain having an amino acid sequence selected from the group consisting of SEQ ID NOs: 551, 553, 555, 557, 561, 563, 565, 567, 569, 571, 573, 575, 577, 579, 581, 583, 585, and 587; and (b) a light chain having an amino acid sequence selected from the group consisting of SEQ ID NOs: 552, 554, 556, 558, 157, 564, 566, 568, 570, 572, 574, 576, 578, 580, 582, 584, 586, and 588; and wherein the second binding arm binds to at least one EGFR molecule and further comprises: (c) a heavy chain having an amino acid sequence selected from the group consisting of SEQ ID NOs: 589 and 591; and (d) a light chain having an amino acid sequence selected from the group consisting of SEQ ID NOs: 590 and 592.

The amino acid sequences of bispecific antibodies described in the preceding paragraph are provided below:

```
Bispecific Antibody Internal Reference Identifier GOMP001_bsAb_007

Full-length Heavy Chain 1 (anti-EGFR; SEQ ID NO: 589)
QVQLVQSGAEVKKPGASVKVSCKASGYTFTSHWMHWVRKAPGQGLEWIGEFNPSNGRTNYNEEFKSKATMTVDTSTNTAYMEL
SSLRSEDTAVYYCASRDYDYDGRYFDYWGQGTLVTVSSASTKGPSVFPLAPSSKSTSGGTAALGCLVADYFPEPVTVSWNSGALTSG
VHTFPAVLQSSGLYSLSSVVTVPSSSLGTQTYICNVNHKPSNTKVDEKVEPKSCDKTHTCPPCPAPEAAGGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISKAKG
QPREPQVYTLPPSREEMTDNQVSLTCLVKGFYPSDIAVEWESNGQPENNYKTTPPVLMSDGSFFLASKLTVDKSRWQQGNVFSCS
VMHEALHNHYTQKSLSLSPG

Full-length Light Chain 1 (anti-EGFR; SEQ ID NO: 590)
RIQMTQSPSSLSASVGDRVTITCSASSSVTYMYWYQDKPGKAPKLLIYDTSNLASGVPSRFSGSGSGTDYTFTISSLQPEDIATYYCQQ
WSSHIFTFGQGTKVEIKRTVAAPSVFIFPPSDKQLKSGTARVVCLLNNFYPREAKVQWKVDNALQSGNSQESVTEQDSKDSTYSLSST
LTLSKADYEKHKVYACEVTHQGLSSPVTKSFNRGEC

Full-length Heavy Chain 2 (anti-CD3; SEQ ID NO: 551)
QAQLVQSGSELKKPGASVKVSCKASGYTFTKHSMNWVRYAPGQGLEWMGWINTNTGNPTYAQRFTGRFVFSLDTSVTTAYLQIS
SLKAEDTAVYYCAREGDYDFWSGFFNFDYWGRGTLVTVSSASTKGPSVFPLAPSSKSTSGGTAALGCLVKDYFPEPVTVSWNSGALT
SGVHTFPAVLQSSGLYSLSSVVTVPSSSLGTQTYICNVNHKPSNTKVDKKVEPKSCDKTHTCPPCPAPEAAGGPSVFLFPPKPKDTLMI
SRTPEVTCVVVDVSHEDPEVKFNWYVDGVEVHNAKTKPREEQYNSTYRVVSVLTVLHQDWLNGKEYKCKVSNKALPAPIEKTISKA
KGQPRRPRVYTLPPSREEMTKNQVSLVCLVKGFYPSDIAVEWESNGQPENNYKTTPPVLDSDGSFFLYSVLTVDKSRWQQGNVFSC
SVMHEALHNHYTQKSLSLSPG

Full-length Light Chain 2 (anti-CD3; SEQ ID NO: 552)
DIQMTQSPSSLSASVGDRVTITCRASQGIRNDLGWYQRKPGDAPKRLIYAASSLQSGVPSRFSGSGSGAEFTLTISSLQPEDFATYYCL
QHNSYPRTFGQGTKVEIKRTVAAPSVFIFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC

Bispecific Antibody Internal Reference Identifier GOMP001_bsAb_008

Full-length Heavy Chain 1 (anti-CD3; SEQ ID NO: 551)
QAQLVQSGSELKKPGASVKVSCKASGYTFTKHSMNWVRKAPGQGLEWMGWINTNTGNPTYAQEFTGRFVFSLDTSVTTAYLQISS
LKAEDTAVYYCAREGDYDFWSGFFNFDYWGQGTLVTVSSASTKGPSVFPLAPSSKSTSGGTAALGCLVADYFPEPVTVSWNSGALT
SGVHTFPAVLQSSGLYSLSSVVTVPSSSLGTQTYICNVNHKPSNTKVDEKVEPKSCDKTHTCPPCPAPEAAGGPSVFLFPPKPKDTLMI
SRTPEVTCVVVDVSHEDPEVKFNWYVDGVEVHNAKTKPREEQYNSTYRVVSVLTVLHQDWLNGKEYKCKVSNKALPAPIEKTISKA
KGQPREPQVYTLPPSREEMTDNQVSLTCLVKGFYPSDIAVEWESNGQPENNYKTTPPVLMSDGSFFLASKLTVDKSRWQQGNVFS
CSVMHEALHNHYTQKSLSLSPG

Full-length Light Chain 1 (anti-CD3; SEQ ID NO: 552)
RIQMTQSPSSLSASVGDRVTITCRASQGIRNDLGWYQDKPGKAPKRLIYAASSLQSGVPSRFSGSGSGAEFTLTISSLQPEDFATYYCL
QHNSYPRTFGQGTKVEIKRTVAAPSVFIFPPSDKQLKSGTARVVCLLNNFYPREAKVQWKVDNALQSGNSQESVTEQDSKDSTYSLS
STLTLSKADYEKHKVYACEVTHQGLSSPVTKSFNRGEC
```

-continued

Full-length Heavy Chain 2 (anti-EGFR; SEQ ID NO: 591)
QVQLVQSGAEVKKPGASVKVSCKASGYTFTSHWMHWVRYAPGQGLEWIGEFNPSNGRTNYNEKFKSKATMTVDTSTNTAYMEL
SSLRSEDTAVYYCASRDYDYDGRYFDYWGRGTLVTVSSASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKVEPKSCDKTHTCPPCPAPEAAGGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISKAKG
QPRRPRVYTLPPSREEMTKNQVSLVCLVKGFYPSDIAVEWESNGQPENNYKTTPPVLDSDGSFFLYSVLTVDKSRWQQGNVFSCSV
MHEALHNHYTQKSLSLSPG Full-length Light Chain 2 (ant-EGFR; SEQ ID NO: 592)
DIQMTQSPSSLSASVGDRVTITCSASSSVTYMYWYQRKPGDAPKLLIYDTSNLASGVPSRFSGSGSGTDYTFTISSLQPEDIATYYCQQ
WSSHIFTFGQGTKVEIKRTVAAPSVFIFPPSDEQLKSGTASVVCLLNNFYPREAKVQWKVDNALQSGNSQESVTEQDSKDSTYSLSST
LTLSKADYEKHKVYACEVTHQGLSSPVTKSFNRGEC Bispecific Antibody Internal Reference Identifier GOMP001_bsAb_011

Full-length Heavy Chain 1 (anti-EGFR; SEQ ID NO: 589)
QVQLVQSGAEVKKPGASVKVSCKASGYTFTSHWMHWVRKAPGQGLEWIGEFNPSNGRTNYNEEFKSKATMTVDTSTNTAYMEL
SSLRSEDTAVYYCASRDYDYDGRYFDYWGQGTLVTVSSASTKGPSVFPLAPSSKSTSGGTAALGCLVADYFPEPVTVSWNSGALTSG
VHTFPAVLQSSGLYSLSSVVTVPSSSLGTQTYICNVNHKPSNTKVDEKVEPKSCDKTHTCPPCPAPEAAGGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISKAKG
QPREPQVYTLPPSREEMTDNQVSLTCLVKGFYPSDIAVEWESNGQPENNYKTTPPVLMSDGSFFLASKLTVDKSRWQQGNVFSCS
VMHEALHNHYTQKSLSLSPG Full-length Light Chain 1 (anti-EGFR; SEQ ID NO: 590)
RIQMTQSPSSLSASVGDRVTITCSASSSVTYMYWYQDKPGKAPKLLIYDTSNLASGVPSRFSGSGSGTDYTFTISSLQPEDIATYYCQQ
WSSHIFTFGQGTKVEIKRTVAAPSVFIFPPSDKQLKSGTARVVCLLNNFYPREAKVQWKVDNALQSGNSQESVTEQDSKDSTYSLSST
LTLSKADYEKHKVYACEVTHQGLSSPVTKSFNRGEC Full-length Heavy Chain 2 (anti-CD3; SEQ ID NO: 553)
EVQLVESGGGLVQPGGSLRLSCAASGFTLSSYTMNWVRYAPGKGLEWVSYISSSSRTIYYSDRVKGRFSISRDNAKNSLYLQMNSLR
DEDTALYYCAREDYYDSSGFDNWGRGTLVTVSSASTKGPSVFPLAPSSKSTSGGTAALGCLVKDYFPEPVTVSWNSGALTSGVHTFP
AVLQSSGLYSLSSVVTVPSSSLGTQTYICNVNHKPSNTKVDKKVEPKSCDKTHTCPPCPAPEAAGGPSVFLFPPKPKDTLMISRTPEVT
CVVVDVSHEDPEVKFNWYVDGVEVHNAKTKPREEQYNSTYRVVSVLTVLHQDWLNGKEYKCKVSNKALPAPIEKTISKAKGQPRRP
RVYTLPPSREEMTKNQVSLVCLVKGFYPSDIAVEWESNGQPENNYKTTPPVLDSDGSFFLYSVLTVDKSRWQQGNVFSCSVMHEAL
HNHYTQKSLSLSPG Full-length Light Chain 2 (anti-CD3; SEQ ID NO: 554)
DIRMTQSPSSFSASTGDRVTITCRASQGISSYLAWYQRKPGDAPKLLIYTASTLQSGVPSRFSGSGSGTDFTLTIRSLQSEDFATYYCQQ
YYSYPRTFGQGTKVEIKRTVAAPSVFIFPPSDEQLKSGTASVVCLLNNFYPREAKVQWKVDNALQSGNSQESVTEQDSKDSTYSLSST
LTLSKADYEKHKVYACEVTHQGLSSPVTKSFNRGEC Bispecific Antibody Internal Reference Identifier GOMP001_bsAb_012

Full-length Heavy Chain 1 (anti-CD3; SEQ ID NO: 5534)
EVQLVESGGGLVQPGGSLRLSCAASGFTLSSYTMNWVRKAPGKGLEWVSYISSSSRTIYYSDEVKGRFSISRDNAKNSLYLQMNSLR
DEDTALYYCAREDYYDSSGFDNWGQGTLVTVSSASTKGPSVFPLAPSSKSTSGGTAALGCLVADYFPEPVTVSWNSGALTSGVHTFP
AVLQSSGLYSLSSVVTVPSSSLGTQTYICNVNHKPSNTKVDEKVEPKSCDKTHTCPPCPAPEAAGGPSVFLFPPKPKDTLMISRTPEVT
CVVVDVSHEDPEVKFNWYVDGVEVHNAKTKPREEQYNSTYRVVSVLTVLHQDWLNGKEYKCKVSNKALPAPIEKTISKAKGQPREP
QVYTLPPSREEMTDNQVSLTCLVKGFYPSDIAVEWESNGQPENNYKTTPPVLMSDGSFFLASKLTVDKSRWQQGNVFSCSVMHEA
LHNHYTQKSLSLSPG Full-length Light Chain 1 (anti-CD3; SEQ ID NO: 554)
RIRMTQSPSSFSASTGDRVTITCRASQGISSYLAWYQDKPGKAPKLLIYTASTLQSGVPSRFSGSGSGTDFTLTIRSLQSEDFATYYCQQ
YYSYPRTFGQGTKVEIKRTVAAPSVFIFPPSDKQLKSGTARVVCLLNNFYPREAKVQWKVDNALQSGNSQESVTEQDSKDSTYSLSST
LTLSKADYEKHKVYACEVTHQGLSSPVTKSFNRGEC Full-length Heavy Chain 2 (anti-EGFR; SEQ ID NO: 591)
QVQLVQSGAEVKKPGASVKVSCKASGYTFTSHWMHWVRYAPGQGLEWIGEFNPSNGRTNYNEKFKSKATMTVDTSTNTAYMEL
SSLRSEDTAVYYCASRDYDYDGRYFDYWGRGTLVTVSSASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKVEPKSCDKTHTCPPCPAPEAAGGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISKAKG
QPRRPRVYTLPPSREEMTKNQVSLVCLVKGFYPSDIAVEWESNGQPENNYKTTPPVLDSDGSFFLYSVLTVDKSRWQQGNVFSCSV
MHEALHNHYTQKSLSLSPG Full-length Light Chain 2 (anti-EGFR; SEQ ID NO: 592)
DIQMTQSPSSLSASVGDRVTITCSASSSVTYMYWYQRKPGDAPKLLIYDTSNLASGVPSRFSGSGSGTDYTFTISSLQPEDIATYYCQQ
WSSHIFTFGQGTKVEIKRTVAAPSVFIFPPSDEQLKSGTASVVCLLNNFYPREAKVQWKVDNALQSGNSQESVTEQDSKDSTYSLSST
LTLSKADYEKHKVYACEVTHQGLSSPVTKSFNRGEC Bispecific Antibody Internal Reference Identifier GOMP001_bsAb_013

Full-length Heavy Chain 1 (anti-EGFR; SEQ ID NO: 589)
QVQLVQSGAEVKKPGASVKVSCKASGYTFTSHWMHWVRKAPGQGLEWIGEFNPSNGRTNYNEEFKSKATMTVDTSTNTAYMEL
SSLRSEDTAVYYCASRDYDYDGRYFDYWGQGTLVTVSSASTKGPSVFPLAPSSKSTSGGTAALGCLVADYFPEPVTVSWNSGALTSG
VHTFPAVLQSSGLYSLSSVVTVPSSSLGTQTYICNVNHKPSNTKVDEKVEPKSCDKTHTCPPCPAPEAAGGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISKAKG
QPREPQVYTLPPSREEMTDNQVSLTCLVKGFYPSDIAVEWESNGQPENNYKTTPPVLMSDGSFFLASKLTVDKSRWQQGNVFSCS
VMHEALHNHYTQKSLSLSPG -continued Full-length Light Chain 1 (anti-EGFR; SEQ ID NO: 590)
RIQMTQSPSSLSASVGDRVTITCSASSSVTYMYWYQDKPGKAPKLLIYDTSNLASGVPSRFSGSGSGTDYTFTISSLQPEDIATYYCQQ
WSSHIFTFGQGTKVEIKRTVAAPSVFIFPPSDKQLKSGTARVVCLLNNFYPREAKVQWKVDNALQSGNSQESVTEQDSKDSTYSLSST
LTLSKADYEKHKVYACEVTHQGLSSPVTKSFNRGEC Full-length Heavy Chain 2 (anti-CD3; SEQ ID NO: 555)
QVQLVQSGAEVKKPGASVKVSCKASGYTFTSYDINWVRYATGQGLEWMGWMNPKSGKTGYAQKFQGRITMTRNTPISTVYMDL
SSLRSEDTAVYYCAREGHYDFWTGYYSFDYWGRGTLVTVSSASTKGPSVFPLAPSSKSTSGGTAALGCLVKDYFPEPVTVSWNSGAL
TSGVHTFPAVLQSSGLYSLSSVVTVPSSSLGTQTYICNVNHKPSNTKVDKKVEPKSCDKTHTCPPCPAPEAAGGPSVFLFPPKPKDTL
MISRTPEVTCVVVDVSHEDPEVKFNWYVDGVEVHNAKTKPREEQYNSTYRVVSVLTVLHQDWLNGKEYKCKVSNKALPAPIEKTIS
KAKGQPRRPRVYTLPPSREEMTKNQVSLVCLVKGFYPSDIAVEWESNGQPENNYKTTPPVLDSDGSFFLYSVLTVDKSRWQQGNVF
SCSVMHEALHNHYTQKSLSLSPG Full-length Light Chain 2 (anti-CD3; SEQ ID NO: 556)
DIQMTQSPSSLSASVGDRVTITCRASQGIRNDLGWYQRTPGDAPKRLIYAASSLQSGVPSRFSGSGSGTEFTLTISSLQPEDFATYYCL
QHYSYPYTFGQGTKLEIKRTVAAPSVFIFPPSDEQLKSGTASVVCLLNNFYPREAKVQWKVDNALQSGNSQESVTEQDSKDSTYSLSS
TLTLSKADYEKHKVYACEVTHQGLSSPVTKSFNRGEC Bispecific Antibody Internal Reference Identifier GOMP001_bsAb_014

Full-length Heavy Chain 1 (anti-CD3; SEQ ID NO: 555)
QVQLVQSGAEVKKPGASVKVSCKASGYTFTSYDINWVRKATGQGLEWMGWMNPKSGKTGYAQEFQGRITMTRNTPISTVYMDL
SSLRSEDTAVYYCAREGHYDFWTGYYSFDYWGQGTLVTVSSASTKGPSVFPLAPSSKSTSGGTAALGCLVADYFPEPVTVSWNSGAL
TSGVHTFPAVLQSSGLYSLSSVVTVPSSSLGTQTYICNVNHKPSNTKVDEKVEPKSCDKTHTCPPCPAPEAAGGPSVFLFPPKPKDTL
MISRTPEVTCVVVDVSHEDPEVKFNWYVDGVEVHNAKTKPREEQYNSTYRVVSVLTVLHQDWLNGKEYKCKVSNKALPAPIEKTIS
KAKGQPREPQVYTLPPSREEMTDNQVSLTCLVKGFYPSDIAVEWESNGQPENNYKTTPPVLMSDGSFFLASKLTVDKSRWQQGNV
FSCSVMHEALHNHYTQKSLSLSPG Full-length Light Chain 1 (anti-CD3; SEQ ID NO: 556)
RIQMTQSPSSLSASVGDRVTITCRASQGIRNDLGWYQDTPGKAPKRLIYAASSLQSGVPSRFSGSGSGTEFTLTISSLQPEDFATYYCL
QHYSYPYTFGQGTKLEIKRTVAAPSVFIFPPSDKQLKSGTARVVCLLNNFYPREAKVQWKVDNALQSGNSQESVTEQDSKDSTYSLSS
TLTLSKADYEKHKVYACEVTHQGLSSPVTKSFNRGEC Full-length Heavy Chain 2 (anti-EGFR; SEQ ID NO: 591)
QVQLVQSGAEVKKPGASVKVSCKASGYTFTSHWMHWVRYAPGQGLEWIGEFNPSNGRTNYNEKFKSKATMTVDTSTNTAYMEL
SSLRSEDTAVYYCASRDYDYDGRYFDYWGRGTLVTVSSASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKVEPKSCDKTHTCPPCPAPEAAGGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISKAKG
QPRRPRVYTLPPSREEMTKNQVSLVCLVKGFYPSDIAVEWESNGQPENNYKTTPPVLDSDGSFFLYSVLTVDKSRWQQGNVFSCSV
MHEALHNHYTQKSLSLSPG Full-length Light Chain 2 (anti-EGFR; SEQ ID NO: 592)
DIQMTQSPSSLSASVGDRVTITCSASSSVTYMYWYQRKPGDAPKLLIYDTSNLASGVPSRFSGSGSGTDYTFTISSLQPEDIATYYCQQ
WSSHIFTFGQGTKVEIKRTVAAPSVFIFPPSDEQLKSGTASVVCLLNNFYPREAKVQWKVDNALQSGNSQESVTEQDSKDSTYSLSST
LTLSKADYEKHKVYACEVTHQGLSSPVTKSFNRGEC Bispecific Antibody Internal Reference Identifier GOMP001_bsAb_015

Full-length Heavy Chain 1 (anti-EGFR; SEQ ID NO: 589)
QVQLVQSGAEVKKPGASVKVSCKASGYTFTSHWMHWVRKAPGQGLEWIGEFNPSNGRTNYNEEFKSKATMTVDTSTNTAYMEL
SSLRSEDTAVYYCASRDYDYDGRYFDYWGQGTLVTVSSASTKGPSVFPLAPSSKSTSGGTAALGCLVADYFPEPVTVSWNSGALTSG
VHTFPAVLQSSGLYSLSSVVTVPSSSLGTQTYICNVNHKPSNTKVDEKVEPKSCDKTHTCPPCPAPEAAGGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISKAKG
QPREPQVYTLPPSREEMTDNQVSLTCLVKGFYPSDIAVEWESNGQPENNYKTTPPVLMSDGSFFLASKLTVDKSRWQQGNVFSCS
VMHEALHNHYTQKSLSLSPG Full-length Light Chain 1 (anti-EGFR; SEQ ID NO: 590)
RIQMTQSPSSLSASVGDRVTITCSASSSVTYMYWYQDKPGKAPKLLIYDTSNLASGVPSRFSGSGSGTDYTFTISSLQPEDIATYYCQQ
WSSHIFTFGQGTKVEIKRTVAAPSVFIFPPSDKQLKSGTARVVCLLNNFYPREAKVQWKVDNALQSGNSQESVTEQDSKDSTYSLSST
LTLSKADYEKHKVYACEVTHQGLSSPVTKSFNRGEC Full-length Heavy Chain 2 (anti-CD3; SEQ ID NO: 557)
QVQLVESGGGVVQPGRSLRLSCAASGFTFSGYGMHWVRYAPGKGLDWVAIIYYNGNNKYYADRVKGRFTISRDNSKNTLYLQMN
SLRAEDTAVYYCARGGGYNWFDPWGRGTLVIVSSASTKGPSVFPLAPSSKSTSGGTAALGCLVKDYFPEPVTVSWNSGALTSGVHT
FPAVLQSSGLYSLSSVVTVPSSSLGTQTYICNVNHKPSNTKVDKKVEPKSCDKTHTCPPCPAPEAAGGPSVFLFPPKPKDTLMISRTPE
VTCVVVDVSHEDPEVKFNWYVDGVEVHNAKTKPREEQYNSTYRVVSVLTVLHQDWLNGKEYKCKVSNKALPAPIEKTISKAKGQPR
RPRVYTLPPSREEMTKNQVSLVCLVKGFYPSDIAVEWESNGQPENNYKTTPPVLDSDGSFFLYSVLTVDKSRWQQGNVFSCSVMHE
ALHNHYTQKSLSLSPG Full-length Light Chain 2 (anti-CD3; SEQ ID NO: 558)
DIQMTQSPSSLSASVGDRVTITCRPSQSISNYLNWYQRKPGDAPKLLIYAASSLQSGVPSRFSGSGSGTDFTLTISSLQPEDFATYYCQ
QSYSTPFTFGRGTRLEIKRTVAAPSVFIFPPSDEQLKSGTASVVCLLNNFYPREAKVQWKVDNALQSGNSQESVTEQDSKDSTYSLSS
TLTLSKADYEKHKVYACEVTHQGLSSPVTKSFNRGEC Bispecific Antibody Internal Reference Identifier GOMP001_bsAb_016

Full-length Heavy Chain 1 (anti-CD3; SEQ ID NO: 557)
QVQLVESGGGVVQPGRSLRLSCAASGFTFSGYGMHWVRKAPGKGLDWVAIIYYNGNNKYYADEVKGRFTISRDNSKNTLYLQMN
SLRAEDTAVYYCARGGGYNWFDPWGQGTLVIVSSASTKGPSVFPLAPSSKSTSGGTAALGCLVADYFPEPVTVSWNSGALTSGVHT
FPAVLQSSGLYSLSSVVTVPSSSLGTQTYICNVNHKPSNTKVDEKVEPKSCDKTHTCPPCPAPEAAGGPSVFLFPPKPKDTLMISRTPE -continued VTCVVVDVSHEDPEVKFNWYVDGVEVHNAKTKPREEQYNSTYRVVSVLTVLHQDWLNGKEYKCKVSNKALPAPIEKTISKAKGQPR
EPQVYTLPPSREEMTDNQVSLTCLVKGFYPSDIAVEWESNGQPENNYKTTPPVLMSDGSFFLASKLTVDKSRWQQGNVFSCSVMH
EALHNHYTQKSLSLSPG Full-length Light Chain 1 (anti-CD3; SEQ ID NO: 558)
RIQMTQSPSSLSASVGDRVTITCRPSQSISNYLNWYQDKPGKAPKLLIYAASSLQSGVPSRFSGSGSGTDFTLTISSLQPEDFATYYCQ
QSYSTPFTFGRGTRLEIKRTVAAPSVFIFPPSDKQLKSGTARVVCLLNNFYPREAKVQWKVDNALQSGNSQESVTEQDSKDSTYSLSS
TLTLSKADYEKHKVYACEVTHQGLSSPVTKSFNRGEC Full-length Heavy Chain 2 (anti-EGFR; SEQ ID NO: 591)
QVQLVQSGAEVKKPGASVKVSCKASGYTFTSHWMHWVRYAPGQGLEWIGEFNPSNGRTNYNEKFKSKATMTVDTSTNTAYMEL
SSLRSEDTAVYYCASRDYDYDGRYFDYWGRGTLVTVSSASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKVEPKSCDKTHTCPPCPAPEAAGGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISKAKG
QPRRPRVYTLPPSREEMTKNQVSLVCLVKGFYPSDIAVEWESNGQPENNYKTTPPVLDSDGSFFLYSVLTVDKSRWQQGNVFSCSV
MHEALHNHYTQKSLSLSPG Full-length Light Chain 2 (anti-EGFR; SEQ ID NO: 592)
DIQMTQSPSSLSASVGDRVTITCSASSSVTYMYWYQRKPGDAPKLLIYDTSNLASGVPSRFSGSGSGTDYTFTISSLQPEDIATYYCQQ
WSSHIFTFGQGTKVEIKRTVAAPSVFIFPPSDEQLKSGTASVVCLLNNFYPREAKVQWKVDNALQSGNSQESVTEQDSKDSTYSLSST
LTLSKADYEKHKVYACEVTHQGLSSPVTKSFNRGEC Bispecific Antibody Internal Reference Identifier GOMP001_bsAb_017

Full-length Heavy Chain 1 (anti-EGFR; SEQ ID NO: 589)
QVQLVQSGAEVKKPGASVKVSCKASGYTFTSHWMHWVRKAPGQGLEWIGEFNPSNGRTNYNEEFKSKATMTVDTSTNTAYMEL
SSLRSEDTAVYYCASRDYDYDGRYFDYWGQGTLVTVSSASTKGPSVFPLAPSSKSTSGGTAALGCLVADYFPEPVTVSWNSGALTSG
VHTFPAVLQSSGLYSLSSVVTVPSSSLGTQTYICNVNHKPSNTKVDEKVEPKSCDKTHTCPPCPAPEAAGGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISKAKG
QPREPQVYTLPPSREEMTDNQVSLTCLVKGFYPSDIAVEWESNGQPENNYKTTPPVLMSDGSFFLASKLTVDKSRWQQGNVFSCS
VMHEALHNHYTQKSLSLSPG Full-length Light Chain 1 (anti-EGFR; SEQ ID NO: 590)
RIQMTQSPSSLSASVGDRVTITCSASSSVTYMYWYQDKPGKAPKLLIYDTSNLASGVPSRFSGSGSGTDYTFTISSLQPEDIATYYCQQ
WSSHIFTFGQGTKVEIKRTVAAPSVFIFPPSDKQLKSGTARVVCLLNNFYPREAKVQWKVDNALQSGNSQESVTEQDSKDSTYSLSST
LTLSKADYEKHKVYACEVTHQGLSSPVTKSFNRGEC Full-length Heavy Chain 2 (anti-CD3; SEQ ID NO: 559)
EVQLVESGGDLVQPGRSLRLSCAASGFTFDDCVIHWVRYAPGKGLEWVSGITWNSGRIGYADRVKGRFTISRDNAKNSLYLQMNSL
RVEDTALYYCAKEGNYDFWSTYYRGYFDLWGRGTLVTVSSASTKGPSVFPLAPSSKSTSGGTAALGCLVKDYFPEPVTVSWNSGALT
SGVHTFPAVLQSSGLYSLSSVVTVPSSSLGTQTYICNVNHKPSNTKVDKKVEPKSCDKTHTCPPCPAPEAAGGPSVFLFPPKPKDTLMI
SRTPEVTCVVVDVSHEDPEVKFNWYVDGVEVHNAKTKPREEQYNSTYRVVSVLTVLHQDWLNGKEYKCKVSNKALPAPIEKTISKA
KGQPRRPRVYTLPPSREEMTKNQVSLVCLVKGFYPSDIAVEWESNGQPENNYKTTPPVLDSDGSFFLYSVLTVDKSRWQQGNVFSC
SVMHEALHNHYTQKSLSLSPG Full-length Light Chain 2 (anti-CD3; SEQ ID NO: 560)
DIQMTQSPSSLSASVGDRVTITCRASQGIRNDLGWYQRKPGDAPKRLIYAASSLQGGVPLRFSGSGSGTEFTLTISSLQPEDFATYYCL
QHNSYPYTFGQGTKLEIKRTVAAPSVFIFPPSDEQLKSGTASVVCLLNNFYPREAKVQWKVDNALQSGNSQESVTEQDSKDSTYSLSS
TLTLSKADYEKHKVYACEVTHQGLSSPVTKSFNRGEC Bispecific Antibody Internal Reference Identifier GOMP001_bsAb_018

Full-length Heavy Chain 1 (anti-CD3; SEQ ID NO: 559)
EVQLVESGGDLVQPGRSLRLSCAASGFTFDDCVIHWVRKAPGKGLEWVSGITWNSGRIGYADEVKGRFTISRDNAKNSLYLQMNSL
RVEDTALYYCAKEGNYDFWSTYYRGYFDLWGRGTLVTVSSASTKGPSVFPLAPSSKSTSGGTAALGCLVADYFPEPVTVSWNSGALT
SGVHTFPAVLQSSGLYSLSSVVTVPSSSLGTQTYICNVNHKPSNTKVDEKVEPKSCDKTHTCPPCPAPEAAGGPSVFLFPPKPKDTLMI
SRTPEVTCVVVDVSHEDPEVKFNWYVDGVEVHNAKTKPREEQYNSTYRVVSVLTVLHQDWLNGKEYKCKVSNKALPAPIEKTISKA
KGQPREPQVYTLPPSREEMTDNQVSLTCLVKGFYPSDIAVEWESNGQPENNYKTTPPVLMSDGSFFLASKLTVDKSRWQQGNVFS
CSVMHEALHNHYTQKSLSLSPG Full-length Light Chain 1 (anti-CD3; SEQ ID NO: 560)
RIQMTQSPSSLSASVGDRVTITCRASQGIRNDLGWYQDKPGIAPKRLIYAASSLQGGVPLRFSGSGSGTEFTLTISSLQPEDFATYYCL
QHNSYPYTFGQGTKLEIKRTVAAPSVFIFPPSDKQLKSGTARVVCLLNNFYPREAKVQWKVDNALQSGNSQESVTEQDSKDSTYSLS
STLTLSKADYEKHKVYACEVTHQGLSSPVTKSFNRGEC Full-length Heavy Chain 2 (anti-EGFR; SEQ ID NO: 591)
QVQLVQSGAEVKKPGASVKVSCKASGYTFTSHWMHWVRYAPGQGLEWIGEFNPSNGRTNYNEKFKSKATMTVDTSTNTAYMEL
SSLRSEDTAVYYCASRDYDYDGRYFDYWGRGTLVTVSSASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKVEPKSCDKTHTCPPCPAPEAAGGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISKAKG
QPRRPRVYTLPPSREEMTKNQVSLVCLVKGFYPSDIAVEWESNGQPENNYKTTPPVLDSDGSFFLYSVLTVDKSRWQQGNVFSCSV
MHEALHNHYTQKSLSLSPG Full-length Light Chain 2 (anti-EGFR; SEQ ID NO: 592)
DIQMTQSPSSLSASVGDRVTITCSASSSVTYMYWYQRKPGDAPKLLIYDTSNLASGVPSRFSGSGSGTDYTFTISSLQPEDIATYYCQQ
WSSHIFTFGQGTKVEIKRTVAAPSVFIFPPSDEQLKSGTASVVCLLNNFYPREAKVQWKVDNALQSGNSQESVTEQDSKDSTYSLSST
LTLSKADYEKHKVYACEVTHQGLSSPVTKSFNRGEC -continued Bispecific Antibody Internal Reference Identifier GOMP001_bsAb_019

Full-length Heavy Chain 1 (anti-EGFR; SEQ ID NO: 589)
QVQLVQSGAEVKKPGASVKVSCKASGYTFTSHWMHWVRKAPGQGLEWIGEFNPSNGRTNYNEEFKSKATMTVDTSTNTAYMEL
SSLRSEDTAVYYCASRDYDYDGRYFDYWGQGTLVTVSSASTKGPSVFPLAPSSKSTSGGTAALGCLVADYFPEPVTVSWNSGALTSG
VHTFPAVLQSSGLYSLSSVVTVPSSSLGTQTYICNVNHKPSNTKVDEKVEPKSCDKTHTCPPCPAPEAAGGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISKAKG
QPREPQVYTLPPSREEMTDNQVSLTCLVKGFYPSDIAVEWESNGQPENNYKTTPPVLMSDGSFFLASKLTVDKSRWQQGNVFSCS
VMHEALHNHYTQKSLSLSPG Full-length Light Chain 1 (anti-EGFR; SEQ ID NO: 590)
RIQMTQSPSSLSASVGDRVTITCSASSSVTYMYWYQDKPGKAPKLLIYDTSNLASGVPSRFSGSGSGTDYTFTISSLQPEDIATYYCQQ
WSSHIFTFGQGTKVEIKRTVAAPSVFIFPPSDKQLKSGTARVVCLLNNFYPREAKVQWKVDNALQSGNSQESVTEQDSKDSTYSLSST
LTLSKADYEKHKVYACEVTHQGLSSPVTKSFNRGEC Full-length Heavy Chain 2 (anti-CD3; SEQ ID NO: 561)
EVQLVDSGGGLVQPGGSLRLSCSGSGFTFSSYWMSWVRYAPGKGLEWVANIKQDGSQKYYVDRVKGRFTISRDNVKNSLYLQMN
SLRVEDTAVYYCARDESSSWYWYFDLWGRGTLVTVSSASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEPKSCDKTHTCPPCPAPEAAGGPSVFLFPPKPKDTLMISRT
PEVTCVVVDVSHEDPEVKFNWYVDGVEVHNAKTKPREEQYNSTYRVVSVLTVLHQDWLNGKEYKCKVSNKALPAPIEKTISKAKGQ
PRRPRVYTLPPSREEMTKNQVSLVCLVKGFYPSDIAVEWESNGQPENNYKTTPPVLDSDGSFFLYSVLTVDKSRWQQGNVFSCSVM
HEALHNHYTQKSLSLSPG Full-length Light Chain 2 (anti-CD3; SEQ ID NO: 562)
DIQMTQSPSTLSASVGDRVTLTCRASQNIVKWLAWYQRKPGDAPKLLIYKASSLESGVPSWFSGSGSGTEFTLTINSLQPDDFATYYC
QQYYTYSRTFGQGTKVEIKRTVAAPSVFIFPPSDEQLKSGTASVVCLLNNFYPREAKVQWKVDNALQSGNSQESVTEQDSKDSTYSL
SSTLTLSKADYEKHKVYACEVTHQGLSSPVTKSFNRGEC Bispecific Antibody Internal Reference Identifier GOMP001_bsAb_020

Full-length Heavy Chain 1 (anti-CD3; SEQ ID NO: 561)
EVQLVDSGGGLVQPGGSLRLSCSGSGFTFSSYWMSWVRKAPGKGLEWVANIKQDGSQKYYVDEVKGRFTISRDNVKNSLYLQMN
SLRVEDTAVYYCARDESSSWYWYFDLWGRGTLVTVSSASTKGPSVFPLAPSSKSTSGGTAALGCLVADYFPEPVTVSWNSGALTSGV
HTFPAVLQSSGLYSLSSVVTVPSSSLGTQTYICNVNHKPSNTKVDEKVEPKSCDKTHTCPPCPAPEAAGGPSVFLFPPKPKDTLMISRT
PEVTCVVVDVSHEDPEVKFNWYVDGVEVHNAKTKPREEQYNSTYRVVSVLTVLHQDWLNGKEYKCKVSNKALPAPIEKTISKAKGQ
PREPQVYTLPPSREEMTDNQVSLTCLVKGFYPSDIAVEWESNGQPENNYKTTPPVLMSDGSFFLASKLTVDKSRWQQGNVFSCSV
MHEALHNHYTQKSLSLSPG Full-length Light Chain 1 (anti-CD3; SEQ ID NO: 562)
RIQMTQSPSTLSASVGDRVTLTCRASQNIVKWLAWYQDKPGKAPKLLIYKASSLESGVPSWFSGSGSGTEFTLTINSLQPDDFATYYC
QQYYTYSRTFGQGTKVEIKRTVAAPSVFIFPPSDKQLKSGTARVVCLLNNFYPREAKVQWKVDNALQSGNSQESVTEQDSKDSTYSL
SSTLTLSKADYEKHKVYACEVTHQGLSSPVTKSFNRGEC Full-length Heavy Chain 2 (anti-EGFR; SEQ ID NO: 591)
QVQLVQSGAEVKKPGASVKVSCKASGYTFTSHWMHWVRYAPGQGLEWIGEFNPSNGRTNYNEKFKSKATMTVDTSTNTAYMEL
SSLRSEDTAVYYCASRDYDYDGRYFDYWGRGTLVTVSSASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKVEPKSCDKTHTCPPCPAPEAAGGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISKAKG
QPRRPRVYTLPPSREEMTKNQVSLVCLVKGFYPSDIAVEWESNGQPENNYKTTPPVLDSDGSFFLYSVLTVDKSRWQQGNVFSCSV
MHEALHNHYTQKSLSLSPG Full-length Light Chain 2 (anti-EGFR; SEQ ID NO: 592)
DIQMTQSPSSLSASVGDRVTITCSASSSVTYMYWYQRKPGDAPKLLIYDTSNLASGVPSRFSGSGSGTDYTFTISSLQPEDIATYYCQQ
WSSHIFTFGQGTKVEIKRTVAAPSVFIFPPSDEQLKSGTASVVCLLNNFYPREAKVQWKVDNALQSGNSQESVTEQDSKDSTYSLSST
LTLSKADYEKHKVYACEVTHQGLSSPVTKSFNRGEC Bispecific Antibody Internal Reference Identifier GOMP001_bsAb_021

Full-length Heavy Chain 1 (anti-EGFR; SEQ ID NO: 589)
QVQLVQSGAEVKKPGASVKVSCKASGYTFTSHWMHWVRKAPGQGLEWIGEFNPSNGRTNYNEEFKSKATMTVDTSTNTAYMEL
SSLRSEDTAVYYCASRDYDYDGRYFDYWGQGTLVTVSSASTKGPSVFPLAPSSKSTSGGTAALGCLVADYFPEPVTVSWNSGALTSG
VHTFPAVLQSSGLYSLSSVVTVPSSSLGTQTYICNVNHKPSNTKVDEKVEPKSCDKTHTCPPCPAPEAAGGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISKAKG
QPREPQVYTLPPSREEMTDNQVSLTCLVKGFYPSDIAVEWESNGQPENNYKTTPPVLMSDGSFFLASKLTVDKSRWQQGNVFSCS
VMHEALHNHYTQKSLSLSPG Full-length Light Chain 1 (anti-EGFR; SEQ ID NO: 590)
RIQMTQSPSSLSASVGDRVTITCSASSSVTYMYWYQDKPGKAPKLLIYDTSNLASGVPSRFSGSGSGTDYTFTISSLQPEDIATYYCQQ
WSSHIFTFGQGTKVEIKRTVAAPSVFIFPPSDKQLKSGTARVVCLLNNFYPREAKVQWKVDNALQSGNSQESVTEQDSKDSTYSLSST
LTLSKADYEKHKVYACEVTHQGLSSPVTKSFNRGEC Full-length Heavy Chain 2 (anti-CD3; SEQ ID NO: 563)
QMLLVESGGGVVQPGRSLTLSCAASGFTFRSYGMHWVRYAPGRGLEWVAIIWYDGSTEYYADRVKGRFTISRANSKNMLYLQMN
SLRAEDTAVYYCAAFDYTNSFDIWGRGTMVTVSSASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTHTCPPCPAPEAAGGPSVFLFPPKPKDTLMISRTPEV
TCVVVDVSHEDPEVKFNWYVDGVEVHNAKTKPREEQYNSTYRVVSVLTVLHQDWLNGKEYKCKVSNKALPAPIEKTISKAKGQPRR
PRVYTLPPSREEMTKNQVSLVCLVKGFYPSDIAVEWESNGQPENNYKTTPPVLDSDGSFFLYSVLTVDKSRWQQGNVFSCSVMHEA
LHNHYTQKSLSLSPG -continued Full-length Light Chain 2 (anti-CD3; SEQ ID NO: 564)
DIVVTQTPLSSPVTLGQPASISCRSSQRFVHSDGNTYLSWLQRRPGDPPRLLIYKISNRISGVPDRFSGSGAGTDFKLKISRVEAEDVGI
YYCMQATQFPYTFGQGTKLEIKRTVAAPSVFIFPPSDEQLKSGTASVVCLLNNFYPREAKVQWKVDNALQSGNSQESVTEQDSKDS
TYSLSSTLTLSKADYEKHKVYACEVTHQGLSSPVTKSFNRGEC Bispecific Antibody Internal Reference Identifier GOMP001_bsAb_022

Full-length Heavy Chain 1 (anti-CD3; SEQ ID NO: 563)
QMLLVESGGGVVQPGRSLTLSCAASGFTFRSYGMHWVRKAPGRGLEWVAIIWYDGSTEYYADEVKGRFTISRANSKNMLYLQMN
SLRAEDTAVYYCAAFDYTNSFDIWGQGTMVTVSSASTKGPSVFPLAPSSKSTSGGTAALGCLVADYFPEPVTVSWNSGALTSGVHTF
PAVLQSSGLYSLSSVVTVPSSSLGTQTYICNVNHKPSNTKVDEKVEPKSCDKTHTCPPCPAPEAAGGPSVFLFPPKPKDTLMISRTPEV
TCVVVDVSHEDPEVKFNWYVDGVEVHNAKTKPREEQYNSTYRVVSVLTVLHQDWLNGKEYKCKVSNKALPAPIEKTISKAKGQPRE
PQVYTLPPSREEMTDNQVSLTCLVKGFYPSDIAVEWESNGQPENNYKTTPPVLMSDGSFFLASKLTVDKSRWQQGNVFSCSVMHE
ALHNHYTQKSLSLSPG Full-length Light Chain 1 (anti-CD3; SEQ ID NO: 564)
RIVVTQTPLSSPVTLGQPASISCRSSQRFVHSDGNTYLSWLQDRPGQPPRLLIYKISNRISGVPDRFSGSGAGTDFKLKISRVEAEDVGI
YYCMQATQFPYTFGQGTKLEIKRTVAAPSVFIFPPSDKQLKSGTARVVCLLNNFYPREAKVQWKVDNALQSGNSQESVTEQDSKDS
TYSLSSTLTLSKADYEKHKVYACEVTHQGLSSPVTKSFNRGEC Full-length Heavy Chain 2 (anti-EGFR; SEQ ID NO: 591)
QVQLVQSGAEVKKPGASVKVSCKASGYTFTSHWMHWVRYAPGQGLEWIGEFNPSNGRTNYNEKFKSKATMTVDTSTNTAYMEL
SSLRSEDTAVYYCASRDYDYDGRYFDYWGRGTLVTVSSASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKVEPKSCDKTHTCPPCPAPEAAGGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISKAKG
QPRRPRVYTLPPSREEMTKNQVSLVCLVKGFYPSDIAVEWESNGQPENNYKTTPPVLDSDGSFFLYSVLTVDKSRWQQGNVFSCSV
MHEALHNHYTQKSLSLSPG Full-length Light Chain 2 (anti-EGFR; SEQ ID NO: 592)
DIQMTQSPSSLSASVGDRVTITCSASSSVTYMYWYQRKPGDAPKLLIYDTSNLASGVPSRFSGSGSGTDYTFTISSLQPEDIATYYCQQ
WSSHIFTFGQGTKVEIKRTVAAPSVFIFPPSDEQLKSGTASVVCLLNNFYPREAKVQWKVDNALQSGNSQESVTEQDSKDSTYSLSST
LTLSKADYEKHKVYACEVTHQGLSSPVTKSFNRGEC Bispecific Antibody Internal Reference Identifier GOMP001_bsAb_023

Full-length Heavy Chain 1 (anti-EGFR; SEQ ID NO: 589)
QVQLVQSGAEVKKPGASVKVSCKASGYTFTSHWMHWVRKAPGQGLEWIGEFNPSNGRTNYNEEFKSKATMTVDTSTNTAYMEL
SSLRSEDTAVYYCASRDYDYDGRYFDYWGQGTLVTVSSASTKGPSVFPLAPSSKSTSGGTAALGCLVADYFPEPVTVSWNSGALTSG
VHTFPAVLQSSGLYSLSSVVTVPSSSLGTQTYICNVNHKPSNTKVDEKVEPKSCDKTHTCPPCPAPEAAGGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISKAKG
QPREPQVYTLPPSREEMTDNQVSLTCLVKGFYPSDIAVEWESNGQPENNYKTTPPVLMSDGSFFLASKLTVDKSRWQQGNVFSCS
VMHEALHNHYTQKSLSLSPG Full-length Light Chain 1 (anti-EGFR; SEQ ID NO: 590)
RIQMTQSPSSLSASVGDRVTITCSASSSVTYMYWYQDKPGKAPKLLIYDTSNLASGVPSRFSGSGSGTDYTFTISSLQPEDIATYYCQQ
WSSHIFTFGQGTKVEIKRTVAAPSVFIFPPSDKQLKSGTARVVCLLNNFYPREAKVQWKVDNALQSGNSQESVTEQDSKDSTYSLSST
LTLSKADYEKHKVYACEVTHQGLSSPVTKSFNRGEC Full-length Heavy Chain 2 (anti-CD3; SEQ ID NO: 565)
QGQLVESGGGVVQPGRSLRLSCEASGFTFRSYGMHWVRYPPGKGLEWVAIIWYDGGKKYYGDRVKGRFTISRDNPKNTLYLQMN
SLRPEDTAVYYCMAYDYSNGFDIWGRGTMVTVSSASTKGPSVFPLAPSSKSTSGGTAALGCLVKDYFPEPVTVSWNSGALTSGVHT
FPAVLQSSGLYSLSSVVTVPSSSLGTQTYICNVNHKPSNTKVDKKVEPKSCDKTHTCPPCPAPEAAGGPSVFLFPPKPKDTLMISRTPE
VTCVVVDVSHEDPEVKFNWYVDGVEVHNAKTKPREEQYNSTYRVVSVLTVLHQDWLNGKEYKCKVSNKALPAPIEKTISKAKGQPR
RPRVYTLPPSREEMTKNQVSLVCLVKGFYPSDIAVEWESNGQPENNYKTTPPVLDSDGSFFLYSVLTVDKSRWQQGNVFSCSVMHE
ALHNHYTQKSLSLSPG Full-length Light Chain 2 (anti-CD3; SEQ ID NO: 566)
DIVMTQTPLSSPVTLGQPASISCRSSQSFVHSDGSTYLSWLQRRPGDPPRLLIYKISNRFSGVPDRFSGRGAGTDFTLKISRVEAEDVGI
YYCMQNTQFPYTFGQGTKLEIKRTVAAPSVFIFPPSDEQLKSGTASVVCLLNNFYPREAKVQWKVDNALQSGNSQESVTEQDSKDS
TYSLSSTLTLSKADYEKHKVYACEVTHQGLSSPVTKSFNRGEC Bispecific Antibody Internal Reference Identifier GOMP001_bsAb_024

Full-length Heavy Chain 1 (anti-CD3; SEQ ID NO: 565)
QGQLVESGGGVVQPGRSLRLSCEASGFTFRSYGMHWVRKPPGKGLEWVAIIWYDGGKKYYGDEVKGRFTISRDNPKNTLYLQMN
SLRPEDTAVYYCMAYDYSNGFDIWGQGTMVTVSSASTKGPSVFPLAPSSKSTSGGTAALGCLVADYFPEPVTVSWNSGALTSGVHT
FPAVLQSSGLYSLSSVVTVPSSSLGTQTYICNVNHKPSNTKVDEKVEPKSCDKTHTCPPCPAPEAAGGPSVFLFPPKPKDTLMISRTPE
VTCVVVDVSHEDPEVKFNWYVDGVEVHNAKTKPREEQYNSTYRVVSVLTVLHQDWLNGKEYKCKVSNKALPAPIEKTISKAKGQPR
EPQVYTLPPSREEMTDNQVSLTCLVKGFYPSDIAVEWESNGQPENNYKTTPPVLMSDGSFFLASKLTVDKSRWQQGNVFSCSVMH
EALHNHYTQKSLSLSPG Full-length Light Chain 1 (anti-CD3; SEQ ID NO: 566)
RIVMTQTPLSSPVTLGQPASISCRSSQSFVHSDGSTYLSWLQDRPGQPPRLLIYKISNRFSGVPDRFSGRGAGTDFTLKISRVEAEDVGI
YYCMQNTQFPYTFGQGTKLEIKRTVAAPSVFIFPPSDKQLKSGTARVVCLLNNFYPREAKVQWKVDNALQSGNSQESVTEQDSKDS
TYSLSSTLTLSKADYEKHKVYACEVTHQGLSSPVTKSFNRGEC Full-length Heavy Chain 2 (anti-EGFR; SEQ ID NO: 591)
QVQLVQSGAEVKKPGASVKVSCKASGYTFTSHWMHWVRYAPGQGLEWIGEFNPSNGRTNYNEKFKSKATMTVDTSTNTAYMEL
SSLRSEDTAVYYCASRDYDYDGRYFDYWGRGTLVTVSSASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKVEPKSCDKTHTCPPCPAPEAAGGPSVFLFPPKPKDTLMISR -continued TPEVTCVVVDVSHEDPEVKFNWYVDGVEVHNAKTKPREEQYNSTYRVVSVLTVLHQDWLNGKEYKCKVSNKALPAPIEKTISKAKG
QPRRPRVYTLPPSREEMTKNQVSLVCLVKGFYPSDIAVEWESNGQPENNYKTTPPVLDSDGSFFLYSVLTVDKSRWQQGNVFSCSV
MHEALHNHYTQKSLSLSPG Full-length Light Chain 2 (anti-EGFR; SEQ ID NO: 592)
DIQMTQSPSSLSASVGDRVTITCSASSSVTYMYWYQRKPGDAPKLLIYDTSNLASGVPSRFSGSGSGTDYTFTISSLQPEDIATYYCQQ
WSSHIFTFGQGTKVEIKRTVAAPSVFIFPPSDEQLKSGTASVVCLLNNFYPREAKVQWKVDNALQSGNSQESVTEQDSKDSTYSLSST
LTLSKADYEKHKVYACEVTHQGLSSPVTKSFNRGEC Bispecific Antibody Internal Reference Identifier GOMP001_bsAb_029

Full-length Heavy Chain 1 (anti-EGFR; SEQ ID NO: 589)
QVQLVQSGAEVKKPGASVKVSCKASGYTFTSHWMHWVRKAPGQGLEWIGEFNPSNGRTNYNEEFKSKATMTVDTSTNTAYMEL
SSLRSEDTAVYYCASRDYDYDGRYFDYWGQGTLVTVSSASTKGPSVFPLAPSSKSTSGGTAALGCLVADYFPEPVTVSWNSGALTSG
VHTFPAVLQSSGLYSLSSVVTVPSSSLGTQTYICNVNHKPSNTKVDEKVEPKSCDKTHTCPPCPAPEAAGGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISKAKG
QPREPQVYTLPPSREEMTDNQVSLTCLVKGFYPSDIAVEWESNGQPENNYKTTPPVLMSDGSFFLASKLTVDKSRWQQGNVFSCS
VMHEALHNHYTQKSLSLSPG Full-length Light Chain 1 (anti-EGFR; SEQ ID NO: 590)
RIQMTQSPSSLSASVGDRVTITCSASSSVTYMYWYQDKPGKAPKLLIYDTSNLASGVPSRFSGSGSGTDYTFTISSLQPEDIATYYCQQ
WSSHIFTFGQGTKVEIKRTVAAPSVFIFPPSDKQLKSGTARVVCLLNNFYPREAKVQWKVDNALQSGNSQESVTEQDSKDSTYSLSST
LTLSKADYEKHKVYACEVTHQGLSSPVTKSFNRGEC Full-length Heavy Chain 2 (anti-CD3; SEQ ID NO: 567)
QVQLVQSGAEVKKPGASVKVSCKASGYTVTGYYMHWVRYAPGQGLEWMGWINPNSGGTNFAQRFQGRVTMTRDTSISTFYMD
LNRLRSDDTAVYYCARGGAPVSYWFFDLWGRGTLVTVSSASTKGPSVFPLAPSSKSTSGGTAALGCLVKDYFPEPVTVSWNSGALTS
GVHTFPAVLQSSGLYSLSSVVTVPSSSLGTQTYICNVNHKPSNTKVDKKVEPKSCDKTHTCPPCPAPEAAGGPSVFLFPPKPKDTLMIS
RTPEVTCVVVDVSHEDPEVKFNWYVDGVEVHNAKTKPREEQYNSTYRVVSVLTVLHQDWLNGKEYKCKVSNKALPAPIEKTISKAK
GQPRRPRVYTLPPSREEMTKNQVSLVCLVKGFYPSDIAVEWESNGQPENNYKTTPPVLDSDGSFFLYSVLTVDKSRWQQGNVFSCS
VMHEALHNHYTQKSLSLSPG Full-length Light Chain 2 (anti-CD3; SEQ ID NO: 568)
DIQMTQSPSSLSASVGDRVTITCRASQSISRYLNWYQRKPGDAPKVLIYNTSSLKSGVPSRFSGSGSGTDFTLTISSLQPEDFGTFYCQ
QSHSTPFTFGPGTKVDIKRTVAAPSVFIFPPSDEQLKSGTASVVCLLNNFYPREAKVQWKVDNALQSGNSQESVTEQDSKDSTYSLSS
TLTLSKADYEKHKVYACEVTHQGLSSPVTKSFNRGEC Bispecific Antibody Internal Reference Identifier GOMP001_bsAb_030

Full-length Heavy Chain 1 (anti-CD3; SEQ ID NO: 567)
QVQLVQSGAEVKKPGASVKVSCKASGYTVTGYYMHWVRKAPGQGLEWMGWINPNSGGTNFAQEFQGRVTMTRDTSISTFYMD
LNRLRSDDTAVYYCARGGAPVSYWFFDLWGRGTLVTVSSASTKGPSVFPLAPSSKSTSGGTAALGCLVADYFPEPVTVSWNSGALTS
GVHTFPAVLQSSGLYSLSSVVTVPSSSLGTQTYICNVNHKPSNTKVDEKVEPKSCDKTHTCPPCPAPEAAGGPSVFLFPPKPKDTLMIS
RTPEVTCVVVDVSHEDPEVKFNWYVDGVEVHNAKTKPREEQYNSTYRVVSVLTVLHQDWLNGKEYKCKVSNKALPAPIEKTISKAK
GQPREPQVYTLPPSREEMTDNQVSLTCLVKGFYPSDIAVEWESNGQPENNYKTTPPVLMSDGSFFLASKLTVDKSRWQQGNVFSC
SVMHEALHNHYTQKSLSLSPG Full-length Light Chain 1 (anti-CD3; SEQ ID NO: 568)
RIQMTQSPSSLSASVGDRVTITCRASQSISRYLNWYQDKPGKAPKVLIYNTSSLKSGVPSRFSGSGSGTDFTLTISSLQPEDFGTFYCQ
QSHSTPFTFGPGTKVDIKRTVAAPSVFIFPPSDKQLKSGTARVVCLLNNFYPREAKVQWKVDNALQSGNSQESVTEQDSKDSTYSLSS
TLTLSKADYEKHKVYACEVTHQGLSSPVTKSFNRGEC Full-length Heavy Chain 2 (anti-EGFR; SEQ ID NO: 591)
QVQLVQSGAEVKKPGASVKVSCKASGYTFTSHWMHWVRYAPGQGLEWIGEFNPSNGRTNYNEKFKSKATMTVDTSTNTAYMEL
SSLRSEDTAVYYCASRDYDYDGRYFDYWGRGTLVTVSSASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKVEPKSCDKTHTCPPCPAPEAAGGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISKAKG
QPRRPRVYTLPPSREEMTKNQVSLVCLVKGFYPSDIAVEWESNGQPENNYKTTPPVLDSDGSFFLYSVLTVDKSRWQQGNVFSCSV
MHEALHNHYTQKSLSLSPG Full-length Light Chain 2 (anti-EGFR; SEQ ID NO: 592)
DIQMTQSPSSLSASVGDRVTITCSASSSVTYMYWYQRKPGDAPKLLIYDTSNLASGVPSRFSGSGSGTDYTFTISSLQPEDIATYYCQQ
WSSHIFTFGQGTKVEIKRTVAAPSVFIFPPSDEQLKSGTASVVCLLNNFYPREAKVQWKVDNALQSGNSQESVTEQDSKDSTYSLSST
LTLSKADYEKHKVYACEVTHQGLSSPVTKSFNRGEC Bispecific Antibody Internal Reference Identifier GOMP001_bsAb_031

Full-length Heavy Chain 1 (anti-EGFR; SEQ ID NO: 589)
QVQLVQSGAEVKKPGASVKVSCKASGYTFTSHWMHWVRKAPGQGLEWIGEFNPSNGRTNYNEEFKSKATMTVDTSTNTAYMEL
SSLRSEDTAVYYCASRDYDYDGRYFDYWGQGTLVTVSSASTKGPSVFPLAPSSKSTSGGTAALGCLVADYFPEPVTVSWNSGALTSG
VHTFPAVLQSSGLYSLSSVVTVPSSSLGTQTYICNVNHKPSNTKVDEKVEPKSCDKTHTCPPCPAPEAAGGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISKAKG
QPREPQVYTLPPSREEMTDNQVSLTCLVKGFYPSDIAVEWESNGQPENNYKTTPPVLMSDGSFFLASKLTVDKSRWQQGNVFSCS
VMHEALHNHYTQKSLSLSPG Full-length Light Chain 1 (anti-EGFR; SEQ ID NO: 590)
RIQMTQSPSSLSASVGDRVTITCSASSSVTYMYWYQDKPGKAPKLLIYDTSNLASGVPSRFSGSGSGTDYTFTISSLQPEDIATYYCQQ
WSSHIFTFGQGTKVEIKRTVAAPSVFIFPPSDKQLKSGTARVVCLLNNFYPREAKVQWKVDNALQSGNSQESVTEQDSKDSTYSLSST
LTLSKADYEKHKVYACEVTHQGLSSPVTKSFNRGEC Full-length Heavy Chain 2 (anti-CD3; SEQ ID NO: 569)
QGQLVESGGGVVQPGRSLRLSCAASGFTFRGFGMHWVRYAPGKGLEWVAIIYYDGKNKYYADRVKGRFTISRDNSKNTLYLQMNS
LRAEDTAVYYCAKGGGYNWFDPWGRGTLVTVSSASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTHTCPPCPAPEAAGGPSVFLFPPKPKDTLMISRTPEV
TCVVVDVSHEDPEVKFNWYVDGVEVHNAKTKPREEQYNSTYRVVSVLTVLHQDWLNGKEYKCKVSNKALPAPIEKTISKAKGQPRR
PRVYTLPPSREEMTKNQVSLVCLVKGFYPSDIAVEWESNGQPENNYKTTPPVLDSDGSFFLYSVLTVDKSRWQQGNVFSCSVMHEA
LHNHYTQKSLSLSPG Full-length Light Chain 2 (anti-CD3; SEQ ID NO: 570)
DIQMTQSPSSLSASVGDRVTITCRASQSISTYLNWYQRKPGDAPKLLIYSASSLQSGVPSRFSGSGSGTDFTLTISNLQPEDFAIYYCQR
SYSPPFTFGPGTKLDIRRTVAAPSVFIFPPSDEQLKSGTASVVCLLNNFYPREAKVQWKVDNALQSGNSQESVTEQDSKDSTYSLSSTL
TLSKADYEKHKVYACEVTHQGLSSPVTKSFNRGEC Bispecific Antibody Internal Reference Identifier GOMP001_bsAb_032

Full-length Heavy Chain 1 (anti-CD3; SEQ ID NO: 569)
QGQLVESGGGVVQPGRSLRLSCAASGFTFRGFGMHWVRKAPGKGLEWVAIIYYDGKNKYYADEVKGRFTISRDNSKNTLYLQMNS
LRAEDTAVYYCAKGGGYNWFDPWGQGTLVTVSSASTKGPSVFPLAPSSKSTSGGTAALGCLVADYFPEPVTVSWNSGALTSGVHTF
PAVLQSSGLYSLSSVVTVPSSSLGTQTYICNVNHKPSNTKVDEKVEPKSCDKTHTCPPCPAPEAAGGPSVFLFPPKPKDTLMISRTPEV
TCVVVDVSHEDPEVKFNWYVDGVEVHNAKTKPREEQYNSTYRVVSVLTVLHQDWLNGKEYKCKVSNKALPAPIEKTISKAKGQPRE
PQVYTLPPSREEMTDNQVSLTCLVKGFYPSDIAVEWESNGQPENNYKTTPPVLMSDGSFFLASKLTVDKSRWQQGNVFSCSVMHE
ALHNHYTQKSLSLSPG Full-length Light Chain 1 (anti-CD3; SEQ ID NO: 570)
RIQMTQSPSSLSASVGDRVTITCRASQSISTYLNWYQDKPGKAPKLLIYSASSLQSGVPSRFSGSGSGTDFTLTISNLQPEDFAIYYCQR
SYSPPFTFGPGTKLDIRRTVAAPSVFIFPPSDKQLKSGTARVVCLLNNFYPREAKVQWKVDNALQSGNSQESVTEQDSKDSTYSLSSTL
TLSKADYEKHKVYACEVTHQGLSSPVTKSFNRGEC Full-length Heavy Chain 2 (anti-EGFR; SEQ ID NO: 591)
QVQLVQSGAEVKKPGASVKVSCKASGYTFTSHWMHWVRYAPGQGLEWIGEFNPSNGRTNYNEKFKSKATMTVDTSTNTAYMEL
SSLRSEDTAVYYCASRDYDYDGRYFDYWGRGTLVTVSSASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKVEPKSCDKTHTCPPCPAPEAAGGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISKAKG
QPRRPRVYTLPPSREEMTKNQVSLVCLVKGFYPSDIAVEWESNGQPENNYKTTPPVLDSDGSFFLYSVLTVDKSRWQQGNVFSCSV
MHEALHNHYTQKSLSLSPG Full-length Light Chain 2 (anti-EGFR; SEQ ID NO: 592)
DIQMTQSPSSLSASVGDRVTITCSASSSVTYMYWYQRKPGDAPKLLIYDTSNLASGVPSRFSGSGSGTDYTFTISSLQPEDIATYYCQQ
WSSHIFTFGQGTKVEIKRTVAAPSVFIFPPSDEQLKSGTASVVCLLNNFYPREAKVQWKVDNALQSGNSQESVTEQDSKDSTYSLSST
LTLSKADYEKHKVYACEVTHQGLSSPVTKSFNRGEC Bispecific Antibody Internal Reference Identifier GOMP001_bsAb_037

Full-length Heavy Chain 1 (anti-EGFR; SEQ ID NO: 589)
QVQLVQSGAEVKKPGASVKVSCKASGYTFTSHWMHWVRKAPGQGLEWIGEFNPSNGRTNYNEEFKSKATMTVDTSTNTAYMEL
SSLRSEDTAVYYCASRDYDYDGRYFDYWGQGTLVTVSSASTKGPSVFPLAPSSKSTSGGTAALGCLVADYFPEPVTVSWNSGALTSG
VHTFPAVLQSSGLYSLSSVVTVPSSSLGTQTYICNVNHKPSNTKVDEKVEPKSCDKTHTCPPCPAPEAAGGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISKAKG
QPREPQVYTLPPSREEMTDNQVSLTCLVKGFYPSDIAVEWESNGQPENNYKTTPPVLMSDGSFFLASKLTVDKSRWQQGNVFSCS
VMHEALHNHYTQKSLSLSPG Full-length Light Chain 1 (anti-EGFR; SEQ ID NO: 590)
RIQMTQSPSSLSASVGDRVTITCSASSSVTYMYWYQDKPGKAPKLLIYDTSNLASGVPSRFSGSGSGTDYTFTISSLQPEDIATYYCQQ
WSSHIFTFGQGTKVEIKRTVAAPSVFIFPPSDKQLKSGTARVVCLLNNFYPREAKVQWKVDNALQSGNSQESVTEQDSKDSTYSLSST
LTLSKADYEKHKVYACEVTHQGLSSPVTKSFNRGEC Full-length Heavy Chain 2 (anti-CD3; SEQ ID NO: 571)
EVQLVESGGVLVKTGGSLRLSCVASGFSFKKAWMNWVRYAPGKGLEWVGRIKRNSDGGAADYAARVKDRFTLSRDDSKNTLYLQ
MNSLKTEDTAVYYCTTLDSSSWYVGYYYMDVWGRGTTVTVSSASTKGPSVFPLAPSSKSTSGGTAALGCLVKDYFPEPVTVSWNSG
ALTSGVHTFPAVLQSSGLYSLSSVVTVPSSSLGTQTYICNVNHKPSNTKVDKKVEPKSCDKTHTCPPCPAPEAAGGPSVFLFPPKPKDT
LMISRTPEVTCVVVDVSHEDPEVKFNWYVDGVEVHNAKTKPREEQYNSTYRVVSVLTVLHQDWLNGKEYKCKVSNKALPAPIEKTIS
KAKGQPRRPRVYTLPPSREEMTKNQVSLVCLVKGFYPSDIAVEWESNGQPENNYKTTPPVLDSDGSFFLYSVLTVDKSRWQQGNVF
SCSVMHEALHNHYTQKSLSLSPG Full-length Light Chain 2 (anti-CD3; SEQ ID NO: 572)
DIHMTQSPSSVSASLGDRVTFTCRASQNINNWLAWYQRKPGDAPKLLIYTASSLQSGVPSRFSGSGSGTDFTLTISSLQPDDFATYYC
QQAHSLPITFGQGTRLGIKRTVAAPSVFIFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC Bispecific Antibody Internal Reference Identifier GOMP001_bsAb_038

Full-length Heavy Chain 1 (anti-CD3; SEQ ID NO: 571)
EVQLVESGGVLVKTGGSLRLSCVASGFSFKKAWMNWVRKAPGKGLEWVGRIKRNSDGGAADYAAEVKDRFTLSRDDSKNTLYLQ
MNSLKTEDTAVYYCTTLDSSSWYVGYYYMDVWGKGTTVTVSSASTKGPSVFPLAPSSKSTSGGTAALGCLVADYFPEPVTVSWNSG
ALTSGVHTFPAVLQSSGLYSLSSVVTVPSSSLGTQTYICNVNHKPSNTKVDEKVEPKSCDKTHTCPPCPAPEAAGGPSVFLFPPKPKDT
LMISRTPEVTCVVVDVSHEDPEVKFNWYVDGVEVHNAKTKPREEQYNSTYRVVSVLTVLHQDWLNGKEYKCKVSNKALPAPIEKTIS
KAKGQPREPQVYTLPPSREEMTDNQVSLTCLVKGFYPSDIAVEWESNGQPENNYKTTPPVLMSDGSFFLASKLTVDKSRWQQGNV
FSCSVMHEALHNHYTQKSLSLSPG -continued Full-length Light Chain 1 (anti-CD3; SEQ ID NO: 572)
RIHMTQSPSSVSASLGDRVTFTCRASQNINNWLAWYQDKPGKAPKLLIYTASSLQSGVPSRFSGSGSGTDFTLTISSLQPDDFATYYC
QQAHSLPITFGQGTRLGIKRTVAAPSVFIFPPSDKQLKSGTARVVCLLNNFYPREAKVQWKVDNALQSGNSQESVTEQDSKDSTYSL
SSTLTLSKADYEKHKVYACEVTHQGLSSPVTKSFNRGEC Full-length Heavy Chain 2 (anti-EGFR; SEQ ID NO: 591)
QVQLVQSGAEVKKPGASVKVSCKASGYTFTSHWMHWVRYAPGQGLEWIGEFNPSNGRTNYNEKFKSKATMTVDTSTNTAYMEL
SSLRSEDTAVYYCASRDYDYDGRYFDYWGRGTLVTVSSASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKVEPKSCDKTHTCPPCPAPEAAGGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISKAKG
QPRRPRVYTLPPSREEMTKNQVSLVCLVKGFYPSDIAVEWESNGQPENNYKTTPPVLDSDGSFFLYSVLTVDKSRWQQGNVFSCSV
MHEALHNHYTQKSLSLSPG Full-length Light Chain 2 (anti-EGFR; SEQ ID NO: 592)
DIQMTQSPSSLSASVGDRVTITCSASSSVTYMYWYQRKPGDAPKLLIYDTSNLASGVPSRFSGSGSGTDYTFTISSLQPEDIATYYCQQ
WSSHIFTFGQGTKVEIKRTVAAPSVFIFPPSDEQLKSGTASVVCLLNNFYPREAKVQWKVDNALQSGNSQESVTEQDSKDSTYSLSST
LTLSKADYEKHKVYACEVTHQGLSSPVTKSFNRGEC Bispecific Antibody Internal Reference Identifier GOMP001_bsAb_039

Full-length Heavy Chain 1 (anti-EGFR; SEQ ID NO: 589)
QVQLVQSGAEVKKPGASVKVSCKASGYTFTSHWMHWVRKAPGQGLEWIGEFNPSNGRTNYNEEFKSKATMTVDTSTNTAYMEL
SSLRSEDTAVYYCASRDYDYDGRYFDYWGQGTLVTVSSASTKGPSVFPLAPSSKSTSGGTAALGCLVADYFPEPVTVSWNSGALTSG
VHTFPAVLQSSGLYSLSSVVTVPSSSLGTQTYICNVNHKPSNTKVDEKVEPKSCDKTHTCPPCPAPEAAGGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISKAKG
QPREPQVYTLPPSREEMTDNQVSLTCLVKGFYPSDIAVEWESNGQPENNYKTTPPVLMSDGSFFLASKLTVDKSRWQQGNVFSCS
VMHEALHNHYTQKSLSLSPG Full-length Light Chain 1 (anti-EGFR; SEQ ID NO: 590)
RIQMTQSPSSLSASVGDRVTITCSASSSVTYMYWYQDKPGKAPKLLIYDTSNLASGVPSRFSGSGSGTDYTFTISSLQPEDIATYYCQQ
WSSHIFTFGQGTKVEIKRTVAAPSVFIFPPSDKQLKSGTARVVCLLNNFYPREAKVQWKVDNALQSGNSQESVTEQDSKDSTYSLSST
LTLSKADYEKHKVYACEVTHQGLSSPVTKSFNRGEC Full-length Heavy Chain 2 (anti-CD3; SEQ ID NO: 573)
EVQLVESGGGLVKTGGSHRLSCVASGFSFKKAWMNWVRYAPGKGLEWVGRIKRNSDGGTTDYAARVKGRFILSRDDSKNTLYLQ
MNSLKTEDTAVYYCTTLDSSSWYVGYYYMDVWGRGTTVTVSSASTKGPSVFPLAPSSKSTSGGTAALGCLVKDYFPEPVTVSWNSG
ALTSGVHTFPAVLQSSGLYSLSSVVTVPSSSLGTQTYICNVNHKPSNTKVDKKVEPKSCDKTHTCPPCPAPEAAGGPSVFLFPPKPKDT
LMISRTPEVTCVVVDVSHEDPEVKFNWYVDGVEVHNAKTKPREEQYNSTYRVVSVLTVLHQDWLNGKEYKCKVSNKALPAPIEKTIS
KAKGQPRRPRVYTLPPSREEMTKNQVSLVCLVKGFYPSDIAVEWESNGQPENNYKTTPPVLDSDGSFFLYSVLTVDKSRWQQGNVF
SCSVMHEALHNHYTQKSLSLSPG Full-length Light Chain 2 (anti-CD3; SEQ ID NO: 574)
DIQMTQSPSSVSASVGDRVTITCRASQDINNWLAWYQRKPGDAPKILIYTASNLQSGVPSRFSGSGSGTDFTLTISSLQPEDFATYFC
QQAHSLPITFGQGTRLEIKRTVAAPSVFIFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC Bispecific Antibody Internal Reference Identifier GOMP001_bsAb_040

Full-length Heavy Chain 1 (anti-CD3; SEQ ID NO: 573)
EVQLVESGGGLVKTGGSHRLSCVASGFSFKKAWMNWVRKAPGKGLEWVGRIKRNSDGGTTDYAAEVKGRFILSRDDSKNTLYLQ
MNSLKTEDTAVYYCTTLDSSSWYVGYYYMDVWGKGTTVTVSSASTKGPSVFPLAPSSKSTSGGTAALGCLVADYFPEPVTVSWNSG
ALTSGVHTFPAVLQSSGLYSLSSVVTVPSSSLGTQTYICNVNHKPSNTKVDEKVEPKSCDKTHTCPPCPAPEAAGGPSVFLFPPKPKDT
LMISRTPEVTCVVVDVSHEDPEVKFNWYVDGVEVHNAKTKPREEQYNSTYRVVSVLTVLHQDWLNGKEYKCKVSNKALPAPIEKTIS
KAKGQPREPQVYTLPPSREEMTDNQVSLTCLVKGFYPSDIAVEWESNGQPENNYKTTPPVLMSDGSFFLASKLTVDKSRWQQGNV
FSCSVMHEALHNHYTQKSLSLSPG Full-length Light Chain 1 (anti-CD3; SEQ ID NO: 574)
RIQMTQSPSSVSASVGDRVTITCRASQDINNWLAWYQDKPGKAPKILIYTASNLQSGVPSRFSGSGSGTDFTLTISSLQPEDFATYFC
QQAHSLPITFGQGTRLEIKRTVAAPSVFIFPPSDKQLKSGTARVVCLLNNFYPREAKVQWKVDNALQSGNSQESVTEQDSKDSTYSLS
STLTLSKADYEKHKVYACEVTHQGLSSPVTKSFNRGEC Full-length Heavy Chain 2 (anti-EGFR; SEQ ID NO: 591)
QVQLVQSGAEVKKPGASVKVSCKASGYTFTSHWMHWVRYAPGQGLEWIGEFNPSNGRTNYNEKFKSKATMTVDTSTNTAYMEL
SSLRSEDTAVYYCASRDYDYDGRYFDYWGRGTLVTVSSASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKVEPKSCDKTHTCPPCPAPEAAGGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISKAKG
QPRRPRVYTLPPSREEMTKNQVSLVCLVKGFYPSDIAVEWESNGQPENNYKTTPPVLDSDGSFFLYSVLTVDKSRWQQGNVFSCSV
MHEALHNHYTQKSLSLSPG Full-length Light Chain 2 (anti-EGFR; SEQ ID NO: 592)
DIQMTQSPSSLSASVGDRVTITCSASSSVTYMYWYQRKPGDAPKLLIYDTSNLASGVPSRFSGSGSGTDYTFTISSLQPEDIATYYCQQ
WSSHIFTFGQGTKVEIKRTVAAPSVFIFPPSDEQLKSGTASVVCLLNNFYPREAKVQWKVDNALQSGNSQESVTEQDSKDSTYSLSST
LTLSKADYEKHKVYACEVTHQGLSSPVTKSFNRGEC Bispecific Antibody Internal Reference Identifier GOMP001_bsAb_041

Full-length Heavy Chain 1 (anti-EGFR; SEQ ID NO: 589)
QVQLVQSGAEVKKPGASVKVSCKASGYTFTSHWMHWVRKAPGQGLEWIGEFNPSNGRTNYNEEFKSKATMTVDTSTNTAYMEL
SSLRSEDTAVYYCASRDYDYDGRYFDYWGQGTLVTVSSASTKGPSVFPLAPSSKSTSGGTAALGCLVADYFPEPVTVSWNSGALTSG
VHTFPAVLQSSGLYSLSSVVTVPSSSLGTQTYICNVNHKPSNTKVDEKVEPKSCDKTHTCPPCPAPEAAGGPSVFLFPPKPKDTLMISR -continued TPEVTCVVVDVSHEDPEVKFNWYVDGVEVHNAKTKPREEQYNSTYRVVSVLTVLHQDWLNGKEYKCKVSNKALPAPIEKTISKAKG
QPREPQVYTLPPSREEMTDNQVSLTCLVKGFYPSDIAVEWESNGQPENNYKTTPPVLMSDGSFFLASKLTVDKSRWQQGNVFSCS
VMHEALHNHYTQKSLSLSPG Full-length Light Chain 1 (anti-EGFR; SEQ ID NO: 590)
RIQMTQSPSSLSASVGDRVTITCSASSSVTYMYWYQDKPGKAPKLLIYDTSNLASGVPSRFSGSGSGTDYTFTISSLQPEDIATYYCQQ
WSSHIFTFGQGTKVEIKRTVAAPSVFIFPPSDKQLKSGTARVVCLLNNFYPREAKVQWKVDNALQSGNSQESVTEQDSKDSTYSLSST
LTLSKADYEKHKVYACEVTHQGLSSPVTKSFNRGEC Full-length Heavy Chain 2 (anti-CD3; SEQ ID NO: 575)
EVQLVESGGGLVKTGGSLRLSCVASGFSFKKAWMNWVRYAPGKGLEWVGRIKRNTDGGPADYAARVKGRFTLSRDDSKKTLYLQ
MNSLKTEDTAVYYCTTLDSSSWYVGYYYMDVWGRGTTVTVSSASTKGPSVFPLAPSSKSTSGGTAALGCLVKDYFPEPVTVSWNSG
ALTSGVHTFPAVLQSSGLYSLSSVVTVPSSSLGTQTYICNVNHKPSNTKVDKKVEPKSCDKTHTCPPCPAPEAAGGPSVFLFPPKPKDT
LMISRTPEVTCVVVDVSHEDPEVKFNWYVDGVEVHNAKTKPREEQYNSTYRVVSVLTVLHQDWLNGKEYKCKVSNKALPAPIEKTIS
KAKGQPRRPRVYTLPPSREEMTKNQVSLVCLVKGFYPSDIAVEWESNGQPENNYKTTPPVLDSDGSFFLYSVLTVDKSRWQQGNVF
SCSVMHEALHNHYTQKSLSLSPG Full-length Light Chain 2 (anti-CD3; SEQ ID NO: 576)
DIQMTQSPSSVSASVGDRVIITCRASQDINNWLAWYLRRPGDAPKLLIYAASSLQSGVPSRFSGSGSGTDFTLTIGSLQPEDFATYYC
QQAHSLPITFGQGTRLEIQRTVAAPSVFIFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC Bispecific Antibody Internal Reference Identifier GOMP001_bsAb_042

Full-length Heavy Chain 1 (anti-CD3; SEQ ID NO: 575)
EVQLVESGGGLVKTGGSLRLSCVASGFSFKKAWMNWVRKAPGKGLEWVGRIKRNTDGGPADYAAEVKGRFTLSRDDSKKTLYLQ
MNSLKTEDTAVYYCTTLDSSSWYVGYYYMDVWGKGTTVTVSSASTKGPSVFPLAPSSKSTSGGTAALGCLVADYFPEPVTVSWNSG
ALTSGVHTFPAVLQSSGLYSLSSVVTVPSSSLGTQTYICNVNHKPSNTKVDEKVEPKSCDKTHTCPPCPAPEAAGGPSVFLFPPKPKDT
LMISRTPEVTCVVVDVSHEDPEVKFNWYVDGVEVHNAKTKPREEQYNSTYRVVSVLTVLHQDWLNGKEYKCKVSNKALPAPIEKTIS
KAKGQPREPQVYTLPPSREEMTDNQVSLTCLVKGFYPSDIAVEWESNGQPENNYKTTPPVLMSDGSFFLASKLTVDKSRWQQGNV
FSCSVMHEALHNHYTQKSLSLSPG Full-length Light Chain 1 (anti-CD3; SEQ ID NO: 576)
RIQMTQSPSSVSASVGDRVIITCRASQDINNWLAWYLDRPGKAPKLLIYAASSLQSGVPSRFSGSGSGTDFTLTIGSLQPEDFATYYC
QQAHSLPITFGQGTRLEIQRTVAAPSVFIFPPSDKQLKSGTARVVCLLNNFYPREAKVQWKVDNALQSGNSQESVTEQDSKDSTYSL
SSTLTLSKADYEKHKVYACEVTHQGLSSPVTKSFNRGEC Full-length Heavy Chain 2 (anti-EGFR; SEQ ID NO: 591)
QVQLVQSGAEVKKPGASVKVSCKASGYTFTSHWMHWVRYAPGQGLEWIGEFNPSNGRTNYNEKFKSKATMTVDTSTNTAYMEL
SSLRSEDTAVYYCASRDYDYDGRYFDYWGRGTLVTVSSASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKVEPKSCDKTHTCPPCPAPEAAGGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISKAKG
QPRRPRVYTLPPSREEMTKNQVSLVCLVKGFYPSDIAVEWESNGQPENNYKTTPPVLDSDGSFFLYSVLTVDKSRWQQGNVFSCSV
MHEALHNHYTQKSLSLSPG Full-length Light Chain 2 (anti-EGFR; SEQ ID NO: 592)
DIQMTQSPSSLSASVGDRVTITCSASSSVTYMYWYQRKPGDAPKLLIYDTSNLASGVPSRFSGSGSGTDYTFTISSLQPEDIATYYCQQ
WSSHIFTFGQGTKVEIKRTVAAPSVFIFPPSDEQLKSGTASVVCLLNNFYPREAKVQWKVDNALQSGNSQESVTEQDSKDSTYSLSST
LTLSKADYEKHKVYACEVTHQGLSSPVTKSFNRGEC Bispecific Antibody Internal Reference Identifier GOMP001_bsAb_043

Full-length Heavy Chain 1 (anti-EGFR; SEQ ID NO: 589)
QVQLVQSGAEVKKPGASVKVSCKASGYTFTSHWMHWVRKAPGQGLEWIGEFNPSNGRTNYNEEFKSKATMTVDTSTNTAYMEL
SSLRSEDTAVYYCASRDYDYDGRYFDYWGQGTLVTVSSASTKGPSVFPLAPSSKSTSGGTAALGCLVADYFPEPVTVSWNSGALTSG
VHTFPAVLQSSGLYSLSSVVTVPSSSLGTQTYICNVNHKPSNTKVDEKVEPKSCDKTHTCPPCPAPEAAGGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISKAKG
QPREPQVYTLPPSREEMTDNQVSLTCLVKGFYPSDIAVEWESNGQPENNYKTTPPVLMSDGSFFLASKLTVDKSRWQQGNVFSCS
VMHEALHNHYTQKSLSLSPG Full-length Light Chain 1 (anti-EGFR; SEQ ID NO: 590)
RIQMTQSPSSLSASVGDRVTITCSASSSVTYMYWYQDKPGKAPKLLIYDTSNLASGVPSRFSGSGSGTDYTFTISSLQPEDIATYYCQQ
WSSHIFTFGQGTKVEIKRTVAAPSVFIFPPSDKQLKSGTARVVCLLNNFYPREAKVQWKVDNALQSGNSQESVTEQDSKDSTYSLSST
LTLSKADYEKHKVYACEVTHQGLSSPVTKSFNRGEC Full-length Heavy Chain 2 (anti-CD3; SEQ ID NO: 577)
EVQLVESGGGLVKTGGSLRLSCVASGFSFKKAWMNWVRYAPGKGLEWVGRIKRNTDGGTADYAARVKGRFTLSRDDSKKTLFLQ
MNSLKTEDTAVYYCTTLDSSSYYVGYYYMDVWGRGTTVTVSSASTKGPSVFPLAPSSKSTSGGTAALGCLVKDYFPEPVTVSWNSG
ALTSGVHTFPAVLQSSGLYSLSSVVTVPSSSLGTQTYICNVNHKPSNTKVDKKVEPKSCDKTHTCPPCPAPEAAGGPSVFLFPPKPKDT
LMISRTPEVTCVVVDVSHEDPEVKFNWYVDGVEVHNAKTKPREEQYNSTYRVVSVLTVLHQDWLNGKEYKCKVSNKALPAPIEKTIS
KAKGQPRRPRVYTLPPSREEMTKNQVSLVCLVKGFYPSDIAVEWESNGQPENNYKTTPPVLDSDGSFFLYSVLTVDKSRWQQGNVF
SCSVMHEALHNHYTQKSLSLSPG Full-length Light Chain 2 (anti-CD3; SEQ ID NO: 578)
DIQMTQSPSSVSASVGDRVTITCRASQDINNWLAWYQRKPGDAPKLLIYTASSLQSGVPSRFSGSGSGTDFTLTIGSLQPEDFATYYC
QQAHSLPITFGQGTRLEIKRTVAAPSVFIFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC -continued Bispecific Antibody Internal Reference Identifier GOMP001_bsAb_044

Full-length Heavy Chain 1 (anti-CD3; SEQ ID NO: 577)
EVQLVESGGGLVKTGGSLRLSCVASGFSFKKAWMNWVRKAPGKGLEWVGRIKRNTDGGTADYAAEVKGRFTLSRDDSKKTLFLQ
MNSLKTEDTAVYYCTTLDSSSYYVGYYYMDVWGKGTTVTVSSASTKGPSVFPLAPSSKSTSGGTAALGCLVADYFPEPVTVSWNSG
ALTSGVHTFPAVLQSSGLYSLSSVVTVPSSSLGTQTYICNVNHKPSNTKVDEKVEPKSCDKTHTCPPCPAPEAAGGPSVFLFPPKPKDT
LMISRTPEVTCVVVDVSHEDPEVKFNWYVDGVEVHNAKTKPREEQYNSTYRVVSVLTVLHQDWLNGKEYKCKVSNKALPAPIEKTIS
KAKGQPREPQVYTLPPSREEMTDNQVSLTCLVKGFYPSDIAVEWESNGQPENNYKTTPPVLMSDGSFFLASKLTVDKSRWQQGNV
FSCSVMHEALHNHYTQKSLSLSPG Full-length Light Chain 1 (anti-CD3; SEQ ID NO: 578)
RIQMTQSPSSVSASVGDRVTITCRASQDINNWLAWYQDKPGKAPKLLIYTASSLQSGVPSRFSGSGSGTDFTLTIGSLQPEDFATYYC
QQAHSLPITFGQGTRLEIKRTVAAPSVFIFPPSDKQLKSGTARVVCLLNNFYPREAKVQWKVDNALQSGNSQESVTEQDSKDSTYSLS
STLTLSKADYEKHKVYACEVTHQGLSSPVTKSFNRGEC Full-length Heavy Chain 2 (anti-EGFR; SEQ ID NO: 591)
QVQLVQSGAEVKKPGASVKVSCKASGYTFTSHWMHWVRYAPGQGLEWIGEFNPSNGRTNYNEKFKSKATMTVDTSTNTAYMEL
SSLRSEDTAVYYCASRDYDYDGRYFDYWGRGTLVTVSSASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKVEPKSCDKTHTCPPCPAPEAAGGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISKAKG
QPRRPRVYTLPPSREEMTKNQVSLVCLVKGFYPSDIAVEWESNGQPENNYKTTPPVLDSDGSFFLYSVLTVDKSRWQQGNVFSCSV
MHEALHNHYTQKSLSLSPG Full-length Light Chain 2 (anti-EGFR; SEQ ID NO: 592)
DIQMTQSPSSLSASVGDRVTITCSASSSVTYMYWYQRKPGDAPKLLIYDTSNLASGVPSRFSGSGSGTDYTFTISSLQPEDIATYYCQQ
WSSHIFTFGQGTKVEIKRTVAAPSVFIFPPSDEQLKSGTASVVCLLNNFYPREAKVQWKVDNALQSGNSQESVTEQDSKDSTYSLSST
LTLSKADYEKHKVYACEVTHQGLSSPVTKSFNRGEC Bispecific Antibody Internal Reference Identifier GOMP001_bsAb_045

Full-length Heavy Chain 1 (anti-EGFR; SEQ ID NO: 589)
QVQLVQSGAEVKKPGASVKVSCKASGYTFTSHWMHWVRKAPGQGLEWIGEFNPSNGRTNYNEEFKSKATMTVDTSTNTAYMEL
SSLRSEDTAVYYCASRDYDYDGRYFDYWGQGTLVTVSSASTKGPSVFPLAPSSKSTSGGTAALGCLVADYFPEPVTVSWNSGALTSG
VHTFPAVLQSSGLYSLSSVVTVPSSSLGTQTYICNVNHKPSNTKVDEKVEPKSCDKTHTCPPCPAPEAAGGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISKAKG
QPREPQVYTLPPSREEMTDNQVSLTCLVKGFYPSDIAVEWESNGQPENNYKTTPPVLMSDGSFFLASKLTVDKSRWQQGNVFSCS
VMHEALHNHYTQKSLSLSPG Full-length Light Chain 1 (anti-EGFR; SEQ ID NO: 590)
RIQMTQSPSSLSASVGDRVTITCSASSSVTYMYWYQDKPGKAPKLLIYDTSNLASGVPSRFSGSGSGTDYTFTISSLQPEDIATYYCQQ
WSSHIFTFGQGTKVEIKRTVAAPSVFIFPPSDKQLKSGTARVVCLLNNFYPREAKVQWKVDNALQSGNSQESVTEQDSKDSTYSLSST
LTLSKADYEKHKVYACEVTHQGLSSPVTKSFNRGEC Full-length Heavy Chain 2 (anti-CD3; SEQ ID NO: 579)
EVQLVESGGGLVQPGRSLRLSCATSGFTFADYTMHWVRYAPGKGLEWVSGISWNSGSIDYADRVKGRFTISRDNAKKSLYLQMNS
LRAEDTALYFCAKDSSGYGHYYFYYLDVWGRGTTVTVSSASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKVEPKSCDKTHTCPPCPAPEAAGGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISKAKG
QPRRPRVYTLPPSREEMTKNQVSLVCLVKGFYPSDIAVEWESNGQPENNYKTTPPVLDSDGSFFLYSVLTVDKSRWQQGNVFSCSV
MHEALHNHYTQKSLSLSPG Full-length Light Chain 2 (anti-CD3; SEQ ID NO: 580)
EIVMTQSPGTLSVSPGKRATLSCRASQSVSSNLAWYQRKPGDGPRLLIYSTSTRATGIPARFSGSGSGTEFTLTISSLQSEDSAVYYCQ
HYNNWPHFGQGTRLEIKRTVAAPSVFIFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC Bispecific Antibody Internal Reference Identifier GOMP001_bsAb_046

Full-length Heavy Chain 1 (anti-CD3; SEQ ID NO: 579)
EVQLVESGGGLVQPGRSLRLSCATSGFTFADYTMHWVRKAPGKGLEWVSGISWNSGSIDYADEVKGRFTISRDNAKKSLYLQMNS
LRAEDTALYFCAKDSSGYGHYYFYYLDVWGKGTTVTVSSASTKGPSVFPLAPSSKSTSGGTAALGCLVADYFPEPVTVSWNSGALTSG
VHTFPAVLQSSGLYSLSSVVTVPSSSLGTQTYICNVNHKPSNTKVDEKVEPKSCDKTHTCPPCPAPEAAGGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISKAKG
QPREPQVYTLPPSREEMTDNQVSLTCLVKGFYPSDIAVEWESNGQPENNYKTTPPVLMSDGSFFLASKLTVDKSRWQQGNVFSCS
VMHEALHNHYTQKSLSLSPG Full-length Light Chain 1 (anti-CD3; SEQ ID NO: 580)
RIVMTQSPGTLSVSPGKRATLSCRASQSVSSNLAWYQDKPGQGPRLLIYSTSTRATGIPARFSGSGSGTEFTLTISSLQSEDSAVYYCQ
HYNNWPHFGQGTRLEIKRTVAAPSVFIFPPSDKQLKSGTARVVCLLNNFYPREAKVQWKVDNALQSGNSQESVTEQDSKDSTYSLS
STLTLSKADYEKHKVYACEVTHQGLSSPVTKSFNRGEC Full-length Heavy Chain 2 (anti-EGFR; SEQ ID NO: 591)
QVQLVQSGAEVKKPGASVKVSCKASGYTFTSHWMHWVRYAPGQGLEWIGEFNPSNGRTNYNEKFKSKATMTVDTSTNTAYMEL
SSLRSEDTAVYYCASRDYDYDGRYFDYWGRGTLVTVSSASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKVEPKSCDKTHTCPPCPAPEAAGGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISKAKG
QPRRPRVYTLPPSREEMTKNQVSLVCLVKGFYPSDIAVEWESNGQPENNYKTTPPVLDSDGSFFLYSVLTVDKSRWQQGNVFSCSV
MHEALHNHYTQKSLSLSPG Full-length Light Chain 2 (anti-EGFR; SEQ ID NO: 592)
DIQMTQSPSSLSASVGDRVTITCSASSSVTYMYWYQRKPGDAPKLLIYDTSNLASGVPSRFSGSGSGTDYTFTISSLQPEDIATYYCQQ
WSSHIFTFGQGTKVEIKRTVAAPSVFIFPPSDEQLKSGTASVVCLLNNFYPREAKVQWKVDNALQSGNSQESVTEQDSKDSTYSLSST
LTLSKADYEKHKVYACEVTHQGLSSPVTKSFNRGEC Bispecific Antibody Internal Reference Identifier GOMP001_bsAb_047

Full-length Heavy Chain 1 (anti-EGFR; SEQ ID NO: 589)
QVQLVQSGAEVKKPGASVKVSCKASGYTFTSHWMHWVRKAPGQGLEWIGEFNPSNGRTNYNEEFKSKATMTVDTSTNTAYMEL
SSLRSEDTAVYYCASRDYDYDGRYFDYWGQGTLVTVSSASTKGPSVFPLAPSSKSTSGGTAALGCLVADYFPEPVTVSWNSGALTSG
VHTFPAVLQSSGLYSLSSVVTVPSSSLGTQTYICNVNHKPSNTKVDEKVEPKSCDKTHTCPPCPAPEAAGGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISKAKG
QPREPQVYTLPPSREEMTDNQVSLTCLVKGFYPSDIAVEWESNGQPENNYKTTPPVLMSDGSFFLASKLTVDKSRWQQGNVFSCS
VMHEALHNHYTQKSLSLSPG Full-length Light Chain 1 (anti-EGFR; SEQ ID NO: 590)
RIQMTQSPSSLSASVGDRVTITCSASSSVTYMYWYQDKPGKAPKLLIYDTSNLASGVPSRFSGSGSGTDYTFTISSLQPEDIATYYCQQ
WSSHIFTFGQGTKVEIKRTVAAPSVFIFPPSDKQLKSGTARVVCLLNNFYPREAKVQWKVDNALQSGNSQESVTEQDSKDSTYSLSST
LTLSKADYEKHKVYACEVTHQGLSSPVTKSFNRGEC Full-length Heavy Chain 2 (anti-CD3; SEQ ID NO: 581)
EVQLVESGGGLVQPGRSLRLSCAASGFTFDDYTMHWVRYAPGKGLEWVSGISWNSGSIGYADRVKGRFTISRDNAKNSLYLQMNS
LRAEDTALYYCAKDSSGYGYYYYYSMDVWGRGTTVTVSSASTKGPSVFPLAPSSKSTSGGTAALGCLVKDYFPEPVTVSWNSGALTS
GVHTFPAVLQSSGLYSLSSVVTVPSSSLGTQTYICNVNHKPSNTKVDKKVEPKSCDKTHTCPPCPAPEAAGGPSVFLFPPKPKDTLMIS
RTPEVTCVVVDVSHEDPEVKFNWYVDGVEVHNAKTKPREEQYNSTYRVVSVLTVLHQDWLNGKEYKCKVSNKALPAPIEKTISKAK
GQPRRPRVYTLPPSREEMTKNQVSLVCLVKGFYPSDIAVEWESNGQPENNYKTTPPVLDSDGSFFLYSVLTVDKSRWQQGNVFSCS
VMHEALHNHYTQKSLSLSPG Full-length Light Chain 2 (anti-CD3; SEQ ID NO: 582)
EIVMTQSPATLSVSPGERATLSCRASQSVSSNLAWYQRKPGDAPRLLIYGASTRATGIPARFSGSGSGTEFTLTISSLQSEDFAVYYCQL
YYNWPHFGQGTRLAIKRTVAAPSVFIFPPSDEQLKSGTASVVCLLNNFYPREAKVQWKVDNALQSGNSQESVTEQDSKDSTYSLSST
LTLSKADYEKHKVYACEVTHQGLSSPVTKSFNRGEC Bispecific Antibody Internal Reference Identifier GOMP001_bsAb_048

Full-length Heavy Chain 1 (anti-CD3; SEQ ID NO: 581)
EVQLVESGGGLVQPGRSLRLSCAASGFTFDDYTMHWVRKAPGKGLEWVSGISWNSGSIGYADEVKGRFTISRDNAKNSLYLQMNS
LRAEDTALYYCAKDSSGYGYYYYYSMDVWGKGTTVTVSSASTKGPSVFPLAPSSKSTSGGTAALGCLVADYFPEPVTVSWNSGALTS
GVHTFPAVLQSSGLYSLSSVVTVPSSSLGTQTYICNVNHKPSNTKVDEKVEPKSCDKTHTCPPCPAPEAAGGPSVFLFPPKPKDTLMIS
RTPEVTCVVVDVSHEDPEVKFNWYVDGVEVHNAKTKPREEQYNSTYRVVSVLTVLHQDWLNGKEYKCKVSNKALPAPIEKTISKAK
GQPREPQVYTLPPSREEMTDNQVSLTCLVKGFYPSDIAVEWESNGQPENNYKTTPPVLMSDGSFFLASKLTVDKSRWQQGNVFSC
SVMHEALHNHYTQKSLSLSPG Full-length Light Chain 1 (anti-CD3; SEQ ID NO: 582)
RIVMTQSPATLSVSPGERATLSCRASQSVSSNLAWYQDKPGQAPRLLIYGASTRATGIPARFSGSGSGTEFTLTISSLQSEDFAVYYCQ
LYYNWPHFGQGTRLAIKRTVAAPSVFIFPPSDKQLKSGTARVVCLLNNFYPREAKVQWKVDNALQSGNSQESVTEQDSKDSTYSLSS
TLTLSKADYEKHKVYACEVTHQGLSSPVTKSFNRGEC Full-length Heavy Chain 2 (anti-EGFR; SEQ ID NO: 591)
QVQLVQSGAEVKKPGASVKVSCKASGYTFTSHWMHWVRYAPGQGLEWIGEFNPSNGRTNYNEKFKSKATMTVDTSTNTAYMEL
SSLRSEDTAVYYCASRDYDYDGRYFDYWGRGTLVTVSSASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKVEPKSCDKTHTCPPCPAPEAAGGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISKAKG
QPRRPRVYTLPPSREEMTKNQVSLVCLVKGFYPSDIAVEWESNGQPENNYKTTPPVLDSDGSFFLYSVLTVDKSRWQQGNVFSCSV
MHEALHNHYTQKSLSLSPG Full-length Light Chain 2 (anti-EGFR; SEQ ID NO: 592)
DIQMTQSPSSLSASVGDRVTITCSASSSVTYMYWYQRKPGDAPKLLIYDTSNLASGVPSRFSGSGSGTDYTFTISSLQPEDIATYYCQQ
WSSHIFTFGQGTKVEIKRTVAAPSVFIFPPSDEQLKSGTASVVCLLNNFYPREAKVQWKVDNALQSGNSQESVTEQDSKDSTYSLSST
LTLSKADYEKHKVYACEVTHQGLSSPVTKSFNRGEC Bispecific Antibody Internal Reference Identifier GOMP001_bsAb_049

Full-length Heavy Chain 1 (anti-EGFR; SEQ ID NO: 589)
QVQLVQSGAEVKKPGASVKVSCKASGYTFTSHWMHWVRKAPGQGLEWIGEFNPSNGRTNYNEEFKSKATMTVDTSTNTAYMEL
SSLRSEDTAVYYCASRDYDYDGRYFDYWGQGTLVTVSSASTKGPSVFPLAPSSKSTSGGTAALGCLVADYFPEPVTVSWNSGALTSG
VHTFPAVLQSSGLYSLSSVVTVPSSSLGTQTYICNVNHKPSNTKVDEKVEPKSCDKTHTCPPCPAPEAAGGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISKAKG
QPREPQVYTLPPSREEMTDNQVSLTCLVKGFYPSDIAVEWESNGQPENNYKTTPPVLMSDGSFFLASKLTVDKSRWQQGNVFSCS
VMHEALHNHYTQKSLSLSPG Full-length Light Chain 1 (anti-EGFR; SEQ ID NO: 590)
RIQMTQSPSSLSASVGDRVTITCSASSSVTYMYWYQDKPGKAPKLLIYDTSNLASGVPSRFSGSGSGTDYTFTISSLQPEDIATYYCQQ
WSSHIFTFGQGTKVEIKRTVAAPSVFIFPPSDKQLKSGTARVVCLLNNFYPREAKVQWKVDNALQSGNSQESVTEQDSKDSTYSLSST
LTLSKADYEKHKVYACEVTHQGLSSPVTKSFNRGEC Full-length Heavy Chain 2 (anti-CD3; SEQ ID NO: 583)
QVQLVESGGGVVQPGRSLRLSCAASGFTFSTYGMHWVRYAPGKGLEWVAVIWYDGSHKYYADRVKGRFTISRDNSKKTLYLQMN
SLRAEDTGIYYCARTGISGNMSYFYFDHWGRGILVTVSSASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKVEPKSCDKTHTCPPCPAPEAAGGPSVFLFPPKPKDTLMISR -continued TPEVTCVVVDVSHEDPEVKFNWYVDGVEVHNAKTKPREEQYNSTYRVVSVLTVLHQDWLNGKEYKCKVSNKALPAPIEKTISKAKG
QPRRPRVYTLPPSREEMTKNQVSLVCLVKGFYPSDIAVEWESNGQPENNYKTTPPVLDSDGSFFLYSVLTVDKSRWQQGNVFSCSV
MHEALHNHYTQKSLSLSPG Full-length Light Chain 2 (anti-CD3; SEQ ID NO: 584)
DIVMTQSPDSLAVSLGERATINCKSSQSVLYSSKNRNYLAWYQRKQGDPPKMFIYWASTRESGVPDRFSGSGSGTDFTLTISSLQAE
DVAVYYCQQYYGPVTFGGGTKVEIKRTVAAPSVFIFPPSDEQLKSGTASVVCLLNNFYPREAKVQWKVDNALQSGNSQESVTEQDS
KDSTYSLSSTLTLSKADYEKHKVYACEVTHQGLSSPVTKSFNRGEC Bispecific Antibody Internal Reference Identifier GOMP001_bsAb_050

Full-length Heavy Chain 1 (anti-CD3; SEQ ID NO: 583)
QVQLVESGGGVVQPGRSLRLSCAASGFTFSTYGMHWVRKAPGKGLEWVAVIWYDGSHKYYADEVKGRFTISRDNSKKTLYLQMN
SLRAEDTGIYYCARTGISGNMSYFYFDHWGQGILVTVSSASTKGPSVFPLAPSSKSTSGGTAALGCLVADYFPEPVTVSWNSGALTSG
VHTFPAVLQSSGLYSLSSVVTVPSSSLGTQTYICNVNHKPSNTKVDEKVEPKSCDKTHTCPPCPAPEAAGGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISKAKG
QPREPQVYTLPPSREEMTDNQVSLTCLVKGFYPSDIAVEWESNGQPENNYKTTPPVLMSDGSFFLASKLTVDKSRWQQGNVFSCS
VMHEALHNHYTQKSLSLSPG Full-length Light Chain 1 (anti-CD3; SEQ ID NO: 584)
RIVMTQSPDSLAVSLGERATINCKSSQSVLYSSKNRNYLAWYQDKQGQPPKMFIYWASTRESGVPDRFSGSGSGTDFTLTISSLQAE
DVAVYYCQQYYGPVTFGGGTKVEIKRTVAAPSVFIFPPSDKQLKSGTARVVCLLNNFYPREAKVQWKVDNALQSGNSQESVTEQDS
KDSTYSLSSTLTLSKADYEKHKVYACEVTHQGLSSPVTKSFNRGEC Full-length Heavy Chain 2 (anti-EGFR; SEQ ID NO: 591)
QVQLVQSGAEVKKPGASVKVSCKASGYTFTSHWMHWVRYAPGQGLEWIGEFNPSNGRTNYNEKFKSKATMTVDTSTNTAYMEL
SSLRSEDTAVYYCASRDYDYDGRYFDYWGRGTLVTVSSASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKVEPKSCDKTHTCPPCPAPEAAGGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISKAKG
QPRRPRVYTLPPSREEMTKNQVSLVCLVKGFYPSDIAVEWESNGQPENNYKTTPPVLDSDGSFFLYSVLTVDKSRWQQGNVFSCSV
MHEALHNHYTQKSLSLSPG Full-length Light Chain 2 (anti-EGFR; SEQ ID NO: 592)
DIQMTQSPSSLSASVGDRVTITCSASSSVTYMYWYQRKPGDAPKLLIYDTSNLASGVPSRFSGSGSGTDYTFTISSLQPEDIATYYCQQ
WSSHIFTFGQGTKVEIKRTVAAPSVFIFPPSDEQLKSGTASVVCLLNNFYPREAKVQWKVDNALQSGNSQESVTEQDSKDSTYSLSST
LTLSKADYEKHKVYACEVTHQGLSSPVTKSFNRGEC Bispecific Antibody Internal Reference Identifier GOMP001_bsAb_051

Full-length Heavy Chain 1 (anti-EGFR; SEQ ID NO: 589)
QVQLVQSGAEVKKPGASVKVSCKASGYTFTSHWMHWVRKAPGQGLEWIGEFNPSNGRTNYNEEFKSKATMTVDTSTNTAYMEL
SSLRSEDTAVYYCASRDYDYDGRYFDYWGQGTLVTVSSASTKGPSVFPLAPSSKSTSGGTAALGCLVADYFPEPVTVSWNSGALTSG
VHTFPAVLQSSGLYSLSSVVTVPSSSLGTQTYICNVNHKPSNTKVDEKVEPKSCDKTHTCPPCPAPEAAGGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISKAKG
QPREPQVYTLPPSREEMTDNQVSLTCLVKGFYPSDIAVEWESNGQPENNYKTTPPVLMSDGSFFLASKLTVDKSRWQQGNVFSCS
VMHEALHNHYTQKSLSLSPG Full-length Light Chain 1 (anti-EGFR; SEQ ID NO: 590)
RIQMTQSPSSLSASVGDRVTITCSASSSVTYMYWYQDKPGKAPKLLIYDTSNLASGVPSRFSGSGSGTDYTFTISSLQPEDIATYYCQQ
WSSHIFTFGQGTKVEIKRTVAAPSVFIFPPSDKQLKSGTARVVCLLNNFYPREAKVQWKVDNALQSGNSQESVTEQDSKDSTYSLSST
LTLSKADYEKHKVYACEVTHQGLSSPVTKSFNRGEC Full-length Heavy Chain 2 (anti-CD3; SEQ ID NO: 585)
QVQLVQSGAEVKKPGASVKVSCKASGYTFTSYYIHWVRYAPGQGLDWMGIINPSGGITGYAQKLQGRVTMTRDTSTTTVYMELSS
LRSDDTAVYYCARGVRGNYYYYYMDVWGRGTTVTVSSASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKVEPKSCDKTHTCPPCPAPEAAGGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISKAKG
QPRRPRVYTLPPSREEMTKNQVSLVCLVKGFYPSDIAVEWESNGQPENNYKTTPPVLDSDGSFFLYSVLTVDKSRWQQGNVFSCSV
MHEALHNHYTQKSLSLSPG Full-length Light Chain 2 (anti-CD3; SEQ ID NO: 586)
EIVLTQSPDFQSVTPKEKVTITCRASQSIGSKLHWYQRKPDDSPKLLIKYASQSFSGVPSRFSGSGSGTDFNLTINSLEAEDAATFYCHQ
SSGLPYTFGQGTKLEIKRTVAAPSVFIFPPSDEQLKSGTASVVCLLNNFYPREAKVQWKVDNALQSGNSQESVTEQDSKDSTYSLSSTL
TLSKADYEKHKVYACEVTHQGLSSPVTKSFNRGEC Bispecific Antibody Internal Reference Identifier GOMP001_bsAb_052

Full-length Heavy Chain 1 (anti-CD3; SEQ ID NO: 585)
QVQLVQSGAEVKKPGASVKVSCKASGYTFTSYYIHWVRKAPGQGLDWMGIINPSGGITGYAQELQGRVTMTRDTSTTTVYMELSS
LRSDDTAVYYCARGVRGNYYYYYMDVWGKGTTVTVSSASTKGPSVFPLAPSSKSTSGGTAALGCLVADYFPEPVTVSWNSGALTSG
VHTFPAVLQSSGLYSLSSVVTVPSSSLGTQTYICNVNHKPSNTKVDEKVEPKSCDKTHTCPPCPAPEAAGGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISKAKG
QPREPQVYTLPPSREEMTDNQVSLTCLVKGFYPSDIAVEWESNGQPENNYKTTPPVLMSDGSFFLASKLTVDKSRWQQGNVFSCS
VMHEALHNHYTQKSLSLSPG Full-length Light Chain 1 (anti-CD3; SEQ ID NO: 586)
RIVLTQSPDFQSVTPKEKVTITCRASQSIGSKLHWYQDKPDQSPKLLIKYASQSFSGVPSRFSGSGSGTDFNLTINSLEAEDAATFYCHQ
SSGLPYTFGQGTKLEIKRTVAAPSVFIFPPSDKQLKSGTARVVCLLNNFYPREAKVQWKVDNALQSGNSQESVTEQDSKDSTYSLSST
LTLSKADYEKHKVYACEVTHQGLSSPVTKSFNRGEC -continued Full-length Heavy Chain 2 (anti-EGFR; SEQ ID NO: 591)
QVQLVQSGAEVKKPGASVKVSCKASGYTFTSHWMHWVRYAPGQGLEWIGEFNPSNGRTNYNEKFKSKATMTVDTSTNTAYMEL
SSLRSEDTAVYYCASRDYDYDGRYFDYWGRGTLVTVSSASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKVEPKSCDKTHTCPPCPAPEAAGGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISKAKG
QPRRPRVYTLPPSREEMTKNQVSLVCLVKGFYPSDIAVEWESNGQPENNYKTTPPVLDSDGSFFLYSVLTVDKSRWQQGNVFSCSV
MHEALHNHYTQKSLSLSPG Full-length Light Chain 2 (anti-EGFR; SEQ ID NO: 592)
DIQMTQSPSSLSASVGDRVTITCSASSSVTYMYWYQRKPGDAPKLLIYDTSNLASGVPSRFSGSGSGTDYTFTISSLQPEDIATYYCQQ
WSSHIFTFGQGTKVEIKRTVAAPSVFIFPPSDEQLKSGTASVVCLLNNFYPREAKVQWKVDNALQSGNSQESVTEQDSKDSTYSLSST
LTLSKADYEKHKVYACEVTHQGLSSPVTKSFNRGEC Bispecific Antibody Internal Reference Identifier GOMP001_bsAb_055

Full-length Heavy Chain 1 (anti-EGFR; SEQ ID NO: 589)
QVQLVQSGAEVKKPGASVKVSCKASGYTFTSHWMHWVRKAPGQGLEWIGEFNPSNGRTNYNEEFKSKATMTVDTSTNTAYMEL
SSLRSEDTAVYYCASRDYDYDGRYFDYWGQGTLVTVSSASTKGPSVFPLAPSSKSTSGGTAALGCLVADYFPEPVTVSWNSGALTSG
VHTFPAVLQSSGLYSLSSVVTVPSSSLGTQTYICNVNHKPSNTKVDEKVEPKSCDKTHTCPPCPAPEAAGGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISKAKG
QPREPQVYTLPPSREEMTDNQVSLTCLVKGFYPSDIAVEWESNGQPENNYKTTPPVLMSDGSFFLASKLTVDKSRWQQGNVFSCS
VMHEALHNHYTQKSLSLSPG Full-length Light Chain 1 (anti-EGFR; SEQ ID NO: 590)
RIQMTQSPSSLSASVGDRVTITCSASSSVTYMYWYQDKPGKAPKLLIYDTSNLASGVPSRFSGSGSGTDYTFTISSLQPEDIATYYCQQ
WSSHIFTFGQGTKVEIKRTVAAPSVFIFPPSDKQLKSGTARVVCLLNNFYPREAKVQWKVDNALQSGNSQESVTEQDSKDSTYSLSST
LTLSKADYEKHKVYACEVTHQGLSSPVTKSFNRGEC Full-length Heavy Chain 2 (anti-CD3; SEQ ID NO: 587)
EVNLVESGGGLVQPGRSLRLSCAASGFTFDDYTMHWVRYVPGKGLEWVSNISWNSGSLGYADRVKGRFTISRDNAKDSLYLQMN
SLRVEDTALYYCAKDSSGYGHYNSYYMDVWGRGTTVTVSSASTKGPSVFPLAPSSKSTSGGTAALGCLVKDYFPEPVTVSWNSGALT
SGVHTFPAVLQSSGLYSLSSVVTVPSSSLGTQTYICNVNHKPSNTKVDKKVEPKSCDKTHTCPPCPAPEAAGGPSVFLFPPKPKDTLMI
SRTPEVTCVVVDVSHEDPEVKFNWYVDGVEVHNAKTKPREEQYNSTYRVVSVLTVLHQDWLNGKEYKCKVSNKALPAPIEKTISKA
KGQPRRPRVYTLPPSREEMTKNQVSLVCLVKGFYPSDIAVEWESNGQPENNYKTTPPVLDSDGSFFLYSVLTVDKSRWQQGNVFSC
SVMHEALHNHYTQKSLSLSPG Full-length Light Chain 2 (anti-CD3; SEQ ID NO: 588)
DIQMTQSPSSLSASVGDRVTITCRASQSIRNYLNWYQRKPGDAPKVLIYSASSLQSGVPSRFSGSGSGTDFTLTISSLQPEDFASFYCQ
QTYSTPITFGQGTRLEIKRTVAAPSVFIFPPSDEQLKSGTASVVCLLNNFYPREAKVQWKVDNALQSGNSQESVTEQDSKDSTYSLSST
LTLSKADYEKHKVYACEVTHQGLSSPVTKSFNRGEC Bispecific Antibody Internal Reference Identifier GOMP001_bsAb_056

Full-length Heavy Chain 1 (anti-CD3; SEQ ID NO: 587)
EVNLVESGGGLVQPGRSLRLSCAASGFTFDDYTMHWVRKVPGKGLEWVSNISWNSGSLGYADEVKGRFTISRDNAKDSLYLQMNS
LRVEDTALYYCAKDSSGYGHYNSYYMDVWGKGTTVTVSSASTKGPSVFPLAPSSKSTSGGTAALGCLVADYFPEPVTVSWNSGALTS
GVHTFPAVLQSSGLYSLSSVVTVPSSSLGTQTYICNVNHKPSNTKVDEKVEPKSCDKTHTCPPCPAPEAAGGPSVFLFPPKPKDTLMIS
RTPEVTCVVVDVSHEDPEVKFNWYVDGVEVHNAKTKPREEQYNSTYRVVSVLTVLHQDWLNGKEYKCKVSNKALPAPIEKTISKAK
GQPREPQVYTLPPSREEMTDNQVSLTCLVKGFYPSDIAVEWESNGQPENNYKTTPPVLMSDGSFFLASKLTVDKSRWQQGNVFSC
SVMHEALHNHYTQKSLSLSPG Full-length Light Chain 1 (anti-CD3; SEQ ID NO: 588)
RIQMTQSPSSLSASVGDRVTITCRASQSIRNYLNWYQDKPGKAPKVLIYSASSLQSGVPSRFSGSGSGTDFTLTISSLQPEDFASFYCQ
QTYSTPITFGQGTRLEIKRTVAAPSVFIFPPSDKQLKSGTARVVCLLNNFYPREAKVQWKVDNALQSGNSQESVTEQDSKDSTYSLSS
TLTLSKADYEKHKVYACEVTHQGLSSPVTKSFNRGEC Full-length Heavy Chain 2 (anti-EGFR; SEQ ID NO: 591)
QVQLVQSGAEVKKPGASVKVSCKASGYTFTSHWMHWVRYAPGQGLEWIGEFNPSNGRTNYNEKFKSKATMTVDTSTNTAYMEL
SSLRSEDTAVYYCASRDYDYDGRYFDYWGRGTLVTVSSASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKVEPKSCDKTHTCPPCPAPEAAGGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISKAKG
QPRRPRVYTLPPSREEMTKNQVSLVCLVKGFYPSDIAVEWESNGQPENNYKTTPPVLDSDGSFFLYSVLTVDKSRWQQGNVFSCSV
MHEALHNHYTQKSLSLSPG Full-length Light Chain 2 (anti-EGFR; SEQ ID NO: 592)
DIQMTQSPSSLSASVGDRVTITCSASSSVTYMYWYQRKPGDAPKLLIYDTSNLASGVPSRFSGSGSGTDYTFTISSLQPEDIATYYCQQ
WSSHIFTFGQGTKVEIKRTVAAPSVFIFPPSDEQLKSGTASVVCLLNNFYPREAKVQWKVDNALQSGNSQESVTEQDSKDSTYSLSST
LTLSKADYEKHKVYACEVTHQGLSSPVTKSFNRGEC Characterization of Anti-CD3 Antibodies Anti-CD3 antibodies disclosed herein exhibit one or more desirable characteristics. Thus, anti-CD3 antibody-producing cells (e.g., human B cells) may be selected, cloned, and further screened for these desirable characteristics including, for example, robust growth, high antibody production, or desirable antibody characteristics. For example, anti-CD3 antibodies may be characterized by their epitope specificity or a number of different physical characteristics including, e.g., binding affinities, melting temperature ($T_m$), and isoelectric points.

Anti-CD3 antibodies disclosed herein may also be characterized by their epitope specificity. Anti-CD3 antibodies disclosed herein will associate with, or bind to, discrete epitopes or determinants presented by the selected target(s). As used herein, the term "epitope" refers to that portion of the target antigen capable of being recognized and specifically bound by a particular antibody. Epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 to 10 amino acids in a unique spatial conformation. More specifically, the skilled artisan will appreciate the term epitope includes any protein determinant capable of specific binding to an immunoglobulin or T-cell receptor or otherwise interacting with a molecule. Epitopic determinants generally consist of chemically active surface groupings of molecules such as amino acids or carbohydrate or sugar side chains and generally have specific three-dimensional structural characteristics, as well as specific charge characteristics. Additionally, an epitope may be linear or conformational. In a linear epitope, all of the points of interaction between the protein and the interacting molecule (such as an antibody) occur linearly along the primary amino acid sequence of the protein. In a conformational epitope, the points of interaction occur across amino acid residues on the protein that are linearly separated from one another.

The term "epitope" refers to the amino acid residues, of an antigen, that are bound by an antibody. An epitope can be a linear epitope, a conformational epitope, or a hybrid epitope. An epitope can be determined according to different experimental techniques, also called "epitope mapping techniques." It is understood that the determination of an epitope may vary based on the different epitope mapping techniques used and may also vary with the different experimental conditions used, e.g., due to the conformational changes or cleavages of the antigen induced by specific experimental conditions. Epitope mapping techniques are known in the art, including, but not limited to, X-ray crystallography, nuclear magnetic resonance (NMR) spectroscopy, electron microscopy, site-directed mutagenesis, species swap mutagenesis, alanine-scanning mutagenesis, hydrogen-deuterium exchange (HDX), and cross-blocking assays.

Once a desired epitope on an antigen is determined, it is possible to generate antibodies to that epitope, e.g., by immunizing with a peptide comprising the epitope using techniques known in the art. Alternatively, during the discovery process, the generation and characterization of antibodies may elucidate information about desirable epitopes. From this information, it is then possible to competitively screen antibodies for binding to the same epitope. An approach to achieve this is to conduct competition studies to find antibodies that competitively bind with one another, i.e., the antibodies compete for binding to the antigen. A high throughput process for binning antibodies based upon their cross-competition is known in the art.

As used herein, the term "binning" refers to a method to group antibodies based on their antigen binding characteristics. The grouping is somewhat arbitrary, depending on how different the observed binding patterns of the antibodies tested. Thus, while the technique is a useful tool for categorizing antibodies, the bins do not always directly correlate with epitopes and such initial determinations of epitope binding should be further confirmed by other art recognized methodology.

With this caveat one can determine whether a selected primary antibody (or fragment thereof) binds to the same epitope or cross competes for binding with a second antibody by using methods known in the art. In one embodiment, one exposes cells expressing CD3, such as a T-cell, to a first antibody under saturating conditions and then measures the ability of a second antibody to bind to the same cells. If the second antibody is able to bind, then the second antibody binds to a different epitope than the first antibody. However, if the second antibody is not able to bind, then the second antibody binds to the same epitope, an overlapping epitope, or an epitope that is in close proximity to the epitope bound by the first antibody. As known in the art, the desired data can be obtained using solid phase direct or indirect radioimmunoassay (RIA), solid phase direct or indirect enzyme immunoassay (EIA), sandwich competition assay, surface plasmon resonance, bio-layer interferometry, or flow cytometric methodology.

As used herein, the term "compete" means competition between antibodies as determined by an assay in which the antibody or immunologically-reactive fragment under test prevents or inhibits specific binding of a reference antibody to a common antigen. Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually, the test immunoglobulin is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Additional details regarding methods for determining competitive binding are provided in the Examples herein. Usually, when a competing antibody is present in excess, it will inhibit specific binding of a reference antibody to a common antigen by at least 40%, 45%, 50%, 55%, 60%, 65%, 70% or 75%. In some instance, binding is inhibited by at least 80%, 85%, 90%, 95%, or 97% or more.

Anti-CD3 antibodies disclosed herein may also be characterized by their binding affinity. In some embodiments, anti-CD3 antibodies specifically bind to a target antigen expressed on a cell, i.e., the dissociation constant $K_d$ ($k_{off}/k_{on}$) is $\leq 10^{-8}$M. The antibody specifically binds it antigen with high affinity when the $K_d$ is $\leq 5\times10^{-9}$M, and with very high affinity when the $K_d$ is $\leq 5\times10^{-10}$M. In particular embodiments, the antibody has a $K_d$ of $\leq 10^{-9}$M and an off-rate of about $1\times10^{-4}$/sec. In other embodiments, the off-rate is $\leq 1\times10^{-5}$/sec. In other embodiments, the antibodies will bind with a $K_d$ of between about $10^{-8}$M and $10^{-10}$M, and in yet other embodiments, antibodies bind with a $K_d \leq 2\times10^{-10}$M. Still other selected embodiments comprise antibodies that have a disassociation constant or $K_d$ ($k_{off}/k_{on}$) of less than $10^{-2}$M, less than $5\times10^{-2}$M, less than $10^{-3}$M, less than $5\times10^{-3}$M, less than $10^{4}$M, less than $5\times10^{-4}$M, less than $10^{-5}$M, less than $5\times10^{-5}$M, less than $10^{-6}$M, less than $5\times10^{-6}$M, less than $10^{-7}$M, less than $5\times10^{-7}$M, less than $10^{-8}$M, less than $5\times10^{-8}$M, less than $10^{-9}$M, less than $5\times10^{-9}$M, less than $10^{-10}$M, less than $5\times10^{-10}$M, less than $10^{-11}$M, less than $5\times10^{-11}$M, less than $10^{-12}$M, less than $5\times10^{-12}$M, less than $10^{-13}$M, less than $5\times10^{-13}$M, less than $10^{-14}$M, less than $5\times10^{-14}$M, less than $10^{-15}$M, or less than $5\times10^{-15}$M.

In another embodiment, an anti-CD3 antibody that specifically binds to its antigen has an association rate constant or $k_{on}$ rate ((Ab)+antigen $(Ag)^{k}{}_{on}\leftarrow$Ab-Ag) of at least $10^5M^{-1}s^{-1}$, at least $2\times10^5M^{-1}s^{-1}$, at least $5\times10^5M^{-1}s^{-1}$, at least $10^6M^{-1}s^{-1}$, at least $5\times10^6M^{-1}s^{-1}$, at least $107M^{-1}s^{-1}$, at least $5\times10^7M^{-1}s^{-1}$, or at least $10^8M^{-1}s^{-1}$.

In another embodiment, an anti-CD3 antibody that specifically binds to its antigen has a disassociation rate constant or $k_{off}$ rate ((Ab)+antigen $(Ag)^{k}{}_{off} \leftarrow$ Ab-Ag) of less than $10^{-1}s^{-1}$, less than $5\times10^{-1}s^{-1}$, less than $10^{-2}s^{-1}$, less than $5\times10^{-2}s^{-1}$, less than $10^{-3}s^{-1}$, less than $5\times10^{-3}s^{-1}$, less than $10^{-4}s^{-1}$, less than $5\times10^{-4}s^{-1}$, less than $10^{-5}s^{-1}$, less than $5\times10^{-5}s^{-1}$, less than $10^{-6}s^{-1}$, less than $5\times10^{-6}s^{-1}$, less than $10^{-7}s^{-1}$, less than $5\times10^{-7}s^{-1}$, less than $10^{8}s^{-1}$, less than $5\times10^{-8}s^{-1}$, less than $10^{-9}s^{-1}$, less than $5\times10^{-9}s^{1}$ or less than $10^{-10}s^{-1}$.

In another embodiment, an anti-CD3 antibody that specifically binds to its antigen (e.g., on a virion or infected cell displaying a viral antigen) will have an affinity constant or $K_a$ ($k_{on}/k_{off}$) of at least $10^2M^{-1}$, at least $5\times10^2M^{-1}$, at least $10^3M^{-1}$, at least $5\times10^3M^{-1}$, at least $10^4M^{-1}$, at least $5\times10^4M^{-1}$, at least $10^5M^{-1}$, at least $5\times10^5M^{-1}$, at least $10^6M^{-1}$, at least $5\times10^6M^{-1}$, at least $10^7M1$, at least $5\times10^7 M^{-1}$, at least $10^8M^{-1}$, at least $5\times10^8M^{-1}$, at least $10^9M^{-1}$, at least $5\times10^9M^{-1}$, at least $10^{10}M^{-1}$, at least $5\times10^{10}M^{-1}$, at least 10 $nM^{-1}$, at least 5×10 $nM^{-1}$, at least $10^{12}M^{-1}$, at least $5\times10^{12}M1$, at least $10^{13}M^{-1}$, at least $5\times10^{13}M^{-1}$, at least $10^{14}M^{-1}$, at least $5\times10^{14}M^{-1}$, at least $10^{15}M^{1}$ or at least $5\times10^{15}M^{-1}$.

Anti-CD3 antibodies disclosed herein may also be characterized by their thermal stability as reflected by their respective melting point ($T_m$). The $T_m$ of the Fab region of an antibody can be a good indicator of the thermal stability of an antibody and may further provide an indication of the shelf life. $T_m$ is merely the temperature of 50% unfolding for a given region or sequence. A lower $T_m$ indicates more aggregation/less stability, whereas a higher $T_m$ indicates less aggregation/more stability. Thus, antibodies or fragments or derivatives having higher $T_m$ are preferable. Moreover, using art-recognized techniques it is possible to alter the composition of antibodies or regions thereof to increase or optimize molecular stability. Thermal melting temperatures ($T_m$) of a protein region (e.g., a Fab region) can be measured using any standard method known in the art, e.g., by differential scanning calorimetry.

In some embodiments, the Fab region of an anti-CD3 antibody disclosed herein has a $T_m$ value higher than at least 50° C., 55° C., 60° C., 65° C., 70° C., 75° C., 80° C., 85° C., 90° C., 95° C., 100° C., 105° C., 110° C., 115° C. or 120° C. In another embodiment, the Fab region of an anti-CD3 antibody disclosed herein has a $T_m$ value higher than at least about 50° C., about 55° C., about 60° C., about 65° C., about 70° C., about 75° C., about 80° C., about 85° C., about 90° C., about 95° C., about 100° C., about 105° C., about 110° C., about 115° C. or about 120° C.

Anti-CD3 antibodies disclosed herein may also be characterized by their isoelectric point (pI), which is generally defined as the pH at which a polypeptide carries no net charge. It is known in the art that protein solubility is typically lowest when the pH of the solution is equal to the isoelectric point (pI) of the protein. Therefore, it is possible to optimize solubility by altering the number and location of ionizable residues in the antibody to adjust the pI. For example, the pI of a polypeptide can be manipulated by making the appropriate amino acid substitutions (e.g., by substituting a charged amino acid such as a lysine, for an uncharged residue such as alanine). Without wishing to be bound by any particular theory, amino acid substitutions of an antibody that result in changes of the pI of the antibody may improve solubility and/or the stability of the antibody. One skilled in the art would understand which amino acid substitutions would be most appropriate for a particular antibody to achieve a desired pI. The pI of a protein may be determined by a variety of methods including, but not limited to, isoelectric focusing and various computer algorithms.

In some embodiments, the pI of an anti-CD3 antibody disclosed herein is higher than about 6.5, about 7.0, about 7.5, about 8.0, about 8.5, or about 9.0. In another embodiment, the pI of an anti-CD3 antibody disclosed herein is higher than 6.5, 7.0, 7.5, 8.0, 8.5, or 9.0. In yet another embodiment, substitutions resulting in alterations in the pI of an anti-CD3 antibody disclosed herein will not significantly diminish its binding affinity. As discussed in more detail below, it is specifically contemplated that the substitution(s) of the Fc region that result in altered binding to FcγR may also result in a change in the pI. In a preferred embodiment, substitution(s) of the Fc region are specifically chosen to effect both the desired alteration in FcγR binding and any desired change in pI. As used herein, the pI value is defined as the pI of the predominant charge form.

Nucleic Acids and Anti-CD3 Antibody Expression

Provided herein are also nucleic acids encoding a heavy chain or light chain, or a VH or VL, of the anti-CD3 antibodies disclosed herein, and vectors comprising one or more such nucleic acids. The terms "nucleic acid" or "polynucleotide", as used interchangeably herein, refer to polymers of nucleotides, including single-stranded and/or double-stranded nucleotide-containing molecules, such as DNA, cDNA, and RNA molecules, incorporating native, modified, and/or analogs of, nucleotides. Polynucleotides of the present disclosure may also include substrates incorporated therein, for example, by DNA or RNA polymerase or a synthetic reaction. In some embodiments, provided herein are nucleic acids encoding a $V_H$ or $V_L$ of the anti-CD3 antibody described herein, e.g., any one of the antibodies identified by internal designation numbers 42-55, 63-91, 93-185, and 187-325. In some embodiments, the nucleic acids encode a $V_H$ or $V_L$ comprising any one of SEQ ID NOs: 1-550.

DNA encoding the anti-CD3 antibodies disclosed herein may be readily isolated and sequenced using conventional procedures (e.g., by using oligonucleotide probes that are capable of binding specifically to genes encoding antibody heavy and light chains). Isolated and subcloned cells (or phage or yeast derived colonies) may serve as a preferred source of such DNA. More particularly, the isolated DNA (which may be modified) can be used to clone constant and variable region sequences for the manufacture of antibodies.

One exemplary method entails extraction of RNA from selected cells, conversion to cDNA, and amplification by PCR using antibody specific primers. Suitable primers are well known in the art, and as exemplified herein, are readily available from numerous commercial sources. It will be appreciated that, to express a recombinant human or non-human antibody isolated by screening of a combinatorial library, the DNA encoding the antibody is cloned into a recombinant expression vector and introduced into host cells including mammalian cells, insect cells, plant cells, yeast, and bacteria. In yet other embodiments, the modulators are introduced into and expressed by simian COS cells, NS0 cells, Chinese Hamster Ovary (CHO) cells or myeloma cells that do not otherwise produce the desired construct. As will be discussed in more detail below, transformed cells expressing the desired modulator may be grown up in relatively large quantities to provide clinical and commercial supplies of the antibody.

In whatever manner the nucleic acid encoding an anti-CD3 antibody disclosed herein is obtained or derived, it should be understood that the inventions disclosed herein encompass nucleic acid molecules and sequences encoding anti-CD3 antibodies, fusion proteins, or antigen-binding fragments or derivatives thereof. The inventions disclosed herein further encompass nucleic acids or nucleic acid molecules (e.g., polynucleotides) that hybridize under high stringency, or alternatively, under intermediate or lower stringency hybridization conditions (e.g., as defined below), to polynucleotides complementary to nucleic acids having a polynucleotide sequence that encodes a modulator of the invention or a fragment or variant thereof. The term nucleic acid molecule or isolated nucleic acid molecule, as used herein, is intended to include at least DNA molecules and RNA molecules. A nucleic acid molecule may be single-stranded or double-stranded, but preferably is double-stranded DNA. Moreover, the present invention comprises any vehicle or construct, incorporating such modulator encoding polynucleotide including, without limitation, vectors, plasmids, host cells, cosmids or viral constructs.

As used herein, the term "isolated nucleic acid" refers to a nucleic acid that was (i) amplified in vitro, for example by polymerase chain reaction (PCR), (ii) recombinantly produced by cloning, (iii) purified, for example by cleavage and gel-electrophoretic fractionation, or (iv) synthesized, for example by chemical synthesis. An isolated nucleic acid is a nucleic acid that is available for manipulation by recombinant DNA techniques.

More specifically, nucleic acids that encode anti-CD3 antibodies described herein, polynucleotides sufficient for use as hybridization probes, PCR primers or sequencing primers for identifying, analyzing, mutating, or amplifying a polynucleotide encoding a polypeptide, anti-sense nucleic acids for inhibiting expression of a polynucleotide, and complementary sequences of the foregoing are also encompassed herein. Such nucleic acids can be any length. They can be, for example, 5, 10, 15, 20, 25, 30, 35, 40, 45, 50, 75, 100, 125, 150, 175, 200, 250, 300, 350, 400, 450, 500, 750, 1,000, 1,500, 3,000, 5,000 or more nucleotides in length, and/or can comprise one or more additional sequences, for example, regulatory sequences, and/or be part of a larger nucleic acid, for example, a vector. These nucleic acids can be single-stranded or double-stranded and can comprise RNA and/or DNA nucleotides, and artificial variants thereof (e.g., peptide nucleic acids).

As indicated, the invention further provides nucleic acids that hybridize to other nucleic acids under particular hybridization conditions. Methods for hybridizing nucleic acids are well known in the art. For example, a moderately stringent hybridization condition uses a prewashing solution containing 5× sodium chloride/sodium citrate (SSC), 0.5% SDS, 1.0 mM EDTA (pH 8.0), hybridization buffer of about 50% formamide, 6×SSC, and a hybridization temperature of 55° C. (or other similar hybridization solutions, such as one containing about 50% formamide, with a hybridization temperature of 42° C.), and washing conditions of 60° C., in 0.5×SSC, 0.1% SDS. A stringent hybridization condition hybridizes in 6×SSC at 45° C., followed by one or more washes in 0.1×SSC, 0.2% SDS at 68° C. One of skill in the art can manipulate the hybridization and/or washing conditions to increase or decrease the stringency of hybridization such that nucleic acids comprising nucleotide sequences that are at least 65, 70, 75, 80, 85, 90, 95, 98 or 99% identical to each other typically remain hybridized to each other. More generally, for the purposes of the instant disclosure the term "substantially identical" with regard to a nucleic acid sequence refers to a sequence of nucleotides exhibiting at least about 85%, or 90%, or 95%, or 97% sequence identity to the reference nucleic acid sequence. The basic parameters affecting the choice of hybridization conditions and guidance for devising suitable conditions are well known, and can be readily determined by those having ordinary skill in the art based on, for example, the length and/or base composition of the nucleic acid.

It will further be appreciated that nucleic acids may be present alone or in combination with other nucleic acids, which may be homologous or heterologous. In preferred embodiments, a nucleic acid is functionally linked to expression control sequences that may be homologous or heterologous with respect to that nucleic acid. In this context, the term "homologous" means that a nucleic acid is also functionally linked to the expression control sequence naturally and the term "heterologous" means that a nucleic acid is not functionally linked to the expression control sequence naturally.

A nucleic acid, such as a nucleic acid expressing RNA and/or protein or peptide, and an expression control sequence are functionally linked to one another, if they are covalently linked to one another in such a way that expression or transcription of the nucleic acid is under the control or under the influence of the expression control sequence. If the nucleic acid is to be translated into a functional protein, then, with an expression control sequence functionally linked to a coding sequence, induction of the expression control sequence results in transcription of the nucleic acid, without causing a frame shift in the coding sequence or the coding sequence not being capable of being translated into the desired protein or peptide. As used herein, the term "expression control sequence" includes promoters, ribosome binding sites, enhancers and other control elements that regulate transcription of a gene or translation of mRNA. In particular embodiments, the expression control sequences can be regulated. The exact structure of expression control sequences may vary as a function of the species or cell type, but generally comprises 5'-untranscribed and 5'- and 3'-untranslated sequences which are involved in initiation of transcription and translation, respectively, such as TATA box, capping sequence, CAAT sequence, and the like. More specifically, 5'-untranscribed expression control sequences comprise a promoter region that includes a promoter sequence for transcriptional control of the functionally linked nucleic acid. Expression control sequences may also comprise enhancer sequences or upstream activator sequences.

As used herein, the term "promoter" or "promoter region" relates to a nucleic acid sequence which is located upstream (5') to the nucleic acid sequence being expressed and controls expression of the sequence by providing a recognition and binding site for RNA-polymerase. The promoter region may include further recognition and binding sites for further factors that are involved in the regulation of transcription of a gene. A promoter may control the transcription of a prokaryotic or eukaryotic gene. Furthermore, a promoter may be inducible and may initiate transcription in response to an inducing agent or may be constitutive if transcription is not controlled by an inducing agent. A gene that is under the control of an inducible promoter is not expressed or only expressed to a small extent if an inducing agent is absent. In the presence of the inducing agent the gene is switched on or the level of transcription is increased. This is mediated, in general, by binding of a specific transcription factor.

Promoters for use in the production of anti-CD3 antibodies (e.g., anti-CD3) disclosed herein include promoters for SP6, T3 and T7 polymerase, human U6 RNA promoter, CMV promoter, and artificial hybrid promoters thereof (e.g., CMV) where a part or parts are fused to a part or parts of promoters of genes of other cellular proteins such as, e.g., human GAPDH (glyceraldehyde-3-phosphate dehydrogenase), and may include (an) additional intron(s).

As used herein, the term "expression" is used in its most general meaning and comprises the production of RNA or of RNA and protein/peptide. It also comprises partial expression of nucleic acids. Furthermore, expression may be carried out transiently or stably.

In a preferred embodiment, a nucleic acid molecule present in a vector, where appropriate with a promoter, which controls expression of the nucleic acid. As used herein, the term "vector" is used here in its most general meaning and comprises any intermediary vehicle for a nucleic acid that enables the nucleic acid, for example, to be introduced into prokaryotic and/or eukaryotic cells and, where appropriate, to be integrated into a genome. Vectors of this kind are preferably replicated and/or expressed in the cells. Vectors may comprise plasmids, phagemids, bacteriophages or viral genomes. As used herein, the term "plasmid" generally relates to a construct of extrachromosomal genetic material, usually a circular DNA duplex, which can replicate independently of chromosomal DNA.

It will be appreciated by those of skill in the art, that many conventional techniques in molecular biology, microbiology, and recombinant DNA technology are optionally used. Such conventional techniques relate to vectors, host cells and recombinant methods as defined herein. In addition, essentially any polynucleotide (including, e.g., labeled or biotinylated polynucleotides) can be obtained from any of a variety of commercial sources.

The inventions disclosed herein also encompass recombinant host cells allowing recombinant expression of antibodies of the invention or portions thereof. Anti-CD3 antibodies disclosed herein produced by expression in such recombinant host cells are referred to herein as recombinant antibodies. The inventions disclosed herein also encompass progeny cells of such host cells, and anti-CD3 antibodies produced by the same.

As used herein, the term "recombinant host cell" or "host cell" means a cell into which a recombinant expression vector has been introduced. It should be understood that recombinant host cell and host cell mean not only the particular subject cell but also the progeny of such a cell. Because certain modifications may occur in succeeding generations due to either mutation or environmental influences, such progeny may not, in fact, be identical to the parent cell, but are still included within the scope of the term host cell as used herein. Such cells may comprise a vector as described above.

The inventions disclosed herein also encompass methods for making anti-CD3 antibodies disclosed herein. According to one embodiment, such a method comprises culturing a cell transfected or transformed with a vector as described above, and isolating the antibody.

As indicated above, expression of an antibody preferably comprises expression vector(s) containing a polynucleotide that encodes the anti-CD3 antibody. Methods that are well known to those skilled in the art can be used to construct expression vectors comprising antibody coding sequences and appropriate transcriptional and translational control signals. These methods include, for example, in vitro recombinant DNA techniques, synthetic techniques, and in vivo genetic recombination. Particular embodiments provide replicable vectors comprising a nucleotide sequence encoding an anti-CD3 antibody disclosed herein operably linked to a promoter. In preferred embodiments, such vectors may include a nucleotide sequence encoding the heavy chain of an antibody molecule (or fragment thereof), a nucleotide sequence encoding the light chain of an antibody (or fragment thereof), or both the heavy and light chain.

Using art recognized molecular biology techniques and current protein expression methodology, substantial quantities of the anti-CD3 antibodies disclosed herein may be produced. More specifically, nucleic acid molecules encoding such antibodies may be integrated into well-known and commercially available protein production systems comprising various types of host cells to provide preclinical, clinical, or commercial quantities of the desired pharmaceutical product. In preferred embodiments the nucleic acid molecules encoding the antibodies are engineered into vectors or expression vectors that provide for efficient integration into the selected host cell and subsequent high expression levels of the antibody.

Preferably, nucleic acid molecules encoding anti-CD3 antibodies disclosed herein and vectors comprising these nucleic acid molecules can be used for transfection of a suitable mammalian, plant, bacterial or yeast host cell though it will be appreciated that prokaryotic systems may also be used. Transfection can be by any known method for introducing polynucleotides into a host cell. Methods for the introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors. Methods of transforming mammalian cells are well known in the art. Methods of transforming plant cells are also well known in the art, including, e.g., *Agrobacterium*-mediated transformation, biolistic transformation, direct injection, electroporation, and viral transformation. Methods of transforming bacterial and yeast cells are also well known in the art.

Moreover, the host cell may be co-transfected with two expression vectors of the invention, for example, the first vector encoding a heavy chain polypeptide and the second vector encoding a light chain polypeptide. The two vectors may contain identical selectable markers that enable substantially equal expression of heavy and light chain polypeptides. Alternatively, a single vector may be used which encodes, and is capable of expressing, both heavy and light chain polypeptides. In such situations, the light chain is preferably placed before the heavy chain to avoid an excess of toxic free heavy chain. The coding sequences for the heavy and light chains may comprise cDNA or genomic DNA.

Varieties of host-expression vector systems, many commercially available, may be used to express anti-CD3 antibodies disclosed herein. Such host-expression systems represent vehicles by which the coding sequences of interest may be expressed and subsequently purified, but also represent cells which may, when transformed or transfected with the appropriate nucleotide coding sequences, express a molecule of the invention in situ. Such systems include, but are not limited to, microorganisms such as bacteria (e.g., *E. coli, B. subtilis, Streptomyces*) transformed with recombinant bacteriophage DNA, plasmid DNA or cosmid DNA expression vectors containing modulator coding sequences; yeast (e.g., *Saccharomyces, Pichia*) transfected with recombinant yeast expression vectors containing modulator coding sequences; insect cell systems infected with recombinant expression vectors (e.g., baculovirus) containing modulator coding sequences; plant cell systems (e.g., *Nicotiana, Ara-*

*bidopsis*, duckweed, corn, wheat, potato, etc.) infected with recombinant expression vectors (e.g., cauliflower mosaic virus, CaMV; tobacco mosaic virus, TMV) or transfected with recombinant plasmid expression vectors (e.g., Ti plasmid) containing modulator coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenolate promoter; the vaccinia 7.5K promoter).

In bacterial systems, a number of expression vectors may be advantageously selected depending upon the use intended for the molecule being expressed. For example, when a large quantity of such a protein is to be produced, for the generation of pharmaceutical compositions, vectors which direct the expression of high levels of fusion protein products that are readily purified may be desirable.

In an insect system, *Autographa californica* nuclear polyhedrosis (AcNPV) may be used as a vector to express foreign genes. The grows in *Spodoptera frugiperda* cells. The coding sequences may be cloned individually into non-essential regions (for example, the polyhedrin gene) of the and placed under control of an AcNPV promoter (for example, the polyhedrin promoter).

In mammalian host cells, a number of viral-based expression systems may be used to introduce the desired nucleotide sequence. In cases where an adeno is used as an expression vector, the coding sequence of interest may be ligated to an adenotranscription/translation control complex, e.g., the late promoter and tripartite leader sequence. This chimeric gene may then be inserted in the adenogenome by in vitro or in vivo recombination. Insertion in a non-essential region of the viral genome (e.g., region E1 or E3) will result in a recombinant that is viable and capable of expressing the molecule in infected hosts. Specific initiation signals may also be required for efficient translation of inserted coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, and the like. Thus, compatible mammalian cell lines available as hosts for expression are well known in the art and include many immortalized cell lines available from the American Type Culture Collection (ATCC). These include, inter alia, Chinese hamster ovary (CHO) cells, NS0 cells, SP2 cells, HEK-293T cells, 293 Freestyle cells (Life Technologies), NIH-3T3 cells, HeLa cells, baby hamster kidney (BHK) cells, African green monkey kidney cells (COS), human hepatocellular carcinoma cells (e.g., Hep G2), A549 cells, and a number of other cell lines.

For long-term, high-yield production of recombinant proteins stable expression is preferred. Accordingly, cell lines that stably express the selected modulator may be engineered using standard art recognized techniques. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1 to 2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the molecule. Such engineered cell lines may be particularly useful in screening and evaluation of compositions that interact directly or indirectly with the molecule.

A number of selection systems are well known in the art and may be used including, but not limited to, the herpes simplex thymidine kinase, hypoxanthineguanine phosphoribosyltransferase, and adenine phosphoribosyltransferase genes can be employed in tk-, hgprt- or aprt-cells, respectively. Also, antimetabolite resistance can be used as the basis of selection for the following genes: dhfr, which confers resistance to methotrexate; gpt, which confers resistance to mycophenolic acid; neo, which confers resistance to the aminoglycoside G-418; and hygro, which confers resistance to hygromycin.

Methods commonly known in the art of recombinant DNA technology may be routinely applied to select the desired recombinant clone. It will be appreciated by those of skill in the art that one particularly preferred method of establishing a stable, high yield cell line comprises the glutamine synthetase gene expression system (the GS system), which provides an efficient approach for enhancing expression under certain conditions.

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function and/or purification of the protein. Different host cells have characteristic and specific mechanisms for the post-translational processing and modification of proteins and gene products. As known in the art, appropriate cell lines or host systems can be chosen to ensure the desired modification and processing of the expressed polypeptide. To this end, eukaryotic host cells that possess the cellular machinery for proper processing of the primary transcript, glycosylation, and phosphorylation of the gene product are particularly effective. Accordingly, some preferred mammalian host lines include, but are not limited to, CHO, VERY, BHK, HeLa, COS, NS0, MDCK, 293, 3T3, and W138. Depending on the anti-CD3 antibody, or anti-CD3× anti-EGFR bispecific antibody, and the selected production system, those of skill in the art may easily select and optimize appropriate host cells for efficient expression of the antibody.

Those of skill in the art will appreciate that anti-CD3 antibodies disclosed herein may be chemically synthesized using techniques known in the art. For example, a peptide corresponding to a polypeptide fragment of the invention can be synthesized by use of a peptide synthesizer. If desired, non-genetically encoded amino acids or synthetic amino acids can be substituted or added into a polypeptide sequence.

Representative non-genetically encoded amino acids include but are not limited to 2-aminoadipic acid; 3-aminoadipic acid; β-aminopropionic acid; 2-aminobutyric acid; 4-aminobutyric acid (piperidinic acid); 6-aminocaproic acid; 2-aminoheptanoic acid; 2-aminoisobutyric acid; 3-aminoisobutyric acid; 2-aminopimelic acid; 2,4-diaminobutyric acid; desmosine; 2,2'-diaminopimelic acid; 2,3-diaminopropionic acid; N-ethylglycine; N-ethylasparagine; hydroxylysine; allo-hydroxylysine; 3-hydroxyproline; 4-hydroxyproline; isodesmosine; allo-isoleucine; N-methylglycine (sarcosine); N-methylisoleucine; N-methylvaline; norvaline; norleucine; and ornithine.

Representative synthetic amino acids include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine.

Anti-CD3 antibodies disclosed herein also can be produced transgenically through the generation of a mammal or plant that is transgenic for the immunoglobulin heavy and light chain sequences (or fragments or derivatives or variants thereof) of interest and production of the desired compounds in a recoverable form. For example, anti-CD3 antibodies can be produced in, and recovered from, e.g., the milk of goats, cows, or other mammals. In some embodiments, non-human transgenic animals that comprise human immunoglobulin loci are immunized with a hyperproliferative or autoimmune disorder virions or an immunogenic portion thereof, as described above.

Non-human transgenic animals or plants may be produced by introducing one or more nucleic acid molecules encoding an anti-CD3 antibody into the animal or plant by standard transgenic techniques. The transgenic cells used for making the transgenic animal can be embryonic stem cells or somatic cells or a fertilized egg. The transgenic non-human organisms can be chimeric, nonchimeric heterozygotes, and nonchimeric homozygotes. In some embodiments, the transgenic non-human animals have a targeted disruption and replacement by a targeting construct that encodes, for example, a heavy chain and/or a light chain of interest. While anti-CD3 antibodies disclosed herein may be produced in any transgenic animal, particularly preferred embodiments include mice, rats, sheep, pigs, goats, cattle, and horses. In particular embodiments, the non-human transgenic animal expresses the desired pharmaceutical product in blood, milk, urine, saliva, tears, mucus, and other bodily fluids from which it is readily obtainable using art recognized purification techniques.

It is likely that modulators, including antibodies, expressed by different cell lines or in transgenic animals will have different glycosylation patterns from each other. However, the instant inventions encompass anti-CD3 antibodies encoded by the nucleic acid molecules provided herein, or comprising the amino acid sequences provided herein, regardless of the glycosylation state of the molecule, and more generally, regardless of the presence or absence of post-translational modification(s). The instant inventions also encompass anti-CD3 antibodies that are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, acetylation, formylation, oxidation, reduction, metabolic synthesis in the presence of tunicamycin, etc. Various post-translational modifications are also encompassed by the invention include, for example, e.g., N-linked or O-linked carbohydrate chains, processing of N-terminal or C-terminal ends, attachment of chemical moieties to the amino acid backbone, chemical modifications of N-linked or O-linked carbohydrate chains, and addition or deletion of an N-terminal methionine residue as a result of prokaryotic host cell expression. Moreover, anti-CD3 antibodies disclosed herein may also be modified with a detectable label, such as an enzymatic, fluorescent, radioisotopic or affinity label to allow for their detection and isolation.

Once anti-CD3 antibodies disclosed herein have been produced by recombinant expression or any one of the other techniques disclosed herein, they may be purified by any method known in the art for purification of immunoglobulins, or more generally by any other standard technique for the purification of proteins. In this respect the anti-CD3 antibody may be isolated. As used herein, an “isolated anti-CD3 antibody” is one that has been identified and separated and/or recovered from a component of its natural environment. Contaminant components of its natural environment are materials that would interfere with diagnostic or therapeutic uses of the antibody and may include enzymes, hormones, and other proteinaceous or non-proteinaceous solutes. Isolated anti-CD3 antibodies include antibodies in situ within recombinant cells because at least one component of the antibody’s natural environment will not be present.

When using recombinant techniques, anti-CD3 antibodies disclosed herein can be produced intracellularly, in the periplasmic space, or directly secreted into the medium. If the desired molecule is produced intracellularly, as a first step, the particulate debris, either host cells or lysed fragments, may be removed, for example, by centrifugation or ultrafiltration. Where the antibody is secreted into the medium, supernatants from such expression systems are generally first concentrated using a commercially available protein concentration filter. A protease inhibitor such as PMSF may be included in any of the foregoing steps to inhibit proteolysis and antibiotics may be included to prevent the growth of adventitious contaminants.

Compositions comprising anti-CD3 antibodies disclosed herein prepared from cells can be purified using, for example, hydroxyapatite chromatography, gel electrophoresis, dialysis, and affinity chromatography. The suitability of protein A as an affinity ligand depends on the species and isotype of any immunoglobulin Fc region that is present in the selected construct. Protein A can be used to purify antibodies that are based on human IgG1, IgG2 or IgG4 heavy chains. Protein G is recommended for all mouse isotypes and for human IgG3. The matrix to which the affinity ligand is attached is most often agarose, but other matrices are available. Mechanically-stable matrices such as controlled pore glass or poly(styrenedivinyl)benzene allow for faster flow rates and shorter processing times than can be achieved with agarose. Where the antibody comprises a $C_H3$ region, the BAKERBOND ABX™ resin is useful for purification. Other techniques for protein purification such as fractionation on an ion-exchange column, ethanol precipitation, reverse phase HPLC, chromatography on silica, chromatography on heparin, SEPHAROSE® chromatography on an anion or cation exchange resin (such as a polyaspartic acid column), chromatofocusing, SDS-PAGE and ammonium sulfate precipitation are also available depending on the antibody to be recovered.

By way of illustration of the foregoing, cDNA sequences encoding an anti-CD3 antibody heavy chain and light chain may be cloned and engineered into an appropriate expression vector. The engineered immunoglobulin expression vector may then be stably transfected into a mammalian (e.g., human) cell. As one skilled in the art will appreciate, mammalian expression of antibodies will result in glycosylation, typically at highly conserved N-glycosylation sites in the Fc region. Positive clones may be expanded into serum-free culture medium for antibody production in bioreactors. Medium, into which an antibody has been secreted, may be purified by conventional techniques. For example, the medium may be conveniently applied to a Protein A or G SEPHAROSE® FF column that has been equilibrated with a compatible buffer, such as phosphate buffered saline. The column is washed to remove nonspecific binding components. The bound antibody is eluted, for example, by pH gradient and antibody fractions are detected, such as by SDS-PAGE, and then pooled. The antibody may be concentrated and/or sterile filtered using common techniques. Soluble aggregate and multimers may be effectively removed by common techniques, including size exclusion, hydrophobic interaction, ion exchange, or hydroxyapatite chromatography. The product may be immediately frozen, for example, at −70° C., or may be lyophilized.

Anti-CD3 Antibody Conjugates

Those skilled in the art will appreciate that anti-CD3 antibodies described herein may be used in conjugated or unconjugated form. That is, the anti-CD3 antibody may be associated with or conjugated to (e.g., covalently or non-covalently) pharmaceutically active compounds, biological response modifiers, diagnostic moieties, or biocompatible modifiers. In this respect it will be understood that such conjugates may comprise peptides, polypeptides, proteins, fusion proteins, nucleic acid molecules, small molecules, mimetic agents, synthetic drugs, inorganic molecules, organic molecules, and radioisotopes. Moreover, a conjugate may be covalently or non-covalently linked to the anti-CD3 antibody in various molar ratios depending, at least in part, on the method used to effect the conjugation.

As used herein the term "conjugate" means any molecule associated with an anti-CD3 antibody disclosed herein regardless of the method of association. In this respect it will be understood that such conjugates may comprise peptides, polypeptides, proteins, polymers, nucleic acid molecules, small molecules, mimetic agents, synthetic drugs, inorganic molecules, organic molecules, and radioisotopes. Moreover, as indicated above the selected conjugate may be covalently or non-covalently linked to the antibody and exhibit various molar ratios depending, at least in part, on the method used to effect the conjugation.

In some embodiments, anti-CD3 antibodies disclosed herein may be conjugated or associated with proteins, polypeptides or peptides that impart selected characteristics (e.g., biotoxins, biomarkers, purification tags, etc.). In particular embodiments, anti-CD3 antibodies disclosed herein are recombinantly fused or chemically conjugated (including both covalent and non-covalent conjugations) to a heterologous protein or polypeptide wherein the polypeptide comprises at least 10, at least 20, at least 30, at least 40, at least 50, at least 60, at least 70, at least 80, at least 90 or at least 100 amino acids. The construct does not necessarily need to be directly linked, but may occur through linker sequences. For example, anti-CD3 antibodies may be used to target heterologous polypeptides to virions or infected cells, either in vitro or in vivo, by fusing or conjugating the antibodies to other antibodies specific for other antigens. Moreover, anti-CD3 antibodies that are fused or conjugated to heterologous polypeptides may also be used in in vitro immunoassays and may be compatible with purification methodology known in the art.

In some embodiments, anti-CD3 antibodies disclosed herein may be conjugated or otherwise associated with biocompatible modifiers that may be used to adjust, alter, improve, or moderate antibody properties. For example, antibodies or fusion constructs with increased in vivo half-lives can be generated by attaching relatively high molecular weight polymer molecules such as commercially available polyethylene glycol (PEG) or similar biocompatible polymers. Those skilled in the art will appreciate that PEG may be obtained in many different molecular weight and molecular configurations that can be selected to impart specific properties to the antibody (e.g., the half-life may be tailored). PEG can be attached to modulators or antibody fragments or derivatives with or without a multifunctional linker either through site-specific conjugation of the PEG to the N- or C-terminus of antibodies or via epsilon-amino groups present on lysine residues. Linear or branched polymer derivatization that results in minimal loss of biological activity may be used. The degree of conjugation can be closely monitored by SDS-PAGE and mass spectrometry to ensure optimal conjugation of PEG molecules to antibody molecules. Unreacted PEG can be separated from antibody-PEG conjugates by, e.g., size exclusion or ion-exchange chromatography. In a similar manner, the disclosed modulators can be conjugated to albumin in order to make the antibody or antibody fragment more stable in vivo or have a longer half-life in vivo. The techniques are well known in the art. Other biocompatible conjugates are evident to those of ordinary skill and may readily be identified and utilized in accordance with the teachings herein.

In other embodiments, anti-CD3 antibodies disclosed herein are conjugated to a diagnostic or detectable agent, marker or reporter which may be a biological molecule (e.g., a peptide or nucleotide), a small molecule, fluorophore, or radioisotope. Labeled modulators can be useful for monitoring the development or progression of a hyperproliferative or autoimmune disorder or as part of a clinical testing procedure to determine the efficacy of a particular therapy including anti-CD3 antibodies disclosed herein (i.e., theragnostics), or to determine a future course of treatment. Such markers or reporters may also be useful in purifying anti-CD3 antibodies disclosed herein.

Diagnosis and detection can be accomplished by coupling the modulator to detectable substances including, but not limited to, various enzymes comprising for example horseradish peroxidase, alkaline phosphatase, beta-galactosidase, or acetylcholinesterase; prosthetic groups, such as but not limited to streptavidin/biotin and avidin/biotin; fluorescent materials, such as but not limited to, umbelliferone, fluorescein, fluorescein isothiocynate, rhodamine, dichlorotriazinylamine fluorescein, dansyl chloride or phycoerythrin; luminescent materials, such as but not limited to, luminol; bioluminescent materials, such as but not limited to, luciferase, luciferin, and aequorin; radioactive materials, such as but not limited to iodine ($^{111}$I, $^{125}$I, $^{123}$I, $^{121}$I), carbon ($^{14}$C), sulfur ($^{35}$S), tritium ($^{3}$H), indium ($^{115}$In, $^{113}$In, $^{112}$In, $^{111}$In), and technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe) fluorine ($^{18}$F), $^{153}$Sm, $^{177}$Lu, $^{59}$Gd, $^{49}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin; positron emitting metals using various positron emission tomographies, non-radioactive paramagnetic metal ions, and molecules that are radiolabeled or conjugated to specific radioisotopes. In such embodiments appropriate detection methodology is well known in the art and readily available from numerous commercial sources.

In other embodiments, anti-CD3 antibodies disclosed herein can be fused to marker sequences, such as a peptide or fluorophore to facilitate purification or diagnostic procedures such as immunohistochemistry or FACs. In some embodiments, the marker amino acid sequence is a hexa-histidine peptide, such as the tag provided in a pQE vector, among others, many of which are commercially available. Other peptide tags useful for purification include, but are not limited to, the hemagglutinin "HA" tag, which corresponds to an epitope derived from the hemagglutinin protein, and the "flag" tag.

In yet other embodiments, anti-CD3 antibodies disclosed herein can be conjugated to an immunomodulator, cytokine, cytotoxic agent, chemotherapeutic agent, or drug. Examples of anti-CD3 antibody conjugates include a murine anti-CD3 antibody conjugated to ricin for the treatment of Steroid-Refractory Acute Graft-versus-Host Disease in combination with an anti-CD7 antibody also conjugated to ricin. See, e.g., Groth et al., Phase I/II Trial of a Combination of Anti-CD3/CD7 Immunotoxins for Steroid-Refractory Acute Graft-versus-Host Disease. *Biol Blood Marrow Transplant.* 2019 April; 25(4):712-719. Bispecific antibody drug conjugates are also under investigation for a variety of hyperproliferative disorders. See, e.g., "Bispecific Antibody Drug Conjugates (ADCs): Emerging Trends" at https://www.biochemp-eg.com/article/290.html.

Pharmaceutical Compositions and Therapeutic Uses

Also provided herein are methods treating a hyperproliferative or autoimmune disorder by administering to a patient a therapeutically effective amount of one or more anti-CD3 antibodies described herein, or a pharmaceutical composition comprising one or more (e.g., two or three) anti-CD3 antibodies described herein in combination with another anti-CD3 antibody or therapy.

As used interchangeably herein, "treatment" or "treating" or "treat" refers to all processes wherein there may be a slowing, interrupting, arresting, controlling, stopping, alleviating, or ameliorating symptoms or complications, or reversing of the progression of a hyperproliferative or autoimmune disorder, but does not necessarily indicate a total elimination of all disease or disorder symptoms.

In some embodiments, methods of preventing or treating a hyperproliferative or autoimmune disorder comprise administering to a patient a pharmaceutical composition comprising one or more (e.g., two or three) anti-CD3 antibodies described herein. In some embodiments, such methods comprise administering to a patient a pharmaceutical composition comprising two or three anti-CD3 antibodies or antigen-binding fragments thereof that bind different epitopes present on an a hyperproliferative or autoimmune disorder virion or infected cell.

In some embodiments, provided herein are methods of treating a hyperproliferative or autoimmune disorder comprising: contacting a sample obtained from a patient with an antibody or antigen-binding fragment thereof described herein, conjugated to a detectable agent; detecting specific binding of the antibody or antigen-binding fragment thereof to an a hyperproliferative or autoimmune disorder-related antigen present in the sample; and administering to the patient a therapeutically effective amount of an antibody or antigen-binding fragment thereof described herein or a pharmaceutical composition comprising such an antibody or antigen-binding fragment thereof.

Also provided are anti-CD3 antibodies or antigen-binding fragments or pharmaceutical compositions comprising one or more (e.g., two or three) anti-CD3 antibodies or antigen-binding fragments for use in therapy. In some embodiments anti-CD3 antibodies or antigen-binding fragments thereof or pharmaceutical compositions comprise one or more (e.g., two or three) anti-CD3 or antigen-binding fragments, for use in the treatment or prevention of a hyperproliferative or autoimmune disorder. Further provided herein are uses of anti-CD3 antibodies or antigen-binding fragments described herein in the manufacture of a medicament for the treatment or prevention of a hyperproliferative or autoimmune disorder.

Depending on the form of anti-CD3 antibody, mode of intended delivery, and numerous other variables, anti-CD3 antibodies disclosed herein may be formulated as desired using art recognized techniques. Various pharmaceutically acceptable carriers, which include vehicles, adjuvants, and diluents, are readily available from numerous commercial sources. Moreover, an assortment of pharmaceutically acceptable auxiliary substances, such as pH adjusting and buffering agents, tonicity adjusting agents, stabilizers, wetting agents, and the like, are also available. Certain non-limiting exemplary carriers include saline, buffered saline, dextrose, water, glycerol, ethanol, and combinations thereof.

In some embodiments, anti-CD3 antibodies may be administered to a patient neat or with a minimum of additional components. In other embodiments, anti-CD3 antibodies may be formulated to contain suitable pharmaceutically acceptable carriers comprising excipients and auxiliaries that are well known in the art and are relatively inert substances that facilitate administration or which aid processing of the active compounds into preparations that are pharmaceutically optimized for delivery. For example, an excipient can give form or consistency or act as a diluent to improve the pharmacokinetics of the antibody. Suitable excipients include but are not limited to stabilizing agents, wetting, and emulsifying agents, salts for varying osmolality, encapsulating agents, buffers, and skin penetration enhancers.

Anti-CD3 antibodies disclosed herein may be formulated for enteral, parenteral, or topical administration. Indeed, all three types of formulation may be used simultaneously to achieve systemic administration of the active ingredient. Excipients as well as formulations for parenteral and non-parenteral drug delivery are known in the art. Suitable formulations for parenteral administration include aqueous solutions of the active compounds in water-soluble form, for example, water-soluble salts. In addition, suspensions of the active compounds as appropriate for oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances that increase the viscosity of the suspension and include, for example, sodium carboxymethyl cellulose, sorbitol, and/or dextran. Optionally, the suspension may also contain stabilizers. Liposomes can also be used to encapsulate the agent for delivery into the cell.

Suitable formulations for enteral administration include hard or soft gelatin capsules, pills, tablets, including coated tablets, elixirs, suspensions, syrups or inhalations and controlled release forms thereof.

In general, anti-CD3 antibodies disclosed herein may be administered in vivo to a subject in need thereof, by various routes, including, but not limited to, oral, intravenous, intra-arterial, subcutaneous, parenteral, intranasal, intramuscular, intracardiac, intraventricular, intratracheal, buccal, rectal, intraperitoneal, intradermal, topical, transdermal, and intrathecal, or otherwise by implantation or inhalation. Compositions may be formulated into preparations in solid, semi-solid, liquid, or gaseous forms; including, but not limited to, tablets, capsules, powders, granules, ointments, solutions, suppositories, enemas, injections, inhalants, and aerosols. The appropriate formulation and route of administration may be selected according to the intended application and therapeutic regimen.

Similarly, the particular dosage regimen, i.e., dose, timing, and repetition, will depend on the particular individual and that individual's medical history. Empirical considerations such as pharmacokinetics (e.g., half-life, clearance rate, etc.) will contribute to the determination of the dosage. Frequency of administration may be determined and adjusted over the course of therapy. Alternatively, sustained continuous release formulations of a subject therapeutic composition may be appropriate. Various formulations and devices for achieving sustained release are known in the art.

Pharmaceutical compositions are administered in therapeutically effective amount for treatment of a hyperproliferative or autoimmune disorder in a subject. As used herein, the term "therapeutically effective amount" means that amount of an anti-CD3 antibody or pharmaceutical composition comprising the same that will elicit the biological or medical response in the subject that is sought by a medical doctor or other clinician. In particular, with regard to hyperproliferative disorders, a "therapeutically effective amount" is intended to include an amount sufficient to achieve one or more of the following effects: (i) decrease in rate of tumor growth; (ii) decrease in tumor size; (iii) disappearance of the tumor.

In some embodiments, a therapeutically effective amount of an anti-CD3 antibody or pharmaceutical composition comprising the same has a beneficial effect but does not cure a hyperproliferative or autoimmune disorder. In certain embodiments, therapy may encompass the administration of multiple doses of an anti-CD3 antibody or pharmaceutical composition comprising the same at a certain frequency to achieve a therapeutic effect.

A therapeutically effective amount is typically dependent on the weight of the subject being treated, his or her physical condition, the extensiveness of the condition to be treated, and the age of the subject being treated. In general, anti-CD3 antibodies disclosed herein may be administered in an amount in the range of about 10 ng/kg body weight to about 100 mg/kg body weight per dose. In certain embodiments, antibodies may be administered in an amount in the range of about 50 μg/kg body weight to about 5 mg/kg body weight per dose. In other embodiments, antibodies may be administered in an amount in the range of about 100 μg/kg body weight to about 10 mg/kg body weight per dose. In other embodiments, antibodies may be administered in an amount in the range of about 100 μg/kg body weight to about 20 mg/kg body weight per dose. In other embodiments, antibodies may be administered in an amount in the range of about 0.5 mg/kg body weight to about 20 mg/kg body weight per dose. In other embodiments, antibodies may be administered in a dose of at least about 100 μg/kg body weight, at least about 250 μg/kg body weight, at least about 750 μg/kg body weight, at least about 3 mg/kg body weight, at least about 5 mg/kg body weight, or at least about 10 mg/kg body weight.

Other dosing regimens may be predicated on Body Surface Area (BSA) calculations. As is well known in the art, a patient's BSA is calculated using the patient's height and weight and provides a measure of a subject's size as represented by the surface area of his or her body. In some embodiments, anti-CD3 antibodies disclosed herein are administered in dosages from 10 mg/m$^2$ to 800 mg/m$^2$. In other embodiments, antibodies are administered in dosages from 50 mg/m$^2$ to 500 mg/m$^2$ and even more preferably at dosages of 100 mg/m$^2$, 150 mg/m$^2$, 200 mg/m$^2$, 250 mg/m$^2$, 300 mg/M$^2$, 350 mg/m$^2$, 400 mg/M$^2$ or 450 mg/m$^2$.

Escalation for an individual patient can occur at the discretion of a clinician in the absence of any clinically significant occurrence that the clinician might reasonably believe would present an undue safety risk for the patient, such as, for example, infusion reactions, acute anaphylaxis, and serum sickness.

Anti-CD3 antibodies disclosed herein are preferably administered as needed to a subject. Determination of the frequency of administration may be made by persons skilled in the art, such as an attending physician based on considerations of the condition being treated, age of the subject being treated, severity of the condition being treated, general state of health of the subject being treated and the like. In some instances, two or more antibodies with different binding specificities may be administered simultaneously, in which case the dosage of each antibody administered falls within the ranges indicated. Intervals between single dosages can be weekly, monthly, or yearly. Intervals can also be irregular depending upon levels of antibody in the blood and other clinical indicia. In some methods, the dosage is adjusted to achieve a plasma antibody concentration of about 1-1000 μg/mL or about 25-300 μg/mL. Alternatively, antibodies can be administered as a sustained release formulation, in which case less frequent administration is required.

Dosage and frequency will vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In therapeutic applications, a relatively high dosage at relatively short intervals is sometimes required until progression of the disease is reduced or terminated, until a partial or complete response is achieved, and/or until the patient shows lessening or amelioration of symptoms of disease.

The duration of a therapeutic regimen depends on a variety of factors that are readily appreciated by one of skill in the art. A clinician can observe the therapy's effects closely and make any adjustments as needed. When agents are used in combination, the two or more therapeutic agents are administered simultaneously or sequentially in any order, i.e., an antibody disclosed herein is administered prior to administering a second therapeutic agent, concurrently with a second therapeutic agent, or subsequent to administration of a second therapeutic agent. For example, a combination therapy may be performed by administering a first therapeutic agent prior to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concurrently with, or subsequent to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) administering a second therapeutic agent.

The dosage, frequency, and mode of administration of each component of a combination therapy can be controlled independently. For example, one therapeutic agent may be administered orally three times per day, while the second therapeutic agent may be administered intravenously once per day. Combination therapy may be given in on-and-off cycles that include rest periods. The compounds may also be admixed or otherwise formulated together such that one administration delivers both therapeutic agents. In this case, each therapeutic agent is generally present in an amount of 1-95% by weight of the total weight of the composition. Alternatively, therapeutic agents can be formulated separately and in individual dosage amounts. Combinations of therapeutic agents for treatment can be provided as components of a pharmaceutical pack.

Preferably, combination therapies elicit a synergistic therapeutic effect, i.e., an effect greater than the sum of their individual effects or therapeutic outcomes, such as those described above. For example, a synergistic therapeutic effect may be an effect of at least about two-fold greater than sum of the therapeutic effects elicited by the single agents of a given combination, or at least about five-fold greater, or at least about ten-fold greater, or at least about twenty-fold greater, or at least about fifty-fold greater, or at least about one hundred-fold greater. A synergistic therapeutic effect may also be observed as an increase in therapeutic effect of at least 10% compared to the sum of the therapeutic effects elicited by the single agents of a given combination, or at least 20%, or at least 30%, or at least 40%, or at least 50%, or at least 60%, or at least 70%, or at least 80%, or at least 90%, or at least 100%, or more. A synergistic effect is also an effect that permits reduced dosing of therapeutic agents when they are used in combination.

Articles of Manufacture

The inventions disclosed herein also encompass pharmaceutical packs and kits comprising one or more containers and comprising one or more doses of an anti-CD3 antibody disclosed herein. In certain embodiments, a unit dosage is provided wherein the unit dosage contains a predetermined amount of a composition comprising, for example, an anti-CD3 antibody disclosed herein, with or without one or more additional agents. For other embodiments, such a unit dosage is supplied in single-use prefilled syringe for injection. In still other embodiments, the composition contained in the unit dosage may comprise saline, sucrose, or the like; a buffer, such as phosphate, or the like; and/or be formulated within a stable and effective pH range. Alternatively, in certain embodiments, the composition may be provided as a lyophilized powder that may be reconstituted upon addition of an appropriate liquid, for example, sterile water. In certain preferred embodiments, the composition comprises one or more substances that inhibit protein aggregation, including, but not limited to, sucrose and arginine. Any label on, or associated with, the container(s) indicates that the enclosed composition is used for diagnosis or treatment.

The present invention also provides kits for producing single-dose or multi-dose administration units of an anti-CD3 antibody disclosed herein and, optionally, one or more other diagnostic or therapeutic agents. The kit comprises a container and a label or package insert on or associated with the container. Suitable containers include, for example, bottles, vials, syringes, etc. The containers may be formed from a variety of materials such as glass or plastic. The container holds a composition that is effective for treating the condition and may have a sterile access port (for example the container may be an intravenous solution bag or a vial having a stopper pierceable by a hypodermic injection needle). Such kits will generally contain in a suitable container a pharmaceutically acceptable formulation of the anti-CD3 antibody and, optionally, one or more other diagnostic or therapeutic agents in the same or different containers. The kits may also contain other pharmaceutically acceptable formulations, either for diagnosis or combined therapy. Such kits may also provide appropriate reagents to conjugate the anti-CD3 antibody with the other diagnostic or therapeutic agent(s).

More specifically the kits may have a single container that contains the anti-CD3 antibody with or without additional components, or they may have distinct containers for each desired agent. Where combined therapeutics are provided for conjugation, a single solution may be pre-mixed, either in a molar equivalent combination, or with one component in excess of the other. Alternatively, the anti-CD3 antibody and any optional diagnostic or therapeutic agent of the kit may be maintained separately within distinct containers prior to administration to a patient. The kits may also comprise a second/third container means for containing a sterile, pharmaceutically acceptable buffer or other diluent such as bacteriostatic water for injection (BWFI), phosphate-buffered saline (PBS), Ringer's solution and dextrose solution.

When the components of the kit are provided in one or more liquid solutions, the liquid solution is preferably an aqueous solution, with a sterile aqueous solution being particularly preferred. However, the components of the kit may be provided as dried powder(s). When reagents or components are provided as a dry powder, the powder can be reconstituted by the addition of a suitable solvent. It is envisioned that the solvent may also be provided in another container.

As indicated briefly above the kits may also contain a means by which to administer the antibody and any optional components to the patient, e.g., one or more needles or syringes, or even an eye dropper, pipette, or other such like apparatus, from which the formulation may be injected or introduced into the patient. Such kits will also typically include a means for containing the vials, or such like, and other component in close confinement for commercial sale, such as, e.g., injection or blow-molded plastic containers into which the desired vials and other apparatus are placed and retained. Any label or package insert indicates that the anti-CD3 antibody composition is used for treating cancer, for example colorectal cancer.

In other preferred embodiments, anti-CD3 antibodies disclosed herein may be used in conjunction with, or comprise, diagnostic or therapeutic devices useful in the diagnosis or treatment of hyperproliferative or autoimmune disorders. For example, in one embodiment, anti-CD3 antibodies may be combined with certain diagnostic devices or instruments that may be used to detect, monitor, quantify or profile cells or marker compounds involved in the etiology or manifestation of a hyperproliferative or autoimmune disorder.

EXAMPLES

The following examples have been included to illustrate aspects of the inventions disclosed herein. In light of the present disclosure and the general level of skill in the art, those of skill appreciate that the following examples are intended to be exemplary only and that numerous changes, modifications, and alterations may be employed without departing from the scope of the disclosure.

Example 1

Cell Lines and Primary Cells

Jurkat E6.1 (ATCC TIB-152) and Jurkat J.RT3-T3.5 (ATCC TIB-153) were cultured in RPMI-1640 (ThermoFisher 11875093) supplemented with 10% heat-inactivated FBS (Gibco 12484028). HeLa (Abcam ab255928) and HeLa EGFR KO cells (Abcam ab255385) were maintained in DMEM/F-12 (Gibco 10565018) supplemented with 10% heat-inactivated FBS. CHO-K1 cells were purchased from Sigma (85051005) and were maintained in Ham's F-12 medium (Gibco 11765054) supplemented with 1 nM L-Glutamine (Gibco 35050061) and 10% heat-inactivated FBS. All cells were cultured at 37° C., 5% $CO_2$ and were routinely tested for mycoplasma contamination.

ExpiCHO-S suspension cells (Gibco A29127) were maintained in ExpiCHO-S expression medium (Gibco A2910001) in a humidified chamber at 37° C., 8% $CO_2$ with 150 rpm shaking. All cells were routinely tested for mycoplasma contamination.

Purified cynomolgus monkey CD3 pan T cells were purchased from iQ Biosciences (IQB-Mn1-T10). Healthy donor human PBMCs were isolated from a leukapheresis sample purchased from StemCell (07850). Leukapheresis samples were collected, resuspended in ammonium chloride solution (StemCell 07850) and incubated on ice for 15 minutes. PBMCs were washed four times by centrifugation at 150×g for 10 minutes, brake off, with PBS+2% FBS before being frozen in 90% FBS+10% DMSO. $CD3^+$ T cells were isolated from human PBMCs using an EasySep human T cell isolation kit (StemCell 17951) according to the manufacturer's instructions.

Generation of γ/δ TCR ExpiCHO-S Cells

ExpiCHO-S cells were transiently transfected with CD3 and γ/δ TCR plasmids by electroporation on the MaxCyte STX. Mock-transfected cells were used as a negative control. Transfection efficiency was assessed by flow cytometry on the CytoFLEX S or LX flow cytometers (Beckman Coulter) using 50 nM anti-CD3 OKT3 (eBioscience 16-0037-85), anti-TCR JOVI.1 (AbCam ab5465) and anti-γ/δ TCR-BV421 antibodies (BD Biosciences 744870) incubated with cells for 30 minutes at 4° C. Binding of OKT3 and JOVI.1 was detected using 100 nM fluorescently labeled secondary antibodies (Jackson ImmunoResearch 115-606-072).

Generation of EGFR-Transduced Cell Lines

To generate CHO-K1 cells overexpressing EGFR at two expression levels, two lentiviral transfer vectors were designed, each containing a C-terminal eGFP-tagged human EGFR driven by the human EF1a promoter. One vector contained a uORF cassette followed by a kozak sequence (ACC), while the other contained a uORF cassette followed by a non-kozak sequence (TTT) in front of the translation initiation site (ATG) of EGFR. Lentiviral vector generation and viral particle production was outsourced to VectorBuilder. Lentiviral transduction was performed by seeding 100,000 CHO-K1 cells per well in 6-well tissue culture-treated plates (Sarstedt 83.3920.500) in 1.5 mL media (described above) supplemented with 5 μg/mL polybrene (VectorBuilder) and lentiviral particles for six hours followed by a medium change and expansion. Thirteen days post-transduction, $GFP^+$ transduced cells were sorted (BD FACSAria Fusion) and the surface expression level of EGFR was evaluated using anti-EGFR antibodies (R&D Systems MAB9577) via flow cytometry using a CytoFLEX S flow cytometer (Beckman Coulter).

Example 2

Affinity-Capture Self-Interaction Nanoparticle Spectroscopy (AC-SINS) Assay

The AC-SINS assay was performed as described previously with modifications (Liu et al., 2014, High-throughput screening for developability during early-stage antibody discovery using self-interaction nanoparticle spectroscopy, *mAbs,* 6:2, 483-492, DOI: 10.4161/mabs.2743).

Gold nanoparticles (15705; Ted Pella Inc.) were coated with 100% capturing anti-human goat IgG Fc (109-005-008; Jackson ImmunoResearch) that was buffer exchanged into 20 mM sodium acetate buffer pH 4.3 prior to the coating reaction. The conjugation reaction was quenched with 0.1 μM polyethylene glycol methyl ether thiol (PEG-SH; 729140; Merck-Sigma) and eluted into 0.1×PBS. The antibodies of interest in PBS were then incubated with the coated gold particles for 4 h at room temperature in 384-well non-binding plates (07000060; Fisher Scientific) and the wavelength shift was measured using a Synergy Neo2 plate reader (Biotek) within the range of 500-570 nm, in increments of 1 nm. Test antibodies were diluted in PBS to a final concentration of 100 μg/mL for incubation. Delta plasma wavelength shift in comparison with PBS is reported. The self-interacting antibodies show a higher wavelength shift away from the buffer controls.

As shown in the self-association plot in FIG. 1, a significant number of human CD3-specific and human/cynomolgus monkey CD3-crossreactive antibodies demonstrated low mean self-interaction.

Example 3

BVP-ELISA

The BVP ELISA was performed as previously described but with modification. (Hötzel, Isidro et al. "A strategy for risk mitigation of antibodies with fast clearance." *mAbs* Vol. 4,6 (2012): 753-60. doi:10.4161/mabs.22189).

Baculovirus particles were purchased from Lake Pharma (Lake Pharma Bac-to-Bac: Baculovirus Particle Production (BVP), 2 mL). BVP were diluted to a 1% solution in carbonate-bicarbonate buffer pH 9.6 (prepared using (Millipore Sigma Cat. No. C3041-50CAP). This solution was further diluted by half in 1×PBS. 12.5 μL of this solution was dispensed into each well of a Nunc MaxiSorp 384 well ELISA plate (Sigma Aldrich Cat. No. P6366-1CS) and incubated overnight at 4° C.

The next day, the BVP solution was aspirated and 70 μL Pierce Protein Free blocking buffer (Thermo Fisher cat no. 37572) dispensed into each well and incubated for a minimum of 1 hour. Normalized samples in 1×PBS at 350 μg/mL were serially diluted with Pierce Protein Free Blocking buffer to 100 μg/mL, 50 μg/mL, 25 μg/mL and 12.5 μg/mL in a Greiner Bio 384 well plate (Fisher cat no. 07000050). After the blocking incubation, the Maxisorp 384 well plate was rinsed with 85 μL of 1×PBS three times. 12.5 μL of each of the four dilutions of the primary antibody was dispensed into the washed Maxisorp 384 well plate and incubated for 1 hour. At the end of the hour, the primary antibody was aspirated and the plate washed three times with 1×PBS. 12.5 μL of goat anti-huIgG-Fc secondary antibody (Cedarlane Cat. No. 109-035-008) at a 1:50000 dilution in Pierce Protein Free blocking buffer was added to each well and incubated for 1 hour. At the end of the incubation, the secondary antibody was aspirated and washed three times in 1×PBS. 12.5 μL Neogen TMB (Cedarlane 308175) was dispensed into each well and incubated for 10 minutes. At the end of the 10 minutes, 12.5 μL of stop solution 0.16 M $H_2SO_4$ (ThermoScientific Ref N600) was added to each well. The absorbance of each well was subsequently read by the Biotek Synergy Neo2 plate reader at a wavelength of 450 nm. The BVP score was calculated by dividing the absorbance of the well incubated with 100 μg/mL of primary antibody and dividing by the absorbance of a control well that was not treated with primary antibody.

Figure 2:
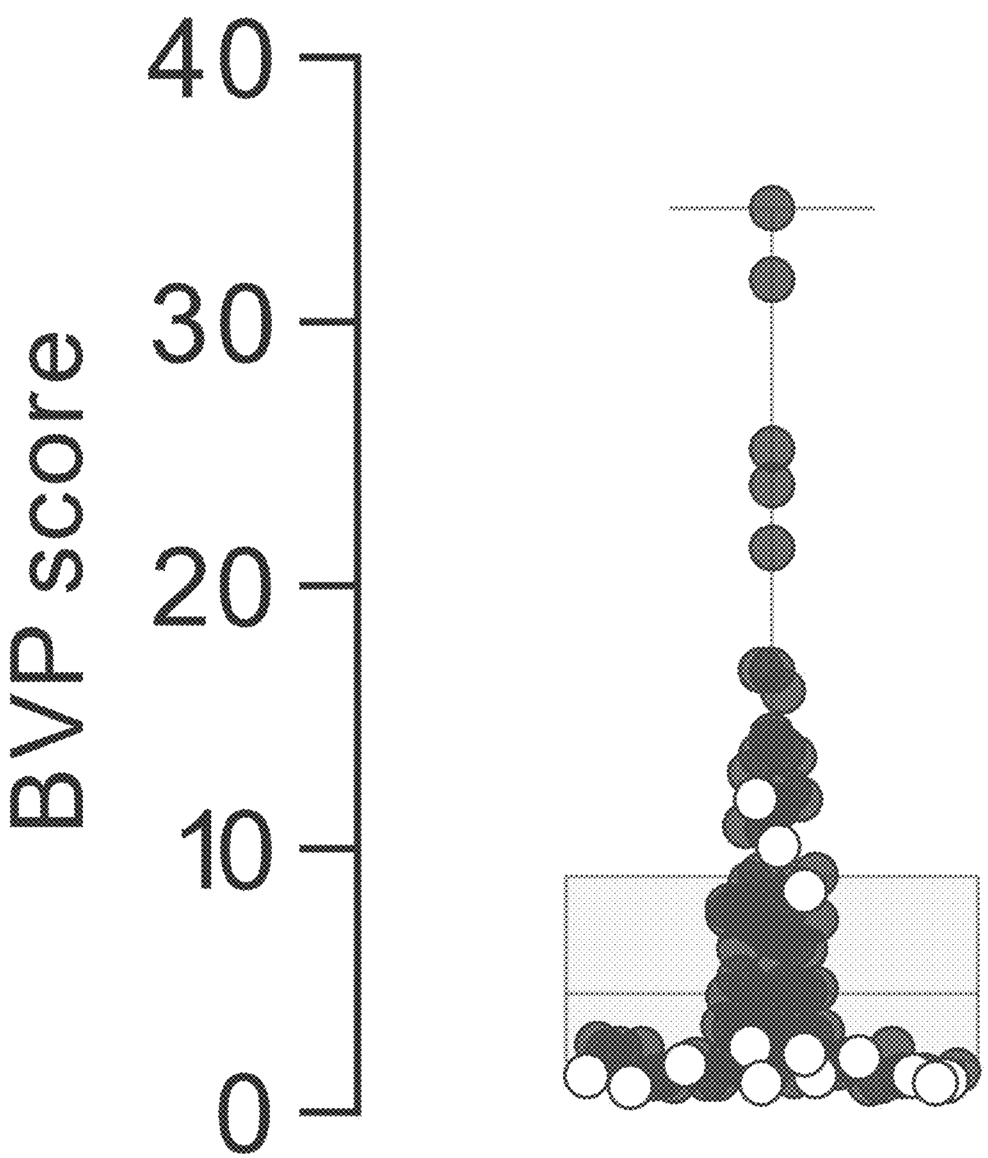
FIG. 2 is a polyspecificity plot. Most of the anti-CD3 antibodies in accordance with the inventions disclosed herein demonstrated low mean polyspecificity, which is associated with slower clearance times in patients.

As shown in the polyspecificity plot in FIG. 2, a significant number of human CD3-specific and human/cynomolgus monkey CD3-crossreactive antibodies demonstrated low mean polyspecificity.

Example 4

Intact Mass

For intact monospecific antibody analysis, purified antibodies were diluted to 87.5 ng/mL with 0.1% formic acid (LC/MS grade, Fisher Scientific A11750). 5 μL corresponding to 0.4 μg of sample was injected and eluted. For bispecific antibody analysis, the samples were treated with RAPID™ PNGase F (non-reducing format) (New England Biolabs P0711S) to remove N-linked glycans then subsequently diluted with 1:1 (v/v) with 0.1% formic acid. 5 μL corresponding to 0.6 μg of sample was injected and eluted.

For the desalting and separation of intact monospecific antibodies and deglycosylated bispecific antibodies, a BioResolve RP mAb Polyphenyl Column was used (450 Å, 2.7 m, 2.1 mm×50 mm, Waters 186008944). The applied flow rate was 0.4 mL/min and the column temperature was kept at 80° C. A binary gradient was employed, with the composition of mobile phases as followed: mobile A contained water (LC/MS grade, Thermo-Fisher W6) with 0.1% formic acid and mobile phase B contained acetonitrile (LC/MS grade, Thermo-Fisher A955) with 0.1% formic acid. The total run time was 6 minutes, of which the first 1 minute was desalting maintained at 5% B, followed by 1.5 minutes of linear gradient separation from 5% to 55% B. The chromatographic run was then quickly ramped up to 95% B in 1 minute, to be concluded by a washing phase of 95% B for 1 minute, and followed by an equilibrium phase at 5% B for another 1.5 minutes.

Example 5

Mass Spectrometry

All analyses were performed using a Vanquish Flex Binary UHPLC system coupled online to a High Resolution ORBITRAP EXPLORIS™ 480 mass spectrometer with Biopharma option (Thermo Fisher Scientific, USA). All spectra were acquired in positive ionization mode with the heater electrospray ionization (HESI) sprayer to which a 3.5 kV voltage was applied. The sheath gas and auxiliary gas flow rates were 50 and 10 units, respectively. The temperature of the high capacity ion transfer tube and the vaporizer were 325° C. and 350° C., respectively. The ion funnel RF was set at 100%. A m/z window of 2200-5000 was selected with a normalized AGC target value of 300% for the MS1 scan. The resolving power was set at 15,000 and 30,000 for the analysis of bispecific antibodies and monospecific antibodies, respectively. Mass spectra were acquired with 10 microscans per spectrum with the maximum injection time of 200 ms and source fragmentation of 100 V at high pressure in intact protein mode.

Deconvolution of raw spectra within the elution time window was performed using the Intact workflow in Protein Metrics BYO S™ software (v.4.2, Protein Metrics, Inc). All full MS scans were deconvoluted using the following parameters: m/z range of 2200-5000, mass range of 143000-163000 with a mass tolerance of 10 Da. For the analysis of monospecific antibodies, the observed masses were compared to the expected masses with the various combinations of glycoforms to identify the intact antibody. For the analysis of bispecific antibodies, possible pairings were identified by matching the observed masses with their theoretical masses. Relative abundance of the correct pair was calculated by dividing its deconvoluted signal intensity by the total intensity of all expected bispecific pairings.

Example 6

Kinetics

High-throughput surface plasmon resonance (SPR) coupled kinetic experiments were performed on a Carterra LSA® instrument equipped with an HC-30M chip type (Carterra, USA). The instrument uses two microfluidic modules, a single-flow cell (SFC) and a 96 printhead, to deliver samples to the chip surface via back-and-forth cycling of a fixed sample volume. An up to 384-ligand array is generated by docking the MFC onto each of the four nested print block locations in a serial manner.

The purified mAbs were immobilized on a Carterra LSA® HC-30M chip by direct coupling. The chip surface was first activated by flowing a freshly prepared 1:1:1 activation mix of 100 mM MES pH 5.5, 100 mM S-NHS, 400 mM EDC for 7 min. mAbs diluted to 10 μg/mL in 10 mM NaOAc pH 4.25+0.01% TWEEN®20 were then injected and printed onto the chip surface simultaneously using the MFC printhead for 10 min. Finally, the chip surface was quenched by flowing 1 M ethanolamine for 7 min (to block the excess reactive esters), followed by 2 wash steps of 15 s each in 25 mM MES pH 5.5. In addition to expressed and purified mAbs, relevant benchmarks and negative control mAbs were also printed on the chip surface.

Affinity determination by single-cycle kinetics of mAbs coupled to the HC-30M chip surface as described above was performed using a Carterra LSA® instrument. The following proteins were screened for kinetic measurements against the immobilized mAbs: human CD3/ed (Sino CT038-H2508H), human CD3e/g (Acro CDD-C52W4), cyno CD3e/d (Acro H52W5), cyno CD3e/g (Acro CDG-52W6), and human EGFR (Genscript z03202).

Each protein in HBSTE (10 mM HEPES pH 7.4, 150 mM NaCl, 3 mM EDTA, 0.01% (v/v) TWEEN® 20)+0.05% BSA at 300 nM, 100 nM, 33.3 nM, 11.1 nM, 3.7 nM, 1.2 nM, 0.4 nM, and 0.1 nM was sequentially injected onto the chip surface. For each concentration, the protein was injected for 10 min (association phase), followed by running buffer injection for 15 min (dissociation phase) and a final buffer stabilizing injection for 2 min. Six regeneration cycles of 25 s were performed between each antigen by injecting 10 mM glycine pH 2.0 on the chip surface.

The data were analyzed using the Carterra Kinetics analysis software. Briefly, the data were referenced with the interstitial reference spots and double-referenced to a buffer cycle, and then fit globally to a 1:1 Langmuir binding model to determine their apparent association (ka) and dissociation (kd) kinetic rate constants and binding affinity constants (KD). See Table 1 below.

TABLE 1

| Affinity & Kinetics | | |
|---|---|---|
| mAb ID | hCD3e/d Affinity (KD, M) | hCD3e/g Affinity (KD, M) |
| 42 | | 1.94E−08 |
| 43 | | 2.17E−08 |
| 44 | | 1.91E−08 |
| 46 | 2.40E−07 | 9.84E−08 |
| 47 | | 2.01E−08 |

TABLE 1-continued

| Affinity & Kinetics | | |
|---|---|---|
| mAb ID | hCD3e/d Affinity (KD, M) | hCD3e/g Affinity (KD, M) |
| 49 | 1.08E−08 | 3.64E−09 |
| 50 | | 3.43E−08 |
| 51 | 3.51E−07 | 1.71E−07 |
| 52 | 1.71E−08 | 1.12E−07 |
| 53 | | 2.58E−07 |
| 54 | 5.53E−07 | 8.32E−08 |
| 55 | | 8.57E−08 |
| 65 | 1.28E−07 | 1.01E−07 |
| 66 | 1.49E−07 | 1.25E−07 |
| 67 | | 1.86E−08 |
| 68 | 4.67E−08 | 9.99E−08 |
| 71 | | 1.13E−07 |
| 72 | 6.06E−07 | 3.94E−07 |
| 73 | | 1.62E−08 |
| 74 | | 9.83E−09 |
| 77 | 2.86E−07 | |
| 78 | 2.83E−07 | 1.26E−06 |
| 79 | 1.24E−07 | 7.48E−08 |
| 81 | 1.01E−07 | 6.96E−08 |
| 83 | 8.65E−08 | 5.34E−08 |
| 85 | 1.17E−07 | 1.02E−07 |
| 86 | 8.21E−08 | 9.19E−08 |
| 90 | 3.33E−08 | 4.10E−08 |
| 93 | 4.78E−08 | 3.58E−08 |
| 94 | 1.57E−09 | 7.80E−09 |
| 95 | 1.79E−09 | 9.22E−09 |
| 96 | 7.73E−09 | 1.19E−08 |
| 97 | 1.65E−08 | 1.78E−08 |
| 98 | 9.71E−09 | 1.12E−08 |
| 99 | 8.92E−09 | 1.16E−08 |
| 100 | 2.05E−08 | 2.55E−08 |
| 101 | 9.06E−09 | 1.09E−08 |
| 106 | 1.71E−08 | 1.06E−08 |
| 109 | 2.17E−08 | |
| 110 | 1.84E−08 | 8.97E−09 |
| 111 | 1.96E−08 | 7.44E−09 |
| 112 | 5.69E−08 | 1.48E−08 |
| 113 | 1.07E−07 | 2.88E−08 |
| 114 | 6.58E−08 | 1.89E−08 |
| 115 | 6.38E−08 | 1.57E−08 |
| 116 | 1.04E−07 | 2.41E−08 |
| 117 | 4.06E−08 | 9.84E−09 |
| 118 | 1.01E−07 | |
| 119 | 3.72E−08 | |
| 120 | 4.44E−08 | 1.21E−08 |
| 121 | 2.10E−08 | |
| 122 | 3.42E−08 | 1.30E−08 |
| 123 | 5.61E−08 | 1.66E−08 |
| 125 | 3.60E−08 | 1.38E−08 |
| 126 | 9.72E−09 | |
| 127 | 6.50E−08 | 1.54E−08 |
| 128 | 1.86E−07 | |
| 129 | 2.64E−08 | 6.62E−09 |
| 130 | 2.17E−08 | 6.07E−09 |
| 131 | 3.21E−08 | 7.45E−09 |
| 133 | 2.72E−08 | 6.64E−09 |
| 134 | 3.11E−08 | 1.09E−08 |
| 137 | 1.81E−07 | 9.50E−07 |
| 140 | 6.35E−07 | |
| 141 | 9.21E−08 | 2.60E−08 |
| 145 | 6.10E−08 | 1.31E−08 |
| 155 | 4.62E−08 | 7.07E−09 |
| 156 | 4.77E−08 | 7.00E−09 |
| 157 | 5.31E−08 | 1.22E−08 |
| 158 | 1.03E−08 | |
| 160 | 1.52E−08 | |
| 161 | 2.41E−08 | |
| 162 | 1.94E−08 | |
| 163 | 4.20E−08 | 8.63E−09 |
| 164 | 7.70E−08 | 1.50E−08 |
| 165 | 4.04E−08 | 1.06E−08 |
| 166 | 4.73E−08 | 1.25E−08 |
| 167 | 6.26E−09 | |
| 169 | 7.38E−08 | 1.26E−08 |
| 170 | 7.19E−08 | |
| 171 | 1.84E−08 | |

TABLE 1-continued

| Affinity & Kinetics | | |
|---|---|---|
| mAb ID | hCD3e/d Affinity (KD, M) | hCD3e/g Affinity (KD, M) |
| 172 | 4.83E−09 | |
| 173 | 7.11E−09 | |
| 176 | 3.49E−09 | |
| 177 | 4.11E−08 | |
| 178 | 9.92E−10 | |
| 179 | 7.72E−09 | |
| 180 | 2.98E−08 | |
| 188 | 3.60E−08 | 1.70E−08 |
| 189 | 1.10E−07 | 6.00E−08 |
| 190 | 9.70E−09 | |
| 191 | 2.80E−08 | 1.50E−08 |
| 192 | 9.20E−09 | 9.30E−09 |
| 193 | 9.30E−08 | 2.90E−08 |
| 194 | 1.90E−08 | 1.20E−08 |
| 195 | 1.10E−08 | 7.10E−09 |
| 196 | 6.90E−09 | 9.10E−09 |
| 197 | 4.90E−08 | 1.70E−08 |
| 198 | 4.10E−08 | 3.00E−08 |
| 199 | 2.60E−08 | 2.90E−08 |
| 200 | 8.60E−09 | |
| 201 | 2.80E−08 | 1.30E−08 |
| 202 | 1.00E−08 | |
| 203 | 1.70E−08 | 9.50E−09 |
| 204 | 2.00E−07 | 9.00E−08 |
| 205 | 1.30E−08 | 8.40E−09 |
| 206 | 7.30E−08 | 3.30E−08 |
| 207 | 1.10E−08 | |
| 208 | 3.00E−09 | |
| 209 | 5.50E−09 | 5.70E−09 |
| 210 | 1.20E−07 | 5.90E−08 |
| 211 | 4.90E−09 | |
| 212 | 1.10E−08 | 2.20E−08 |
| 213 | 1.30E−08 | 8.60E−09 |
| 214 | 1.30E−08 | 2.50E−08 |
| 215 | 7.60E−08 | 3.40E−08 |
| 216 | 9.30E−09 | 6.80E−09 |
| 217 | 3.80E−08 | 1.70E−08 |
| 218 | 6.20E−08 | 3.40E−08 |
| 219 | 1.00E−08 | 6.30E−09 |
| 220 | 1.60E−08 | 1.10E−08 |
| 221 | 3.80E−08 | 2.50E−08 |
| 222 | 1.60E−08 | 8.20E−09 |
| 223 | 9.70E−08 | |
| 224 | 3.90E−08 | 1.80E−08 |
| 225 | 1.10E−08 | 6.20E−09 |
| 226 | 7.50E−08 | 3.20E−08 |
| 227 | 6.90E−09 | |
| 228 | 2.50E−08 | |
| 229 | 2.20E−08 | 4.70E−08 |
| 230 | 1.80E−08 | |
| 231 | 3.60E−08 | |
| 232 | 8.80E−09 | |
| 233 | 2.90E−09 | |
| 234 | 1.80E−08 | |
| 235 | 1.40E−08 | |
| 236 | 1.20E−08 | |
| 237 | 2.50E−08 | 5.60E−09 |
| 238 | 5.90E−08 | 1.70E−08 |
| 239 | 1.50E−08 | |
| 240 | 1.80E−08 | |
| 241 | 6.40E−09 | |
| 242 | 1.30E−09 | |
| 243 | 1.10E−08 | |
| 244 | 8.50E−09 | |
| 245 | 5.30E−09 | |
| 246 | 4.90E−08 | |
| 247 | 9.40E−09 | |
| 249 | 5.80E−08 | |
| 251 | 2.40E−08 | 8.10E−09 |
| 252 | 3.00E−08 | 1.30E−08 |
| 258 | 2.40E−08 | |
| 259 | 6.30E−08 | 1.30E−08 |
| 260 | 2.80E−08 | 4.20E−09 |
| 261 | 1.60E−08 | 3.00E−09 |
| 262 | 2.60E−08 | 1.00E−08 |
| 263 | 9.00E−09 | 4.10E−09 |

TABLE 1-continued

| Affinity & Kinetics | | |
|---|---|---|
| mAb ID | hCD3e/d Affinity (KD, M) | hCD3e/g Affinity (KD, M) |
| 264 | 3.20E−08 | 7.40E−09 |
| 265 | 4.10E−08 | |
| 273 | 7.50E−08 | 4.60E−08 |
| 276 | 1.50E−08 | 9.60E−09 |
| 283 | 1.60E−07 | 2.00E−08 |
| 284 | 4.50E−07 | |
| 285 | 1.50E−07 | |
| 286 | 5.80E−07 | |
| 288 | 1.30E−07 | |
| 290 | 3.20E−06 | |
| 291 | 4.20E−08 | |
| 292 | 9.10E−08 | 4.70E−08 |
| 293 | 5.70E−08 | |
| 295 | | 2.10E−07 |
| 296 | 3.70E−07 | 1.80E−07 |
| 297 | 6.60E−08 | 1.80E−08 |
| 298 | 4.30E−08 | |
| 299 | 4.10E−08 | |
| 301 | 1.10E−07 | |
| 302 | 5.80E−08 | |
| 303 | 4.70E−08 | 5.50E−09 |
| 304 | 1.20E−07 | |
| 305 | 8.30E−08 | |
| 306 | 2.50E−07 | |
| 307 | 1.00E−07 | |
| 308 | 5.40E−08 | |
| 309 | 7.40E−08 | |
| 313 | 6.20E−08 | |
| 314 | 1.00E−07 | |
| 315 | 5.30E−08 | |
| 316 | 7.00E−08 | |
| 317 | 6.70E−08 | |
| 318 | 8.40E−08 | |
| 320 | | 6.90E−10 |
| 321 | 1.20E−07 | |
| 322 | 1.10E−07 | |

Example 7

Analytical Hydrophobic Interaction Chromatography (aHIC)

Relative surface hydrophobicity of the purified mAbs was assessed by analytical hydrophobic interaction chromatography (aHIC). Using a Vanquish Duo UH-PLC System (Thermo Fisher Scientific), 5 μL of each mAb at 0.35 mg/mL was injected onto a hydrophobic interaction column (TSKgel Butyl-NPR, 2.5 μm, 4.6 mm TD×3.5 cm, TOSOH #0014947). A linear gradient method from 5800 to 0% buffer A over 6 minutes with a flow rate of 0.5 mL/min was used to separate mAbs based on their surface hydrophobicity properties (Buffer A: 25 mM sodium phosphate pH 7.0, 2.5 M ammonium sulfate; Buffer B: 25 mM sodium phosphate pH 7.0; Fisher Scientific #S468-500, #S373-500, and #A702-3). Chromatograms monitoring absorbance at 280 nm were acquired and analyzed using CHROMELEON™ software (Thermo Fisher Scientific, v 7.3). Relative hydrophobicity of each mAb was determined based on retention time of the largest peak by integrated area.

Figure 3:
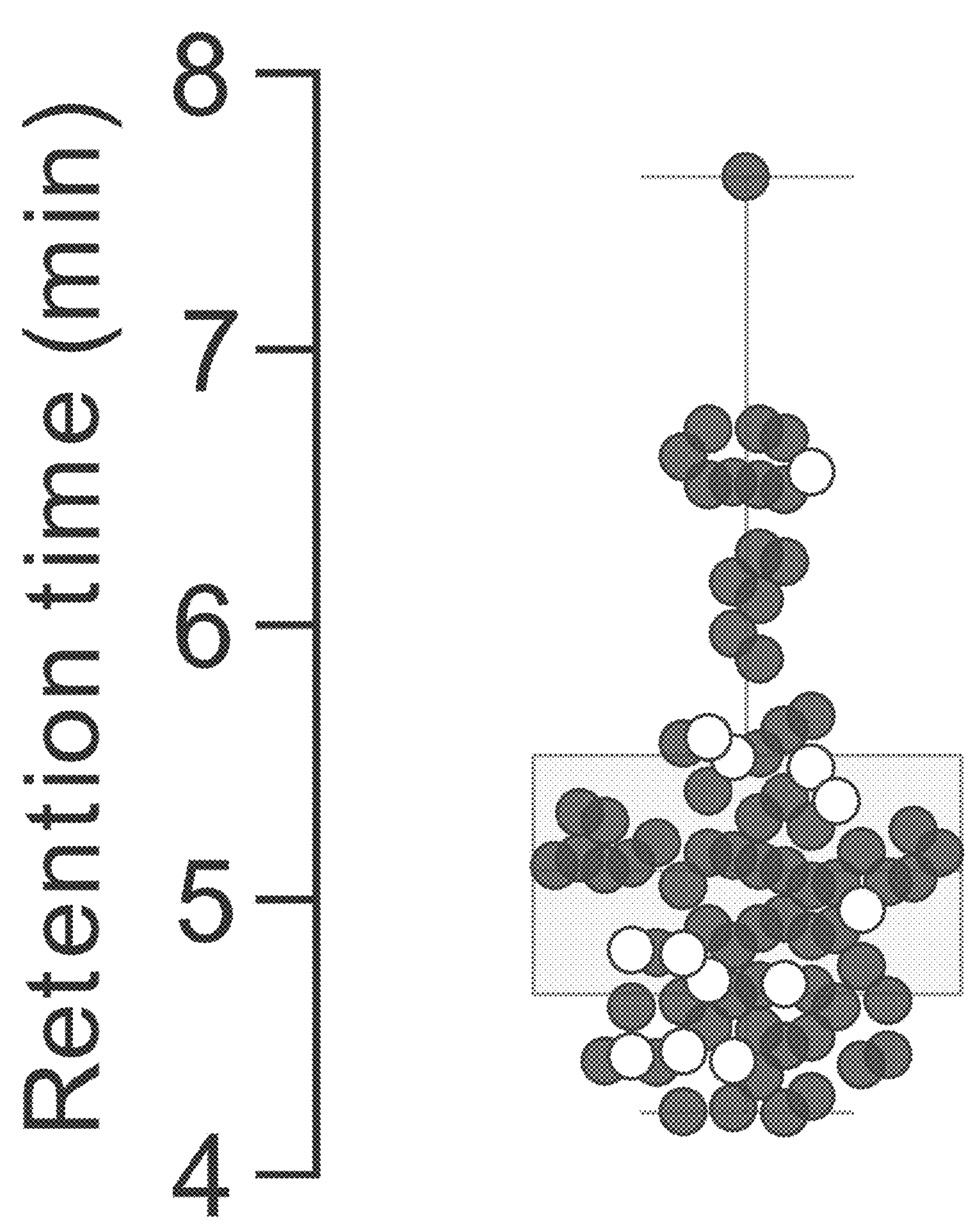
FIG. 3 is a hydrophobicity plot. Most of the anti-CD3 antibodies in accordance with the inventions disclosed herein demonstrated low hydrophobicity, which translates to a lower propensity to aggregate, which in turn causes lower therapeutic efficacy and induces anti-antibody immune responses in patients.

As shown in the hydrophobicity plot in FIG. 3, a significant number of human CD3-specific and human/cynomolgus monkey CD3-crossreactive antibodies demonstrated low mean hydrophobicity.

Example 8

Cell-Based Binding Assay

Purified antibodies were confirmed to bind CD3 expressed on cells using the CytoFLEX S or LX flow cytometers (Beckman Coulter). Antibodies were diluted to 25 nM in FACS buffer (PBS+2% FBS) and were incubated with CD3-expressing cells for 30 minutes at 4° C. Cells were washed with FACS buffer, and binding was detected using 75 nM fluorescently labeled anti-human secondary detection antibodies (Jackson ImmunoResearch 109-606-098). The median fluorescence intensity of the binding signal for each antibody was normalized to the isotype control to obtain a fold over isotype value. An antibody with a fold over isotype (FOI) of ≥10 was considered to be positive for binding. See Table 2 below.

TABLE 2

| mAb ID | Jurkat Cell Binding (FOI) | Jurkat CD3 KO Cell Binding (FOI) | Human primary T Cell Binding (FOI) | Cyno primary T Cell Binding (FOI) |
|---|---|---|---|---|
| 42 | 110.718 | 1.496 | 96.193 | 1.097 |
| 43 | 107.539 | 1.591 | 83.28 | 0.95 |
| 44 | 130.996 | 1.753 | 109.987 | 0.938 |
| 45 | 0.918 | 0.807 | 0.891 | 0.955 |
| 46 | 107.174 | 1.198 | 96.921 | 0.908 |
| 47 | 111.994 | 1.552 | 135.997 | 1.016 |
| 48 | 1.426 | 0.853 | 1.303 | 0.995 |
| 49 | 177.67 | 2.28 | 190.715 | 1.02 |
| 50 | 92.487 | 1.312 | 86.377 | 0.956 |
| 51 | 99.835 | 1.206 | 101.86 | 0.944 |
| 52 | 181.321 | 2.195 | 185.137 | 1.013 |
| 53 | 44.573 | 1.126 | 34.758 | 0.874 |
| 54 | 110.866 | 1.275 | 98.49 | 1.085 |
| 55 | 151.023 | 1.532 | 103.94 | 1.052 |
| 63 | 0.98 | 1.08 | 0.842 | 0.97 |
| 64 | 0.97 | 0.925 | 0.816 | 0.977 |
| 65 | 184.295 | 1.852 | 199.394 | 1.015 |
| 66 | 171.919 | 1.783 | 191.593 | 0.954 |
| 67 | 70.159 | 1.558 | 72.367 | 0.99 |
| 68 | 112.934 | 1.747 | 116.858 | 56.024 |
| 69 | 144.648 | 3.067 | 122.597 | 244.77 |
| 70 | 140.369 | 2.986 | 130.626 | 238.491 |
| 71 | 100.229 | 1.61 | 108.267 | 0.966 |
| 72 | 98.67 | 1.17 | 91.385 | 0.843 |
| 73 | 108.651 | 2.034 | 74.539 | 1.26 |
| 74 | 150.617 | 2.497 | 145.998 | 1.02 |
| 75 | 1.073 | 1.059 | 0.694 | 0.978 |
| 76 | 0.92 | 0.814 | 0.921 | 0.876 |
| 77 | 105.555 | 1.592 | 125.36 | 6.859 |
| 78 | 104.218 | 1.381 | 116.101 | 41.586 |
| 79 | 171.243 | 1.96 | 198.669 | 0.958 |
| 80 | 1.14 | 0.952 | 0.905 | 0.944 |
| 81 | 164.876 | 1.676 | 157.944 | 0.885 |
| 82 | 1.011 | 0.971 | 0.954 | 0.869 |
| 83 | 160.872 | 1.769 | 173.407 | 1.031 |
| 84 | 1.752 | 1.088 | 0.805 | 0.804 |
| 85 | 181.406 | 2.123 | 195.056 | 1.115 |
| 86 | 175.384 | 2.158 | 189.486 | 0.943 |
| 87 | 1.017 | 0.934 | 0.715 | 0.923 |
| 88 | 0.953 | 0.855 | 0.885 | 0.933 |
| 89 | 0.975 | 0.909 | 0.594 | 0.909 |
| 90 | 3.988 | 12.134 | 1.373 | 0.979 |
| 91 | 0.962 | 0.896 | 0.746 | 0.94 |
| 93 | 174.812 | 2.757 | 197.773 | 0.986 |
| 94 | 170.05 | 2.279 | 173.571 | 0.915 |
| 95 | 177.286 | 2.655 | 206.499 | 0.918 |
| 96 | 173.69 | 2.668 | 188.95 | 0.927 |
| 97 | 191.959 | 2.66 | 210.976 | 0.868 |
| 98 | 180.727 | 2.745 | 173.83 | 0.981 |
| 99 | 197.644 | 2.664 | 217.607 | 0.961 |
| 100 | 241.314 | 3.399 | 229.082 | 0.98 |
| 101 | 216.386 | 2.825 | 232.959 | 0.912 |
| 102 | 100.762 | 1.488 | 98.89 | 0.966 |
| 103 | 0.927 | 0.815 | 0.526 | 0.929 |
| 104 | 0.939 | 0.845 | 0.778 | 0.872 |
| 105 | 0.951 | 0.855 | 0.842 | 0.858 |
| 106 | 185.629 | 3.057 | 209.642 | 0.927 |
| 107 | 1.079 | 1.062 | 0.743 | 0.927 |
| 108 | 1.192 | 1.462 | 0.772 | 0.921 |
| 109 | 1.662 | 1.235 | 1.404 | 1.012 |

TABLE 2-continued

| mAb ID | Jurkat Cell Binding (FOI) | Jurkat CD3 KO Cell Binding (FOI) | Human primary T Cell Binding (FOI) | Cyno primary T Cell Binding (FOI) |
|---|---|---|---|---|
| 110 | 197.379 | 3.533 | 214.195 | 0.953 |
| 111 | 159.642 | 2.439 | 168.119 | 1.063 |
| 112 | 157.501 | 1.855 | 173.791 | 0.908 |
| 113 | 156.95 | 1.635 | 172.932 | 0.968 |
| 114 | 167.405 | 10.244 | 178.587 | 1.016 |
| 115 | 157.411 | 1.836 | 173.802 | 0.899 |
| 116 | 159.328 | 1.603 | 174.422 | 0.9 |
| 117 | 154.758 | 1.86 | 169.981 | 0.931 |
| 118 | 83.831 | 1.449 | 84.738 | 0.88 |
| 119 | 90.409 | 1.7 | 95.363 | 0.861 |
| 120 | 167.834 | 12.817 | 166.94 | 0.981 |
| 121 | 100.825 | 1.699 | 101.018 | 12.159 |
| 122 | 198.562 | 57.175 | 174.142 | 0.913 |
| 123 | 158.874 | 4.495 | 171.134 | 0.901 |
| 124 | 0.962 | 0.834 | 0.835 | 0.862 |
| 125 | 184.527 | 42.357 | 180.356 | 0.939 |
| 126 | 96.989 | 1.499 | 97.565 | 0.865 |
| 127 | 154.798 | 1.773 | 172.059 | 0.88 |
| 128 | 97.06 | 1.449 | 100.516 | 0.93 |
| 129 | 156.537 | 2.005 | 169.088 | 1.032 |
| 130 | 155.178 | 2.041 | 164.593 | 1.105 |
| 131 | 154.993 | 1.921 | 170.845 | 0.892 |
| 132 | 156.852 | 5.01 | 163.782 | 0.966 |
| 133 | 161.157 | 4.118 | 169.081 | 0.927 |
| 134 | 170.874 | 26.463 | 176.086 | 0.975 |
| 135 | 0.958 | 0.93 | 0.821 | 0.883 |
| 136 | 90.888 | 1.145 | 85.999 | 0.945 |
| 137 | 151.297 | 1.328 | 158.227 | 0.929 |
| 138 | 0.915 | 0.793 | 0.796 | 0.852 |
| 139 | 0.943 | 0.799 | 0.678 | 0.869 |
| 140 | 134.835 | 1.238 | 147.846 | 2.018 |
| 141 | 182.977 | 2.433 | 310.076 | 0.883 |
| 142 | 65.492 | 1.046 | 59.616 | 0.854 |
| 143 | 15.495 | 38.63 | 1.797 | 1.847 |
| 144 | 139.432 | 1.29 | 157.103 | 3.127 |
| 145 | 190.834 | 2.032 | 216.945 | 0.884 |
| 146 | 194.349 | 4.765 | 340.412 | 136.225 |
| 147 | 1.381 | 2.193 | 1.583 | 1.049 |
| 148 | 0.726 | 0.665 | 1.435 | 0.865 |
| 149 | 0.755 | 0.702 | 1.454 | 0.895 |
| 150 | 1.503 | 2.97 | 1.675 | 1.072 |
| 151 | 1.118 | 1.345 | 1.363 | 0.907 |
| 152 | 3.623 | 0.804 | 12.574 | 0.935 |
| 153 | 98.529 | 1.067 | 261.601 | 26.149 |
| 154 | 55.197 | 106.311 | 4.726 | 6.474 |
| 155 | 163.374 | 9.622 | 274.003 | 0.981 |
| 156 | 171.302 | 11.402 | 242.591 | 0.982 |
| 157 | 162.691 | 1.99 | 265.024 | 1.081 |
| 158 | 117.142 | 1.821 | 164.425 | 10.907 |
| 159 | 124.524 | 1.621 | 170.679 | 0.971 |
| 160 | 114.542 | 1.857 | 168.865 | 1.758 |
| 161 | 106.232 | 1.622 | 170.085 | 8.432 |
| 162 | 111.329 | 1.56 | 160.179 | 1.146 |
| 163 | 117.564 | 7.09 | 277.58 | 0.966 |
| 164 | 136.836 | 15.999 | 236.856 | 1.029 |
| 165 | 153.715 | 15.611 | 241.372 | 1.011 |
| 166 | 158.809 | 1.676 | 265.977 | 0.909 |
| 167 | 124.245 | 1.73 | 167.034 | 6.717 |
| 168 | 0.971 | 0.899 | 1.483 | 1.05 |
| 169 | 172.896 | 12.076 | 264.305 | 0.953 |
| 170 | 116.844 | 1.275 | 119.572 | 0.996 |
| 171 | 108.141 | 1.541 | 164.727 | 20.13 |
| 172 | 110.94 | 1.586 | 166.627 | 7.809 |
| 173 | 109.481 | 1.508 | 169.035 | 3.971 |
| 174 | 130.071 | 1.66 | 230.522 | 1.215 |
| 175 | 96.583 | 1.091 | 117.528 | 0.969 |
| 176 | 114.019 | 1.716 | 146.617 | 34.025 |
| 177 | 121.188 | 1.68 | 146.329696 | 45.072 |
| 178 | 127.644 | 1.868 | 171.5 | 157.666 |
| 179 | 128.867 | 1.821 | 177.395 | 54.194 |
| 180 | 143.923 | 1.603 | 154.139 | 90.212 |
| 181 | 1.669 | 0.803 | 1.031 | 0.886 |
| 182 | 0.802 | 0.857 | 1.267 | 0.925 |
| 183 | 0.699 | 0.623 | 1.269 | 0.809 |
| 184 | 0.908 | 0.683 | 1.286 | 1.262 |

TABLE 2-continued

| mAb ID | Jurkat Cell Binding (FOI) | Jurkat CD3 KO Cell Binding (FOI) | Human primary T Cell Binding (FOI) | Cyno primary T Cell Binding (FOI) |
|---|---|---|---|---|
| 185 | 0.787 | 0.779 | 1.175 | 0.933 |
| 187 | 1.020164198 | 0.990941406 | 1.162517716 | 0.955608458 |
| 188 | 170.9002855 | 1.892061308 | 216.4804666 | 0.95404005 |
| 189 | 165.1162331 | 1.88632802 | 184.3191845 | 0.942669094 |
| 190 | 179.0685543 | 2.384283148 | 222.717084 | 0.952415628 |
| 191 | 170.174572 | 2.073042082 | 212.0352509 | 0.92972973 |
| 192 | 175.5001334 | 2.548599167 | 223.0397209 | 0.96950007 |
| 193 | 163.2861024 | 2.07938692 | 205.6626449 | 0.934266909 |
| 194 | 199.2002687 | 2.484692122 | 216.5792783 | 0.995658871 |
| 195 | 169.6179176 | 2.529105989 | 226.4101101 | 0.916510293 |
| 196 | 171.5375967 | 2.546993846 | 223.7236254 | 0.959417449 |
| 197 | 182.7938628 | 2.215839162 | 259.5793146 | 0.983279653 |
| 198 | 182.3281795 | 2.173986164 | 230.7815532 | 0.998235541 |
| 199 | 171.5547476 | 2.299621603 | 225.1165825 | 0.992690099 |
| 200 | 180.6875389 | 2.391239537 | 219.5602718 | 0.9380759 |
| 201 | 165.5589563 | 2.131101173 | 210.2269143 | 0.91169304 |
| 202 | 180.8732748 | 2.639796659 | 221.8328306 | 0.945749895 |
| 203 | 201.3010996 | 3.003287085 | 284.9155795 | 0.928721468 |
| 204 | 161.9245399 | 1.921186408 | 181.4935494 | 0.966811371 |
| 205 | 180.0711724 | 2.444711998 | 215.9722717 | 0.922223778 |
| 206 | 185.9601853 | 1.985590337 | 197.5529309 | 0.94703823 |
| 207 | 168.5869649 | 2.27164316 | 219.2860414 | 0.943621342 |
| 208 | 187.2406169 | 2.655505867 | 286.0763165 | 0.902618681 |
| 209 | 185.5859078 | 2.528953102 | 227.8325762 | 0.962610279 |
| 210 | 168.2337506 | 2.034017506 | 192.3078824 | 0.950175046 |
| 211 | 183.5069305 | 2.555288002 | 221.4733074 | 0.947206274 |
| 212 | 150.4676 | 1.958873218 | 159.8668823 | 0.947822434 |
| 213 | 191.5125421 | 2.599166762 | 247.8054294 | 0.969107968 |
| 214 | 150.1576581 | 1.87394412 | 161.7671985 | 0.972636886 |
| 215 | 167.2478487 | 1.9361694 | 202.2712868 | 0.912925361 |
| 216 | 182.4970411 | 2.552497802 | 217.771305 | 0.945581851 |
| 217 | 173.0805481 | 2.161258265 | 213.709634 | 0.915726089 |
| 218 | 179.1574309 | 1.94496044 | 191.8550714 | 0.949950987 |
| 219 | 174.6833302 | 2.452662156 | 244.6117673 | 0.943285254 |
| 220 | 181.460951 | 2.329969805 | 242.9839372 | 0.993362274 |
| 221 | 180.7298235 | 2.263349004 | 238.7224261 | 1.000028007 |
| 222 | 180.257422 | 2.458089669 | 215.683323 | 0.984624002 |
| 223 | 168.2522847 | 1.894201735 | 194.9028601 | 0.951295337 |
| 224 | 181.101967 | 2.039177464 | 212.3520369 | 0.957512953 |
| 225 | 209.9799445 | 2.87734587 | 266.7349275 | 0.938187929 |
| 226 | 176.38064 | 2.150403241 | 199.3170404 | 0.940876628 |
| 227 | 193.0594058 | 2.891335092 | 270.5527856 | 0.903851001 |
| 228 | 158.7840228 | 2.566831021 | 105.3258349 | 0.867665593 |
| 229 | 179.9183157 | 2.222107556 | 250.2144129 | 0.890407506 |
| 230 | 141.1617582 | 2.559568857 | 55.32674347 | 0.908052094 |
| 231 | 174.6661002 | 2.021977602 | 279.2402878 | 0.940372497 |
| 232 | 187.6671376 | 2.445323549 | 296.6650434 | 0.946926201 |
| 233 | 183.7182347 | 6.268623629 | 214.1088055 | 1.903879009 |
| 234 | 182.4947095 | 2.575086955 | 300.918196 | 0.931970312 |
| 235 | 184.7716733 | 5.252646868 | 223.5874914 | 0.999523876 |
| 236 | 180.9545639 | 2.890723541 | 217.6746012 | 1.004005041 |
| 237 | 217.2199686 | 2.762680121 | 292.6926991 | 0.925416608 |
| 238 | 184.5279246 | 2.11906127 | 266.1693499 | 0.945021706 |
| 239 | 175.7375987 | 2.610136452 | 194.3720972 | 0.932026327 |
| 240 | 177.3478102 | 3.292474105 | 216.2357452 | 0.96434673 |
| 241 | 202.7242711 | 2.967664259 | 287.0211869 | 0.952471643 |
| 242 | 198.1461978 | 10.18159233 | 201.0419014 | 1.893852402 |
| 243 | 163.0480443 | 2.912127814 | 236.9560999 | 0.949782944 |
| 244 | 172.6647764 | 2.504835072 | 279.8253807 | 0.926872987 |
| 245 | 169.105168 | 2.588464626 | 222.6575208 | 0.916958409 |
| 246 | 182.9150654 | 2.099797424 | 248.4034597 | 0.931466181 |
| 247 | 186.6972406 | 2.61009823 | 286.2115056 | 0.949446856 |
| 248 | 174.0999615 | 5.72476398 | 202.5718647 | 1.092508052 |
| 249 | 183.5913415 | 2.106753813 | 249.7419777 | 0.940428511 |
| 250 | 124.8568352 | 2.695791767 | 108.9531199 | 1.057779023 |
| 251 | 215.0674478 | 4.312617055 | 297.2926918 | 1.049992998 |
| 252 | 183.8462739 | 3.880059626 | 269.6755097 | 1.044111469 |
| 253 | 1.087345261 | 1.100676528 | 1.175200785 | 0.842403025 |
| 254 | 0.996216125 | 1.006956389 | 0.992768107 | 0.904803249 |
| 255 | 161.6780644 | 1.68906471 | 198.357052 | 1.164990898 |
| 256 | 61.5091633 | 1.324160073 | 72.99698368 | 1.025402605 |
| 257 | 62.33932364 | 1.407713183 | 77.70105753 | 0.992746114 |
| 258 | 147.2724291 | 2.149638803 | 113.4846459 | 0.964290716 |
| 259 | 169.0956836 | 2.117570615 | 213.7375441 | 1.009326425 |
| 260 | 178.3927128 | 2.156251194 | 218.9456336 | 0.976333847 |

TABLE 2-continued

| mAb ID | Jurkat Cell Binding (FOI) | Jurkat CD3 KO Cell Binding (FOI) | Human primary T Cell Binding (FOI) | Cyno primary T Cell Binding (FOI) |
|---|---|---|---|---|
| 261 | 188.1509993 | 2.405993196 | 228.5146273 | 1.000532138 |
| 262 | 164.9680396 | 2.405534534 | 218.9672203 | 1.011286935 |
| 263 | 187.8667049 | 3.460841647 | 247.5181161 | 0.979134575 |
| 264 | 173.5762653 | 2.068073233 | 220.0770433 | 0.921103487 |
| 265 | 161.0170027 | 2.073538967 | 221.9681651 | 0.941660832 |
| 266 | 85.04972387 | 1.677445247 | 71.90427736 | 0.929449657 |
| 267 | 61.28430433 | 1.742651837 | 88.76152924 | 0.931466181 |
| 268 | 0.921289481 | 0.915567787 | 1.064214849 | 0.933930822 |
| 269 | 0.967130677 | 0.979321943 | 0.982774285 | 0.913541521 |
| 270 | 6.589474308 | 1.174215495 | 3.812370535 | 0.925416608 |
| 271 | 4.965826574 | 1.143446852 | 3.362394156 | 0.960425711 |
| 272 | 5.67359883 | 1.163972022 | 3.58596504 | 0.973253046 |
| 273 | 53.06557069 | 2.280548867 | 24.24355853 | 3.284469962 |
| 274 | 1.027317006 | 1.009593701 | 0.938365374 | 0.957905055 |
| 275 | 1.019769016 | 1.026908229 | 0.968782934 | 0.89953788 |
| 276 | 156.048726 | 2.279172878 | 149.111313 | 0.932082341 |
| 277 | 1.142710361 | 1.094905019 | 0.97983065 | 0.890687579 |
| 278 | 0.963494996 | 0.965141612 | 0.895955228 | 0.931522196 |
| 279 | 1.229532005 | 1.065359477 | 1.107933278 | 0.979358633 |
| 280 | 1.069601557 | 1.081221572 | 1.184140713 | 0.961658031 |
| 281 | 1.039686225 | 1.055880442 | 1.211105862 | 0.933594735 |
| 282 | 2.164257699 | 2.942667125 | 1.066068249 | 0.913429492 |
| 283 | 215.8222468 | 2.000726216 | 127.8325035 | 0.956112589 |
| 284 | 225.533309 | 2.345220349 | 209.3349202 | 0.885198152 |
| 285 | 231.8265938 | 1.983373466 | 228.5716466 | 1.066517294 |
| 286 | 231.5038086 | 2.412338035 | 185.2224806 | 1.044167484 |
| 287 | 156.2816072 | 2.017085197 | 106.5352328 | 0.957905055 |
| 288 | 229.4288227 | 1.99900623 | 243.3924483 | 0.88984736 |
| 289 | 1.106234995 | 1.143943737 | 1.080277647 | 0.89315222 |
| 290 | 134.8555508 | 1.787639032 | 99.82854236 | 0.977342109 |
| 291 | 243.7449886 | 2.471161564 | 276.5969764 | 0.91488587 |
| 292 | 226.620101 | 1.991132515 | 255.2318567 | 0.950343089 |
| 293 | 269.5154467 | 2.448610633 | 249.4550641 | 0.938804089 |
| 294 | 1.11528468 | 1.137675343 | 1.307664353 | 0.878028287 |
| 295 | 172.3674014 | 1.656193862 | 172.5901806 | 0.909620501 |
| 296 | 167.1462472 | 1.77961243 | 182.7548061 | 0.946198012 |
| 297 | 219.8341813 | 2.065474143 | 211.1369335 | 1.013527517 |
| 298 | 217.4399273 | 2.429423231 | 211.2352727 | 1.00030808 |
| 299 | 251.5153084 | 3.003554638 | 246.7726133 | 0.942052934 |
| 300 | 68.00150169 | 1.70064595 | 26.7163935 | 0.899873967 |
| 301 | 253.385313 | 1.960019875 | 283.0521132 | 0.903178827 |
| 302 | 202.8679991 | 2.474028208 | 220.7311844 | 0.933706764 |
| 303 | 247.3189421 | 2.591637045 | 256.3239089 | 0.942220978 |
| 304 | 234.2083206 | 2.005121737 | 226.080314 | 0.936955609 |
| 305 | 262.2966044 | 2.263119673 | 250.1197442 | 0.969276012 |
| 306 | 215.503611 | 1.942820013 | 219.0331068 | 0.932418429 |
| 307 | 286.5966666 | 2.543630318 | 228.1071338 | 0.933818793 |
| 308 | 261.5584821 | 2.787868364 | 241.97209 | 0.943957429 |
| 309 | 251.9973128 | 2.248939342 | 239.2834248 | 0.984287915 |
| 310 | 1.463045476 | 1.403776325 | 1.304139259 | 0.969668114 |
| 311 | 1.077623766 | 1.098153881 | 1.124577534 | 0.868561826 |
| 312 | 1.07754473 | 1.103963613 | 1.190318712 | 0.911132895 |
| 313 | 249.2757289 | 3.302067806 | 242.4245739 | 0.988096905 |
| 314 | 254.8914729 | 2.100447196 | 266.9910601 | 0.900602157 |
| 315 | 243.551191 | 2.277911554 | 243.9114002 | 0.937963871 |
| 316 | 252.6456891 | 2.386156022 | 241.2517716 | 1.018792886 |
| 317 | 275.9854178 | 2.134082483 | 254.8704801 | 0.959417449 |
| 318 | 210.5418943 | 2.40706341 | 211.4927136 | 0.929337628 |
| 319 | 1.09125757 | 1.117761725 | 0.986372061 | 0.919142977 |
| 320 | 1.067902271 | 1.024118029 | 1.219064578 | 1.702058535 |
| 321 | 233.2053073 | 2.363261094 | 171.5127376 | 0.994650609 |
| 322 | 244.7474486 | 2.979283721 | 223.6116946 | 0.971908696 |
| 323 | 1.045653484 | 1.036081489 | 0.998837083 | 0.924968492 |
| 324 | 1.06015669 | 1.070901655 | 0.951557219 | 0.929393642 |
| 325 | 0.97507385 | 0.986736995 | 0.969037322 | 0.87965271 |

Example 9

CD3 T Cell Activation and CD69/CD25 Upregulation

To assess T cell activation, 100 μL of purified antibodies were coated onto 96-well flat bottom plates at a two-fold, seven-point dilution range starting at 100 nM and were incubated overnight at 4° C. or for two hours at 37° C. Following incubation, the plates were washed with PBS and 200,000 healthy donor human T cells were added and incubated for 24 hours at 37° C. Cells were then collected and stained in FACS buffer (PBS+2% FBS) containing anti-CD69 APC (Biolegend 310909), anti-CD25 FITC (Biolegend 356106), anti-CD4 PeCy7 (Biolegend 317413), anti-CD8 PE (Biolegend 301008) and eFluor450 fixable viability dye (Thermo Fisher 65-0863-14) for 30 minutes at 4° C. The cells were washed with FACS buffer and T cell activation was assessed using a CytoFLEX S flow cytometer (Beckman Coulter). Data was analyzed using FlowJo V10 and $EC_{50}$ plotted with 4PL nonlinear regression using GraphPad Prism 9 software. See Table 3 below.

TABLE 3

| mAb ID | CD8 $EC_{50}$ (nM) | CD4 $EC_{50}$ (nM) |
|---|---|---|
| 42 | 25.49 | 25.41 |
| 43 | 25.56 | 24.64 |
| 44 | 20.91 | 20.36 |
| 47 | 23.8 | 23.4 |
| 49 | 6.653 | 6.758 |
| 50 | 24.46 | 26.3 |
| 52 | 9.485 | 8.794 |
| 53 | 18.3 | 18.28 |
| 54 | 15.23 | 13.31 |
| 55 | 8.913 | 8.536 |
| 66 | 13.18 | 13.01 |
| 67 | 21.32 | 21.97 |
| 68 | 12.56 | 12.5 |
| 71 | 19.22 | 19.28 |
| 72 | 18.21 | 16.37 |
| 73 | 22.97 | 24.76 |
| 74 | 19.57 | 20.92 |
| 77 | 13.05 | 12.95 |
| 78 | 12.15 | 12.25 |
| 79 | 11.04 | 10.45 |
| 85 | 10.32 | 9.432 |
| 94 | 12.43 | 11.73 |
| 95 | 15.49 | 14.44 |
| 96 | 19.46 | 17.2 |
| 97 | 13.95 | 12.57 |
| 98 | 12.04 | 11.34 |
| 99 | 12.1 | 11.67 |
| 100 | 13.27 | 13.07 |
| 101 | 14.5 | 12.88 |
| 102 | 16.95 | 15.56 |
| 106 | 12.92 | 13.55 |
| 110 | 15.32 | 13.51 |
| 111 | 9.422 | 6.96 |
| 112 | 6.556 | 6.483 |
| 113 | 8.892 | 8.811 |
| 114 | 12.51 | 12.56 |
| 115 | 7.163 | 6.997 |
| 116 | 7.007 | 6.962 |
| 117 | 6.592 | 6.493 |
| 118 | 11.23 | 10.38 |
| 119 | 13.81 | 12.89 |
| 120 | 6.455 | 6.407 |
| 121 | 12.29 | 12.34 |
| 123 | 11.62 | 11.67 |
| 126 | 11.04 | 10.22 |
| 127 | 10.29 | 10.23 |
| 128 | 11.68 | 11.56 |
| 129 | 12.5 | 12.54 |
| 130 | 10.82 | 10.86 |
| 131 | 13.31 | 13.26 |
| 132 | 6.343 | 6.386 |
| 133 | 13.6 | 13.9 |
| 137 | 14.05 | 13.05 |
| 140 | 17.8 | 13.68 |
| 141 | 22.78 | 22.08 |
| 142 | 32.03 | 26.94 |
| 145 | 14.94 | 13.31 |
| 146 | 12.58 | 12.53 |
| 153 | 8.56 | 8.761 |
| 155 | 6.295 | 6.246 |

TABLE 3-continued

| mAb ID | CD8 $EC_{50}$ (nM) | CD4 $EC_{50}$ (nM) |
|---|---|---|
| 156 | 6.252 | 6.251 |
| 157 | 6.567 | 6.416 |
| 158 | 6.625 | 6.67 |
| 159 | 11.92 | 12.04 |
| 160 | 8.475 | 6.948 |
| 161 | 7.887 | 6.76 |
| 162 | 12.71 | 12.62 |
| 163 | 6.994 | 6.296 |
| 164 | 6.621 | 6.845 |
| 165 | 6.569 | 6.481 |
| 166 | 10.62 | 10.52 |
| 167 | 6.358 | 6.298 |
| 169 | 6.667 | 6.487 |
| 170 | 15.09 | 14.58 |
| 171 | 6.712 | 6.862 |
| 172 | 22.91 | 23.16 |
| 173 | 12.34 | 12.48 |
| 174 | 19.41 | 19.47 |
| 175 | 21.16 | 21.6 |
| 176 | 6.369 | 6.383 |
| 177 | 14.17 | 14.33 |
| 178 | 12.59 | 12.59 |
| 179 | 9.871 | 10.41 |
| 180 | 6.57 | 6.54 |

Example 10

T Cell Activation Bioassay (NEAT)

The T cell activation bioassay was purchased from Promega (catalog J1621). Briefly, 3000 CHO-K1 or CHO-K1 cells stably expressing EGFR were plated in 384-well plates and were allowed to adhere for 24 hours at 37° C. The following day, 20,000 Jurkat NEAT T cells were added per well along with CD3×EGFR bispecific antibodies at a five-fold, seven-point dilution series starting at 100 nM. The plate was incubated at 37° C., and after six hours, BIO-GLO™ Luciferase Reagent was added to each well and incubated for 5-10 minutes. Luminescence was read on the Synergy Neo2 (BioTek), and $EC_{50}$ values calculated using the nonlinear regression log (agonist) vs. response (three parameters) with GraphPad Prism 9 software. See Table 4 below.

TABLE 4

| bsAb ID | $EC_{50}$ CHO-K1 | $EC_{50}$ CHO-K1 EGFR Low (nM) | $EC_{50}$ CHO-K1 EGFR Med (nM) |
|---|---|---|---|
| 0011 | N/D | 0.1064 | 0.02634 |
| 0012 | N/D | 0.1475 | 0.02338 |
| 0013 | N/D | 1.314 | 0.2392 |
| 0014 | N/D | 0.2378 | 0.07223 |
| 0015 | N/D | 0.5146 | 0.02665 |
| 0016 | 11.76 | 0.05306 | 0.00316 |
| 0017 | N/D | 0.9445 | 0.1025 |
| 0018 | N/D | 0.3768 | 0.0442 |
| 0019 | N/D | 4.272 | 0.2572 |
| 0020 | N/D | 0.2347 | 0.01022 |
| 0021 | N/D | 1.79 | 0.3727 |
| 0022 | N/D | 0.07805 | 0.05073 |
| 0023 | N/D | 8.335 | 1.709 |
| 0024 | N/D | 0.2451 | 0.1219 |
| 0029 | 7.637 | 0.2713 | 0.0226 |
| 0030 | 2.497 | 0.06444 | 0.002722 |
| 0031 | N/D | 1.658 | 0.4456 |
| 0032 | N/D | 0.1218 | 0.04819 |
| 0037 | N/D | 0.1833 | 0.02804 |
| 0038 | 13.85 | 0.02479 | 0.004887 |
| 0039 | 8.649 | 0.3687 | 0.02569 |
| 0040 | 1.214 | 0.04992 | 0.003803 |
| 0041 | N/D | 0.2974 | 0.02197 |

TABLE 4-continued

| bsAb ID | $EC_{50}$ CHO-K1 | $EC_{50}$ CHO-K1 EGFR Low (nM) | $EC_{50}$ CHO-K1 EGFR Med (nM) |
|---|---|---|---|
| 0042 | N/D | 0.04386 | 0.002228 |
| 0043 | 4.742 | 0.07063 | 0.0122 |
| 0044 | 0.5483 | 0.01359 | 0.004103 |
| 0045 | N/D | 0.07104 | 0.007917 |
| 0046 | N/D | 0.02002 | 0.004085 |
| 0047 | N/D | 0.3675 | 0.02443 |
| 0048 | N/D | 0.09985 | 0.005579 |
| 0049 | N/D | N/D | 0.1381 |
| 0050 | N/D | 1.671 | 0.0606 |
| 0051 | N/D | 1.225 | 0.09216 |
| 0055 | N/D | 0.1192 | 0.01393 |
| 0056 | N/D | 0.02909 | 0.004119 |

Example 11

Target Cell Lysis Using XCELLIGENCE® Real-Time Cell Analysis (RTCA) and Cytokine Analysis The XCELLIGENCE® RTCA MP instrument (Agilent) was utilized to monitor T cell-mediated cytotoxicity of EGFR-expressing cell lines. RPMI-1640+10% FBS was added to each well of an E-plate (Agilent 300600900) and a baseline impedance measurement was recorded. 10,000 HeLa or HeLa EGFR knockout target cell lines were then seeded on the E-plate and cell impedance measurements were recorded every 15 min for five hours while the cells adhered. CD3×EGFR bispecific antibodies at a five-fold, seven-point dilution series starting at 25 nM, and 100,000 purified healthy donor human T cells (E:T ratio 10:1) were then added to appropriate wells and measurements were recorded every 15 min for 48 hours. Cell index (CI) values were normalized to the pre-effector addition, and cytotoxicity was calculated using XCELLIGENCE® RTCA Pro software. $EC_{50}$ values were calculated using the nonlinear regression log (agonist) vs. response (three parameters) with GraphPad Prism 9 software.

Following the 48 hour incubation, cells were pelleted and 100 μL of supernatant was collected from each well and snap frozen. Quantitation of IFNγ, IL-2, IL-6 and TNFα was performed using the ProcartaPlex Immunoassay (Thermo Fisher) using the Luminex FlexMap3D platform according to the manufacturer's instructions. See Table 5 below.

TABLE 5

| bsAb ID | XCELLIGENCE ® HeLa $EC_{50}$ (nM) | Max killing % |
|---|---|---|
| 0011 | 0.06931 | 77.76 |
| 0012 | 0.03952 | 93.35 |
| 0013 | 0.6681 | 80.84 |
| 0014 | 0.1311 | 94.991 |
| 0015 | 0.1786 | 100 |
| 0016 | 0.01922 | 91.99 |
| 0017 | 0.7053 | 91.42 |
| 0018 | 0.1108 | 97.27 |
| 0019 | N/D | 48.26 |
| 0020 | 0.1025 | 79.6 |
| 0021 | N/D | 25.43635 |
| 0022 | 0.4777 | 60.56 |
| 0023 | N/D | 27.4935 |
| 0024 | 0.8948 | 72.54 |
| 0029 | 0.1355 | 81.06 |
| 0030 | 0.04543 | 92.6205 |
| 0031 | N/D | 68.7834 |
| 0032 | 0.06097 | 98.0542 |
| 0037 | 0.1736 | 83.5602 |
| 0038 | 0.03315 | 93.6356 |
| 0039 | 0.3741 | 81.10025 |

TABLE 5-continued

| bsAb ID | XCELLIGENCE ® HeLa $EC_{50}$ (nM) | Max killing % |
|---|---|---|
| 0040 | 0.03907 | 89.5457 |
| 0041 | 0.4487 | 78.6465 |
| 0042 | 0.03415 | 84.753 |
| 0043 | 0.1021 | 76.2459 |
| 0044 | 0.02006 | 84.1279 |
| 0045 | 0.1788 | 69.46735 |
| 0046 | 0.02643 | 92.63 |
| 0047 | 0.4736 | 63.556 |
| 0048 | 0.1147 | 86.75415 |
| 0049 | N/D | 55.8594 |
| 0050 | N/D | 57.0449 |
| 0051 | N/D | 60.23 |
| 0055 | 0.1818 | 77.972 |
| 0056 | 0.01353 | 96.2959 |

While this invention has been disclosed with reference to particular embodiments, it is apparent that other embodiments and variations of the inventions disclosed herein can be devised by others skilled in the art without departing from the true spirit and scope thereof. The appended claims include all such embodiments and equivalent variations.

What is claimed is:

1. An antibody or antigen-binding fragment thereof that binds to at least one human or cynomolgus monkey CD3 molecule, wherein the antibody and antigen-binding fragment thereof comprises:

(a) three CDRs of a heavy chain variable region set forth as SEQ ID NO: 1 and three CDRs of a light chain variable region set forth as SEQ ID NO: 2; or (b) three CDRs of a heavy chain variable region set forth as SEQ ID NO: 3 and three CDRs of a light chain variable region set forth as SEQ ID NO: 4; or (c) three CDRs of a heavy chain variable region set forth as SEQ ID NO: 5 and three CDRs of a light chain variable region set forth as SEQ ID NO: 6; or (d) three CDRs of a heavy chain variable region set forth as SEQ ID NO: 7 and three CDRs of a light chain variable region set forth as SEQ ID NO: 8; or (e) three CDRs of a heavy chain variable region set forth as SEQ ID NO: 9 and three CDRs of a light chain variable region set forth as SEQ ID NO: 10; or (f) three CDRs of a heavy chain variable region set forth as SEQ ID NO: 11 and three CDRs of a light chain variable region set forth as SEQ ID NO: 12; or (g) three CDRs of a heavy chain variable region set forth as SEQ ID NO: 13 and three CDRs of a light chain variable region set forth as SEQ ID NO: 14; or (h) three CDRs of a heavy chain variable region set forth as SEQ ID NO: 15 and three CDRs of a light chain variable region set forth as SEQ ID NO: 16; or (i) three CDRs of a heavy chain variable region set forth as SEQ ID NO:17 and three CDRs of a light chain variable region set forth as SEQ ID NO: 18; or (j) three CDRs of a heavy chain variable region set forth as SEQ ID NO: 19 and three CDRs of a light chain variable region set forth as SEQ ID NO: 20; or (k) three CDRs of a heavy chain variable region set forth as SEQ ID NO: 21 and three CDRs of a light chain variable region set forth as SEQ ID NO: 22; or (l) three CDRs of a heavy chain variable region set forth as SEQ ID NO: 23 and three CDRs of a light chain variable region set forth as SEQ ID NO: 24; or (m)three CDRs of a heavy chain variable region set forth as SEQ ID NO: 41 and three CDRs of a light chain variable region set forth as SEQ ID NO: 42, wherein the CDR numbering is according to Kabat, Chothia, or MacCallum.

2. A composition comprising the antibody or antigen-binding fragment thereof of claim 1 and one or more pharmaceutically acceptable carriers, diluents, or excipients.

3. A nucleic acid encoding:

(a) a heavy chain variable region having an amino acid sequence that is identical to one of the heavy chain variable region sequences set forth in claim 1; or (b) a light chain variable region having an amino acid sequence that is identical to one of the light chain variable region sequences set forth in claim 1; or (c) a heavy chain variable region having an amino acid sequence that is identical to one of the heavy chain variable region sequences set forth in claim 1 and a light chain variable region having an amino acid sequence that is at identical to the light chain variable region sequence corresponding to the heavy chain variable region sequence.

4. A vector comprising the nucleic acid of claim 3.

5. A host cell comprising the nucleic acid of claim 3.

6. A process for producing an antibody comprising:

(a) cultivating the host cell of claim 5 under conditions such that the antibody is expressed; and (b) recovering the expressed antibody.

* * * * *